United States Patent
Tsuzuki et al.

(10) Patent No.: US 8,575,338 B2
(45) Date of Patent: Nov. 5, 2013

(54) PYRIMIDINE, PYRIDINE AND TRIAZINE DERIVATIVES AS MAXI-K CHANNEL OPENERS

(75) Inventors: Yasuyuki Tsuzuki, Osaka (JP); Miki Hirai, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 47 days.

(21) Appl. No.: 12/936,987

(22) PCT Filed: Apr. 8, 2009

(86) PCT No.: PCT/JP2009/057541
§ 371 (c)(1),
(2), (4) Date: Oct. 8, 2010

(87) PCT Pub. No.: WO2009/125870
PCT Pub. Date: Oct. 15, 2009

(65) Prior Publication Data
US 2011/0034435 A1    Feb. 10, 2011

(30) Foreign Application Priority Data
Apr. 9, 2008   (JP) .................. 2008-101078
Aug. 6, 2008   (JP) .................. 2008-203378

(51) Int. Cl.
C07D 239/47   (2006.01)
C07D 239/46   (2006.01)
C07D 239/34   (2006.01)
C07D 401/04   (2006.01)
C07D 401/14   (2006.01)
C07D 403/04   (2006.01)
C07D 403/14   (2006.01)
A61K 31/506   (2006.01)
A61P 13/10    (2006.01)
A61P 11/06    (2006.01)

(52) U.S. Cl.
USPC ........... 544/242; 544/317; 544/320; 544/321; 544/323; 544/324; 544/326; 544/328; 544/330; 544/331; 514/256; 514/269; 514/275

(58) Field of Classification Search
USPC ......... 544/242, 317, 320, 321, 323, 324, 326, 544/328, 330, 331; 514/256, 269, 275
See application file for complete search history.

(56) References Cited

U.S. PATENT DOCUMENTS

| | | | |
|---|---|---|---|
| 5,998,459 A | 12/1999 | Tsuda et al. | |
| 6,440,963 B1 | 8/2002 | Leonardi et al. | |
| 7,385,083 B2 | 6/2008 | Imaizumi et al. | |
| 7,495,127 B2 | 2/2009 | Imaizumi et al. | |
| 7,531,655 B2 | 5/2009 | Hosaka et al. | |
| 2004/0116482 A1 | 6/2004 | Imaizumi et al. | |
| 2006/0135597 A1 | 6/2006 | Hosaka et al. | |
| 2006/0235072 A1 | 10/2006 | Imaizumi et al. | |
| 2007/0185116 A1 | 8/2007 | Hirai et al. | |
| 2010/0256165 A1 | 10/2010 | Hongu et al. | |

FOREIGN PATENT DOCUMENTS

| | | |
|---|---|---|
| EP | 0629622 A1 | 12/1994 |
| EP | 1302463 A1 | 4/2003 |
| EP | 1400243 A1 | 3/2004 |
| JP | 2000-351773 A | 12/2000 |
| JP | 2000-516925 A | 12/2000 |
| WO | WO-96/40634 A1 | 12/1996 |
| WO | WO-98/04135 A1 | 2/1998 |
| WO | WO-00/34244 A1 | 6/2000 |
| WO | WO-02/083111 A2 | 10/2002 |
| WO | WO-2004/011442 A | 2/2004 |
| WO | WO-2005/007648 A2 | 1/2005 |
| WO | WO-2006/030977 A2 | 3/2006 |
| WO | WO-2006/034473 A2 | 3/2006 |
| WO | WO-2006/084017 A2 | 8/2006 |
| WO | WO-2007/051133 A2 | 5/2007 |
| WO | WO-2007/066102 A1 | 6/2007 |

OTHER PUBLICATIONS

N'Gouemo, P. Expert Opin. Ther. Targets (2011) 15(11):1283-1295.*
Grimm, R.P. Kidney Int. Nov. 2010; 78(10): 956-962.*
European Office Action for Application No. 09730805.0 dated Apr. 20, 2011.
Benassayag et al., "About 500 Cases of Pollakiuria and Cystalgia Treated with an Anti-inflammatory Drug (*)", Therapy, vol. XXV, 1970, pp. 1051-1057.
Bresalier et al., "Cardiovascular Events Associated with Rofecoxib in a Colorectal Adenoma Chemoprevention Trial", The New England Journal of Medicine, vol. 352, No. 11, Mar. 17, 2005, pp. 1092-1102.
Database Beilstein, Beilstein Institute for Organic Chemistry, Frankfurt-Main, DE; XP002534190, Database accession No. 4006449 (BRN) cited in the application, N-[4-phenyl-6-(1-phenylethylamino)-[1,3,5]triazin-2-yl]-glycine & Krasnovskaya et al., Zhurnal Obshchei Khimii, vol. 42, 1972, pp. 2280-2285.

(Continued)

*Primary Examiner* — Venkataraman Balasubramanian
(74) *Attorney, Agent, or Firm* — Birch, Stewart, Kolasch & Birch, LLP

(57) ABSTRACT

A compound of formula (A); wherein ring A is an aromatic ring or a heteroaromatic ring; $R^1$ is independently halogen, cyano, etc., each of $X^1$, $X^2$ and $X^3$ is $CR^2$ or nitrogen, $R^2$ is independently hydrogens, etc., n is 0, 1, 2, 3 or 4; -D-Y is —O—$CH_2$COOH, etc, and G is a substituted amino, a substituted heterocyclic group, etc, or a pharmaceutical acceptable salt thereof, has activities of opening BK channels.

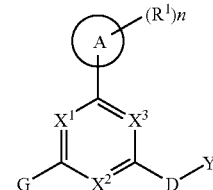

(A)

8 Claims, No Drawings

(56) References Cited

OTHER PUBLICATIONS

Database Beilstein, Beilstein Institute for Organic Chemistry, Frankfurt-Main, DE; XP002534191, Database accession No. 7498395 (BRN), [4-(4-Chloro-phenyl)-6-(2-methoxy-naphthalen-1-yl)-pyrimidin-2-ylamino]-acetic acid & Essawy et al., Egyptian Journal of Chemistry, vol. 37, No. 4, 1994.

Database Beilstein, Beilstein Institute for Organic Chemistry, Frankfurt-Main, DE; XP002534192, Database accession No. 4539335 (BRN), (4,6-Diphenyl-pyrimidin-2-yloxy)-acetic acid ethyl ester & Gefenas et al., Chemistry of Heterocyclic Compounds, vol. 20, No. 10, 1984.

Database WPI Week 200421, Thomson Scientific, London, GB; AN 2004-226296; XP002534193.

Nussmeier et al., "Complications of the COX-2 Inhibitors Parecoxib and Valdecoxib after Cardiac Surgery", The New England Journal of Medicine, vol. 352, No. 11, 2005, pp. 1081-1091.

Patel et al., "Inhibition of Cholinergic Neurotransmission in Guinea Pig Trachea by NS1619, a Putative Activator of Large-Conductance, Calcium-Activated Potassium Channels[1,2]", The Journal of Pharmacology and Experimental Therapeutics, vol. 286, No. 2, 1998, pp. 952-958.

Romine et al., "4,5-Diphenyltriazol-3-ones: Openers of Large-Conductance $Ca^{2+}$-Activated Potassium (Maxi-K) Channels", Journal of Medicinal Chemistry, vol. 45, No. 14, 2002, pp. 2942-2952.

Solomon et al., "Cardiovascular Risk Associated with Celecoxib in a Clinical Trial for Colorectal Adenoma Prevention, The New England Journal of Medicine", vol. 352, No. 11, 2005, pp. 1071-1080.

Wang et al., "Synthesis and Antivirus Activity of 1,3,5-Triazine Derivatives", Heteroatom Chemistry, vol. 14, No. 6, 2003, pp. 542-545; XP002534189.

International Search Report, dated Jul. 8, 2009, issued in corresponding International Application PCT/JP2009/057541.

\* cited by examiner

PYRIMIDINE, PYRIDINE AND TRIAZINE DERIVATIVES AS MAXI-K CHANNEL OPENERS

TECHNICAL FIELD

The present invention relates to a new compound and a large conductance calcium-activated potassium channel opener comprising the compound, which is useful for treatment of diseases such as pollakiuria, urinary incontinence, asthma, chronic obstructive pulmonary diseases (COPD), cerebral infarction, subarachnoid hemorrhage, overactive bladder and the like.

BACKGROUND ART

Potassium is the most abundant intracelluar cation, and is very important in maintaining physiological homeostasis. Potassium channels are present in almost all vertebrate cells, and the potassium influx through these channels is indispensable for maintaining hyperpolarized resting membrane potential.

Large conductance calcium activated potassium channels (also referred to as BK channels or maxi-K channels) are expressed especially in neurons and smooth muscle cells. Because both of the increase of intracellular calcium concentration and membrane depolarization can activate maxi-K channels, maxi-K channels have been thought to play a pivotal role in regulating voltage-dependent calcium influx. Increase in the intracellular calcium concentration mediates many processes such as release of neurotransmitters, contraction of smooth muscles, cell growth and death, and the like. Actually, the opening of maxi-K channels causes strong membrane hyperpolarization, and inhibits these calcium-induced responses thereby. Accordingly, by inhibiting various depolarization-mediated physiological responses, a substance having an activity of opening maxi-K channels is useful for the treatment of diseases such as cerebral infarction, subarachnoid hemorrhage, pollakiuria, urinary incontinence, and the like.

There has been a report that a medicine which opens BK channels has activities to inhibit electrically induced contraction of respiratory tract preparation of guinea pig (nonpatent document 1). Therefore, it is effective for treatment of, for example, asthma, COPD, etc. Also, there has been suggested that a medicine which opens BK channels can be an agent for treatment of sexual function disorder such as erectile dysfunction, etc. (patent document 1).

There have been various reports on large conductance calcium-activated potassium channel openers. For example, pyrrole derivatives (patent document furan derivatives (patent document 3), nitrogen-containing 5-membered ring derivatives in which the nitrogen atom is substituted by phenyl or benzyl (patent document 4), diphenyltriazole derivatives (nonpatent document 2), Celecoxib derivative, etc. (patent document 5), diphenylheterocyclic compounds (patent document 6), nitrogen-containing 5-membered heterocyclic ring compounds (patent document 7), imidazole compounds (patent document 8), thiazole compounds (patent document 9) etc.

There has been a report on a method of treating neuromuscular dysfunction of the lower urinary tract in mammal comprising administrating a cyclooxygenase inhibitor (patent document 10) and a report on a method of treating pollakiuria comprising administrating Niflumic acid known as cyclooxygenase inhibitor (nonpatent document 3). However, there have also been various reports on side effects caused by inhibiting cyclooxygenases, known as COX-1 and COX-2. The primary side effects associated with the administration of Nonsteroidal anti-inflammatory drugs ("NSAIDs"), whose primary pharmacological action is the inhibition of both COX-1 and COX-2, are gastrointestinal upset and injury. It is generally understood that these effects are primarily due to the inhibition of protective prostaglandins produced through the COX-1 pathway. As regards side effects associated with COX-2 inhibitors, there have been reported for increased incidence of cardiovascular events (nonpatent documents 4 to 6, etc).

There have been various reports on pyrimidine, pyridine and triadine derivatives. For example, pyrimidine derivatives (patent documents 11, 12, and 13), triadine derivatives (nonpatent document 7), etc.

[patent document 1] WO 00/34244
[patent document 2] WO 96/40634
[patent document 3] JP 2000-351773
[patent document 4] WO 98/04135
[patent document 5] EP 1400243
[patent document 6] JP 2000-516925
[patent document 7] WO 02/83111
[patent document 8] WO 2006/030977
[patent document 9] WO 2007/51133
[patent document 10] U.S. Pat. No. 6,440,963
[patent document 11] WO 2006034473
[patent document 12] WO 2004011442
[patent document 13] WO 2006084017
[nonpatent document 1] J. Pharmacol. Exp. Ther., (1998) 286: 952-958
[nonpatent document 2] J. Med. Chem., Vol. 45, p. 2942-2952 (2002)
[nonpatent document 3] Therapy, 1970, XXV, 1051
[nonpatent document 4] N. Engl. J. Med., 352, 1071 (2005)
[nonpatent document 5] N. Engl. J. Med., 352, 1081 (2005)
[nonpatent document 6] N. Engl. J. Med., 352, 1092 (2005)
[nonpatent document 7] Zhurnal Obshchei Khimii (1972), 42(10), 2280

DISCLOSURE OF INVENTION

An object of the present invention is to provide a compound having an excellent large conductance calcium-activated K channel opening activity, and useful for the treatment of diseases such as pollakiuria, urinary incontinence, asthma, COPD, cerebral infarction, subarachnoid hemorrhage, overactive bladder and the like, with less or no side effects which include ones caused by inhibiting COX s.

The present inventors have studied intensively to solve the above-mentioned problem, and as a result, they have found that a compound of the formulae shown below has an excellent large conductance calcium-activated K channel opening activity, whereby they have accomplished the present invention.

That is, the present invention is described as follows.

(1) A compound of formula (A):

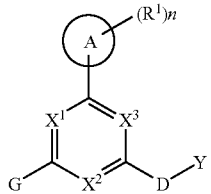
(A)

wherein ring A is an aromatic ring or a heteroaromatic ring;

$R^1$ is independently a halogen, cyano, an alkylthio, a cycloalkyl, an alkanoyl, an amino optionally substituted by alkyl(s), an alkylsulfonyl, an alkoxy optionally substituted by one to three substituent(s) independently selected from a halogen, an alkoxy and hydroxy, or an alkyl optionally substituted by one to three substituent(s) independently selected from a halogen, an alkoxy and hydroxy;

n is 0, 1, 2, 3 or 4;

Each of $X^1$, $X^2$ and $X^3$ is independently $CR^2$ or nitrogen, provided that at least one of $X^1$, $X^2$ and $X^3$ is nitrogen;

$R^2$ is independently hydrogen, a halogen, an alkoxy optionally substituted by one to three substituent(s) independently selected from a halogen, an alkoxy and hydroxy, or an alkyl optionally substituted by one or more substituent(s) independently selected from halogen, an alkoxy and hydroxy;

Y is carboxy, tetrazolyl or an alkoxycarbonyl;

D is a group of formula:

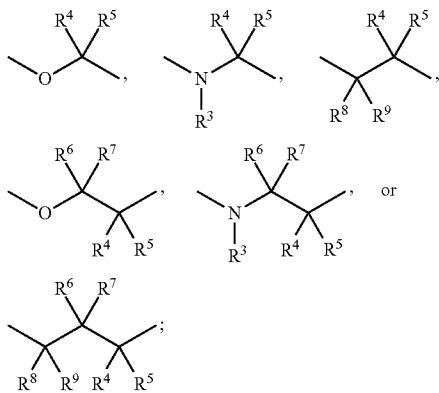

$R^3$ is hydrogen or an alkyl optionally substituted by one or more substituent(s) independently selected from an alkoxy and a heteroaryl;

Each of $R^4$, $R^5$, $R^6$, $R^7$, $R^8$ and $R^9$ is independently hydrogen, or an alkyl, or two of $R^3$, $R^4$, $R^5$, $R^6$, $R^7$, $R^8$ and $R^9$, taken together with the atom(s) to which they are bonded, may form a carbocyclic ring optionally substituted by one or more alkyl(s) or a heterocyclic ring optionally substituted by one or more alkyl(s);

G is $-NR^{10}R^{11}$, $-OR^{14}$, a phenyl optionally substituted by one or more $R^{15}(s)$ or a group of formula:

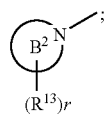

$R^{10}$ is an alkyl optionally substituted by one or more substituent(s) selected from an alkoxy, hydroxy, and a group of formula:

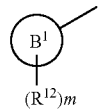

or a cycloalkyl optionally substituted by one or more $R^{12}(s)$;

$R^{11}$ is hydrogen, or an alkyl optionally substituted by one to three substituent(s) independently selected from an alkoxy and hydroxy;

$R^{12}$ is independently a halogen, cyano, an alkylthio, a cycloalkyl, an alkanoyl, an amino optionally substituted by alkyl(s), an alkylsulfonyl, an alkoxy optionally substituted by one to three substituent(s) independently selected from a halogen, an alkoxy and hydroxy, or an alkyl optionally substituted by one to three substituent(s) independently selected from a halogen, an alkoxy and hydroxy;

$R^{13}$ is independently hydroxy, an alkoxy optionally substituted by one to three substituent(s) independently selected from a halogen, an alkoxy, a cycloalkyl and hydroxy, an alkylsulfonyl, oxo, a halogen, cyano, an aryl, a heteroary, an aryloxy, a heteroaryloxy, an alkoxycarbonyl or an alkyl optionally substituted by one to three substituent(s) independently selected from a halogen, hydroxy, and an optionally substituted alkoxy;

$R^{14}$ is an alkyl substituted by a group of formula

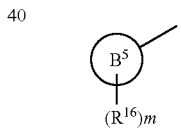

or a group of formula

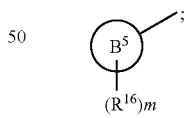

Ring $B^1$ is a carbocyclic ring, a heterocyclic ring, an aromatic ring or a hetero aromatic ring;

Ring $B^2$ is a nitrogen containing heterocyclic ring;

Ring $B^5$ is a carbocyclic ring, a heterocyclic ring, an aromatic ring or a heteroaromatic ring;

$R^{15}$ is independently a halogen, cyano, an alkylthio, a cycloalkyl, a cycloalkyloxy, an alkanoyl, an amino optionally substituted by alkyl(s), an alkylsulfonyl, an alkoxy optionally substituted by one to three substituent(s) independently selected from a halogen, an alkoxy, a cycloalkyl and hydroxy, or an alkyl optionally substituted by one to three substituent(s) independently selected from a halogen, an alkoxy and hydroxy;

$R^{16}$ is independently a halogen, cyano, an alkylthio, a cycloalkyl, an alkanoyl, an amino optionally substituted by alkyl(s), an alkylsulfonyl, an alkoxy optionally substituted by one to three substituent(s) independently selected from a halogen, an alkoxy and hydroxy, or an alkyl optionally substituted by one to three substituent(s) independently selected from a halogen, an alkoxy and hydroxy;

m is 0, 1, 2 or 3; and
r is 0, 1, 2 or 3;
or a pharmaceutically acceptable salt thereof.

(2) The compound according to (1) or a pharmaceutically acceptable salt thereof, wherein a group of formula:

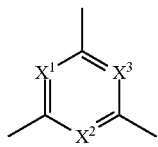

is pyrimidine which is substituted by $R^2$ or triadine.

(3) The compound according to (1) or a pharmaceutically acceptable salt thereof, wherein a group of formula:

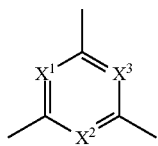

is pyrimidine which is substituted by $R^2$.

(4) The compound according to (1) or a pharmaceutically acceptable salt thereof, wherein a group of formula:

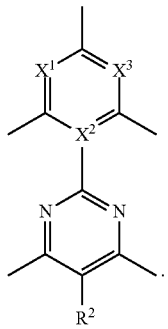 is 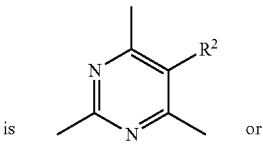 or (5) The compound according to (1) or a pharmaceutically acceptable salt thereof, wherein a group of formula:

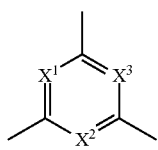 is 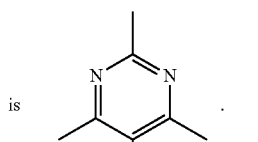.

(6) The compound according to any one of (1) to (5) or a pharmaceutically acceptable salt thereof, wherein $R^2$ is hydrogen.

(7) The compound according to any one of (1) to (6) or a pharmaceutically acceptable salt thereof, wherein ring A is an aromatic ring.

(8) The compound according to any one of (1) to (6) or a pharmaceutically acceptable salt thereof, wherein ring A is benzene.

(9) The compound according to any one of (1) to (6) or a pharmaceutically acceptable salt thereof, wherein ring A is a heteroaromatic ring.

(10) The compound according to any one of (1) to (6) or a pharmaceutically acceptable salt thereof, wherein ring A is thiophene.

(11) The compound according to any one of (1) to (10) or a pharmaceutically acceptable salt thereof, wherein $R^1$ is independently a halogen, an alkoxy, or an alkyl optionally substituted by one to three halogen(s).

(12) The compound according to any one of (1) to (11) or a pharmaceutically acceptable salt thereof, wherein $R^1$ is independently a halogen, or an alkyl optionally substituted by one to three halogen(s).

(13) The compound according to any one of (1) to (12) or a pharmaceutically acceptable salt thereof, wherein n is 1 or 2.

(14) The compound according to any one of (1) to (13) or a pharmaceutically acceptable salt thereof, wherein Y is carboxy or alkoxycarbonyl.

(15) The compound according to any one of (1) to (14) or a pharmaceutically acceptable salt thereof, wherein G is a group of formula:

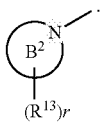

(16) The compound according to any one of (1) to (14) or a pharmaceutically acceptable salt thereof, wherein G is $-NR^{10}R^{11}$.

(17) The compound according to any one of (1) to (14) or a pharmaceutically acceptable salt thereof, wherein G is a phenyl optionally substituted by one or more $R^{15}$(s).

(18) The compound according to (16) or a pharmaceutically acceptable salt thereof, wherein ring $B^1$ is benzene or a monocyclic heteroaromatic ring.

(19) The compound according to (15) or a pharmaceutically acceptable salt thereof, wherein ring $B^2$ is a monocyclic nitrogen containing heterocyclic ring.

(20) The compound according to (16) or (18) or a pharmaceutically acceptable salt thereof, wherein $R^{10}$ is an alkyl optionally substituted by one or more group(s) of formula:

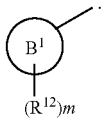

(21) The compound according to (16) or (18) or a pharmaceutically acceptable salt thereof, wherein $R^{10}$ is an alkyl substituted by a group of formula:

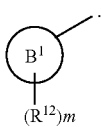

(22) The compound according to (16) or (18) or a pharmaceutically acceptable salt thereof, wherein $R^{10}$ is a cycloalkyl optionally substituted by one or more $R^{12}$(s).

(23) The compound according to any one of (1) to (22) or a pharmaceutically acceptable salt thereof, wherein D is a group of formula:

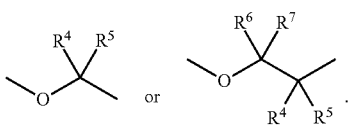

(24) The compound according to any one of (1) to (22) or a pharmaceutically acceptable salt thereof, wherein D is a group of formula:

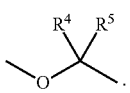

(25) The compound according to any one of (1) to (22) or a pharmaceutically acceptable salt thereof, wherein D is a group of formula:

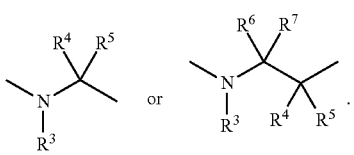

(26) The compound according to any one of (1) to (22) or a pharmaceutically acceptable salt thereof, wherein D is a group of formula:

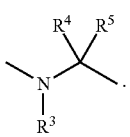

(27) The compound according to (25) or (26) or a pharmaceutically acceptable salt thereof, wherein $R^3$ is hydrogen or an alkyl optionally substituted by a heteroaryl.

(28) The compound according to any one of (23) to (27) or a pharmaceutically acceptable salt thereof, wherein $R^4$ is ethyl and $R^5$ is ethyl.

(29) The compound according to any one of (23) to (27) or a pharmaceutically acceptable salt thereof, wherein $R^4$ is methyl and $R^5$ is methyl.

(30) The compound according to any one of (23) to (27) or a pharmaceutically acceptable salt thereof, wherein $R^4$ is hydrogen and $R^5$ is hydrogen.

(31) The compound according to (25) or (26) or a pharmaceutically acceptable salt thereof, wherein $R^3$ and $R^4$, taken together with the atom(s) to which they are bonded, form a heterocyclic ring optionally substituted by one or more alkyl(s).

(32) The compound according to any one of (1) to (27) or a pharmaceutically acceptable salt thereof, wherein $R^4$ and $R^5$, taken together with the atom(s) to which they are bonded, form a heterocyclic ring optionally substituted by one or more alkyl(s).

(33) The compound according to any one of (1) to (27) or a pharmaceutically acceptable salt thereof, wherein $R^4$ and $R^5$, taken together with the atom(s) to which they are bonded, form a carbocyclic ring optionally substituted by one or more alkyl(s).

(34) The compound according to (33) or a pharmaceutically acceptable salt thereof, wherein $R^4$ and $R^5$, taken together with the atom(s) to which they are bonded, form a cyclopropane ring optionally substituted by one or more alkyl(s).

(35) The compound according to (33) or a pharmaceutically acceptable salt thereof, wherein $R^4$ and $R^5$, taken together with the atom(s) to which they are bonded, form a cyclopentane ring optionally substituted by one or more alkyl(s).

(36) The compound according to any one of (1) to (35) or a pharmaceutically acceptable salt thereof,
provided that when D is a group of formula:

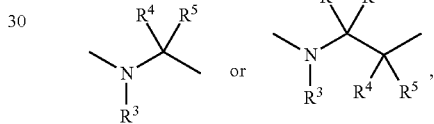

G is not a group of formula:

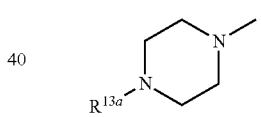

wherein $R^{13a}$ is an unsubstituted or substituted aryl or an unsubstituted or substituted heteroaryl.

(37) The compound according to any one of (1) to (36) or a pharmaceutically acceptable salt thereof,
provided that when G is phenyl or a phenyl substituted by one or more $R^{15}$, Ring A is an aromatic ring.

(38) The compound according to any one of (1) to (37) or a pharmaceutically acceptable salt thereof,
provided that when G is phenyl or a phenyl substituted by one $R^{15}$, D is a group of formulae:

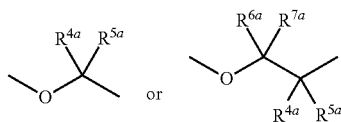

wherein two of $R^{4a}$, $R^{5a}$, $R^{6a}$ and $R^{7a}$, taken together with the atom(s) to which they are bonded, form a carbocyclic ring optionally substituted by one or more alkyl(s) or a heterocyclic ring optionally substituted by one or more alkyl(s).

(39) The compound according to any one of (1) to (38) or a pharmaceutically acceptable salt, wherein G is —$OR^{14}$.

(40) The compound according to any one of (1) to (39) or a pharmaceutically acceptable salt thereof for use in therapy.
(41) The compound according to any one of (1) to (40) or a pharmaceutically acceptable salt thereof for the prophylaxis and/or treatment for a disorder or disease responsive to opening of BK channels.
(42) A method for the prophylaxis and/or treatment for a disorder or disease responsive to opening BK channels, comprising administrating an effective amount of the compound according to any one of (1) to (39) or a pharmaceutically acceptable salt thereof.
(43) A large conductance calcium-activated K channel opener comprising the compound according to any one of (1) to (39) or a pharmaceutically acceptable salt thereof.
(44) A medicine comprising the compound according to any one of (1) to (39) or a pharmaceutically acceptable salt thereof.

DETAILED DESCRIPTION OF THE INVENTION

Hereinafter, each group of the respective symbols in the present specification will be explained.

"Alkyl" is exemplified by a straight or branched $C_{1-6}$, preferably $C_{1-4}$ alkyl, more specifically by methyl, ethyl, propyl, isopropyl, butyl, isobutyl, 1-methylpropyl, pentyl, hexyl, etc.

"Alkoxy" is exemplified by a straight or branched $C_{1-6}$, preferably $C_{1-4}$ alkoxy, more specifically by methoxy, ethoxy, propoxy, isopropoxy, butoxy, isobutoxy, tert-butoxy, pentyloxy, hexyloxy, etc.

"Alkanoyl" is exemplified by a straight or branched $C_{1-6}$, preferably $C_{1-4}$ alkanoyl, more specifically by formyl, acetyl, propionyl, butyryl, pentanoyl, hexanoyl, etc.

"Aromatic ring" is exemplified by a monocyclic, bicyclic or tricyclic 6 to 14-membered, preferably 6 to 10-membered aromatic ring, more specifically by benzene, naphthalene, phenanthrlene, anthracene, etc., particularly preferably by benzene and naphthalene.

"Aryl" is exemplified by a monocyclic, bicyclic or tricyclic 6 to 14-membered, preferably 6 to 10-membered aryl, more specifically by phenyl, naphthyl, phenanthlyl, anthlyl, etc., particularly preferably by phenyl and naphthyl.

"Carbocyclic ring" is exemplified by a monocyclic or bicyclic 3 to 14-membered carbocyclic ring, which is partially or wholly saturated, and it is more preferably exemplified by a monocyclic carbocyclic ring.

The monocyclic carbocyclic ring is preferably exemplified by a 3 to 8-membered carbocyclic group which is partially or wholly saturated, and it is more preferably exemplified by a cycloalkane and cycloalkene, etc, and it is further preferably exemplified by a cycloalkane.

"Cycloalkane" is exemplified by a 3 to 8-membered cycloalkane, preferably 3 to 6-membered cycloalkane, more specifically by cyclopropane, cyclobutane, cyclopentane, cyclohexane, etc., preferably cyclopropane, and cyclopentane.

"Cycloalkene" is exemplified by a 4 to 8-membered cycloalkene, preferably 5 to 7-membered cycloalkene, more specifically by cyclopropene, cyclobutene, cyclopentene, cyclohexene, etc., preferably cyclopropene, and cyclopentene.

The bicyclic carbocyclic ring is preferably exemplified by a 7 to 14-membered carbocyclic group which is partially or wholly saturated, and it is more preferably exemplified by a cycloalkane fused with an aromatic ring or monocyclic carbocyclic ring and cycloalkene fused with an aromatic ring or monocyclic carbocyclic ring, etc.

"Cycloalkyl" is exemplified by a $C_{3-8}$, preferably $C_{3-6}$ cycloalkyl, more specifically by cyclopropyl, cyclobutyl, cyclopentyl, cyclohexyl, etc.

"Halogen" is exemplified by fluorine, chlorine, bromine, and iodine.

"Heterocyclic ring" is exemplified by a monocyclic or bicyclic 4 to 10-membered heterocyclic ring, which is partially or wholly saturated, containing 1 to 4 hetero atom(s) selected from nitrogen, oxygen and sulfur. The monocyclic or bicyclic heterocyclic group which may be partially or wholly saturated may be substituted by oxo.

The monocyclic heterocyclic ring is preferably exemplified by a 4 to 7-membered heterocyclic group which is partially or wholly saturated, containing 1 to 4 hetero atom(s) selected from nitrogen, oxygen and sulfur, and it is specifically exemplified by azetidine, pyrrolidine, piperidine, piperazine, morpholine, thiomorpholine, homopiperazine, homomorpholine, homothiomorpholine, homopiperidine, tetrahydropyrane, tetrahydrofuran, oxazolidine, etc.

The bicyclic heterocyclic ring is exemplified by a bicyclic heterocyclic group in which two of the same or different monocyclic heterocyclic ring above are fused, or a bicyclic heterocyclic ring in which the above monocyclic heterocyclic group and benzene ring or heteroaromatic ring are fused, and it is specifically exemplified by dihydroindole, tetrahydroquinoline, etc.

"Heteroaromatic ring" is exemplified by a monocyclic or bicyclic 5 to 10-membered heteroaromatic ring containing 1 to 4 hetero atom(s) selected from nitrogen, oxygen and sulfur. It is exemplified by preferably 5 to 10-membered heteroaromatic ring, more specifically by oxazole, pyrrole, pyrazole, pyridine, pyrimidine, pyridazine, triazine, pyrazine, tetrazole, thiazole, furan, thiophene, benzofuran, benzthiophene, benzimidazole, benzothiazole, etc.

"Heteroaryl" is exemplified by a monocyclic, bicyclic or tricyclic 5 to 14-membered heteroaryl, preferably 5 to 10-membered heteroaryl, more specifically by oxazolyl, pyrrolyl, pyrazolyl, pyridyl, pyrimidinyl, pyrazinyl, pyridazinyl, triadinyl, tetrazolyl, thiazolyl, furanyl, thienyl, benzofuranyl, benzthienyl, benzimidazolyl, benzothiazolyl etc.

"Nitrogen containing heterocyclic ring" is exemplified by a monocyclic or bicyclic 4 to 10-membered heterocyclic ring, which is partially or wholly saturated, containing 1 to 4 nitrogen and 0 to 3 hetero atom(s) selected from oxygen and sulfur.

A) A Group of Formula:

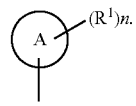

Preferable "heteroaromatic ring" of ring A is exemplified by thiophene, oxazole, thiazole, furan, pyrimidine, benzofuran, benzothiophene, pyridine, etc., more preferably furan, thiophene, benzofuran, and benzothiophene, further preferably thiophene.

Preferable ring A is exemplified by an aromatic ring, and a heteroaromatic ring containing one heteroatom selected from sulfur atom and oxygen atom, and more preferable ring A is benzene, and thiophene.

"Alkoxy substituted by one to three substituent(s) independently selected from a halogen, an alkoxy and hydroxy" of $R^1$ is exemplified by alkoxy-$C_{2-6}$-alkoxy, hydroxy-$C_{2-6}$-alkoxy and trihaloalkoxy, more preferably by 2-alkoxyethoxy, 3-alkoxypropoxy, 2-hydroxyethoxy, 3-hydroxypropoxy, and trifluoromethoxy.

"Alkyl substituted by one to three substituent(s) independently selected from a halogen, an alkoxy and hydroxy" of $R^1$ is exemplified by alkoxy-$C_{1-6}$-alkyl, hydroxy-$C_{1-6}$-alkyl and trihaloalkyl, more preferably by an alkoxymethyl, a 2-alkoxyethyl, a 3-alkoxypropyl, hydroxymethyl, 2-hydroxyethyl, 3-hydroxypropyl, and trifluoromethyl.

$R^1$ is preferably a halogen, cyano, an alkoxy optionally substituted by one to three substituent(s) independently selected from a halogen, an alkoxy and hydroxy, or an alkyl optionally substituted by one to three substituent(s) independently selected from a halogen, an alkoxy and hydroxyl, and more preferably a halogen, an alkoxy, an alkyl optionally substituted by three halogens, and further preferably a halogen.

Preferable groups of formula:

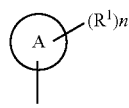

are exemplified by benzene substituted by one or two halogen(s), and thiophene substituted by one or two halogen(s).

Other preferable groups of formula:

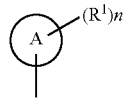

are exemplified by groups of formulae:

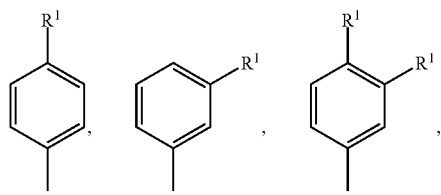

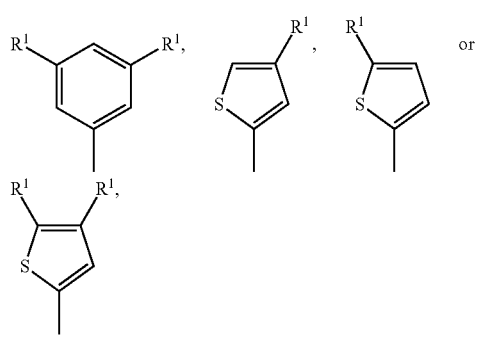

and are further preferably exemplified by groups of formulae:

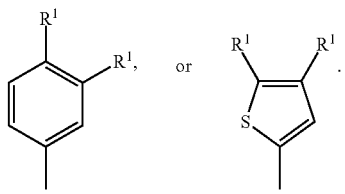

Other preferable groups of formula:

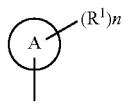

are exemplified by groups of formulae:

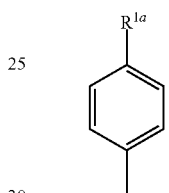

wherein $R^{1a}$ is $R^1$.

Preferable $R^{1a}$ are exemplified by halogen atom, an alkoxy optionally substituted by one to three substituent(s) independently selected from a halogen and an alkoxy, or an alkyl optionally substituted by one to three substituent(s) independently selected from a halogen and an alkoxy, and is specifically exemplified by fluorine atom, chlorine atom, trifluoromethyl, methoxy, and ethoxy.

When G is a phenyl optionally substituted by one or more $R^{15}$(s), preferable "heteroaromatic ring" of ring A is monocyclic heteroaromatic ring, and is specifically exemplified by pyridine, pyrimidine, thiophene, furan, thazole, oxazole, and pyrrazole, and more preferably pyridine, thiophene, thazole, and pyrrazole.

B) A Group of Formula:

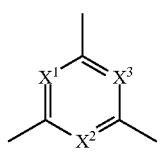

There are seven patterns in combinations of $X^1$, $X^2$ and $X^3$, as follows:

(1) $X^1$ is nitrogen, $X^2$ is nitrogen, and $X^3$ is nitrogen,
(2) $X^1$ is $CR^2$, $X^2$ is nitrogen, and $X^3$ is nitrogen,
(3) $X^1$ is nitrogen, $X^2$ is $CR^2$, and $X^3$ is nitrogen,
(4) $X^1$ is nitrogen, $X^2$ is nitrogen, and $X^3$ is $CR^2$,
(5) $X^1$ is $CR^2$, $X^2$ is $CR^2$, and $X^3$ is nitrogen,
(6) $X^1$ is nitrogen, $X^2$ is $CR^2$, and $X^3$ is $CR^2$, and
(7) $X^1$ is $CR^2$, $X^2$ is nitrogen, and $X^3$ is $CR^2$.

"An alkyl substituted by one or more substituent(s) independently selected from an alkoxy and hydroxy" of $R^2$ is exemplified by alkoxy-$C_{1-6}$-alkyl, hydroxy-$C_{1-6}$-alkyl and trihaloalkyl, more preferably by an alkoxymethyl, a 2-alkoxyethyl, a 3-alkoxypropyl, hydroxymethyl, 2-hydroxyethyl, and 3-hydroxypropyl.

$R^2$ is preferably hydrogen, an alkoxy, and an alkyl, and more preferably hydrogen.

C) -D-Y

"Heteroaryl" of "an alkyl substituted by a heteroaryl" of $R^3$ is exemplified by a monocyclic heteroaryl, more preferably by pyridine.

$R^4$ and $R^5$ are preferably the same.

$R^6$ and $R^7$ are preferably the same.

$R^8$ and $R^9$ are preferably the same.

"Alkyl" of each of $R^4$, $R^5$, $R^6$, $R^7$, $R^8$ and $R^9$ is preferably exemplified by $C_{1-3}$ alkyl, more preferably by methyl and ethyl.

A heterocyclic ring optionally substituted by one or more alkyl(s) which two of $R^3$, $R^4$, $R^5$, $R^6$, $R^7$, $R^8$ and $R^9$ form taken together with the atoms to which they are bonded is exemplified by following formulae (a) to (d), more preferably formulae (a) to (c):

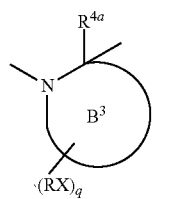

(a)

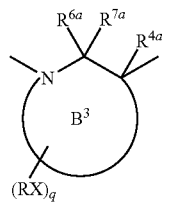

(b)

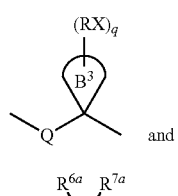

(c)

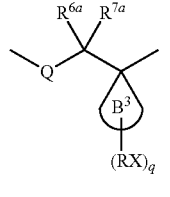

(d)

wherein each of $R^{4a}$, $R^{6a}$, and $R^{7a}$ is independently hydrogen or an alkyl, ring $B^3$ is a heterocyclic ring, Q is —O—, —$CR^8R^9$— or —$NR^3$—, RX is independently an alkyl, and q is 0, 1, 2 or 3, and the other symbols are as defined above.

Preferable $R^3$ is an alkyl optionally substituted by one or more substituent(s) independently selected from an alkoxy, and a heteroaryl.

Each of $R^4$, $R^5$, $R^6$, $R^7$, $R^8$ and $R^9$ is preferably an alkyl.

Preferable ring $B^3$ of formula (a) is exemplified by pyrrolidine, piperidine, piperazine, morpholine, and thiomorpholine, preferably by pyrrolidine, piperidine and morpholine.

Preferable ring $B^3$ of formula (b) is exemplified by azetidine, pyrrolidine, piperidine, piperazine, morpholine, and thiomorpholine, preferably by azetidine, pyrrolidine and piperidine.

Preferable ring $B^3$ of formula (c) or (d) is exemplified by tetrahydrofuran, tetrahydropyran, and piperidine.

A carbocyclic ring optionally substituted by one or more alkyl(s) which two of $R^3$, $R^4$, $R^5$, $R^6$, $R^7$, $R^8$ and $R^9$ may form taken together with the atom(s) to which they are bonded is exemplified by following formulae (e) and (f), more preferably formulae (e):

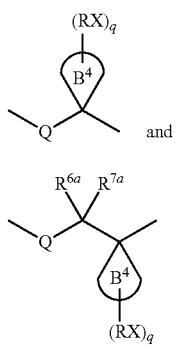

wherein ring $B^4$ is cycloalkane, and the other symbols are as defined above.

Preferable ring $B^4$ is exemplified by 3 to 6-membered cycloalkane, and more preferably by cyclopropane and cyclopentane, further preferably by cyclopropane.

Preferable -D-Y is exemplified by formula:

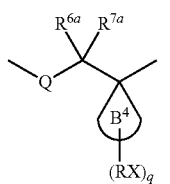

D) -G

D1) —$NR^{10}R^{11}$ $R^{10}$ is preferably exemplified by an alkoxy-$C_{2-6}$-alkyl, and a $C_{1-6}$-alkyl substituted by a group of formula:

Alkoxy-$C_{2-6}$-alkyl of $R^{10}$ is exemplified by 2-alkoxyethyl, and 3-alkoxypropyl.

"Aromatic ring" of ring $B^1$ is preferably benzene.

"Heteroaromatic ring" of ring $B^1$ is preferably pyridine.

"Carbocyclic ring" of $B^1$ is preferably a cycloalkane which may be fused with an aromatic ring.

"Alkoxy optionally substituted by one to three substituent(s) independently selected from a halogen, an alkoxy and hydroxy" of $R^{12}$ is exemplified by unsubstituted alkoxy, alkoxy-$C_{2-6}$-alkoxy, hydroxy-$C_{2-6}$-alkoxy and trihaloalkoxy, more preferably by unsubstituted alkoxy.

"Alkyl substituted by one to three substituent(s) independently selected from a halogen, an alkoxy and hydroxy" of $R^{12}$ is exemplified by alkoxy-$C_{1-6}$-alkyl, hydroxy-$C_{1-6}$-alkyl and trihaloalkyl, more preferably by an alkoxymethyl, a 2-alkoxyethyl, a 3-alkoxypropyl, hydroxymethyl, 2-hydroxyethyl, 3-hydroxypropyl, and trifluoromethyl.

$R^{12}$ is preferably exemplified by cyano, a halogen, an alkoxy, an alkyl substituted by one to three substituent(s) independently selected from a halogen, an alkoxy and hydroxyl.

Ring $B^1$ is preferably exemplified by an aromatic ring, a heteroaromatic ring and a carbocyclic ring.

Preferable $C_{1-6}$-alkyl substituted by a group of formula:

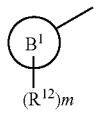

is exemplified by a phenylalkyl, a cycloalkylalkyl, and a pyridylalkyl.

"Alkyl substituted by one to three substituent(s) independently selected from an alkoxy and hydroxy" of $R^{11}$ is preferably exemplified by alkoxy-$C_{2-6}$-alkyl, and hydroxy-$C_{2-6}$-alkyl, more preferably by 2-alkoxyethyl, 3-alkoxypropyl, 2-hydroxyethyl, and 3-hydroxypropyl.

One of preferable —$NR^{10}R^{11}$ is an amino substituted by one or two alkyl independently substituted by one to three substituent(s) independently selected from a halogen, hydroxyl and alkoxy.

One of preferable —$NR^{10}R^{11}$ is a group wherein $R^{10}$ is an alkyl substituted by a group of formula:

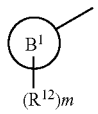

and $R^{11}$ is hydrogen.

D2) A Group of Formula:

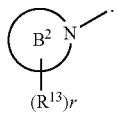

Ring $B^2$ is preferably exemplified by a monocyclic 4 to 8-membered heterocyclic ring or bicyclic 8 to 10-membered heterocyclic ring, which is partially or wholly saturated, containing 1 to 4 nitrogen(s) and 0 to 3 heteroatom(s) selected from oxygen and sulfur.

The monocyclic heterocyclic ring of ring $B^2$ is preferably exemplified by a 4 to 7-membered heterocyclic group which is partially or wholly saturated, containing 1 or 2 nitrogen(s) and 0 or 1 heteroatom selected from oxygen and sulfur, and it is specifically exemplified by azetidine, pyrrolidine, piperidine, piperazine, morpholine, thiomorpholine, homopiperazine, homomorpholine, homopiperidine, and homothiomorpholine.

The bicyclic heterocyclic ring of ring $B^2$ is preferably exemplified by a bicyclic heterocyclic group in which the above nitrogen containing monocyclic heterocyclic ring and benzene ring or heteroaromatic ring are fused, and it is specifically exemplified by dihydroindole, tetrahydroquinoline, and tetrahydroiso indo line.

Ring $B^2$ is preferably exemplified by a monocyclic heterocyclic ring, and specifically exemplified by pyrrolidine and piperidine.

"Alkoxy substituted by one to three substituent(s) independently selected from a halogen, a cycloalkyl, an alkoxy and hydroxy" of $R^{13}$ is exemplified by alkoxy-$C_{2-6}$-alkoxy, hydroxy-$C_{2-6}$-alkoxy, $C_{3-6}$-cycloalkyl-$C_{2-6}$-alkoxy and trihaloalkoxy, more preferably by 2-alkoxyethoxy, 3-alkoxypropoxy, 2-hydroxyethoxy, 3-hydroxypropoxy, cyclopropylmethoxy, trifluoroethoxy, difluoroethoxy, and trifluoromethoxy.

"Alkyl substituted by one to three substituent(s) independently selected from a halogen, an alkoxy and hydroxy" of $R^{13}$ is exemplified by alkoxy-$C_{1-6}$-alkyl, hydroxy-$C_{1-6}$-alkyl and haloalkyl, more preferably by an alkoxymethyl, a 2-alkoxyethyl, a 3-alkoxypropyl, hydroxymethyl, 2-hydroxyethyl, and 3-hydroxypropyl, further preferably by methoxymethyl, ethoxymethyl, methoxyethyl, 1-methyl-1-hydroxy-1-ethyl and fluoromethyl.

"Heteroaryl" of $R^{13}$ is exemplified by pyrimidine and pyridine.

Preferable $R^{13}$ is exemplified by an alkoxy optionally substituted by one to three substituent(s) independently selected from a halogen, an alkoxy, a cycloalkyl and hydroxy, oxo, a halogen, an aryl, an alkoxycarbonyl or an alkyl optionally substituted by one to three substituent(s) independently selected from a halogen, an alkoxy and hydroxy, more preferably an alkoxy optionally substituted by one to three substituent(s) independently selected from a halogen, an alkoxy, a cycloalkyl, and hydroxyl, an alkyl optionally substituted by one to three substituent(s) independently selected from a halogen, an alkoxy and hydroxyl, further preferably alkoxyalkyl and alkoxy.

One of preferable groups of formulae:

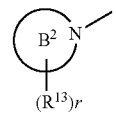

is a pyrrolidyl substituted on 2-position by an alkyl substituted by one to three substituent(s) independently selected from a halogen, an alkoxy and hydroxyl, further preferably 2-methoxymethylpyrrolidyl.

One of preferable groups of formulae:

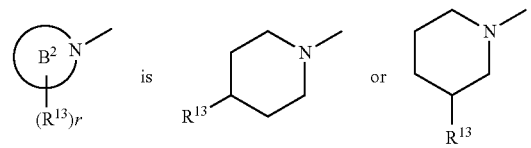

D3) A Phenyl Optionally Substituted by One or More $R^{15}$(s)

"Alkoxy optionally substituted by one to three substituent(s) independently selected from a halogen, an alkoxy, a cycloalkyl and hydroxy" of $R^{15}$ is exemplified by unsubstituted alkoxy, alkoxy-$C_{2-6}$-alkoxy, hydroxy-$C_{2-6}$-alkoxy and trihaloalkoxy, more preferably by unsubstituted alkoxy.

"Alkyl substituted by one to three substituent(s) independently selected from a halogen, an alkoxy and hydroxy" of $R^{15}$ is exemplified by alkoxy-$C_{1-6}$-alkyl, hydroxy-$C_{1-6}$-alkyl and trihaloalkyl, more preferably by an alkoxymethyl, a 2-alkoxyethyl, a 3-alkoxypropyl, hydroxymethyl, 2-hydroxyethyl, 3-hydroxypropyl, and trifluoromethyl.

$R^{15}$ is preferably a halogen, an alkoxy optionally substituted by one to three substituent(s) independently selected from a halogen, an alkoxy, a cycloalkyl and hydroxy, or an alkyl optionally substituted by one to three substituent(s) independently selected from a halogen, an alkoxy and hydroxyl, more preferably a halogen and an alkoxy.

Preferable "phenyl optionally substituted by one or more $R^{15}(s)$" is exemplified by a phenyl substituted by one or two $R^{15}(s)$, further preferably a phenyl substituted by two $R^{15}s$, specifically a group of formula:

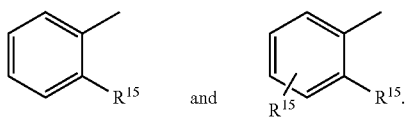

D4) —$OR^{14}$

Ring $B^5$ is a carbocyclic ring, a heterocyclic ring, an aromatic ring or a heteroaromatic ring.

Preferable Ring $B^5$ is an aromatic ring or a heteroaromatic ring.

A preferable aromatic ring of Ring $B^5$ is exemplified by benzene.

A preferable heteroaromatic ring of Ring $B^5$ is exemplified by thiophene, pyridine, pyrimidine, quinoline and isoquinoline.

Preferable $R^{16}$ is exemplified by a halogen, cyano, an alkylthio, a cycloalkyl, an alkanoyl, an amino optionally substituted by alkyl(s), an alkylsulfonyl, an alkoxy optionally substituted by one to three substituent(s) independently selected from a halogen and an alkoxy, or an alkyl optionally substituted by one to three substituent(s) independently selected from a halogen and an alkoxy.

$R^{16}$ is preferably a halogen, an alkoxy optionally substituted by one to three substituent(s) independently selected from a halogen, an alkoxy and a cycloalkyl, or an alkyl optionally substituted by one to three substituent(s) independently selected from a halogen and an alkoxy, more preferably a halogen, or an alkoxy.

A preferable alkyl in "an alkyl substituted by a group of formula

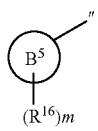

of $R^{14}$ is exemplified by methyl and ethyl.

Examples of pharmaceutically acceptable salts of the compound of formula (A) of the present invention may include, for example, inorganic acid salts such as hydrochloride, sulfate, phosphate or hydrobromide, and organic acid salts such as acetate, fumarate, oxalate, citrate, methanesulfonate, benzenesulfonate, tosylate or maleate, and the like. Also, in case of a compound having an acidic group such as carboxy, salts with a base (for example, alkali metal salts such as a sodium salt and a potassium salt, alkaline earth metal salts such as a calcium salt, organic base salts such as a triethylamine salt, or amino acid salts such as a lysine salt) can be mentioned.

The compound of formula (A) or a pharmaceutically acceptable salt thereof includes any of its internal salts, and solvates such as hydrates.

In the compound of formula (A) of the present invention, an optical isomer based on an asymmetric carbon may be present, and any of the isomers and a mixture thereof may be encompassed in the present invention. In addition, cis form and trans form may be present, in case that the compound of formula (A) of the present invention has a double bond or a cycloalkanediyl moiety, and a tautomer may be present based on an unsaturated bond such as carbonyl, etc. in the compound of formula (A) of the present invention, and any of these isomers and a mixture thereof may be encompassed in the compound of formula (A) of the present invention.

The compound of formula (A) of the present invention or a pharmaceutically acceptable salt thereof can be used for the present medical use in the free form or in the form of a pharmaceutically acceptable salt. Examples of pharmaceutically acceptable salts of the compound of formula (A) may include, for example, inorganic acid salts such as hydrochloride, sulfate, phosphate or hydrobromide, and organic acid salts such as acetate, fumarate, oxalate, citrate, methanesulfonate, benzenesulfonate, tosylate or maleate. In addition, in case of compound having an acidic group such as carboxy, salts with a base (for example, alkali metal salts such as a sodium salt and a potassium salt, alkaline earth metal salts such as a calcium salt, organic base salts such as a triethylamine salt, or amino acid salts such as a lysine salt) can be mentioned.

The compound of formula (A) of the present invention or a pharmaceutically acceptable salt thereof includes its internal salts, and solvates such as hydrates.

The compound of formula (A) of the present invention or a pharmaceutically acceptable salt thereof can be administered orally or parenterally, and used as common pharmaceutical preparations such as tablets, granules, capsules, powders, injection and inhalants with a pharmaceutically acceptable carrier or diluent.

A pharmaceutically acceptable carrier for a preparation of oral administration includes a material commonly used, for example, a binder (such as syrup, Gum Arabic, gelatin, sorbit, tragacanth and polyvinyl pyrrolidone), an excipient (such as lactose, sugar, corn starch, potassium phosphate, sorbit and glycine), a lubricant (such as magnesium stearate, talc, polyethylene glycol and silica), a disintegrator (such as potato starch) and a humectant (such as anhydrous lauryl sodium sulfate).

On the other hand, when the active ingredient of the present invention is administered parenterally, it may be formulated into the form of an injection or a drip infusion by using distilled water for injection, physiological saline, an aqueous glucose solution and the like, or a suppository.

A dose of the compound of formula (A) of the present invention or a pharmaceutically acceptable salt thereof may vary depending on an administration route, an age, weight, conditions or a kind or degree of disease of a patient, and generally about 0.1 to 50 mg/kg body weight per day, particularly preferably about 0.3 to 30 mg/kg body weight per day.

The compound of formula (A) of the present invention or a pharmaceutically acceptable salt thereof has an excellent large conductance calcium-activated K channel opening activity and hyperpolarizes a membrane electric potential of cells, so that it may be used as an agent for a prophylactic, relief and/or treatment of, for example, hypertension, irritable bowel syndrome, chronic heart failure, angina, cardiac infarction, cerebral infarction, subarachnoid hemorrhage, cerebral vasospasm, cerebral hypoxia, peripheral blood vessel disorder, anxiety, erectile dysfunction, diabetes, diabetic peripheral nerve disorder, other diabetic complication, urolithiasis and pain accompanied thereby, pollakiuria, urinary incontinence, nocturnal enuresis, asthma, chronic obstructive pulmonary disease (COPD), cough accompanied by asthma or COPD, intracerebral hemorrhage, traumatic encephalopathy, interstitial cystitis, prostatitis, pain accompanied by prostatitis, overactive bladder and the like.

Some of the compounds of formula (A) or a pharmaceutically acceptable salt thereof of the present invention have very week or no COXs inhibition activities, so that the compound is useful for the prophylaxis and/or treatment for a disorder or disease responsive to opening of BK channels with less or no side effects.

The compound of the present invention represented by a formula (A) may be prepared by the following methods.

Further, unless otherwise specified, the following abbreviations as used herein mean the following meanings, respectively.

DMF: N,N-dimethylformamide

THF: tetrahydrofuran

DMSO: dimethyl sulfoxide

DMA: N,N-dimethylacetamide

Bz: benzoyl

Me: methyl

Et: ethyl $^i$Pr: isopropyl $^t$Bu: tertiary butyl

Ac: acetyl

General Synthetic Scheme:

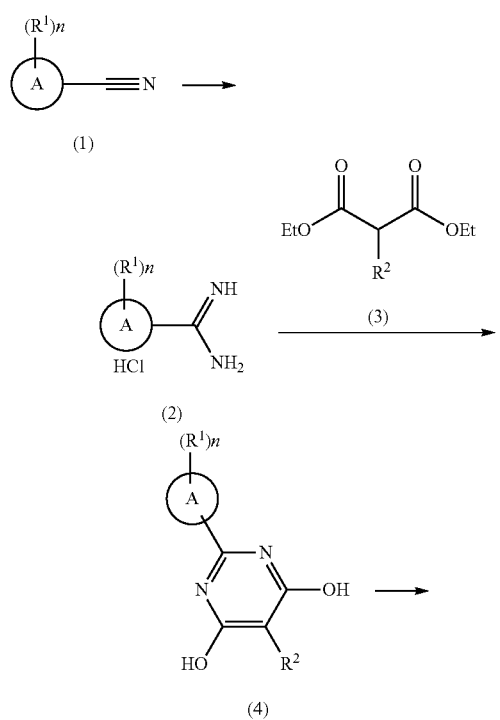

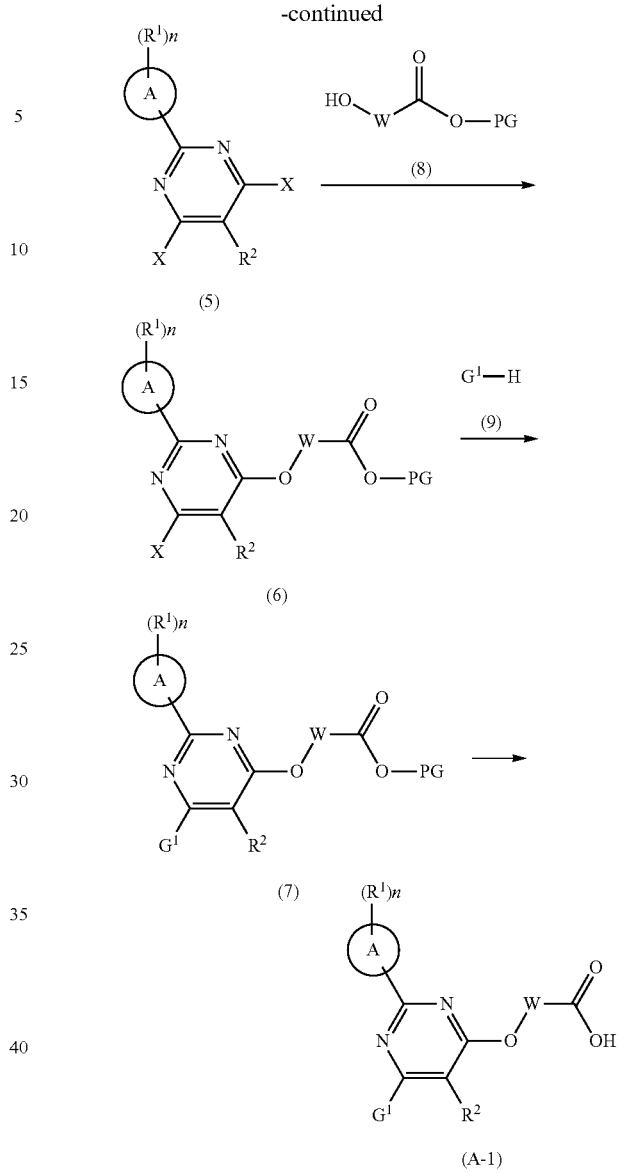

wherein X is chlorine or bromine atom,
PG is a protective group for carboxy,
W is a group of formula:

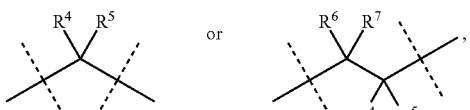

$G^1$ is $—OR^{14}$, $—NR^{10}R^{11}$, or a group of formula:

and the other symbols have the same meanings as defined above.

The compound (2) can be synthesized from the compound (1) by referring to Tetrahedron Letters, 36, 8761 (1995). The compound (2) is reacted with the compound (3) in the presence of a base such as an alkali metal alkoxide in a solvent such as alkanol at the reflux temperature of the solvent for 1 to 24 hours to give the compound (4). The compound (4) is reacted with a halogenating agent such as POCl$_3$ etc, at room temperature to reflux temperature for 1 to 24 hours to give the compound (5). The compound (5) is reacted with the compound (8) in the presence of a base such as sodium hydride etc., in an aprotic solvent such as THF, DMF, etc., under −78° C. to room temperature for 1 to 24 hours to give the compound (6). The compound (7) can be synthesized by reacting the compound (6) with the compound (9) in the presence of a base in a solvent, under −78° C. to reflux temperature of the solvent for 1 to 24 hours. The solvent is not specifically limited so long as it does not exert any bad effect on the reaction. The base is exemplified by inorganic bases such as an alkali metal carbonate, an alkali metal hydroxide, an alkali metal phosphate and an alkali metal fluoride, or organic bases such as triethylamine, and they are suitably used. The compound (7) is deprotected to give the compound (A-1) under ordinary method. PG is exemplified by an alkyl such as methyl, ethyl, and t-butyl, etc., a substituted methyl such as methoxymethyl, 2-trimethylsilylethoxymethyl and α-methoxyphenylmethy, etc., 2-substituted ethyl such as 2-haloethyl, etc., allyl, and a trialkylsilyl such as t-butyldimethyksilyl, triethylsilyl, etc., preferably a protective group which is not removed under basic condition such as the condition to give the compound (6) described above.

The compound of formula

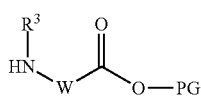

(8-2)

can be used in the scheme as an alternative to the compound (8).

Scheme 2:

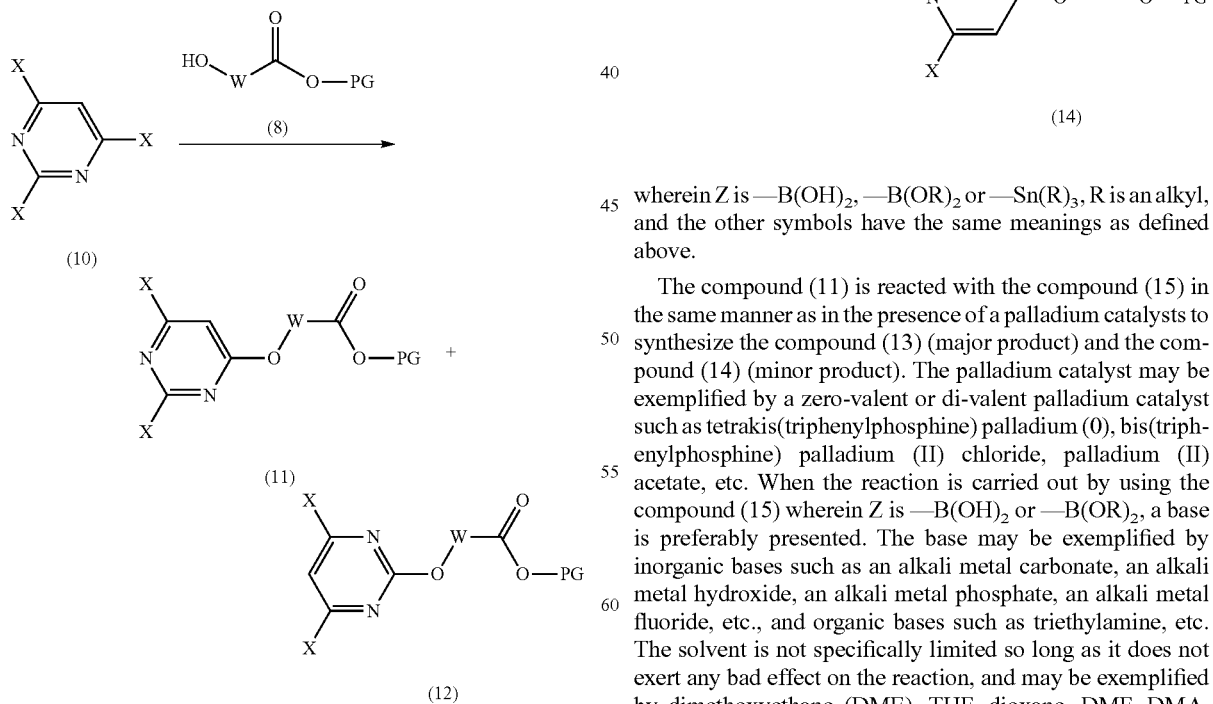

wherein the symbols have the same meanings as defined above.

The compound (10) is reacted with the compound (8) in the presence of a base such as sodium hydride, etc., in an aprotic solvent such as THF, DMF, etc., under −78° C. to room temperature for 1 to 24 hours to give the compound (11) (major product) and the compound (12) (minor product).

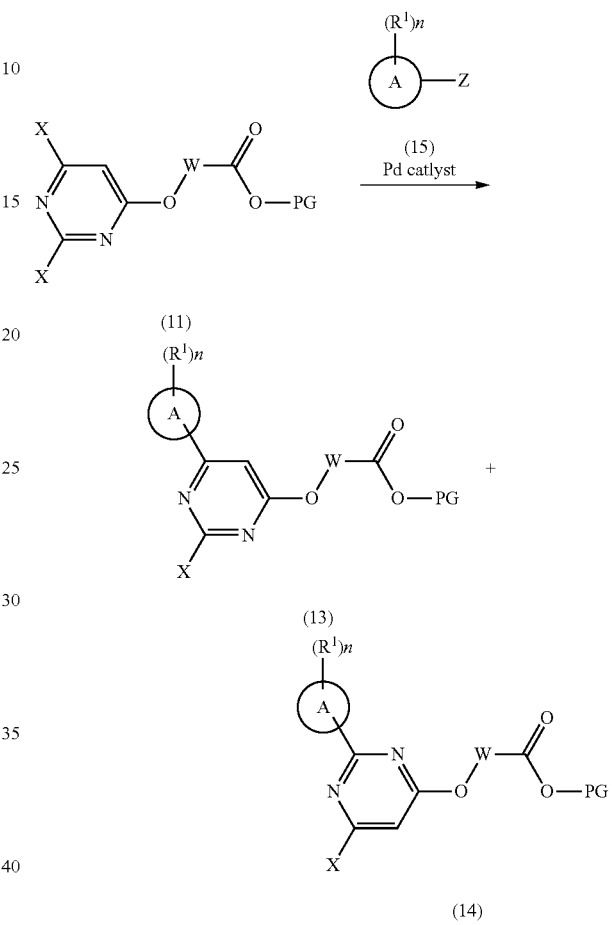

wherein Z is —B(OH)$_2$, —B(OR)$_2$ or —Sn(R)$_3$, R is an alkyl, and the other symbols have the same meanings as defined above.

The compound (11) is reacted with the compound (15) in the same manner as in the presence of a palladium catalysts to synthesize the compound (13) (major product) and the compound (14) (minor product). The palladium catalyst may be exemplified by a zero-valent or di-valent palladium catalyst such as tetrakis(triphenylphosphine) palladium (0), bis(triphenylphosphine) palladium (II) chloride, palladium (II) acetate, etc. When the reaction is carried out by using the compound (15) wherein Z is —B(OH)$_2$ or —B(OR)$_2$, a base is preferably presented. The base may be exemplified by inorganic bases such as an alkali metal carbonate, an alkali metal hydroxide, an alkali metal phosphate, an alkali metal fluoride, etc., and organic bases such as triethylamine, etc. The solvent is not specifically limited so long as it does not exert any bad effect on the reaction, and may be exemplified by dimethoxyethane (DME), THF, dioxane, DMF, DMA, toluene, benzene or a mixture thereof. The reaction proceeds generally at 60 to 150° C., preferably 80 to 120° C., and for generally from 1 to 24 hours.

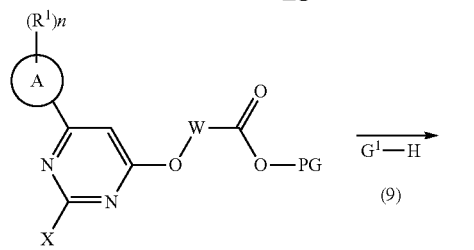

(13)

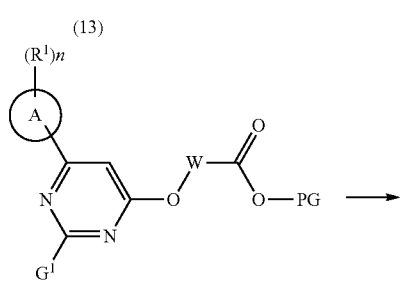

(47)

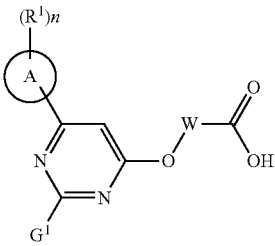

(A-2)

wherein the symbols have the same meanings as defined above.

The compound (13) is reacted with the compound (9) in the same manner as in Scheme 1 to synthesize the compound (47).

The compound (47) is deprotected in the same manner as in Scheme 1 to give the compound (A-2).

The compound of formula

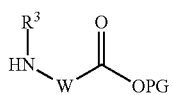

(8-2)

can be used in Scheme as an alternative to the compound (8).

Scheme 3:

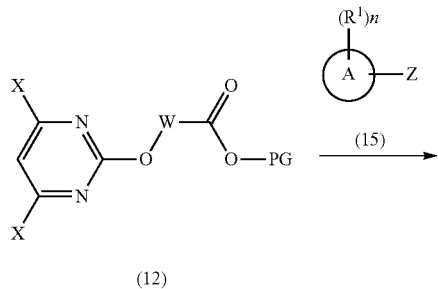

(12)

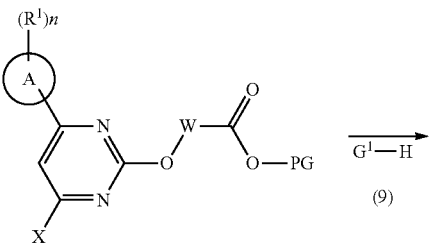

(16)

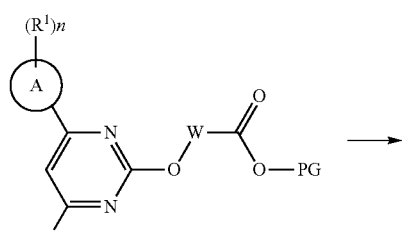

(17)

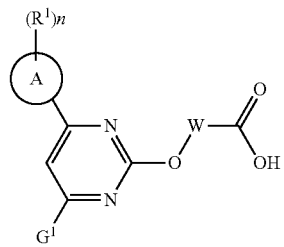

(A-3)

wherein the symbols have the same meanings as defined above.

The compound (17) can be prepared from the compound (12) in the same manner as in Scheme 1.

From the compound (14) in Scheme 2, the corresponding compound of formula (I) can be prepared in the same manner.

Instead of the compound (8), the compound (8-2) described in Scheme 1 can also be used.

The compound (17) is deprotected in the same manner as in Scheme 1 to give the compound (A-3).

Scheme 4:

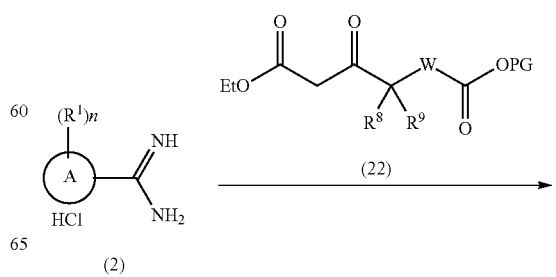

(2)

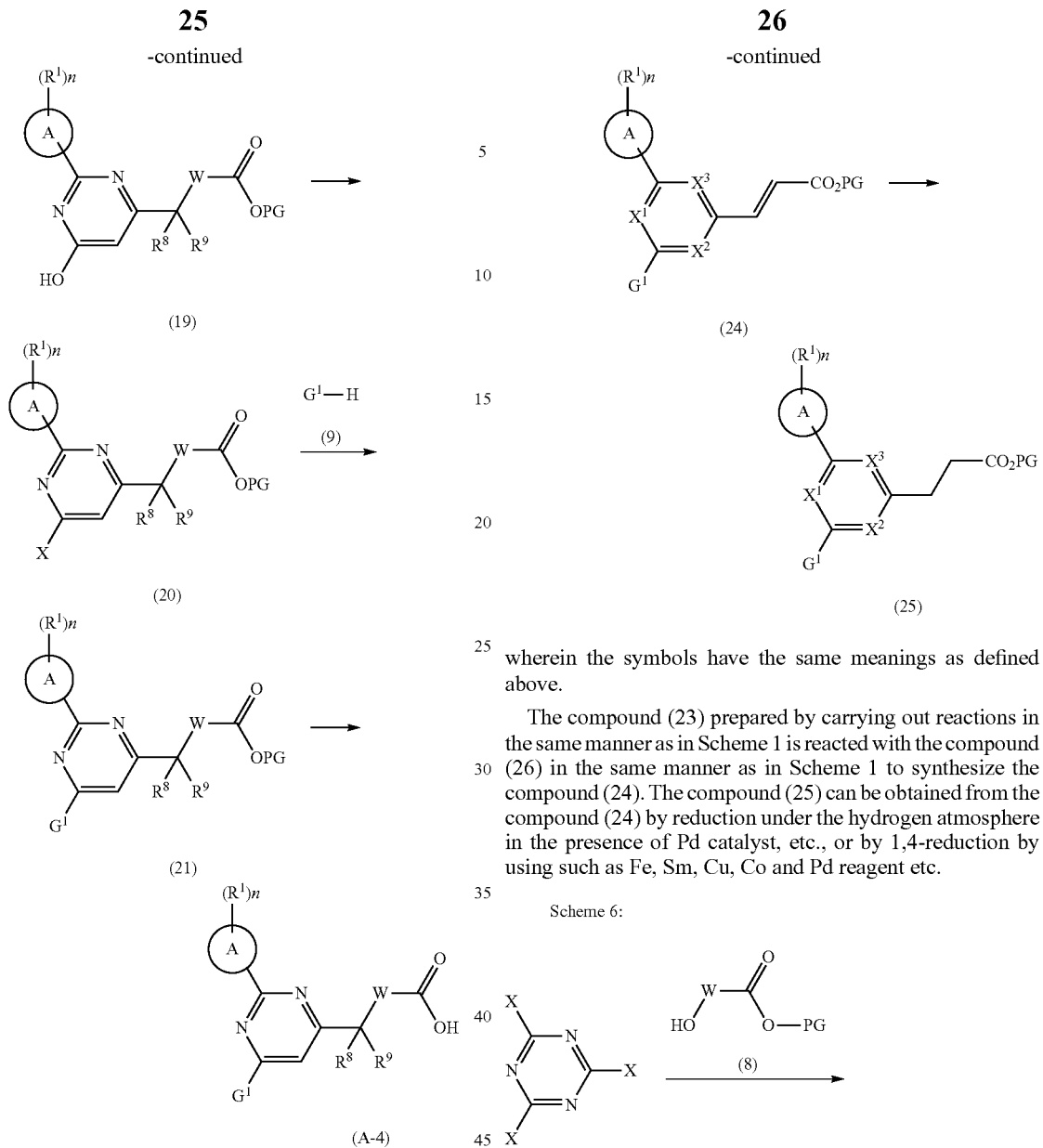

wherein the symbols have the same meanings as defined above.

The compound (21) can be prepared in the same manner as in Schemes 1 to 3 from the compound (2).

The compound (21) is deprotected in the same manner as in Scheme 1 to give the compound (A-4).

Scheme 5:

wherein the symbols have the same meanings as defined above.

The compound (23) prepared by carrying out reactions in the same manner as in Scheme 1 is reacted with the compound (26) in the same manner as in Scheme 1 to synthesize the compound (24). The compound (25) can be obtained from the compound (24) by reduction under the hydrogen atmosphere in the presence of Pd catalyst, etc., or by 1,4-reduction by using such as Fe, Sm, Cu, Co and Pd reagent etc.

Scheme 6:

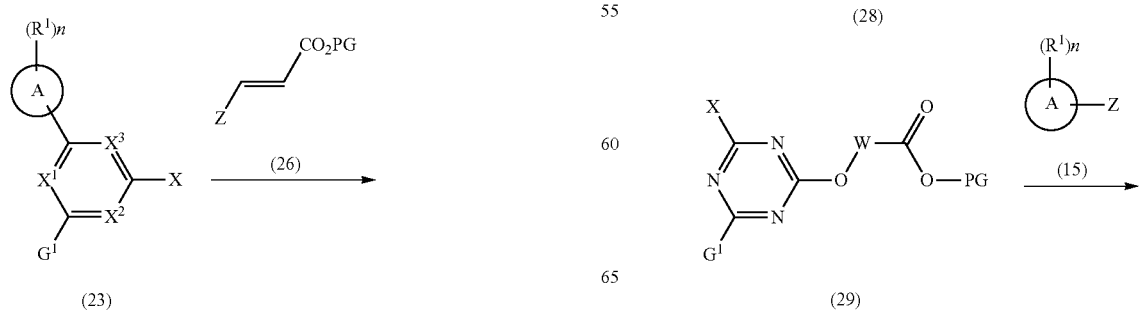

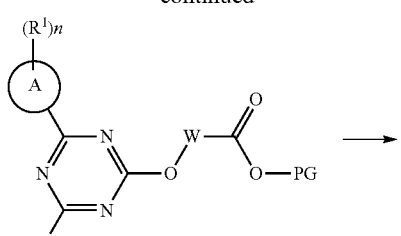

(30)

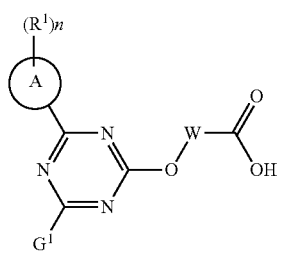

(A-5)

wherein the symbols have the same meanings as defined above.

The compound (30) can be prepared by carrying out reactions in the same manner as in Schemes 1 to 5.

The compound of formula

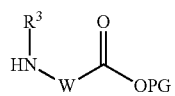

(8-2)

can be used in the scheme as an alternative to the compound (8).

The compound (30) is deprotected in the same manner as in Scheme 1 to give the compound (A-5).

Scheme 7:

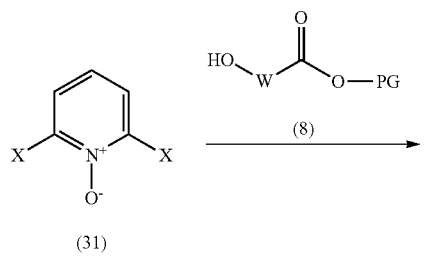

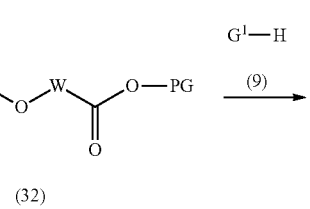

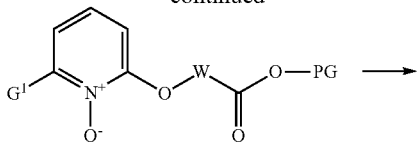

(33)

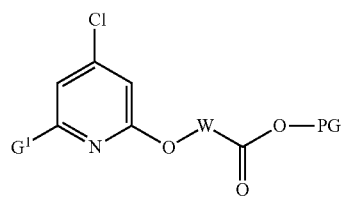 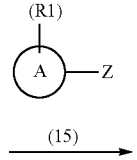

(34)    (15)

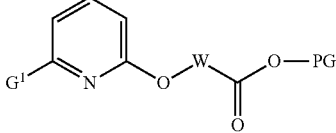

(35)

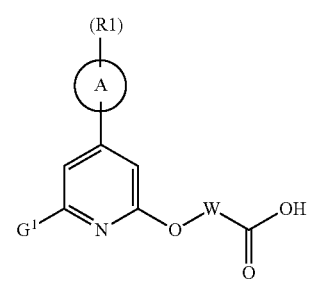

(A-6)

wherein the symbols have the same meanings as defined above.

The compound (33) can be prepared by carrying out reactions in the same manner as in Schemes 1 to 6 from the compound (31). The compound (33) is reacted with triphosgene in the presence of an organic base such as triethylamine under −78° C. to 0° C., preferably −10° C. to −5° C. to give the compound (34). The compound (35) can be prepared by reacting the compound (34) with the compound (15) in the same manner as in Schemes 1 to 6.

The compound of formula

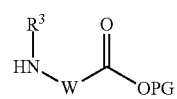

(8-2)

can be used in the scheme as an alternative to the compound (8).

The compound (35) is deprotected in the same manner as in Scheme 1 to give the compound (A-6).

Scheme 8:

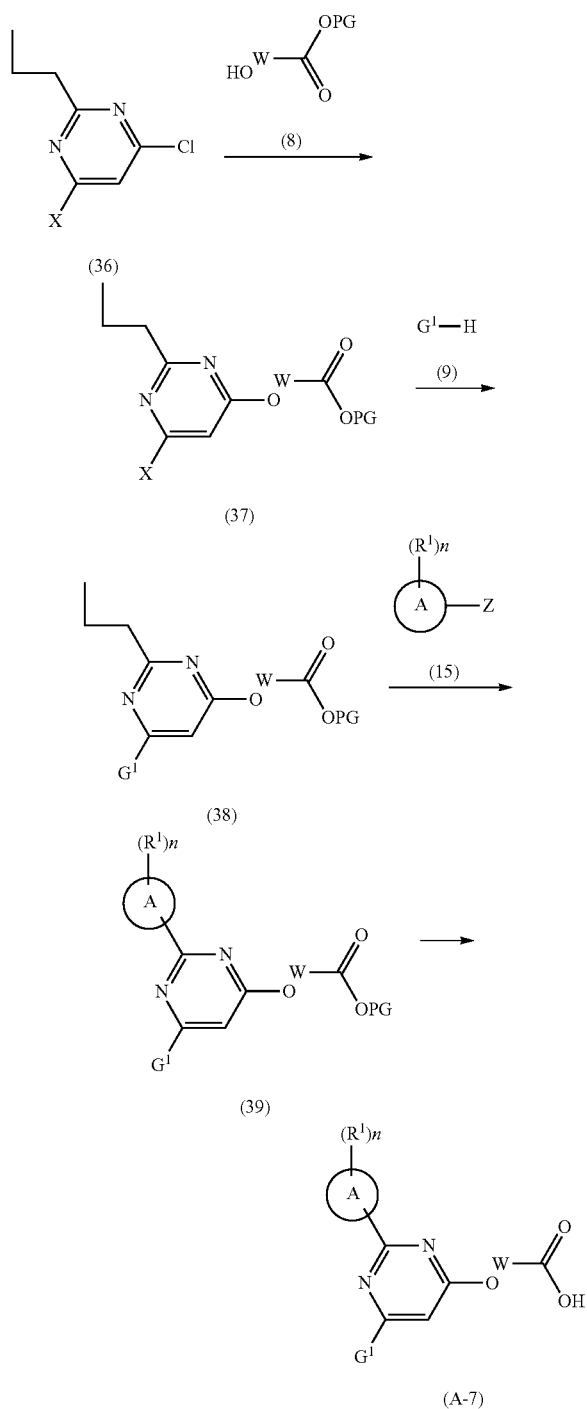

The compound of formula

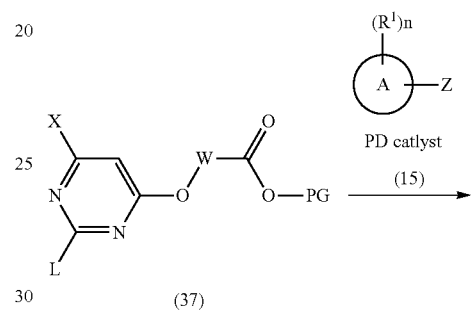

(8-2)

can be used in the scheme as an alternative to the compound (8).

The compound (39) is deprotected in the same manner as in Scheme 1 to give the compound (A-7).

Scheme 9:

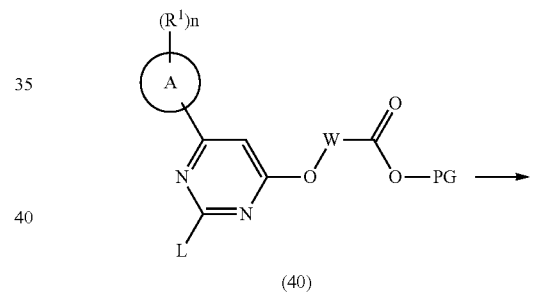

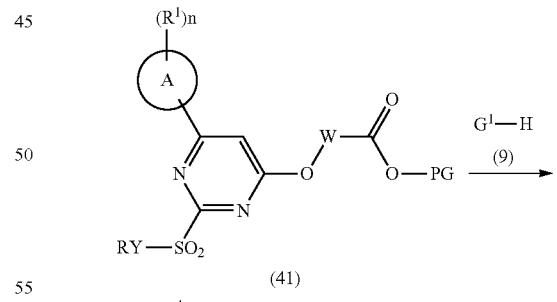

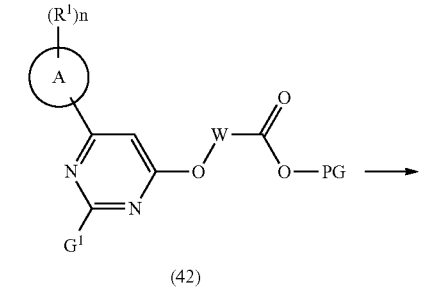

wherein L is an alkylthio or an arylthio, and the symbols have the same meanings as defined above.

The compound (37) can be prepared by carrying out reactions in the same manner as in Schemes 1 to 6 from the compound (36). The compound (38) can be prepared by carrying out reactions in the same manner as in Schemes 1 to 6 from the compound (37).

The compound (39) can be prepared by carrying out reactions in the manner described in Org. Lett. 2002, 4(6), 979 from the compound (38).

-continued

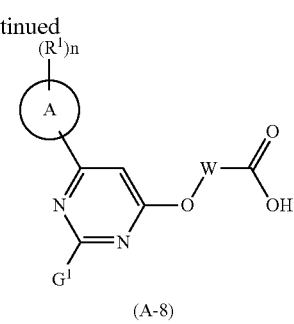

(A-8)

wherein RY is an alkyl or an aryl, and the symbols have the same meanings as defined above.

The compound (40) can be prepared by carrying out reactions in the same manner as in Schemes 1 to 6 from the compound (37).

The compound (42) is deprotected in the same manner as in Scheme 1 to give the compound (A-8).

Scheme 10:

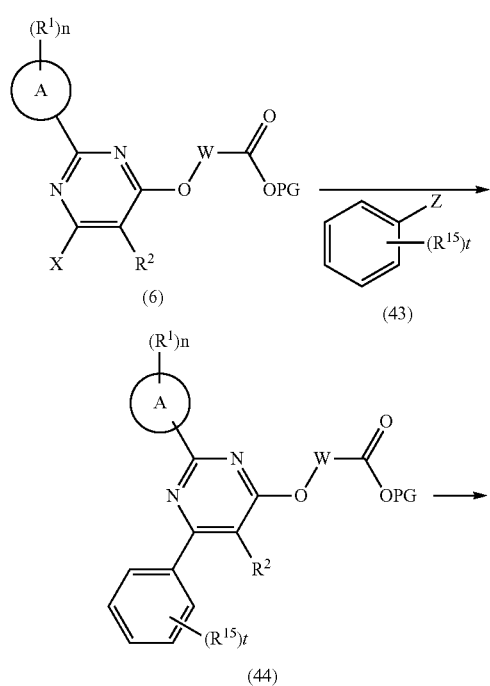

wherein t is 0, 1, 2, 3 or 4, and the other symbols have the same meanings as defined above.

The compound (44) can be synthesized by reacting the compound (6) with the compound (43) in the presence of a palladium catalyst. The compound (44) is deprotected by an ordinary method to give the compound (A-10).

The compound of formula

(8-2)

can be used in the scheme as an alternative to the compound (8).

Scheme 11:

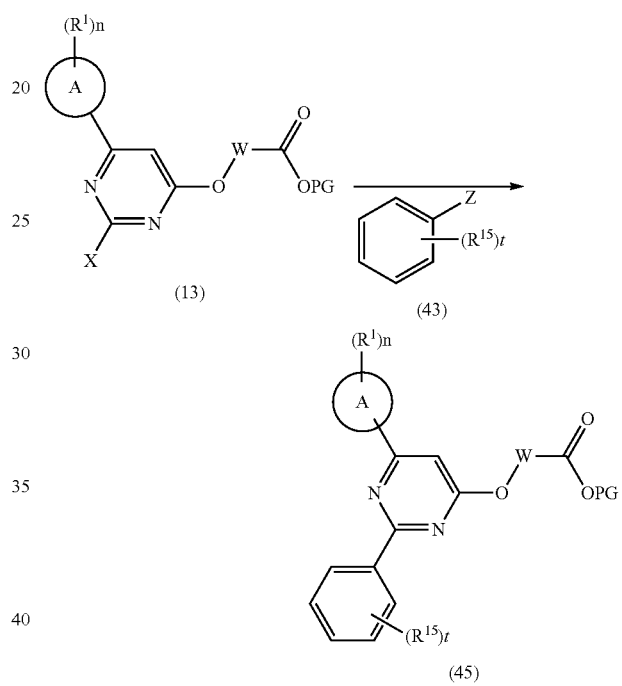

wherein the symbols have the same meanings as defined above.

The compound (13) is reacted with the compound (43) in the same manner as in Scheme 1 to synthesize the compound (45).

The compound (8-2) described in Scheme 10 can be used as an alternative to the compound (8).

Scheme 12:

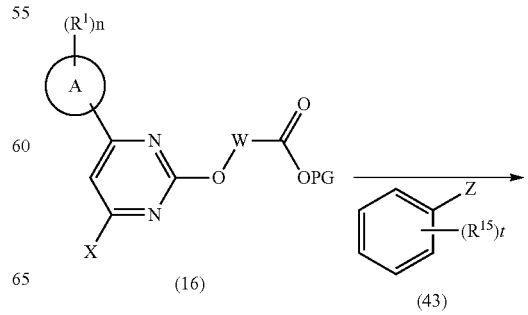

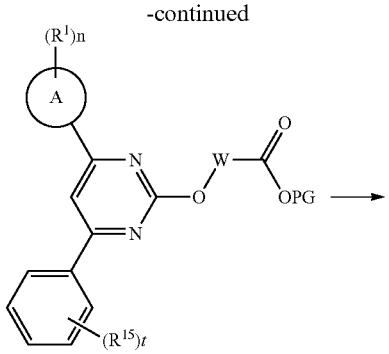

(46)

(A-11)

wherein the symbols have the same meanings as defined above.

The compound (46) can be prepared from the compound (12) in the same manner as in Scheme 1.

The compound (46) is deprotected in the same manner as in Scheme 1 to give the compound (A-11).

The compound (8-2) described in Scheme 1 can be used as an alternative to the compound (8).

Incidentally, in the above-mentioned schemes, when the compound of the present invention, an intermediate compound, a starting compound, etc. have a functional group (hydroxyl, amino, carboxy, etc.), the functional group may be protected with a protective group generally used in an organic synthesis chemistry. The protective group for hydroxyl may include tetrahydropyranyl, trimethylsilyl, benzyl, etc. The protective group for amino may include tert-butoxycarbonyl, benzyloxycarbonyl, etc. The protective group for carboxy may include an alkyl such as methyl, ethyl, etc., benzyl, and the like.

Further, after the compound of the present invention and the intermediate compound are prepared according to the above-mentioned schemes, the functional group can be converted or modified according to the conventional method, if necessary. Specifically, the following methods are mentioned.

(1) Modification of Amino

After an amino is optionally protected, (i) a reaction with an alkyl halide, etc. may be carried out in the presence of a base (sodium hydride, triethylamine, sodium carbonate, potassium carbonate, etc.), or (ii) an alcohol, etc. may be subjected to Mitsunobu Reaction using dialkyl azodicarboxylate and triphenylphosphine, and deprotection may be optionally carried out to convert the amino to a mono- or di-alkylamino.

(2) Conversion of Amino to Amide

An amino may be converted to a corresponding amide by reacting with an acyl halide.

(3) Conversion of Carboxy to Carbamoyl

Carboxy may be converted to a corresponding carbamoyl by reacting with an amine.

(4) Hydrogenation of C=C Double Bond

A C=C double bond may be converted to a corresponding single bond by catalytic reduction using a transition metal (platinum, palladium, rhodium, ruthenium, nickel, etc.) catalyst.

(5) Hydrolysis of Ester

An ester may be converted to a corresponding carboxy by hydrolysis using an alkali (sodium hydroxide, potassium hydroxide, etc.).

(6) Conversion of Carbamoyl to Nitrile

Carbamoyl may be converted to a corresponding nitrile by reacting with trifluoroacetic anhydride.

(7) Conversion of Carboxy to 4,5-dihydroxazol-2-yl

Carboxy may be converted to a corresponding 4,5-dihydroxazol-2-yl by reacting with 2-haloethylamine in the presence of a condensing agent.

(8) Halogenation and Alkylation of Hydroxyl

Hydroxyl may be converted to a corresponding halide by reacting with a halogenating agent. Also, the halide may be converted to a corresponding alkoxy by reacting with an alcohol.

(9) Reduction of Ester

Ester may be converted to a corresponding hydroxyl by reduction using a reducing agent (a metal reducing agent such as lithium aluminum hydride, sodium borohydride, lithium borohydride, etc., diborane, etc.).

(10) Oxidation of Hydroxyl

Hydroxyl may be converted to an aldehyde, ketone or carboxy by oxidation.

(11) Amination of Ketone or Aldehyde

Ketone or aldehyde may be converted to a mono- or di-substituted aminomethyl by reductive amination with an amine in the presence of a reducing agent (sodium borohydride, sodium cyanoborohydride, etc.).

(12) Conversion of Ketone or Aldehyde to Double Bond

Ketone or aldehyde may be converted to a double bond by Wittig reaction.

(13) Conversion of Sulfonamide to Salt

Sulfonamide may be converted to a corresponding sulfonamide salt (a sodium salt, a potassium salt, etc.) by treating with sodium hydroxide, potassium hydroxide, etc. in an alcohol (methanol, ethanol, etc.).

(14) Conversion of Aldehyde to Oxime, Etc.

Aldehyde may be converted to a corresponding oxime by reacting with hydroxylamine or O-alkylhydroxylamine in the presence of a base (sodium bicarbonate, etc.) in an alcohol (methanol, ethanol, etc.).

(15) Conversion of Halide to Nitrile

Halide may be converted to a corresponding nitrile by reacting with a cyanating agent.

(16) Amination of Halide

A halide may be converted to a corresponding amine according to the method disclosed in Tetrahedron, 2002, p. 2041.

(17) Conversion of Carboxylic Acid to Carbamoyl or Hydroxymethyl

Carboxylic acid may be converted to a corresponding carbamoyl by condensating with N-hydroxysuccinimide to give succinimide ester, and reacting with an amine. Also, the succinimide ester may be converted to a corresponding hydroxymethyl by treating with a reducing agent (sodium borohydride, etc.).

(18) Dehalogenation

A halogen-substituted aromatic ring may be dehalogenated by catalytic reduction. Also, it can be dehalogenated by reacting with potassium methoxide in the presence of a palladium catalyst according to the method disclosed in Organometallics 2001, 20, 3607.

(19) Conversion of Aryl Halide

A halide may be converted to a corresponding amino, alkoxy or aryloxy by reacting an aryl halide or heteroaryl halide with a nucleophilic reagent (a primary amine, a secondary amine, an alcohol, phenol, etc.) by using Pd catalysts etc.

(20) Alkylation of heteroaryl halide

A halogen may be converted to an alkyl according to the method disclosed in Chem. Commun., 1996, 2719, J. Chem. Soc., Chem. Commun., 1988, 638, or Tetrahedron Lett., 37, 1309 (1996).

EXAMPLES

In the following, the present invention will be explained in more detail by referring to Examples, Reference examples and Experimental examples, but the present invention is not limited by Examples, etc.

Example 1

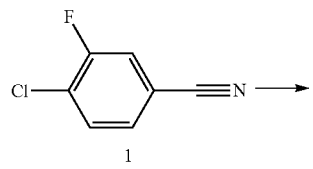

1

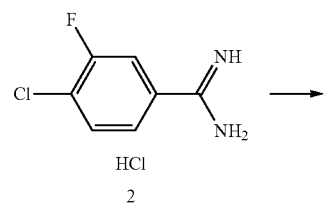

2

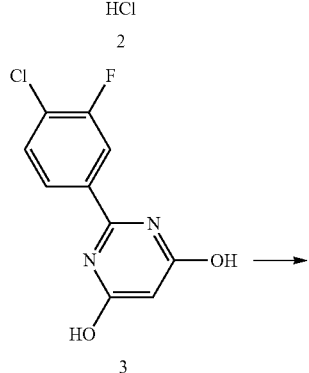

3

-continued

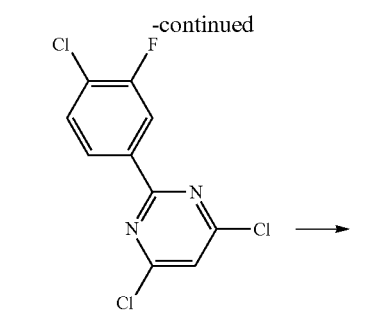

4

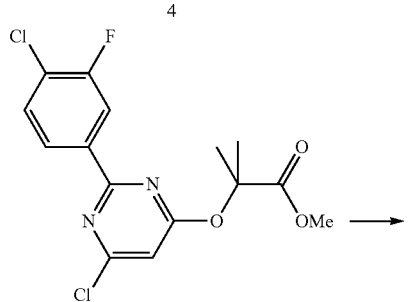

5

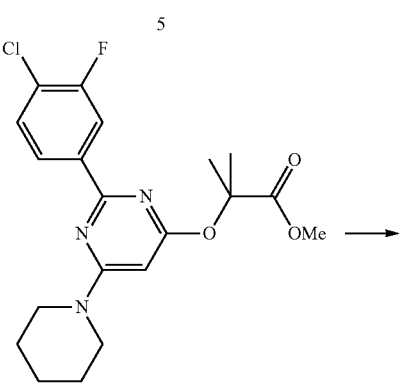

6

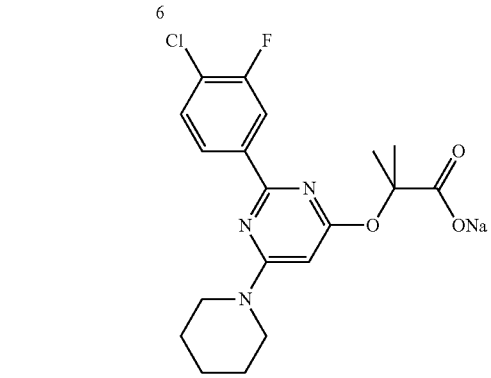

7

To a suspension of ammonium chloride (15.0 g, 280 mmol) in toluene (103 mL) was added dropwise trimethylalminum (2.0 M solution in toluene; 127 ml, 255 mmol) at 0° C. under argon atmosphere and the mixture was stirred at room temperature for 2 hours. Compound 1 (19.8 g, 127 mmol) was added thereto and the mixture was stirred at 80° C. overnight. After cooling, the reaction mixture was slowly poured into a slurry of silica gel and water in chloroform. The mixture was stirred for 30 minutes, filtered, and concentrated under reduced pressure. The residue was triturated with ethyl acetate to give Compound 2 (18.9 g, 71%) as a solid.

MS: 173/175 [M+H]$^+$, APCI.

A solution of sodium ethoxide was prepared by dissolving sodium (5.87 g, 256 mmol) in absolute EtOH (170 mL). Compound 2 (17.8 g, 85.3 mmol) and diethyl malonate (16.4 g, 102 mmol) were added thereto at 0° C. The mixture was refluxed for 3 hours. After cooling, the reaction mixture was concentrated under reduced pressure. The residue was dissolved in water and acidified with 36% aqueous hydrochloric acid. The precipitate was collected by filtration to give Compound 3 (20.0 g, 97%) as powders.

MS: 241/243 [M+H]+, APCI.

A mixture of Compound 3 (10.0 g, 41.6 mmol), phosphoryl chloride (39 mL) and N,N-diethylaniline (13 mL) was refluxed for 22 hours. The reaction mixture was concentrated under reduced pressure. The residue was poured into ice-water, which was extracted with ethyl acetate. The organic layer was washed with water and brine, dried over anhydrous sodium sulfate, and concentrated under reduced pressure. The residue was purified by silica gel column chromatography (hexane:ethyl acetate=50:1) to give Compound 4 (11.2 g, 97%) as a solid.

1H NMR (500 MHz, DMSO-d6): δ 7.82 (1H, t, J=8.4 Hz), 8.06 (1H, s), 8.14-8.19 (2H, m).

To a solution of Compound 4 (9.00 g, 32.4 mmol) and methyl 2-hydroxyisobutyrate (4.60 g, 38.9 mmol) in THF (180 mL) was added sodium hydride (60%, 1.56 g, 38.9 mmol) at −78° C. and the mixture was stirred at room temperature overnight. The reaction mixture was quenched with 1 M aqueous citric acid and extracted with ethyl acetate. The organic layer was washed with water and brine, dried over anhydrous sodium sulfate, and concentrated under reduced pressure. The residue was purified by silica gel column chromatography (hexane:ethyl acetate=15:1) and triturated with diisopropyl ether to give Compound 5 (9.02 g, 77%) as powders.

MS: 359/361 [M+H]+, APCI.

To a solution of Compound 5 (60.0 mg, 167 μmol) in THF (1.67 mL) was added piperidine (82.5 μl, 835 μmol) and the mixture was stirred at room temperature overnight. The reaction mixture was poured into water and extracted with ethyl acetate. The organic layer was concentrated under reduced pressure. The residue was purified by silica gel column chromatography (hexane→hexane:ethyl acetate=19:1) to give Compound 6 (67.6 mg, 99%) as a solid.

MS: 408/410 [M+H]+, APCI.

To a solution of Compound 6 (66.4 mg, 163 μmol) in MeOH (1.00 mL) and THF (1.00 mL) was added 2 M aqueous sodium hydroxide (407 μL, 814 μmol) and the mixture was stirred at room temperature for 3 days. The reaction mixture was concentrated under reduced pressure. The residue was acidified with 1 M aqueous citric acid and extracted with ethyl acetate. The organic layer was filtered through Chem Elut® (Varian Inc.) and concentrated under reduced pressure. The obtained free acid (58.5 mg, 149 μmol) was dissolved in acetone and treated with 2 N aqueous sodium hydroxide (72.8 μl, 146 μmol), then concentrated under reduced pressure. The residue was triturated with diethyl ether to give Compound 7 (48.4 mg, 73%) as powders.

MS: 392/394 [M−Na]−, ESI.

Example 2

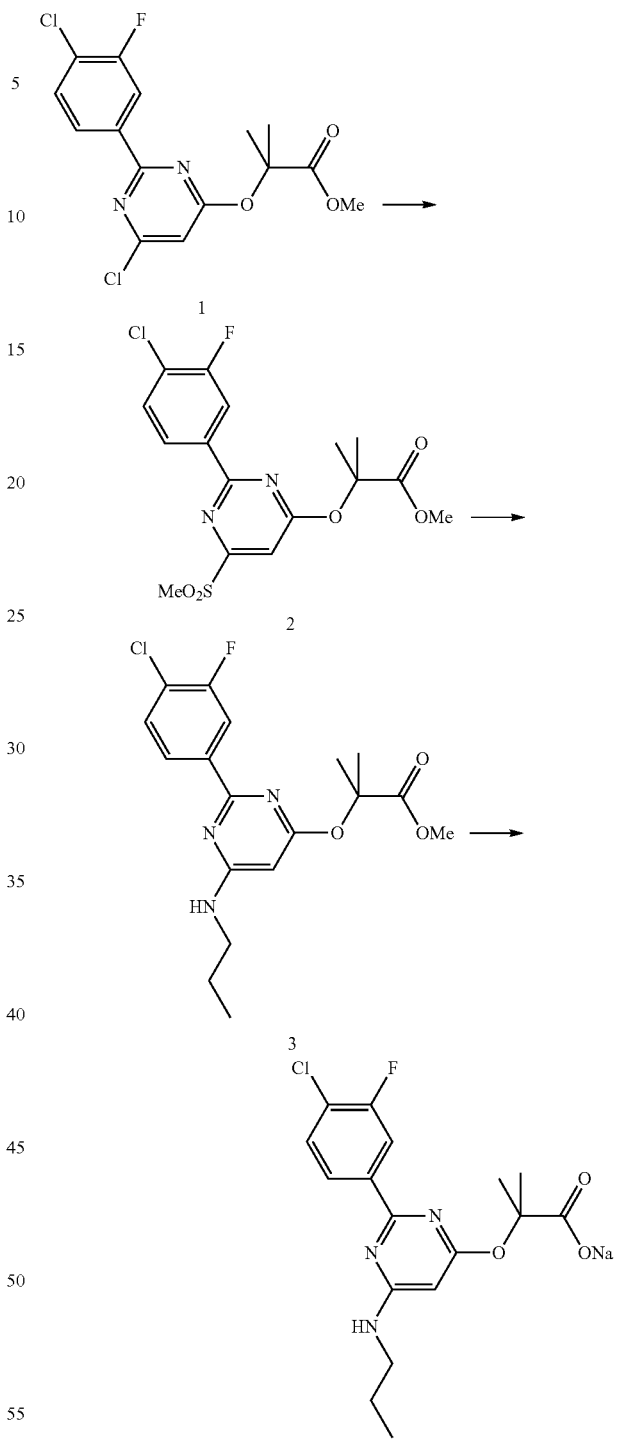

A mixture of Compound 1 (2.00 g, 5.57 mmol) and sodium methanesulfinate (2.01 g, 16.7 mmol) in DMF (27.8 mL) was stirred at 50° C. overnight. After cooling to room temperature, the mixture was diluted with ethyl acetate, washed with water and brine, dried over anhydrous sodium sulfate, and concentrated under reduced pressure. The residue was triturated with diisopropyl ether to give Compound 2 (2.16 g, 96%) as powders.

MS: 403/405 [M+H]+, APCI.

To a solution of Compound 2 (60.0 mg, 149 µmol) in THF (1.67 mL) were added propylamine (68.7 µl, 835) and triethylamine (27.9 µl, 201 µmol), and the mixture was stirred at room temperature for 3 days. The reaction mixture was poured into water and extracted with ethyl acetate. The organic layer was concentrated under reduced pressure. The residue was purified by silica gel column chromatography (hexane→hexane:ethyl acetate=4:1) to give Compound 3 (55.3 mg, 97%) as a viscous oil.

MS: 382/384 [M+H]+, APCI.

Compound 4 was prepared by reacting and treating in the same manner as in Example 1 using Compound 3.

Compound 4: MS: 366/368 [M-Na]−, ESI.

Example 3

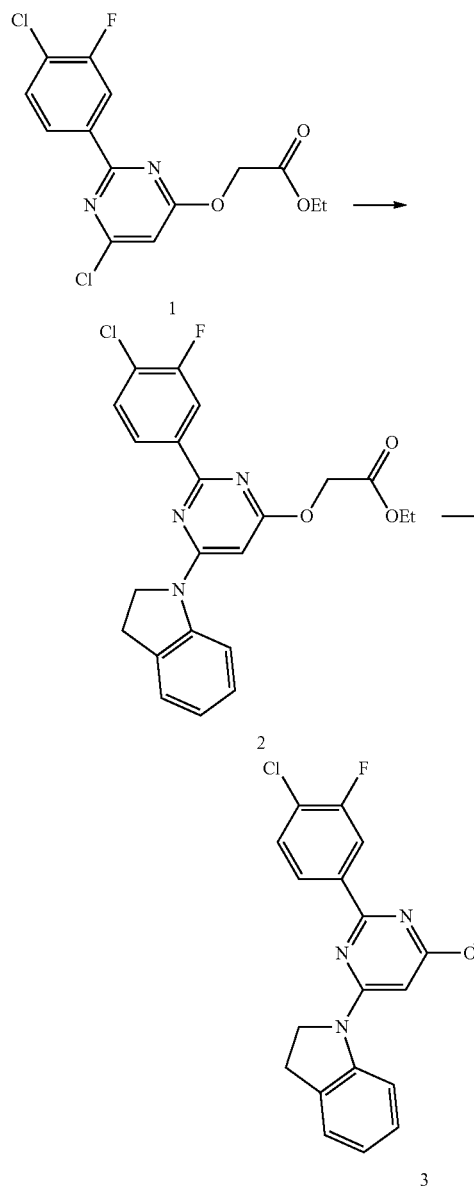

dium (13.3 mg, 14.5 µmol), 4,5-bis(diphenylphosphino)-9,9-dimethylxanthene (25.2 mg, 43.5 µmol) and cesium carbonate (189 mg, 579 µmol) in 1,4-dioxane (2.90 mL) was refluxed overnight under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane:ethyl acetate=9:1→4:1) to give Compound 2 (33.5 mg, 27%) as a solid.

MS: 428/430 [M+H]+, APCI.

Compound 3 was prepared by reacting and treating in the same manner as in example 1 using Compound 2.

Compound 3: MS: 398/400 [M-Na]−, ESI.

Example 4

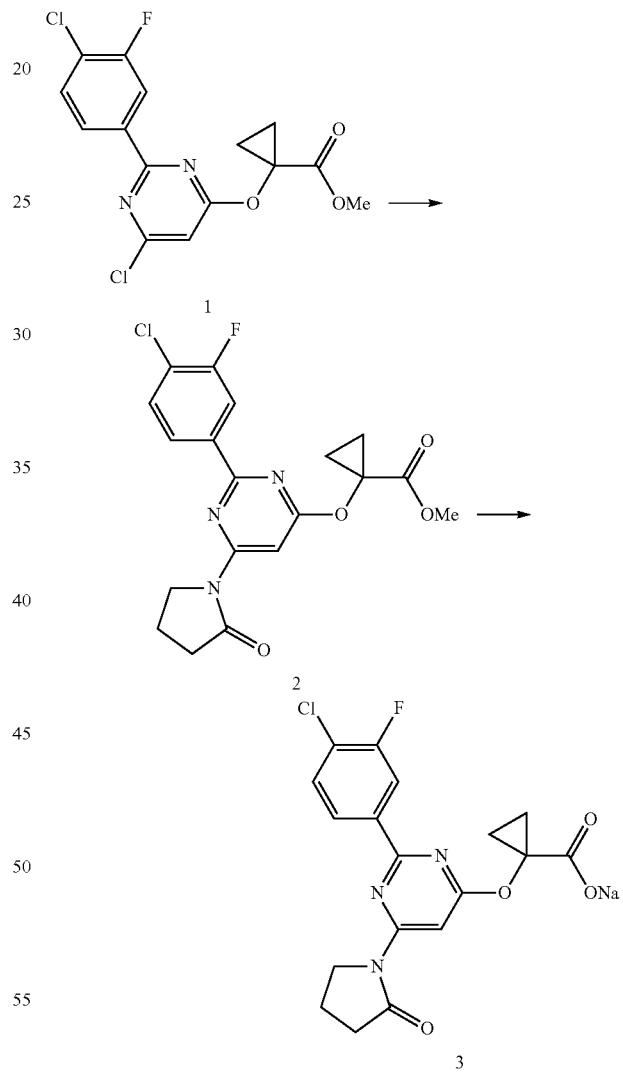

A mixture of Compound 1 (60 mg, 168 µmol), 2-pyrrolidinone (16 µL, 204 µmol), tris(dibenzylideneacetone)dipalladium(0) (8 mg, 8 µmol), 4,5-bis(diphenylphosphino)-9,9-dimethylxanthene (15 mg, 25 µmol), and potassium phosphate tribasic (50 mg, 236 µmol) in 1,4-dioxane (3 mL) was refluxed for 6 hours under argon atmosphere. After cooling, the mixture was diluted with ethyl acetate, filtered through Chem Elut® (Varian Inc.) and Bond Elut® (Varian A suspension of Compound 1 (100 mg, 290 µmol), indoline (51.8 mg, 435 µmol), tris(dibenzylideneacetone)dipalla- Inc.), and concentrated under reduced pressure. The residue was purified by silica gel column chromatography (hexane:ethyl acetate=19:1→13:7) to give Compound 2 (62.3 mg, 91%) as a solid.

MS: 406/408 [M+H]+, APCI.

A mixture of Compound 2 (47 mg, 116 µmol) and lithium iodide (109 mg, 814 µmol) in collidine (4 mL) was refluxed for 30 minutes under argon atmosphere. After cooling, the mixture was diluted with ethyl acetate, washed with 10% aqueous hydrochloric acid and brine, dried over anhydrous sodium sulfate, and concentrated under reduced pressure. The residue was purified by silica gel column chromatography (chloroform:methanol=49:1). The solid was suspended in THF and MeOH, treated with 0.5 M aqueous sodium bicarbonate (91 µL, 46 µmol), and concentrated under reduced pressure. The residue was triturated with diethyl ether to give Compound 3 (19.3 mg, 40%) as powders.

MS: 390/392 [M-Na]−, ESI.

Example 5

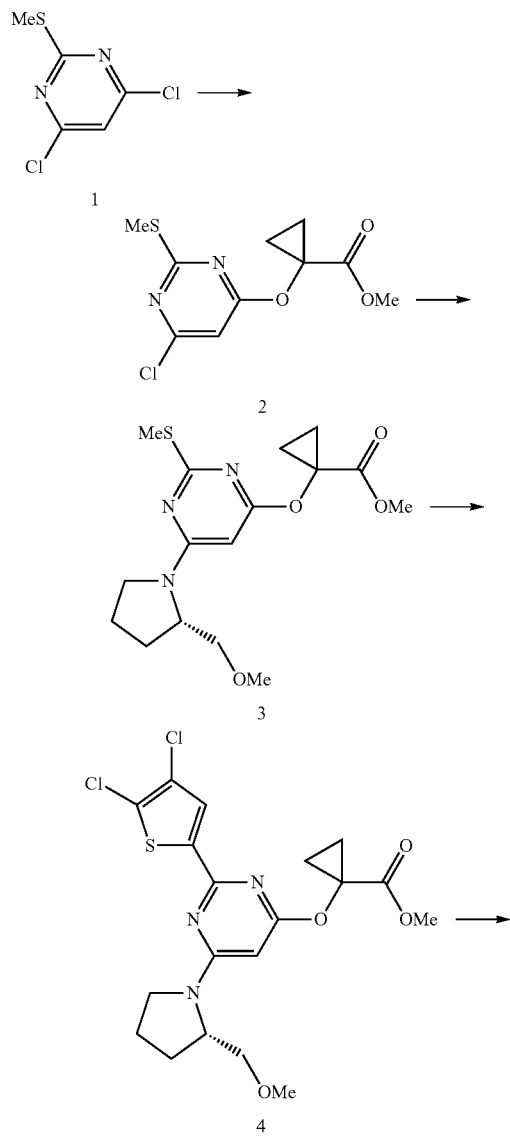

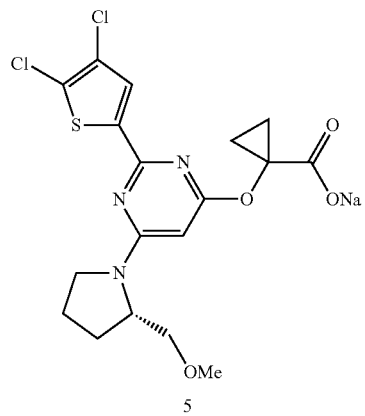

To a solution of Compound 1 (5.00 g, 25.6 mmol) and methyl 1-hydroxy-1-cyclopropane carboxylate (3.97 g, 30.8 mmol) in THF (100 mL) was added sodium hydride (60%, 1.23 g, 30.8 mmol) at −78° C. and the mixture was stirred at room temperature for 3 hours. The reaction mixture was quenched with 1 M aqueous citric acid and extracted with ethyl acetate. The organic layer was washed with water and brine, dried over anhydrous sodium sulfate, and concentrated under reduced pressure. The residue was purified by silica gel column chromatography (hexane:ethyl acetate=15:1) to give Compound 2 (6.91 g, 98%) as a solid.

MS: 275/277 [M+H]+, APCI.

To a solution of Compound 2 (5.00 g, 18.2 mmol) in THF (18.2 mL) were added (S)-(+)-2-(methoxymethyl)pyrrolidine (3.37 ml, 27.3 mmol) and triethylamine (3.81 ml, 27.3 mmol), and the mixture was stirred at room temperature for 18 hours and further stirred at 50° C. for 22 hours. The reaction mixture was poured into water and extracted with ethyl acetate. The organic layer was washed with water and brine, dried over anhydrous sodium sulfate, and concentrated under reduced pressure. The residue was purified by silica gel column chromatography (hexane:ethyl acetate=7:1) to give Compound 3 (6.72 mg, quant.) as a viscous oil.

MS: 354 [M+H]+, APCI.

A mixture of Compound 3 (70 mg, 198 µmol), 4,5-dichlorothiophene-2-boronic acid (117 mg, 594 µmol), tetrakis(triphenylphosphine)palladium(0) (24 mg, 20 µmol), copper (I) thiophene-2-carboxylate (117 mg, 594 µmol) and THF (2 mL) was refluxed for 2 hours under argon atmosphere. Additional 4,5-dichlorothiophene-2-boronic acid (117 mg, 594 µmol), tetrakis(triphenylphosphine)palladium(0) (24 mg, 20 µmol), and copper(I) thiophene-2-carboxylate (117 mg, 594 µmol) were added and the mixture was refluxed for 15 hours under argon atmosphere. After cooling, the reaction mixture was diluted with saturated aqueous ammonium hydroxide and ethyl acetate, filtered through Chem Elut® (Varian Inc.) and Bond Elut® (Varian Inc.), and concentrated under reduced pressure. The residue was purified by NH silica gel column chromatography (hexane→hexane:ethyl acetate=4:1) to give Compound 4 (51 mg, 67%) as a solid.

MS: 458/460 [M+H]+, APCI.

Compound 5 was prepared by reacting and treating in the same manner as in Example 1 using Compound 4.

Compound 5: MS: 442/444 [M-Na]−, ESI.

Example 6

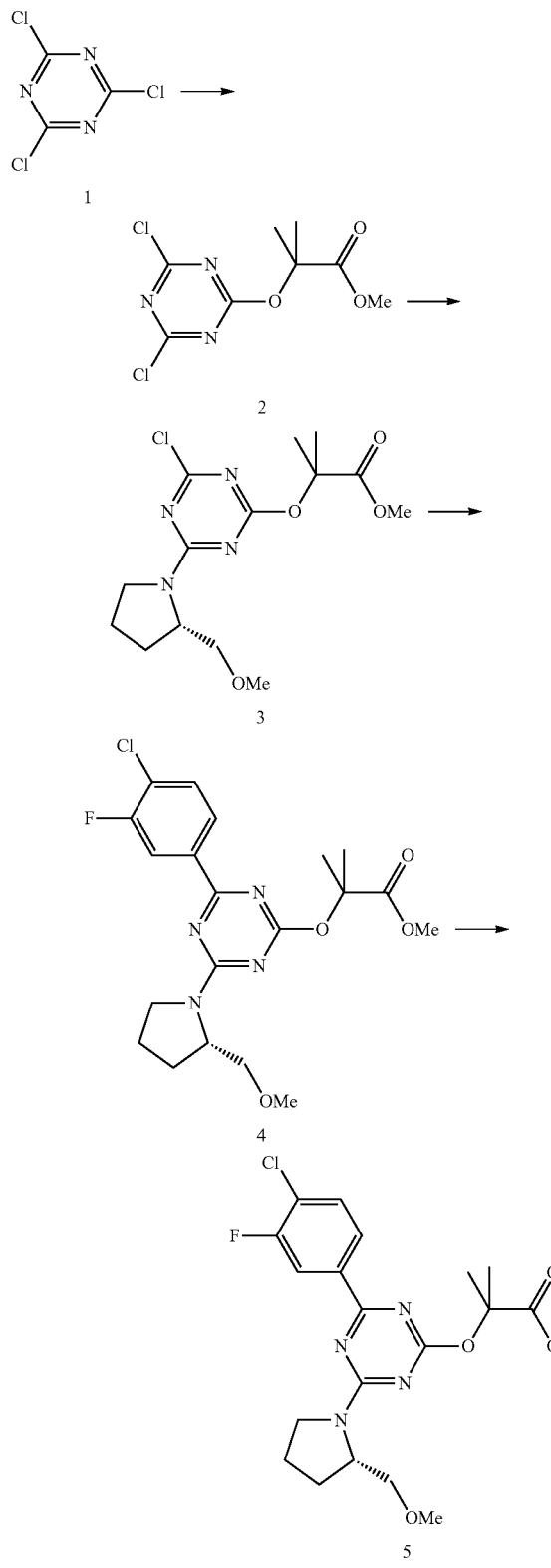

To a solution of Compound 1 (3.00 g, 15.9 mmol) and methyl 2-hydroxyisobutyrate (2.26 g, 19.1 mmol) in THF (30.0 mL) was added sodium hydride (60%, 765 mg, 19.1 mmol) at −78° C. and the mixture was stirred at room temperature overnight. The reaction mixture was quenched with 1 M aqueous citric acid and extracted with ethyl acetate. The organic layer was washed with water and brine, dried over anhydrous sodium sulfate, and concentrated under reduced pressure. The residue was purified by silica gel column chromatography (hexane:ethyl acetate=20:1) to give Compound 2 (3.34 g, 79%) as a solid.

1H NMR (400 MHz, CDCl3): δ 1.76 (6H, s), 3.75 (3H, s).

To a solution of Compound 2 (150 mg, 564 mmol) in THF (2.82 mL) were added (S)-(+)-2-(methoxymethyl)pyrrolidine (73.1 µl, 592 µmol) and triethylamine (118 µl, 667 µmol) at 0° C., and the mixture was stirred at room temperature overnight. The reaction mixture was poured into water and extracted with ethyl acetate. The organic layer was filtered through Chem Elut® (Varian Inc.) and Bond Elut® (Varian Inc.), and concentrated under reduced pressure. The residue was purified by silica gel column chromatography (hexane→hexane:ethyl acetate=4:1) to give Compound 3 (218 mg, quant.) as a solid.

MS: 345/347 [M+H]$^+$, APCI.

A suspension of Compound 3 (102 mg, 277 µmol), 4-chloro-3-fluorophenylboronic acid (74.1 mg, 416 µmol), dichlorobis(triphenylphosphine)palladium (19.9 mg, 27.7 µmol) and 2 M aqueous sodium carbonate (416 µL, 831 µmol) in 1,2-dimethoxyethane (2.77 mL) was refluxed for 2 hours under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane→hexane:ethyl acetate=4:1) to give Compound 4 (108 mg, 89%) as a viscous oil.

MS: 439/441 [M+H]$^+$, APCI.

Compound 5 was prepared by reacting and treating in the same manner as in Example 1 using Compound 4.

Compound 5: MS: 423/425 [M-Na]−, ESI.

Example 7

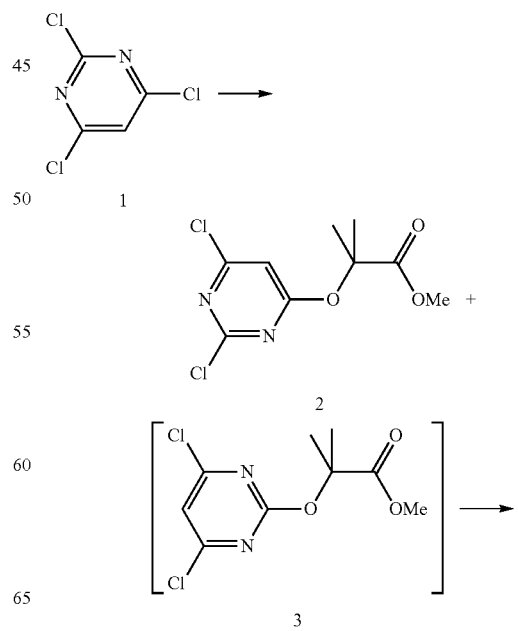

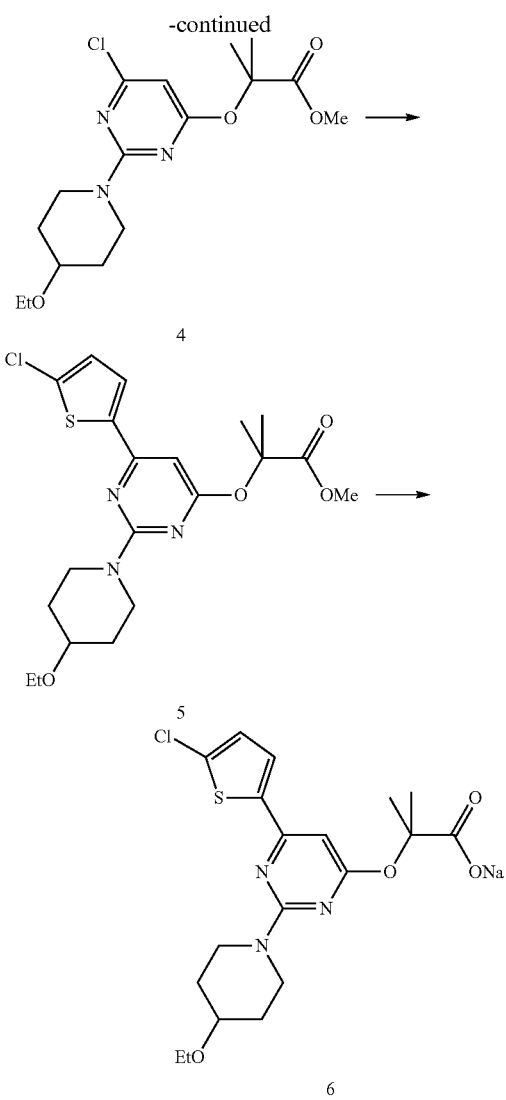

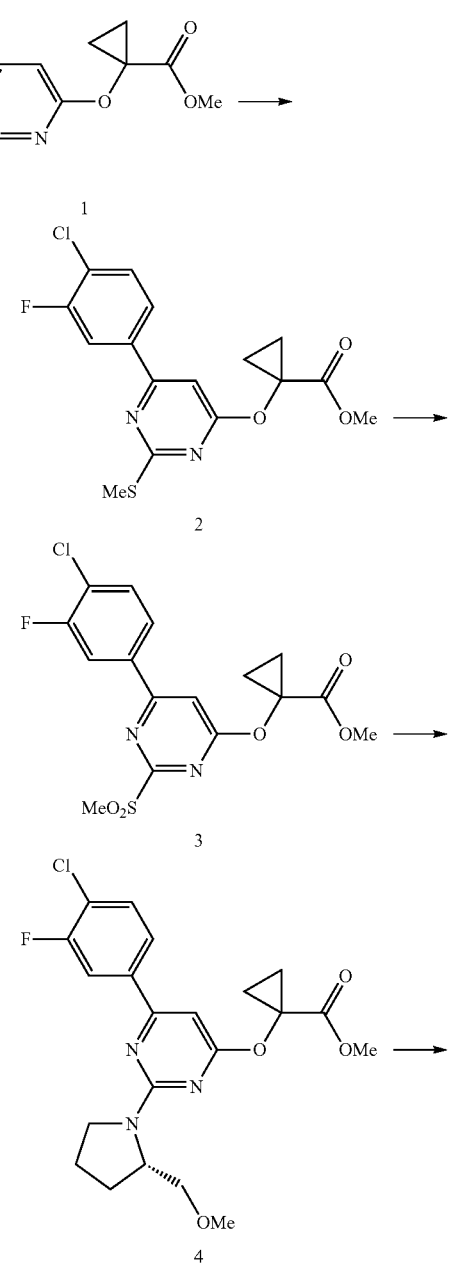

A suspension of Compound 4 (70 mg, 196 μmol), potassium 5-chloro-2-thiophenetrifluoroborate (88 mg, 392 μmol), dichlorobis(triphenylphosphine)palladium (16 mg, 19.6 μmol) and diisopropylethylamine (103 μL, 589 μmol) in dioxane/water (10:1, 2 mL) was refluxed for 4 hours under argon atmosphere. After cooling, potassium 5-chloro-2-thiophenetrifluoroborate (88 mg, 392 μmol), dichlorobis(triphenylphosphine)palladium (16 mg, 19.6 μmol) and diisopropylethylamine (103 μL, 589 μmol) were added thereto and the mixture was refluxed for 3 hours under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane→hexane:ethyl acetate=23:2) to give Compound 5 (39 mg, 45%) as a powder.

Compound 6 was prepared by reacting and treating in the same manner as in Example 1 using Compound 5.

Compound 6: MS: 424 [M-Na]−, ESI.

Example 8

To a solution of Compound 1 (5.00 g, 27.3 mmol) and methyl 2-hydroxyisobutyrate (3.38 g, 29.3 mmol) in THF (100 mL) was added sodium hydride (60%, 1.15 g, 28.6 mmol) at 0° C. After 1 hour at 0° C., the mixture was stirred at room temperature overnight. The reaction mixture was quenched with 1 M aqueous citric acid and extracted with ethyl acetate. The organic layer was washed with water and brine, dried over anhydrous sodium sulfate, and concentrated under reduced pressure. The residue was purified by silica gel column chromatography (hexane:ethyl acetate=19:1) to give the mixture of Compounds 2 and 3 (5.56 g, total 77%, mol ratio=1:1.2) as a liquid.

MS: 265/267 [M+H]+, APCI.

To a solution of Compounds 2 and 3 (3.00 g, total 11.3 mmol) in THF (50 mL) were added 4-ethoxypiperidine (1.54 g, 11.9 mmol) and triethylamine (3.16 ml, 22.7 mmol), and the mixture was stirred at room temperature for 14 hours. The reaction mixture was concentrated under reduced pressure to dryness. The residue was diluted with ethyl acetate, washed with 1 M aqueous citric acid, dried over anhydrous sodium sulfate, and concentrated under reduced pressure. The residue was purified by silica gel column chromatography (hexane:ethyl acetate=9:1→7:3) to give Compound 4 (1.78 mg, 34% 2 steps) as a viscous oil.

MS: 358/360 [M+H]+, APCI.

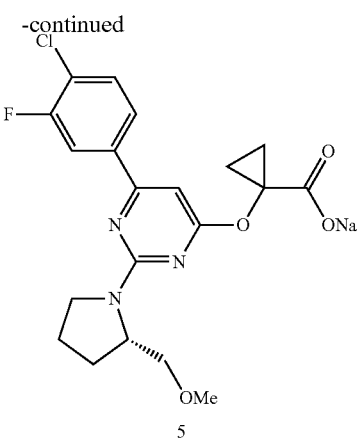

A suspension of Compound 1 (500 mg, 1.82 mmol), 4-chloro-3-fluorophenylboronic acid (486 mg, 2.73 mmol), dichlorobis(triphenylphosphine)palladium (130 mg, 182 µmol) and 2 M aqueous sodium carbonate (2.73 mL, 5.46 mmol) in 1,2-dimethoxyethane (18.2 mL) was refluxed for 1.5 hours under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane→hexane:ethyl acetate=17:3) to give Compound 2 (657 mg, 98%) as a powder.

MS: 369/371 [M+H]$^+$, APCI

To a solution of Compound 2 (653 mg, 1.77 mmol) in chloroform (8.85 mL) was added 3-chloroperoxybenzoic acid (896 mg, 3.89 mmol) at 0° C. and the mixture was stirred at the same temperature for 1.5 hours. Sat. aqueous sodium sulfite and sat. aqueous sodium bicarbonate were added thereto and the mixture was extracted with chloroform. The combined organic layer was washed with sat. aqueous sodium bicarbonate and brine, dried over anhydrous sodium sulfate, and concentrated under reduced pressure. The residue was purified by silica gel column chromatography (hexane:ethyl acetate=9:1→6:4) to give Compound 3 (594 mg, 84%) as powders.

MS: 401/403 [M+H]$^+$, APCI.

To a solution of Compound 3 (70 mg, 175 µmol) in THF (1.75 mL) were added (S)-(+)-2-(methoxymethyl)pyrrolidine (65 µl, 524 µmol) and triethylamine (37 µl, 262 µmol), and the mixture was stirred at room temperature overnight. The reaction mixture was poured into water and extracted with ethyl acetate. The organic layer was washed with water and brine, dried over anhydrous sodium sulfate, and concentrated under reduced pressure. The residue was purified by silica gel column chromatography (hexane→hexane:ethyl acetate=4:1) to give Compound 4 (77 mg, quant.) as powders.

MS: 436/438 [M+H]$^+$, APCI.

To a solution of Compound 4 (73.1 mg, 166 µmol) in MeOH (1.00 mL) and THF (1.00 mL) was added 2 M aqueous sodium hydroxide (415 µL, 830 µmol) and the mixture was stirred at room temperature overnight. The reaction mixture was concentrated under reduced pressure. The residue was acidified with 1 M aqueous citric acid and extracted with ethyl acetate. The organic layer was filtered through Chem Elut® (Varian Inc.) and concentrated under reduced pressure. The obtained free acid (71.9 mg, 166 µmol) was dissolved in acetone and treated with 2 M aqueous sodium hydroxide (81 µl, 162 µmol), then concentrated under reduced pressure. The residue was triturated with diethyl ether to give Compound 5 (71.1 mg, 98%) as powders.

MS: 420/422 [M-Na]−, ESI.

Corresponding starting compounds were treated in the similar manner to any of the above examples to give the following compounds.

Example 9

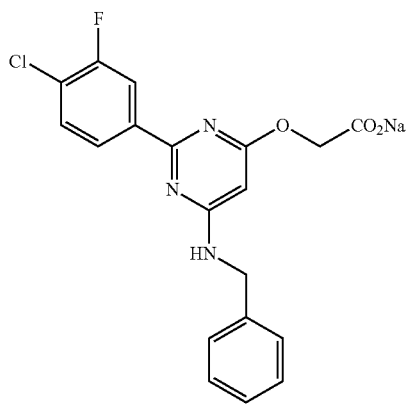

MS: 386/388 [M-Na]−, ESI.

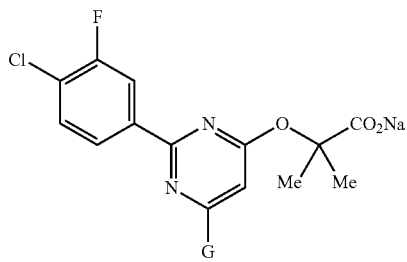

| Example | G | MS (ESI) |
|---|---|---|
| 10 | —N(morpholine) | 394/396 [M − Na]− |
| 11 | —NMe$_2$ | 352/354 [M − Na]− |
| 12 | —N(2-(methoxymethyl)pyrrolidinyl) | 422/424 [M − Na]− |
| 13 | —N(CH$_2$CH$_2$OMe)$_2$ | 440/442 [M − Na]− |
| 14 | —N(pyrrolidinyl) | 378/380 [M − Na]− |
| 15 | —N(3,3-difluoropyrrolidinyl) | 414/416 [M − Na]− |

-continued

| | | |
|---|---|---|
| 16 | 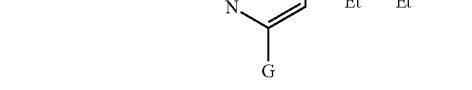 | 450/452 [M − Na]⁻ |
| 17 | 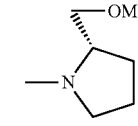 | 436/438 [M − Na]⁻ |
| 18 | 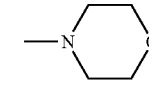 | 410/412 [M − Na]⁻ |
| 19 | 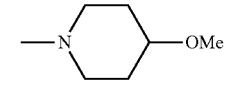 | 428/430 [M − Na]⁻ |
| 20 |  | 428/430 [M − Na]⁻ |
| 21 |  | 451/453 [M − Na]⁻ |
| 22 | 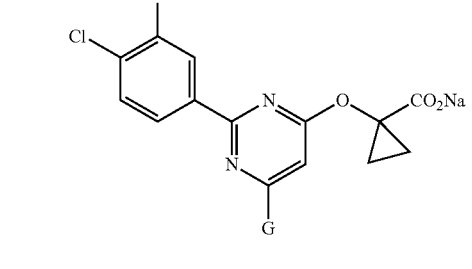 | 410/412 [M − Na]⁻ |
| 23 | 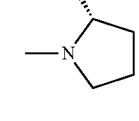 | 450/452 [M − Na]⁻ |
| 24 | 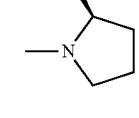 | 450/452 [M − Na]⁻ |
| 25 | 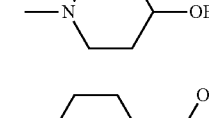 | 436/438 [M − Na]⁻ |
| 26 | | 422/424 [M − Na]⁻ |
| 27 | | 436/438 [M − Na]⁻ |
| 28 | —NHMe | 338/340 [M − Na]⁻ |
| 29 | —NHEt | 352/354 [M − Na]⁻ |
| 30 | —NHCHMe₂ | 366/368 [M − Na]⁻ |

-continued

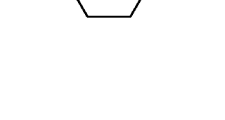

| Example | G | MS (ESI) |
|---|---|---|
| 31 | pyrrolidine-CH₂OMe | 450/452 [M − Na]⁻ |
| 32 | morpholine | 422/424 [M − Na]⁻ |
| 33 | N-Me-piperidine-OMe | 450/452 [M − Na]⁻ |
| 34 | —NHCH₂CH₂OMe | 410/412 [M − Na]⁻ |
| 35 | —NMe₂ | 380/382 [M − Na]⁻ |

| Example | G | MS (ESI) |
|---|---|---|
| 36 | pyrrolidine-CH₂OMe | 420/422 [M − Na]⁻ |
| 37 | pyrrolidine-CH₂OMe | 420/422 [M − Na]⁻ |
| 38 | N-Me-piperidine-OEt | 434/436 [M − Na]⁻ |
| 39 | N-Me-piperidine-CH₂OMe | 434/436 [M − Na]⁻ |

-continued

| Example | Structure | MS (ESI) |
|---|---|---|
| 40 | 2,6-dimethyl-4-methylmorpholine | 420/422 [M − Na]⁻ |
| 41 | 1-methyl-4-(2-hydroxypropan-2-yl)piperidine | 448/450 [M − Na]⁻ |
| 42 | 2-(1-methylpiperidin-4-yl)ethanol | 434/436 [M − Na]⁻ |
| 43 | 1-methyl-3-methoxypyrrolidine | 406/408 [M − Na]⁻ |
| 44 | N-methylbenzylamine | 412/414 [M − Na]⁻ |
| 45 | N-methyl-4-fluorobenzylamine | 430/432 [M − Na]⁻ |
| 46 | N-methyl-3-fluorobenzylamine | 430/432 [M − Na]⁻ |
| 47 | N-methylcyclopentylamine | 390/392 [M − Na]⁻ |
| 48 | 1-methyl-3-ethoxypiperidine | 434/436 [M − Na]⁻ |
| 49 | 1-methyl-3-methoxypiperidine | 420/422 [M − Na]⁻ |
| 50 | 1-methyl-3-ethoxypiperidine | 434/436 [M − Na]⁻ |
| 51 | 1-methyl-3-ethoxypyrrolidine | 420/422 [M − Na]⁻ |
| 52 | 1-methyl-4-(1-methylethoxy)piperidine | 448/450 [M − Na]⁻ |

-continued

| Example | Structure | MS (ESI) |
|---|---|---|
| 53 | 1-methyl-4-(propoxy)piperidine | 448/450 [M − Na]⁻ |

Structure:

4-chloro-3-fluorophenyl-pyrimidine-4-oxy-cyclopentane-CO₂Na with G substituent at 6-position

| Example | G | MS (ESI) |
|---|---|---|
| 54 | (S)-1-methyl-2-(methoxymethyl)pyrrolidine | 448/450 [M − Na]⁻ |
| 55 | (S)-1-methyl-2-(hydroxymethyl)pyrrolidine | 434/436 [M − Na]⁻ |
| 56 | 1-methyl-4-methoxypiperidine | 448/450 [M − Na]⁻ |
| 57 | 1-methyl-4-ethoxypiperidine | 462/464 [M − Na]⁻ |
| 58 | 1-methyl-4-(2-hydroxypropan-2-yl)piperidine | 476/478 [M − Na]⁻ |
| 59 | 2-(1-methylpiperidin-4-yl)ethanol | 462/464 [M − Na]⁻ |
| 60 | N-methyl-(pyridin-2-yl)methylamine | 441/443 [M − Na]⁻ |

Example 61
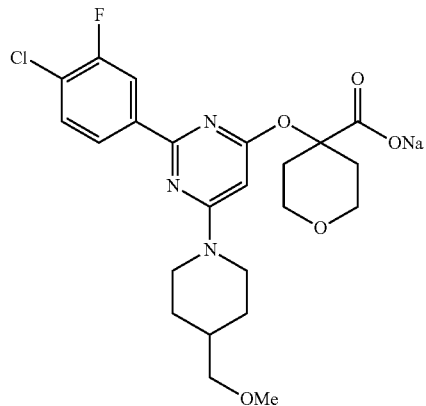
MS: 478/480 [M-Na]−, ESI.
| Example | Ring A1 | MS (ESI) |
|---|---|---|
| 62 | 3-CF₃-phenyl | 436 [M-Na]− |
| 63 | 4-CF₃-phenyl | 436 [M-Na]− |
| 64 | 3-Cl-phenyl | 402/404 [M-Na]− |
| 65 | 3-EtO-phenyl | 412 [M-Na]− |
| 66 | 4-Me-phenyl | 382 [M-Na]− |
| 67 | 5-Cl-2-thienyl | 408/410 [M-Na]− |
| 68 | 2-Cl-3,5-diMe-thienyl | 422/424 [M-Na]− |
| Example | Ring A1 | MS (ESI) |
|---|---|---|
| 69 | 5-Cl-2-thienyl | 422/424 [M-Na]− |
| 70 | 3-Cl-phenyl | 416/418 [M-Na]− |
| 71 | 4-Me-phenyl | 396 [M-Na]− |
| 72 | 3-F-phenyl | 400 [M-Na]− |
| 73 | 4-F-phenyl | 400 [M-Na]− |
| 74 | 3,4-diF-phenyl | 418 [M-Na]− |

55
-continued

[Structure: Ring A1 attached to pyrimidine with O-cyclopropane-CO2Na and piperidine-O-CH(Me)2 substituents]

| Example | Ring A1 | MS (ESI) |
|---|---|---|
| 75 | 4-F-phenyl | 414 [M-Na]⁻ |
| 76 | 3,4-diF-phenyl | 432 [M-Na]⁻ |
| 77 | 3,5-diF-phenyl | 432 [M-Na]⁻ |

[Structure: Ring A1 attached to pyrimidine with O-cyclopropane-CO2Na and piperidine-O-CH2CH2-Me substituents]

| Example | Ring A1 | MS (ESI) |
|---|---|---|
| 77 | 3,5-diF-phenyl | 432 [M-Na]⁻ |
| 78 | 4-F-phenyl | 414 [M-Na]⁻ |
| 79 | 3-F-phenyl | 414 [M-Na]⁻ |

56
-continued

| | | |
|---|---|---|
| 80 | 3,4-diF-phenyl | 432 [M-Na]⁻ |

[Structure: Ring A1 attached to pyrimidine with O-cyclopropane-CO2Na and piperidine-OEt substituents]

| Example | Ring A1 | MS (ESI) |
|---|---|---|
| 82 | 3-Cl-phenyl | 416/418 [M-Na]⁻ |
| 83 | 4-F-phenyl | 400 [M-Na]⁻ |
| 84 | 3,4-diF-phenyl | 418 [M-Na]⁻ |
| 85 | 5-Cl-thiophen-2-yl | 422/424 [M-Na]⁻ |

[Structure: Ring A1 attached to pyrimidine with O-C(Me)2-CO2Na and pyrrolidine-CH2OMe substituents]

| Example | Ring A1 | MS (ESI) |
|---|---|---|
| 86 | 4-CF3-phenyl | 438/440 [M-Na]⁻ |
| 87 | 2,3-diCl-thiophen-5-yl | 444/446 [M-Na]⁻ |

-continued
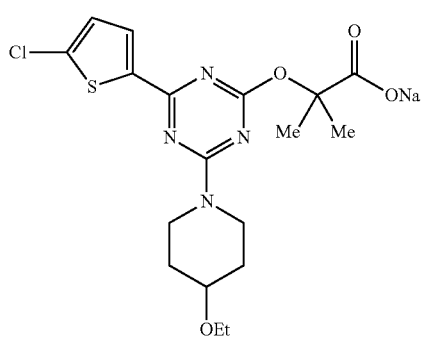
| Example | G | MS (ESI) |
|---|---|---|
| 88 | 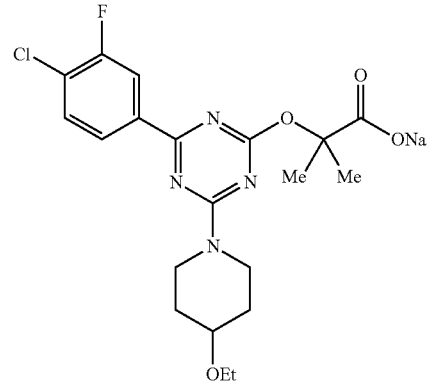 (OMe on pyrrolidine) | 421/423 [M-Na]⁻ |
| 89 | N-methyl-piperidine-OEt | 435/437 [M-Na]⁻ |
Example 90
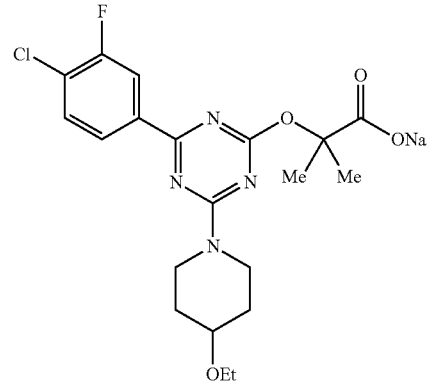
MS: 437/439 [M-Na]⁻, ESI.
Example 91
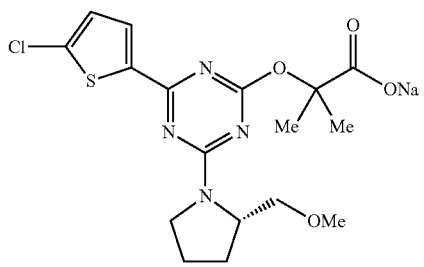
MS: 411/413 [M-Na]⁻, ESI.
Example 92
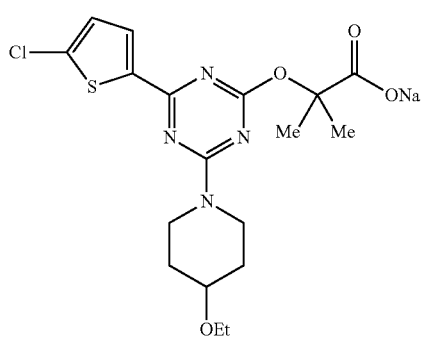
MS: 425/427 [M-Na]⁻, ESI.
Example 93
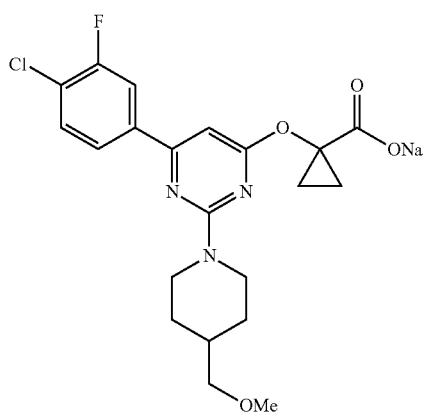
MS: 434/436 [M-Na]⁻, ESI.
| Example | G | MS (ESI) |
|---|---|---|
| 94 | pyrrolidine-CH₂-OMe | 422/424 [M-Na]⁻ |

-continued

| | | | |
|---|---|---|---|
| 95 | ![piperidine-CH2OMe] N-methylpiperidine-4-CH2OMe | 436/438 [M−Na]− | |
| 96 | N-methylpiperidine-4-OEt | 436/438 [M−Na]− | |

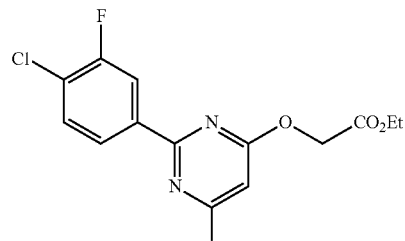

| Example | G | MS (ESI) |
|---|---|---|
| 97 | —NH-CH2-Ph | 416/418 [M + H]+ |
| 98 | 1-methylindoline | 428/430 [M + H]+ |

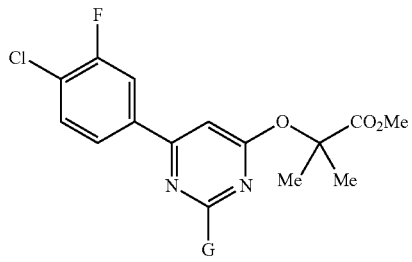

| Example | G | MS (APCI) |
|---|---|---|
| 99 | 4-methylmorpholine | 410/412 [M + H]+ |
| 100 | —NMe2 | 368/370 [M + H]+ |
| 101 | (S)-1-methyl-2-(methoxymethyl)pyrrolidine | 438/440 [M + H]+ |
| 102 | —N(CH2CH2OMe)2 | 456/458 [M + H]+ |
| 103 | 1-methylpyrrolidine | 394/396 [M + H]+ |
| 104 | 1-methyl-3,3-difluoropyrrolidine | 430/432 [M + H]+ |

-continued

| | | |
|---|---|---|
| 105 | 1-methyl-4-(2-hydroxyprop-2-yl)piperidine | 466/468 [M + H]+ |
| 106 | 1-methyl-4-(methoxymethyl)piperidine | 452/454 [M + H]+ |
| 107 | 1-methyl-4-fluoropiperidine | 426/428 [M + H]+ |
| 108 | 1-methyl-4,4-difluoropiperidine | 444/446 [M + H]+ |
| 109 | 1-methyl-3,3-difluoropiperidine | 444/446 [M + H]+ |
| 110 | 4-methyl-1-(methoxycarbonyl)piperazine | 467/469 [M + H]+ |
| 111 | (S)-1-methyl-2-(fluoromethyl)pyrrolidine | 426/428 [M + H]+ |
| 112 | 1-methyl-4-(n-propoxy)piperidine | 466/468 [M + H]+ |
| 113 | 1-methyl-4-(isopropoxy)piperidine | 466/468 [M + H]+ |
| 114 | (3R)-1-methyl-3-ethoxypiperidine | 452/454 [M + H]+ |
| 115 | (3R)-1-methyl-3-methoxypiperidine | 438/440 [M + H]+ |
| 116 | (3S)-1-methyl-3-ethoxypiperidine | 452/454 [M + H]+ |
| 117 | —NHMe | 354/356 [M + H]+ |
| 118 | —NHEt | 368/370 [M + H]+ |
| 119 | —NHCHMe2 | 382/384 [M + H]+ |

-continued

| Example | G | MS (APCI) |
|---|---|---|
| 120 | pyrrolidine-CH2OMe (N-Me) | 466/468 [M + H]+ |
| 121 | N-methylmorpholine | 438/440 [M + H]+ |
| 122 | N-methyl-4-OMe-piperidine | 466/468 [M + H]+ |
| 123 | —NHCH2CH2OMe | 426/428 [M + H]+ |
| 124 | —NMe2 | 396/398 [M + H]+ |

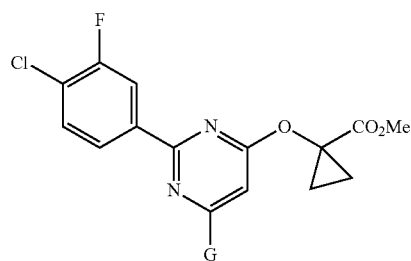

| Example | G | MS (APCI) |
|---|---|---|
| 125 | pyrrolidine-CH2OMe (N-Me) | 436/438 [M + H]+ |
| 126 | pyrrolidine-CH2OMe (N-Me) | 436/438 [M + H]+ |
| 127 | N-methyl-4-OEt-piperidine | 450/452 [M + H]+ |
| 128 | N-methyl-4-CH2OMe-piperidine | 450/452 [M + H]+ |
| 129 | 2,6-dimethyl-N-methylmorpholine | 436/438 [M + H]+ |
| 130 | N-methyl-4-(C(Me)2OH)-piperidine | 464/466 [M + H]+ |
| 131 | N-methyl-4-CH2CH2OH-piperidine | 450/452 [M + H]+ |
| 132 | N-methyl-3-OMe-pyrrolidine | 422/424 [M + H]+ |
| 133 | —NHCH2Ph | 428/430 [M + H]+ |
| 134 | —NHCH2(4-F-Ph) | 446/448 [M + H]+ |
| 135 | —NHCH2(3-F-Ph) | 446/448 [M + H]+ |
| 136 | —NH-cyclopentyl | 406/408 [M + H]+ |
| 137 | N-methyl-3-OEt-piperidine | 450/452 [M + H]+ |
| 138 | N-methyl-3-OMe-piperidine | 436/438 [M + H]+ |
| 139 | N-methyl-3-OEt-piperidine | 450/452 [M + H]+ |
| 140 | N-methyl-3-OEt-pyrrolidine | 436/438 [M + H]+ |

-continued

| | | |
|---|---|---|
| 141 | [N-methylpiperidine-4-O-CH(Me)Me] | 464/466 [M + H]+ |
| 142 | [N-methylpiperidine-4-O-CH2CH2Me] | 464/466 [M + H]+ |

[Structure: 4-chloro-3-fluorophenyl-pyrimidine with G substituent and cyclopentane bearing CO2Me, with Cl at other position]

| Example | G | MS (APCI) |
|---|---|---|
| 143 | (S)-1-methyl-2-(methoxymethyl)pyrrolidine | 464/466 [M + H]+ |
| 144 | 1-methyl-2-(hydroxymethyl)pyrrolidine | 450/452 [M + H]+ |
| 145 | 4-methoxy-1-methylpiperidine | 464/466 [M + H]+ |
| 146 | 4-ethoxy-1-methylpiperidine | 478/480 [M + H]+ |
| 147 | 4-(2-hydroxypropan-2-yl)-1-methylpiperidine | 492/494 [M + H]+ |
| 148 | 4-(2-hydroxyethyl)-1-methylpiperidine | 478/480 [M + H]+ |
| 149 | N-(pyridin-2-ylmethyl)amino | 457/459 [M + H]+ |

Example 150

[Structure of Example 150: 2-(4-chloro-3-fluorophenyl)-6-{4-(methoxymethyl)piperidin-1-yl}pyrimidin-4-yloxy tetrahydropyran-4-carboxylic acid 4-methoxybenzyl ester]

MS: 600/602 [M+H]+, APCI.

[General structure with Ring A1, pyrimidine, O-cyclopropane-CO2Me, and (S)-2-(methoxymethyl)pyrrolidin-1-yl]

| Example | Ring A1 | MS (APCI) |
|---|---|---|
| 151 | 3-(trifluoromethyl)phenyl | 452 [M + H]+ |
| 152 | 4-(trifluoromethyl)phenyl | 452 [M + H]+ |
| 153 | 3-chlorophenyl | 418/420 [M + H]+ |
| 154 | 3-ethoxyphenyl | 428 [M + H]+ |
| 155 | 4-methylphenyl | 398 [M + H]+ |
| 156 | 5-chloro-2-methylthien-... | 424/426 [M + H]+ |

| 157 | 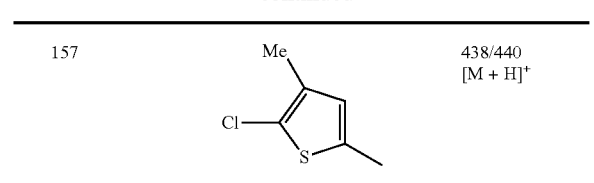 | 438/440 [M + H]+ |
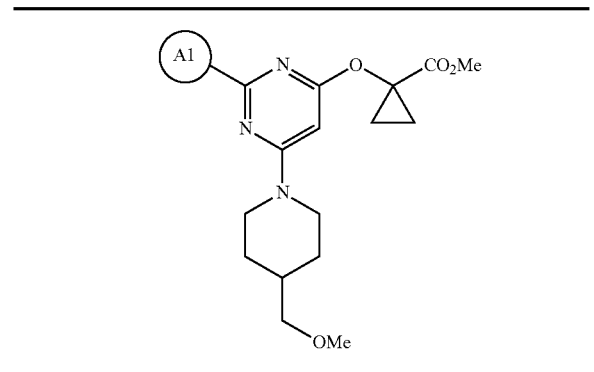
| Example | Ring A1 | MS (APCl) |
|---|---|---|
| 158 | 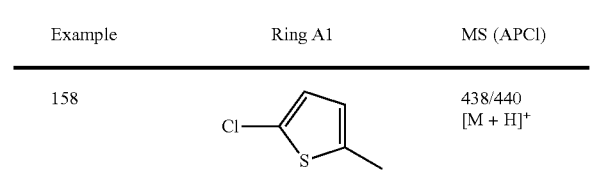 | 438/440 [M + H]+ |
| 159 | 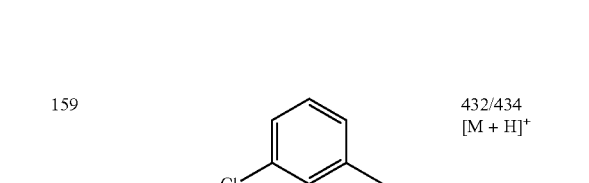 | 432/434 [M + H]+ |
| 160 | 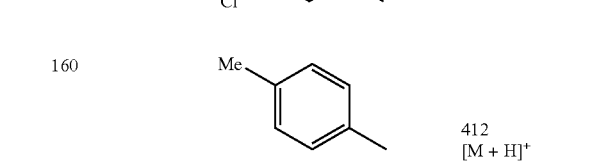 | 412 [M + H]+ |
| 161 | 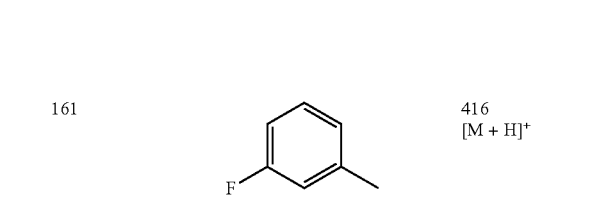 | 416 [M + H]+ |
| 162 | 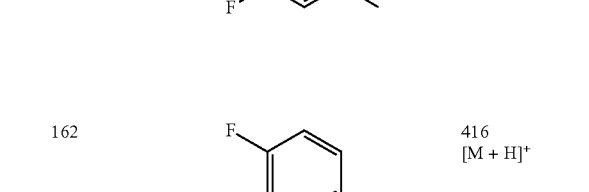 | 416 [M + H]+ |
| 163 | 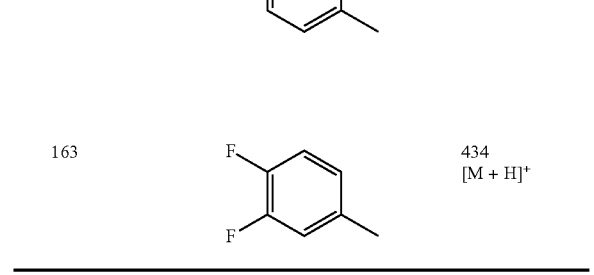 | 434 [M + H]+ |
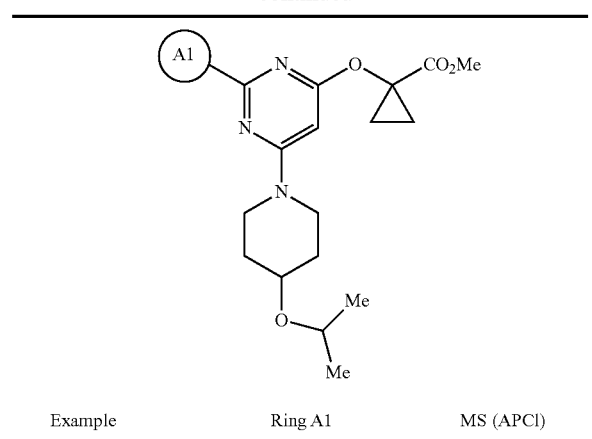
| Example | Ring A1 | MS (APCl) |
|---|---|---|
| 164 | 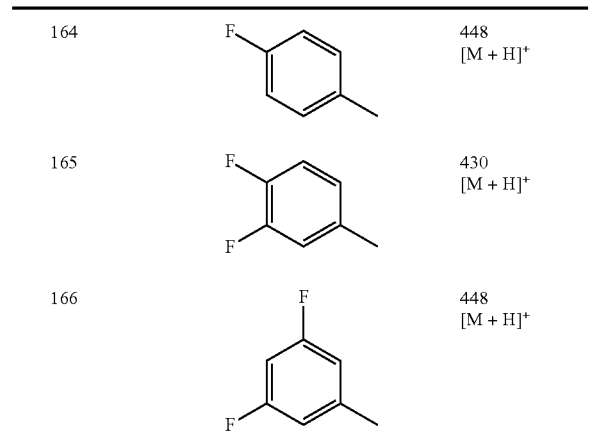 | 448 [M + H]+ |
| 165 | | 430 [M + H]+ |
| 166 | | 448 [M + H]+ |
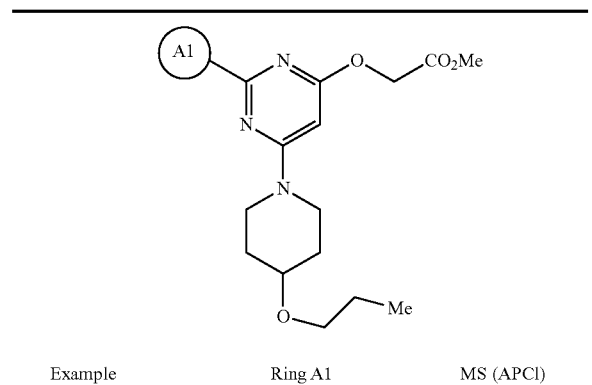
| Example | Ring A1 | MS (APCl) |
|---|---|---|
| 167 | 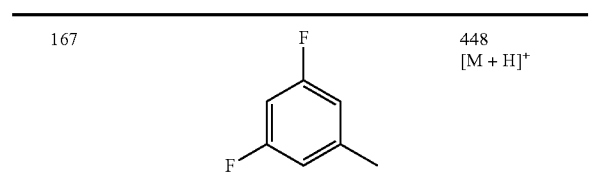 | 448 [M + H]+ |
| 168 | | 430 [M + H]+ |
| 169 | 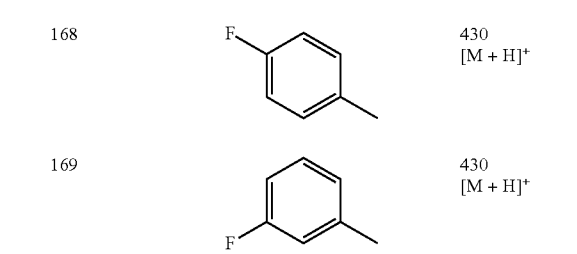 | 430 [M + H]+ |

-continued
| 170 | 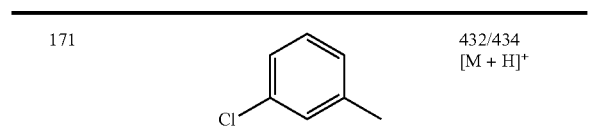 | 448 [M + H]+ |
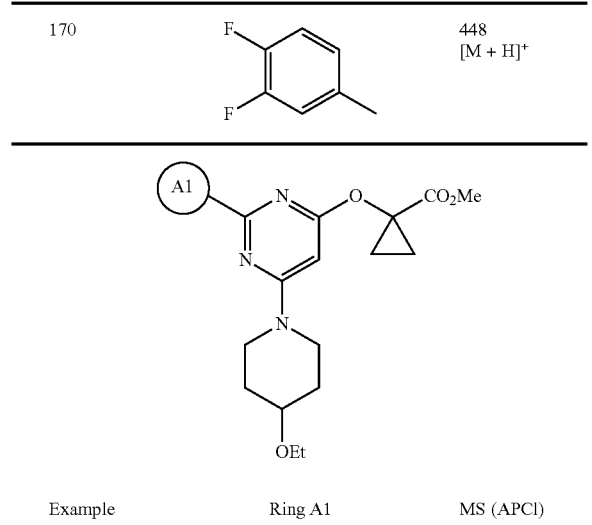
| Example | Ring A1 | MS (APCl) |
|---|---|---|
| 171 | 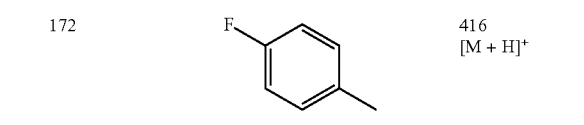 | 432/434 [M + H]+ |
| 172 | 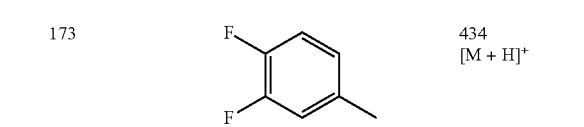 | 416 [M + H]+ |
| 173 | 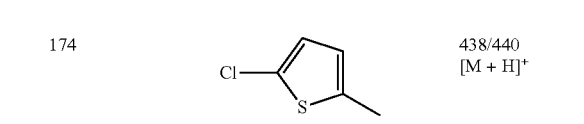 | 434 [M + H]+ |
| 174 | | 438/440 [M + H]+ |
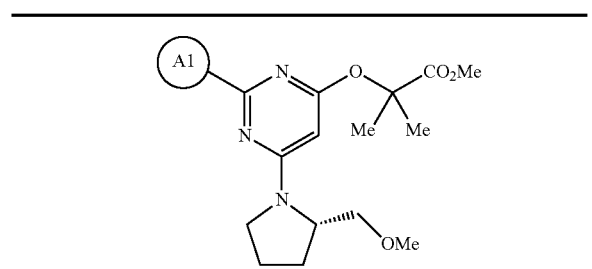
| Example | Ring A1 | MS (APCl) |
|---|---|---|
| 175 |  | 454 [M + H]+ |
| 176 | 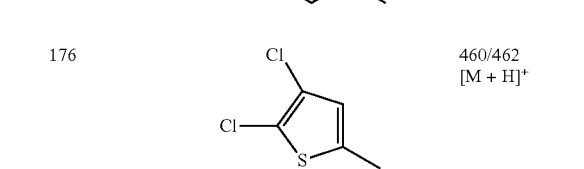 | 460/462 [M + H]+ |
-continued
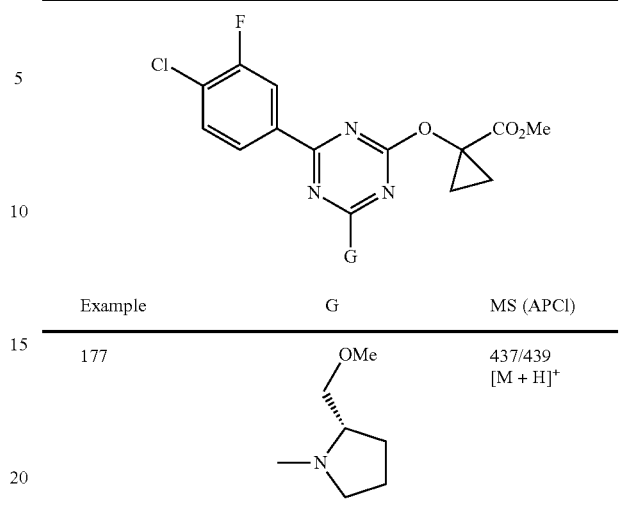
| Example | G | MS (APCl) |
|---|---|---|
| 177 | 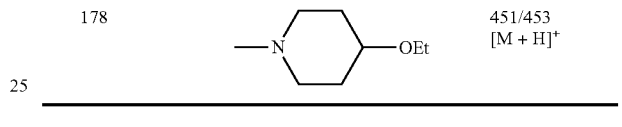 | 437/439 [M + H]+ |
| 178 | 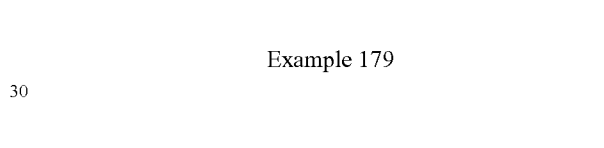 | 451/453 [M + H]+ |
Example 179
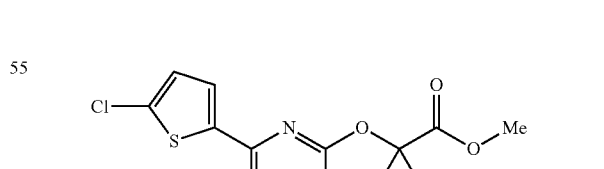
MS: 453/455 [M+H]+, APCI.
Example 180
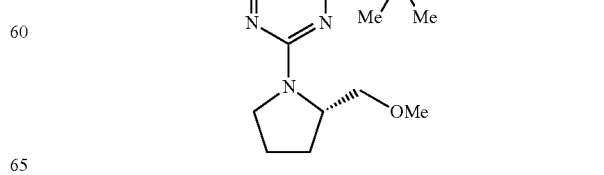
MS: 427/429 [M+H]+, APCI.

Example 181
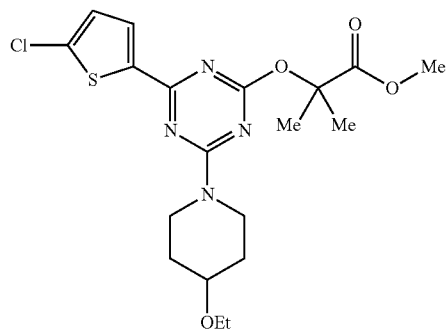 [SMILES: CCOC1CCN(c2nc(OC(C)(C)C(=O)OC)nc(-c3ccc(Cl)s3)n2)CC1]
MS: 441/443 [M+H]+, APCI.
Example 182
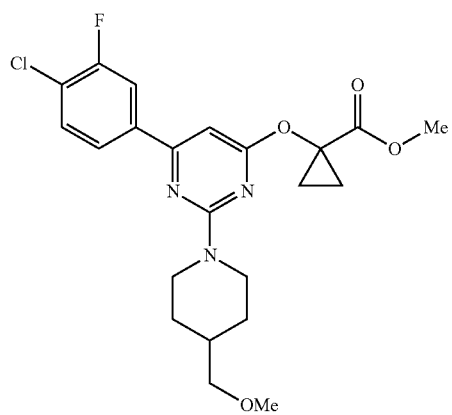 [SMILES: COCC1CCN(c2nc(OC3(C(=O)OC)CC3)cc(-c3ccc(Cl)c(F)c3)n2)CC1]
MS: 450/452 [M+H]+, APCI.
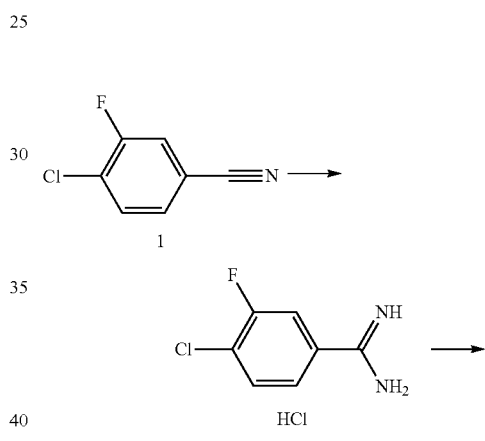
| Example | G | MS (APCI) |
|---|---|---|
| 183 | (2S)-1-methyl-2-(methoxymethyl)pyrrolidin-2-yl | 438/440 [M + H]+ |
| 184 | 1-methyl-4-(methoxymethyl)piperidin-4-yl | 452/454 [M + H]+ |
-continued
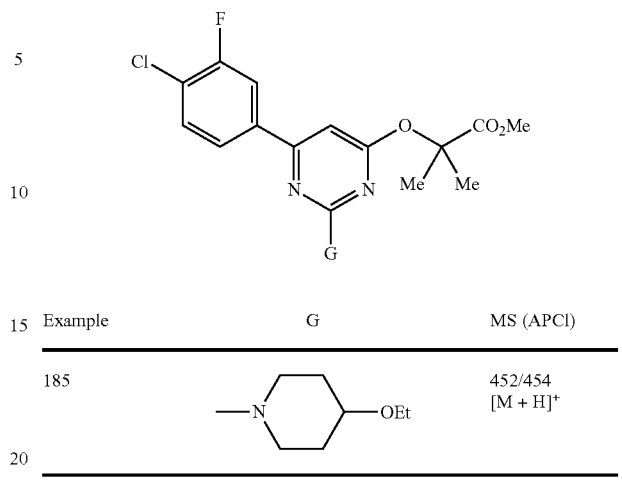
| Example | G | MS (APCI) |
|---|---|---|
| 185 | 1-methyl-4-ethoxypiperidin-4-yl | 452/454 [M + H]+ |
Example 186
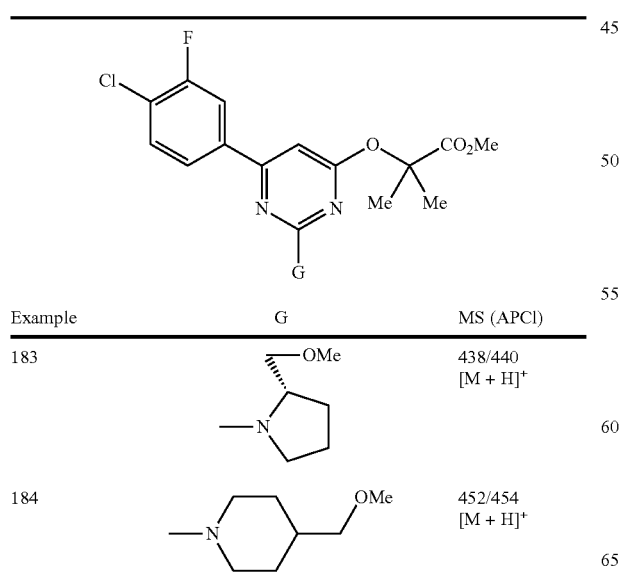

-continued

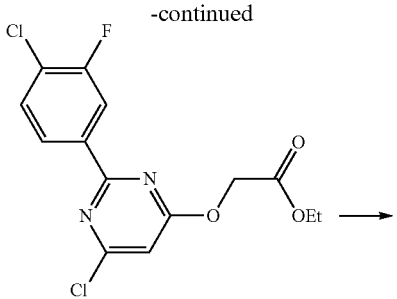

5

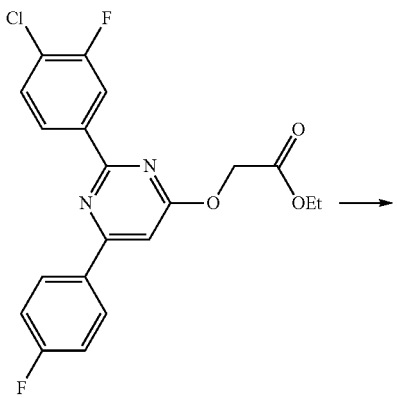

6

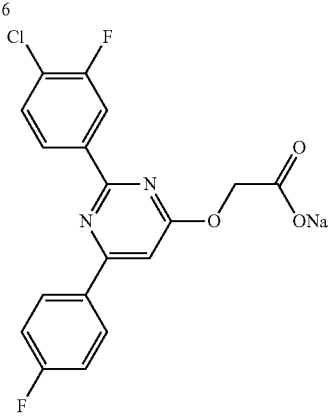

7

To a suspension of ammonium chloride (15.0 g, 280 mmol) in toluene (103 mL) was added dropwise trimethylalminum (2.0 M solution in toluene; 127 ml, 255 mmol) at 0° C. under argon atmosphere and the mixture was stirred at room temperature for 2 hours. Compound 1 (19.8 g, 127 mmol) was added thereto and the mixture was stirred at 80° C. overnight. After cooling, the reaction mixture was slowly poured into a slurry of silica gel and water in chloroform. The mixture was stirred for 30 minutes, filtered, and concentrated under reduced pressure. The residue was triturated with ethyl acetate to give Compound 2 (18.9 g, 71%) as a solid.

MS: 173/175 [M+H]$^+$, APCI.

A solution of sodium ethoxide was prepared by dissolving sodium (5.87 g, 256 mmol) in absolute EtOH (170 mL). Compound 2 (17.8 g, 85.3 mmol) and diethyl malonate (16.4 g, 102 mmol) were added thereto at 0° C. The mixture was refluxed for 3 hours. After cooling, the reaction mixture was concentrated under reduced pressure. The residue was dissolved in water and acidified with 36% aqueous hydrochloric acid. The precipitate was collected by filtration to give Compound 3 (20.0 g, 97%) as a solid.

MS: 241/243 [M+H]$^+$, APCI.

A mixture of Compound 3 (10.0 g, 41.6 mmol), phosphoryl chloride (39 mL) and N,N-diethylaniline (13 mL) was refluxed for 22 hours. The reaction mixture was concentrated under reduced pressure. The residue was poured into ice-water, which was extracted with ethyl acetate. The organic layer was washed with water and brine, dried over anhydrous sodium sulfate, and concentrated under reduced pressure. The residue was purified by silica gel column chromatography (hexane:ethyl acetate=50:1) to give Compound 4 (11.2 g, 97%) as a solid.

1H NMR (500 MHz, DMSO-d6): δ 7.82 (1H, t, J=8.4 Hz), 8.06 (1H, s), 8.14-8.19 (2H, m).

To a solution of Compound 4 (6.00 g, 21.6 mmol) and ethyl glycolate (2.48 g, 23.8 mmol) in THF (60.0 mL) was added sodium hydride (60%, 951 mg, 23.8 mol) at −78° C. and the mixture was stirred at room temperature overnight. The reaction mixture was quenched with 1 M aqueous citric acid and extracted with ethyl acetate. The organic layer was washed with water, filtered through Chem Elut® (Varian Inc.), and concentrated under reduced pressure. The residue was purified by silica gel column chromatography (hexane:ethyl acetate=15:1) to give Compound 5 (6.37 g, 85%) as a solid.

MS: 345/347 [M+H]$^+$, APCI.

A suspension of Compound 5 (42.0 mg, 121 μmol), 4-fluorophenylboronic acid (25.5 mg, 183 μmol), dichlorobis(triphenylphosphine)palladium (8.72 mg, 12.2 μmol) and 2 M aqueous sodium carbonate (122 μL, 243 μmol) in 1,2-dimethoxyethane (1.22 mL) was refluxed for 2 hours under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane:ethyl acetate=93:7→17:3) to give Compound 6 (34.5 mg, 70%) as a solid.

MS: 405/407 [M+H]$^+$, APCI.

To a solution of Compound 6 (32.2 mg, 79.5 μmol) in EtOH (1.00 mL) and THF (1.00 mL) was added 2 M aqueous sodium hydroxide (39.8 μL, 79.5 μmol) and the mixture was stirred at room temperature overnight. The reaction mixture was concentrated under reduced pressure. The residue was triturated with diethyl ether to give Compound 7 (31.1 mg, 98%) as a solid.

MS: 375/377 [M−Na]−, ESI.

Example 187

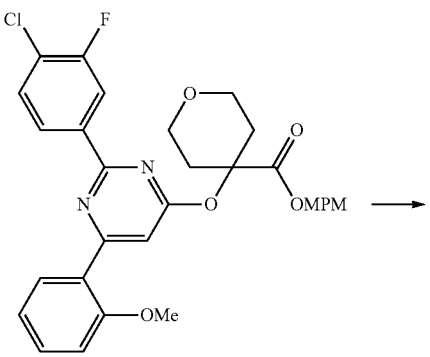

1

-continued

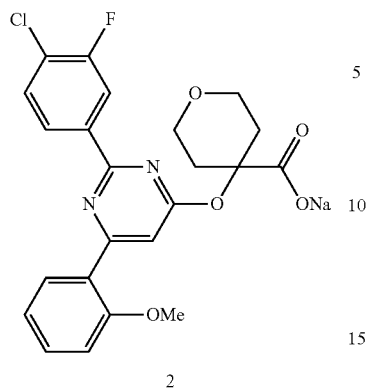

To a mixture of Compound 1 (91 mg, 157 μmol) and 1,3-dimethoxybenzene (205 μL, 1.57 mmol) was added trifluoroacetic acid (1.6 mL) at 0° C. and the reaction mixture was stirred at room temperature for 3 hours. The volatile was removed under reduced pressure. The residue was purified by silica gel column chromatography (chloroform→chloroform:methanol=10:1) to give the free carboxylic acid (72 mg, 157 μmol). The free carboxylic acid was dissolved in THF (2 mL) and 2 M NaOH (77 μL, 154 μmol) was added thereto. The volatile was removed under reduced pressure and the residue was triturated with hexane/diethylether to give Compound 2 (66 mg, 88%) as a powder.

Compound 2: MS: 457/459 [M-Na]−, ESI.

Example 188

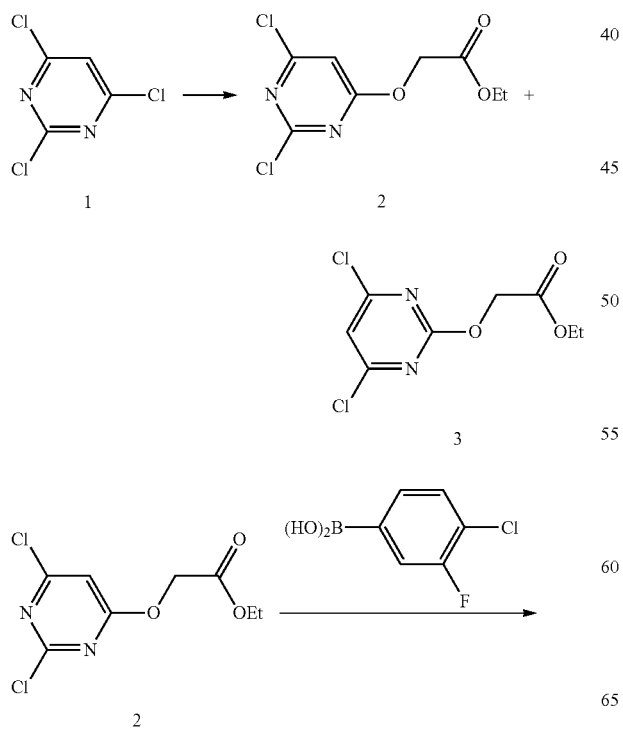

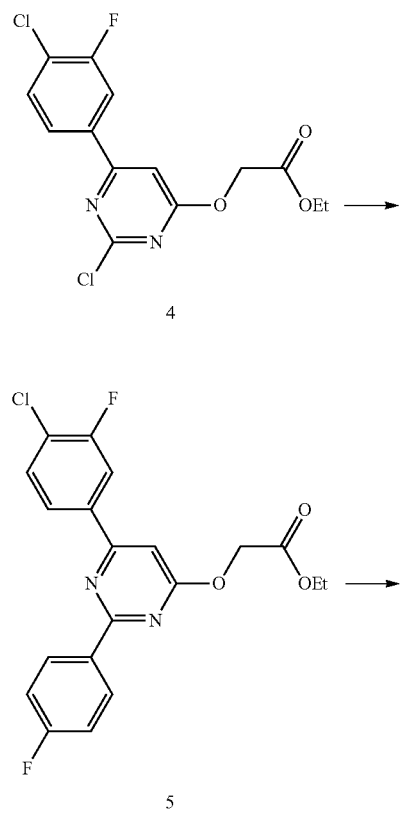

Compounds 2 and 3 were prepared by reacting and treating in the same manner as in Example 186 using Compound 1.

Compound 2: MS: 251/253 [M+H]+, APCI.

Compound 3: MS: 251/253 [M+H]+, APCI.

Compound 4 was prepared by reacting and treating in the same manner as in Example 186 using Compound 2.

Compound 4: MS: 345/347 [M+H]+, APCI.

Compound 5 was prepared by reacting and treating in the same manner as in Example 186 using Compound 4.

Compound 5: MS: 405/407 [M+H]+, APCI.

Compound 6 was prepared by reacting and treating in the same manner as in Example 186 using Compound 5.

Compound 6: MS: 375/377 [M-Na]−, ESI.

Example 189

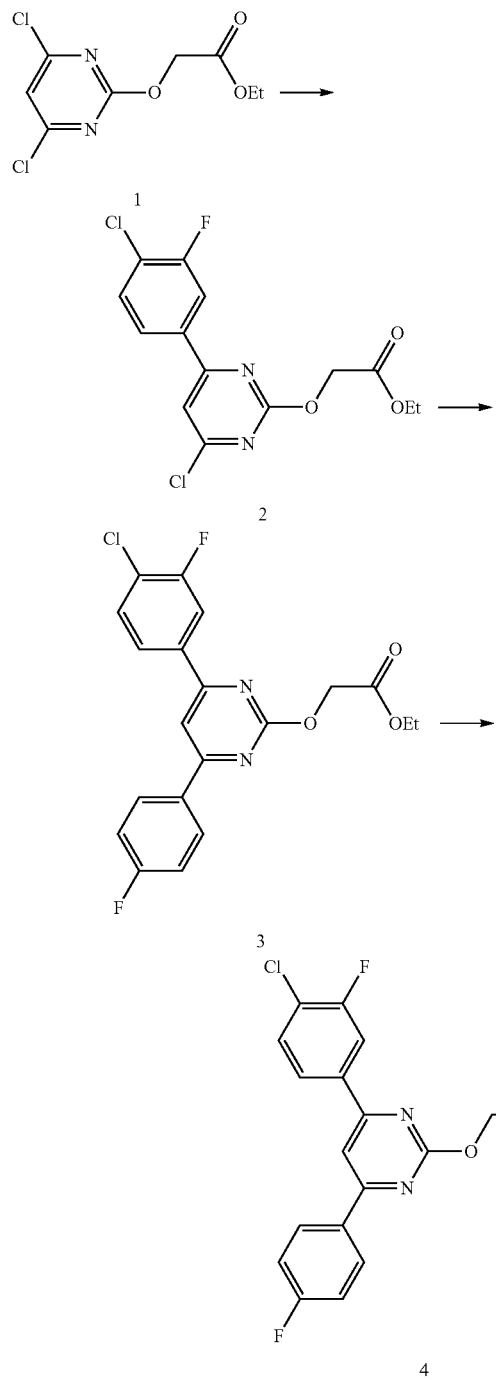

Compound 2 was prepared by reacting and treating in the same manner as in Example 186 using Compound 1.
Compound 2: MS: 345/347 [M+H]+, APCI.
Compound 3 was prepared by reacting and treating in the same manner as in Example 186 using Compound 2.
Compound 3: MS: 405/407 [M+H]+, APCI.
Compound 4 was prepared by reacting and treating in the same manner as in Example 186 using Compound 3
Compound 4: MS: 375/377 [M-Na]−, ESI.

Example 190

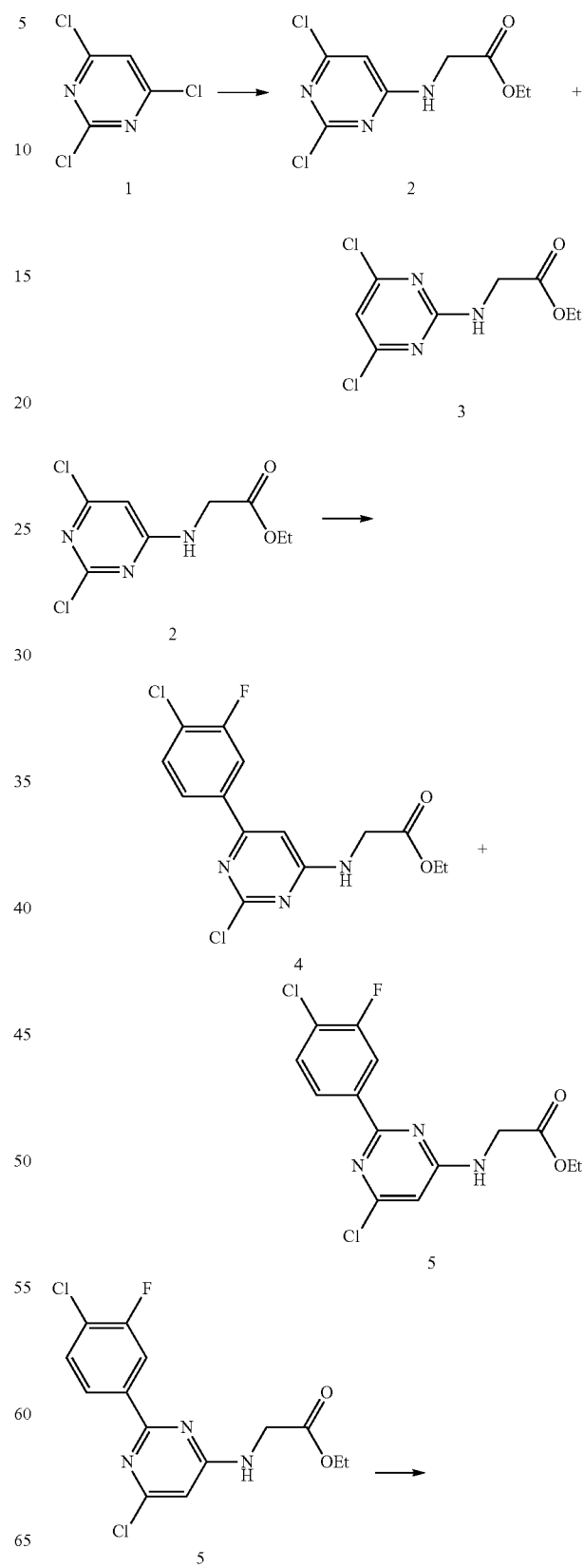

-continued

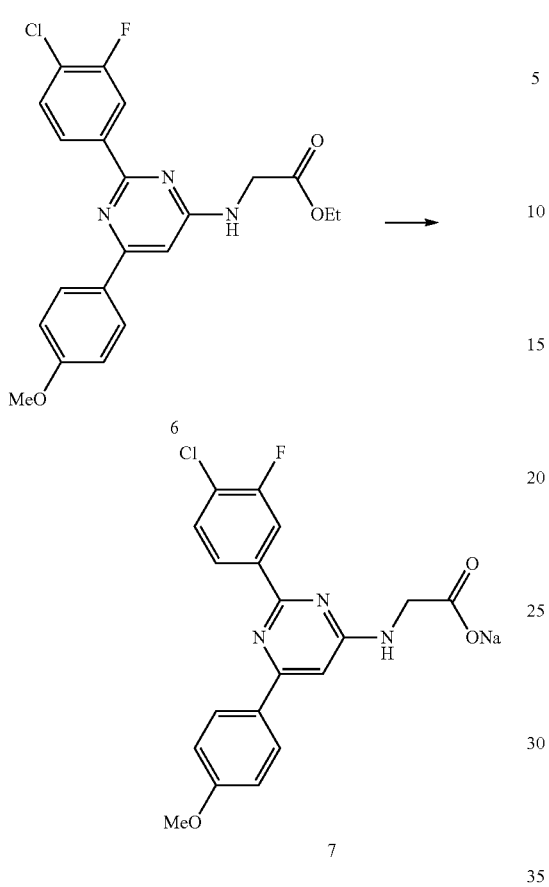

To a solution of Compound 1 (5.00 g, 27.3 mmol) and glycine ethyl ester hydrochloride (3.80 g, 27.3 mmol) in THF (50.0 mL) was added N,N-diisopropylethylamine (10.0 ml, 57.2 mmol) at 0° C. and the mixture was stirred at room temperature overnight. Glycine ethyl ester hydrochloride (761 mg, 5.45 mmol) and N,N-diisopropylethylamine (1.91 ml, 10.9 mmol) were added thereto at 0° C. and the mixture was stirred at room temperature for 5 hours. The reaction mixture was partitioned between water and ethyl acetate. The organic layer was washed with brine, filtered through Chem Elute® (Varian Inc.), and concentrated under reduced pressure. The residue was purified by silica gel column chromatography (hexane:ethyl acetate=4:1) to give Compound 2 (3.90 g, 57) as a solid and Compound 3 (26.6 mg, 39%) as a solid.

Compound 2: MS: 250/252 [M+H]+, APCI.

Compound 3: MS: 250/252 [M+H]+, APCI.

Compounds 4 and 5 were prepared by reacting and treating in the same manner as in Example 186 using Compound 2.

Compound 4: MS: 344/346 [M+H]+, APCI.

Compound 5: MS: 344/346 [M+H]+, APCI.

Compound 6 was prepared by reacting and treating in the same manner as in Example 186 using Compound 5.

Compound 6: MS: 416/418 [M+H]+, APCI.

Compound 7 was prepared by reacting and treating in the same manner as in Example 186 using Compound 6.

Compound 7: MS: 386/388 [M-Na]−, ESI.

Example 191

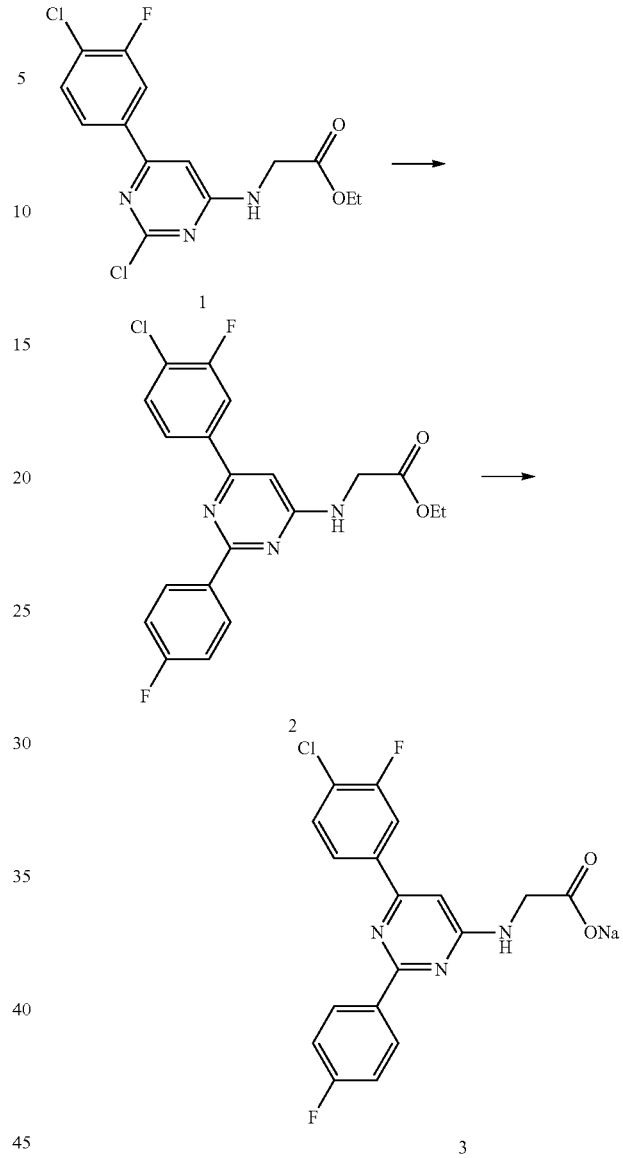

Compound 2 was prepared by reacting and treating in the same manner as in Example 186 using Compound 1.

Compound 2: MS: 404/406 [M+H]+, APCI.

Compound 3 was prepared by reacting and treating in the same manner as in Example 186 using Compound 2.

Compound 3: MS: 374/376 [M-Na]−, ESI.

Example 192

-continued

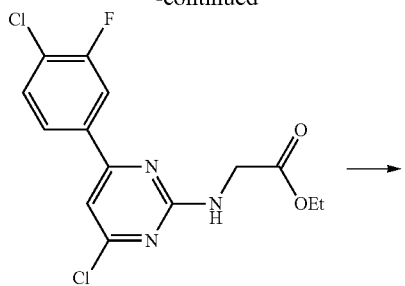

2

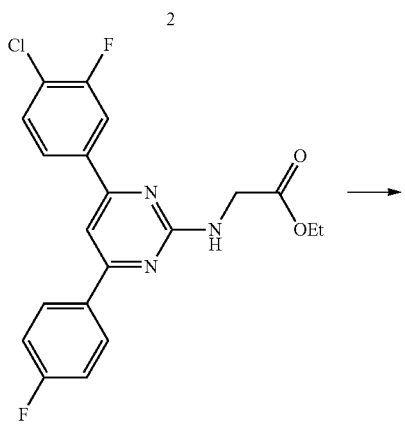

3

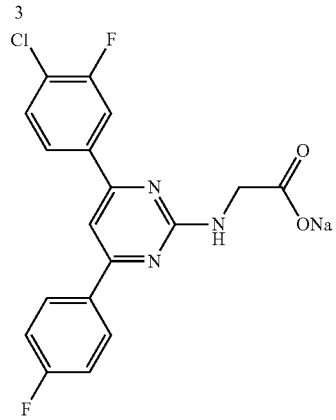

4

Compound 2 was prepared by reacting and treating in the same manner as in Example 186 using Compound 1.
Compound 2: MS: 344/346 [M+H]+, APCI.
Compound 3 was prepared by reacting and treating in the same manner as in Example 186 using Compound 2.
Compound 3: MS: 404/406 [M+H]+, APCI.
Compound 4 was prepared by reacting and treating in the same manner as in Example 186 using Compound 3.
Compound 4: MS: 374/376 [M−Na]−, ESI.

Example 193

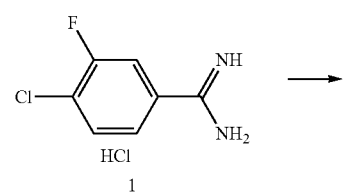

1

-continued

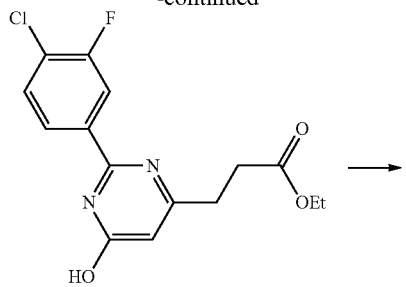

2

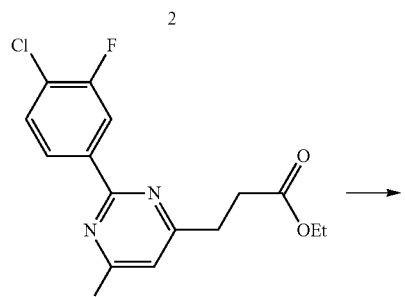

3

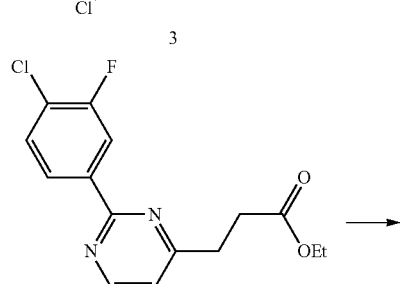

4

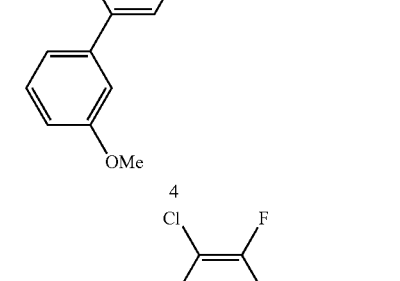

5

Compound 2 was prepared by reacting and treating in the same manner as in Example 186 using Compound 1.
Compound 2: MS: 325/327 [M+H]+, APCI.
Compound 3 was prepared by reacting and treating in the same manner as in Example 186 using Compound 2.
Compound 3: MS: 343/345 [M+H]+, APCI.
Compound 4 was prepared by reacting and treating in the same manner as in Example 186 using Compound 3.
Compound 4: MS: 415/417 [M+H]+, APCI.

Compound 5 was prepared by reacting and treating in the same manner as in Example 186 using Compound 4.

Compound 5: MS: 385/387 [M-Na]−, ESI.

Example 194

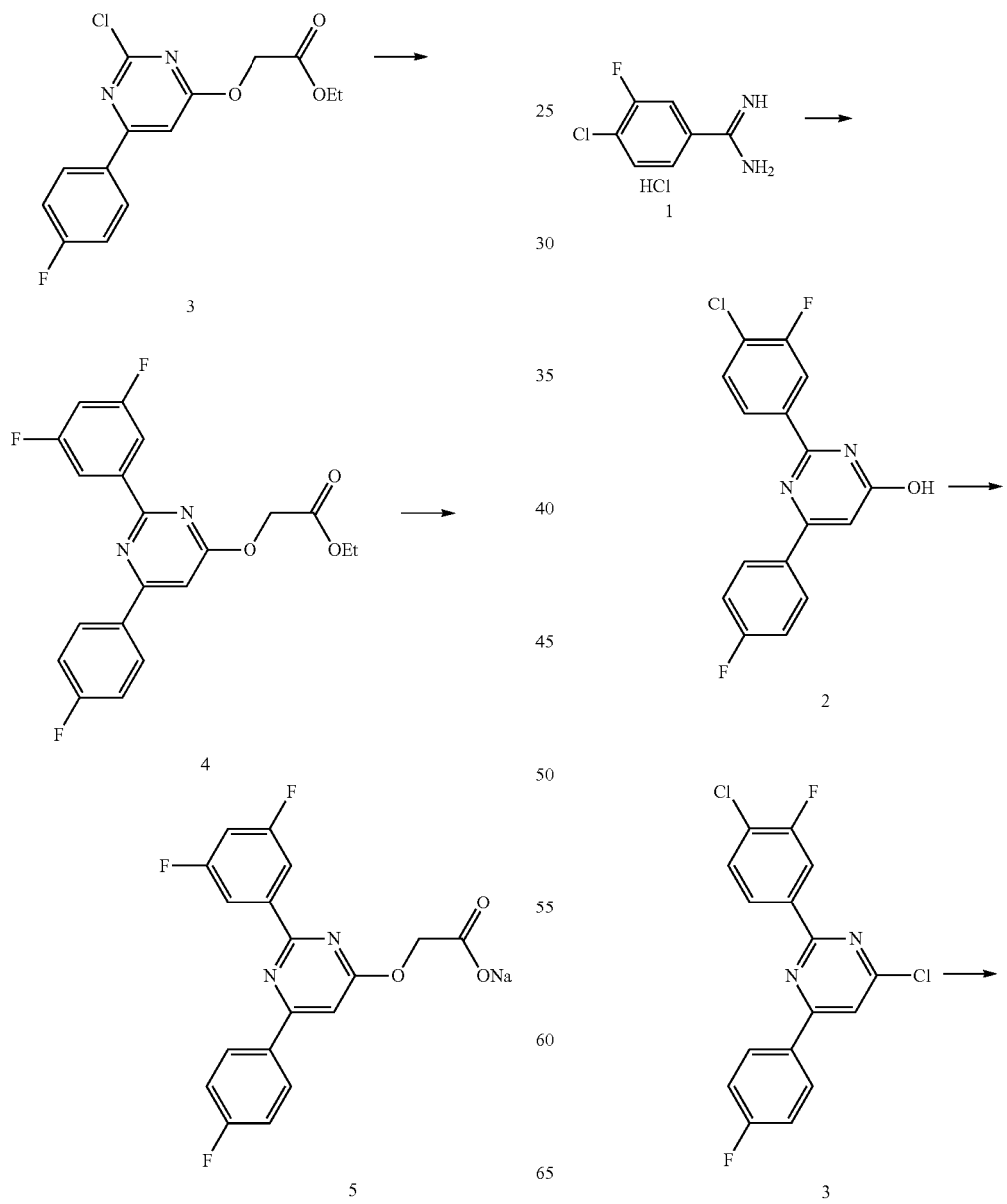

Compound 2 was prepared by reacting and treating in the same manner as in Example 186 using Compound 1.

Compound 2: MS: 243/245 [M+H]+, APCI.

Compound 3 was prepared by reacting and treating in the same manner as in Example 186 using Compound 2.

Compound 3: MS: 311/313 [M+H]+, APCI.

Compound 4 was prepared by reacting and treating in the same manner as in Example 186 using Compound 3.

Compound 4: MS: 389 [M+H]+, APCI.

Compound 5 was prepared by reacting and treating in the same manner as in Example 186 using Compound 4.

Compound 5: MS: 359 [M-Na]−, ESI.

Example 195

-continued

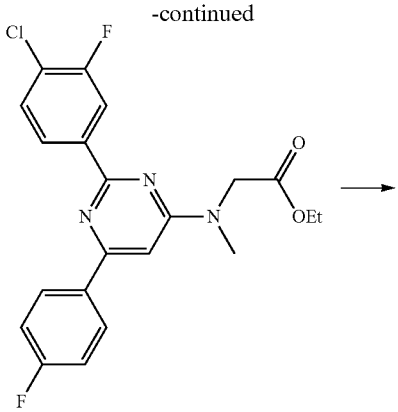

4

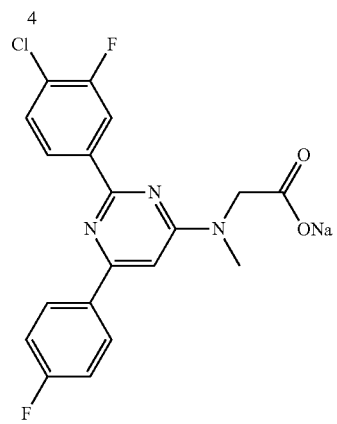

5

Compound 2 was prepared by reacting and treating in the same manner as in Example 186 using Compound 1.
Compound 2: MS: 319/321 [M+H]+, APCI
Compound 3 was prepared by reacting and treating in the same manner as in Example 186 using Compound 2.
Compound 3: MS: 337/339 [M+H]+, APCI.
Compound 4 was prepared by reacting and treating in the same manner as in Example 186 using Compound 3.
Compound 4: MS: 418/420 [M+H]+, APCI.
Compound 5 was prepared by reacting and treating in the same manner as in Example 186 using Compound 4.
Compound 5: MS: 388/390 [M-Na]−, ESI.

Example 196

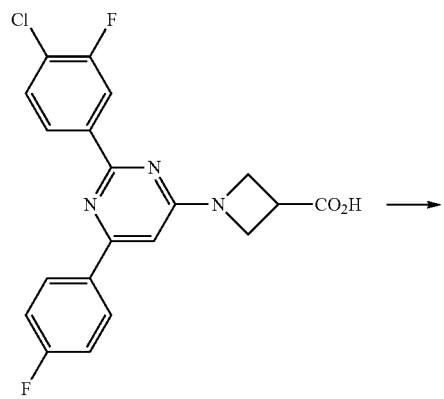

1

-continued

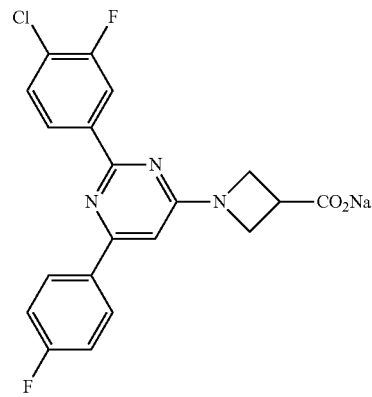

2

Compound 1 (74.7 mg, 186 μmol) was suspended in acetone and 2 M aqueous sodium hydroxide (91.1 μl, 182 μmol) was added thereto. The mixture was concentrated under reduced pressure. The residue was triturated with diethyl ether to give Compound 2 (73.7 mg, 96%) as a solid.
MS: 400/402 [M-Na]−, ESI.

Example 197

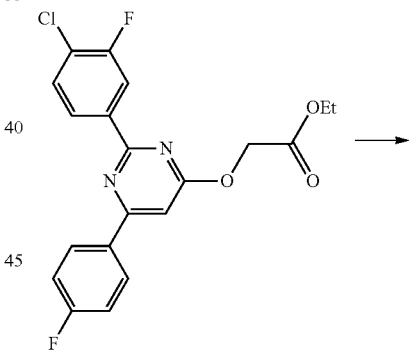

1

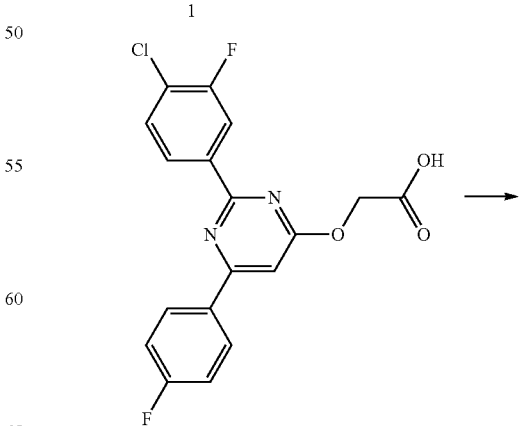

2

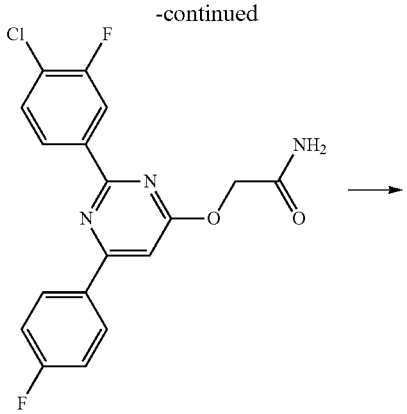

3

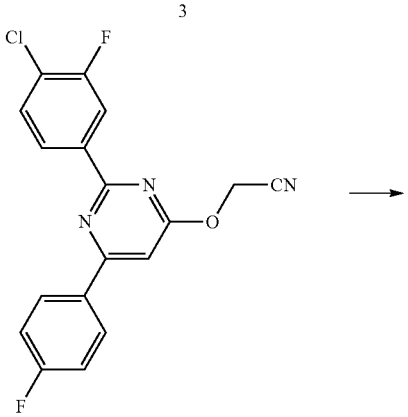

4

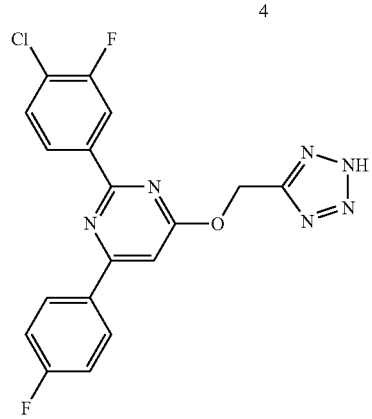

5

To a solution of Compound 1 (1.03 g, 2.56 mmol) in EtOH (5.11 mL) and THF (5.11 mL) was added 2 M aqueous sodium hydroxide (1.53 mL, 3.07 mmol) and the mixture was stirred at room temperature overnight. The reaction mixture was concentrated under reduced pressure. The residue was acidified with 1 M aqueous citric acid and extracted with ethyl acetate. The organic layer was washed with water and brine, dried over anhydrous sodium sulfate, and concentrated under reduced pressure. The residue was triturated with diisopropyl ether to give Compound 2 (733 mg, 76%) as a solid.

MS: 375/377 [M−H]−, ESI.

To a suspension of Compound 2 (300 mg, 796 μmol) and DMF (6.2 μL, 80 μmol) in chloroform (6.00 mL) was added oxalyl chloride (139 μL, 1.59 mmol) and the mixture was stirred at room temperature for 1 hour. The reaction mixture was concentrated under reduced pressure. The residue was suspended in ethyl acetate (6.0 ml) and poured into saturated aqueous ammonium hydroxide (6.0 mL) at 0° C. The mixture was stirred at room temperature for 1 hour. The organic layer was separated, washed with water and brine, dried over sodium sulfate, and concentrated under reduced pressure. The residue was triturated with diethyl ether to give Compound 3 (276 mg, 92%) as a solid.

MS: 376/378 [M+H]+, APCI.

To a suspension of Compound 3 (250 mg, 665 μmol) and pyridine (323 μL, 3.99 mmol) in chloroform (5.00 mL) was added trifluoroacetic anhydride (419 μL, 2.00 mmol) at 0° C. and the mixture was stirred at room temperature for 1.5 hour. The reaction mixture was diluted with chloroform, washed with water, and concentrated under reduced pressure. The residue was purified by silica gel column chromatography (hexane:ethyl acetate=9:1→7:3) to give Compound 4 (179 mg, 75%) as a solid.

MS: 358/360 [M+H]+, APCI.

A mixture of compound 4 (100 mg, 280 μmol), azidotributyltin (191 mg, 559 μmol) and toluene (2.80 mL) was refluxed for 8 hours. Then 10% aqueous hydrochloric acid was added thereto and the mixture was refluxed for 1 hour. After cooling, the precipitate was collected by filtration to give Compound 5 (76.5 mg, 68%) as a solid.

MS: 399/401 [M−H]−, ESI.

Example 198

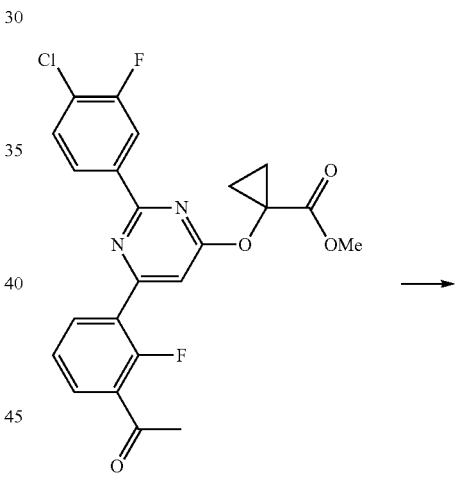

1

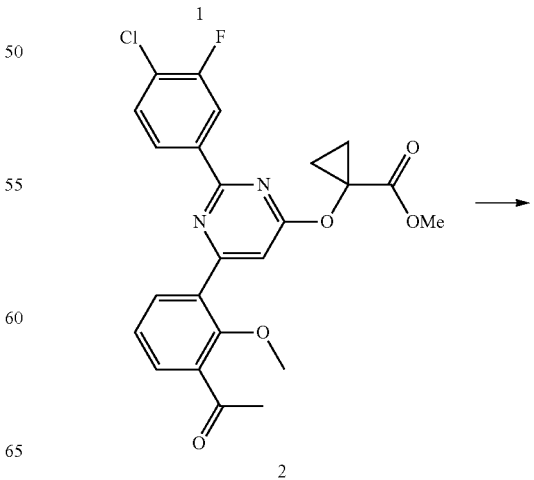

2

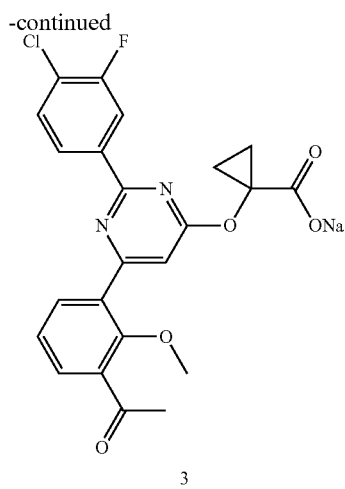

Compound 2 was prepared by reacting and treating in the same manner as in Example 186 using Compound 1.

Compound 2: MS: 471/473 [M+H]+, APCI.

Compound 3 was prepared by reacting and treating in the same manner as in Example 186 using Compound 2.

Compound 3: MS: 455/457 [M-Na]−, ESI.

Example 199

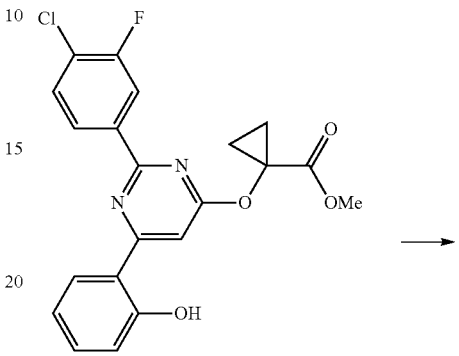

To a solution of Compound 1 (61.1 mg, 133 μmol) in THF (1 mL) and MeOH (1 mL) was added 2 M aqueous sodium hydroxide (333 μL, 666 μmol) and the mixture was stirred at room temperature overnight. The volatiles were removed under reduced pressure. The residue was acidified with 1 M aqueous citric acid, extracted with ethyl acetate. The organic layer was dried, and concentrated under reduced pressure. The residue was purified by silica gel column chromatography (hexane:ethyl acetate=1:1→0:1), and dissolved in ethyl acetate. 2 M aqueous sodium hydroxide (44 μl, 88 μmol) was added thereto, and concentrated under reduced pressure. The residue was triturated with ethyl ether to give Compound 2 (40 mg, 63%) as a solid.

MS: 455/457 [M-Na]−, ESI.

Example 200

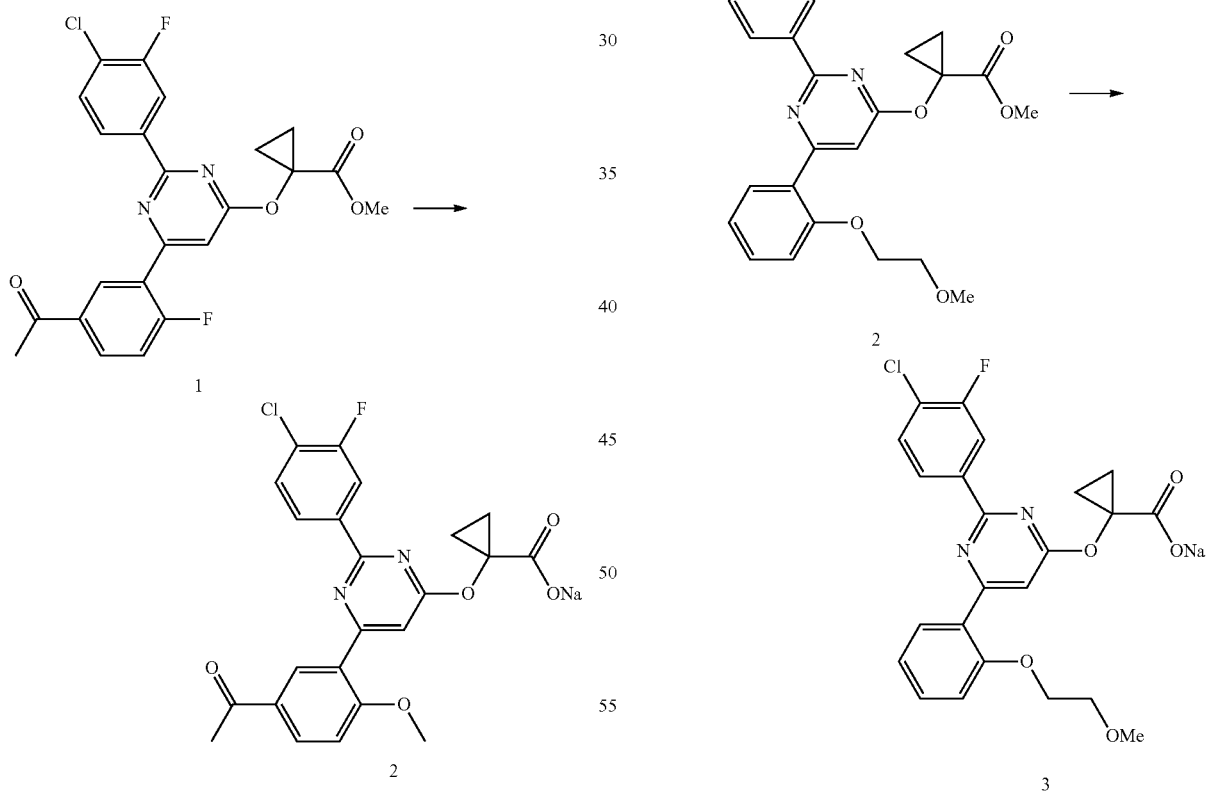

A suspension of Compound 1 (25 mg, 60 μmol), 2-bromoethyl methyl ether (8.5 μL, 90 μmol), and potassium carbonate (25 mg, 181 μmol) in DMA (2 mL) was stirred at 60° C. for 15 hours. After cooling, water (3 ml) was added thereto. The resulting precipitate was collected by filtration, rinsed with water, and dried to give Compound 2 (25 mg, 87%) as a solid.

MS: 473/475 [M+H]+, APCI.

Compound 3 was prepared by reacting and treating in the same manner as in Example 186 using Compound 2.

Compound 3: MS: 457/459 [M-Na]−, ESI.

Example 201

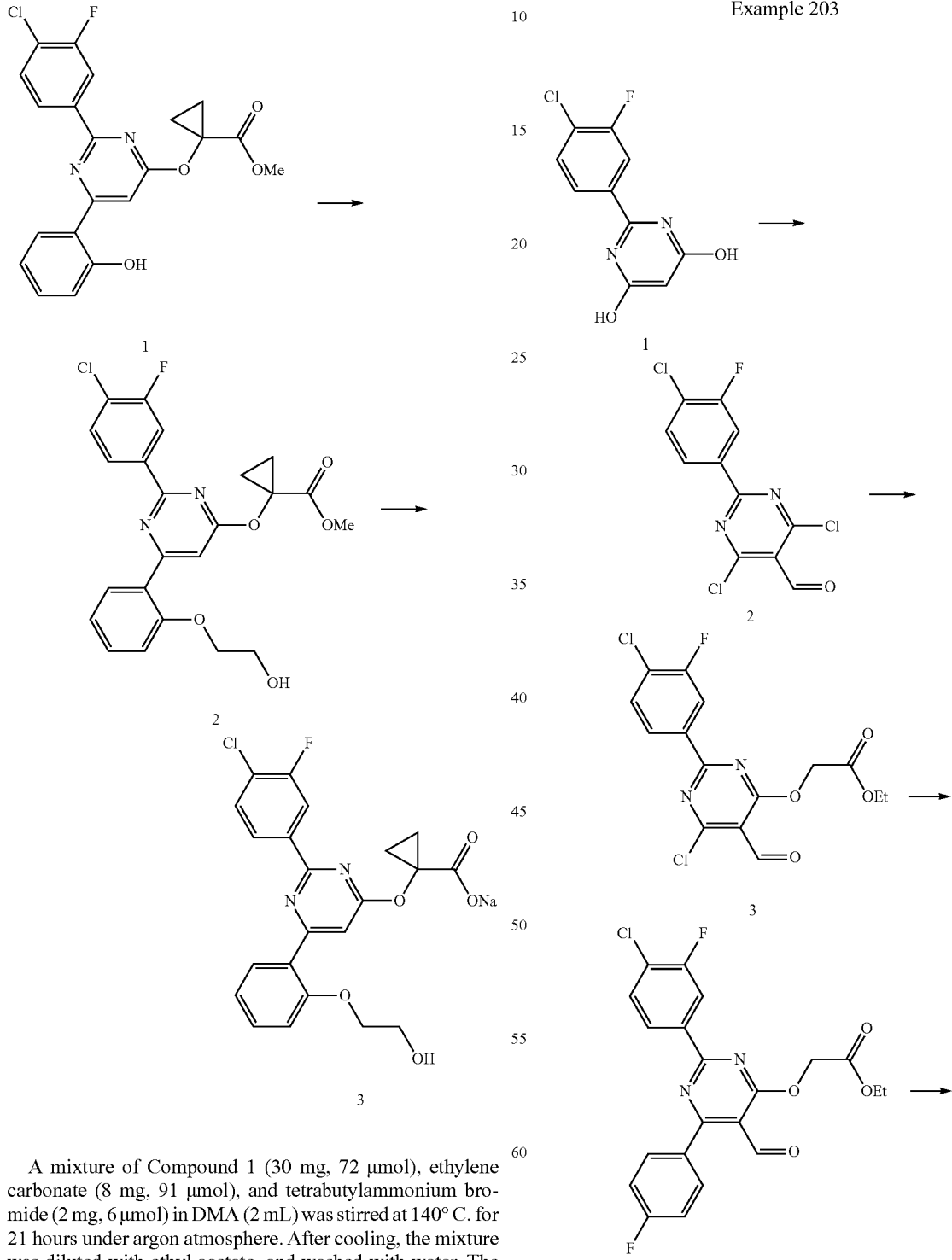

A mixture of Compound 1 (30 mg, 72 μmol), ethylene carbonate (8 mg, 91 μmol), and tetrabutylammonium bromide (2 mg, 6 μmol) in DMA (2 mL) was stirred at 140° C. for 21 hours under argon atmosphere. After cooling, the mixture was diluted with ethyl acetate, and washed with water. The organic layer was dried over anhydrous sodium sulfate, and concentrated under reduced pressure. The residue was purified by silica gel column chromatography (hexane:ethyl acetate=9:1→1:1) to give Compound 2 (10 mg, 31%) as a solid.

MS: 459/461 [M+H]+, APCI.

Compound 3 was prepared by reacting and treating in the same manner as in Example 186 using Compound 2.

Compound 3: MS: 443/445 [M-Na]−, ESI.

Example 203

-continued

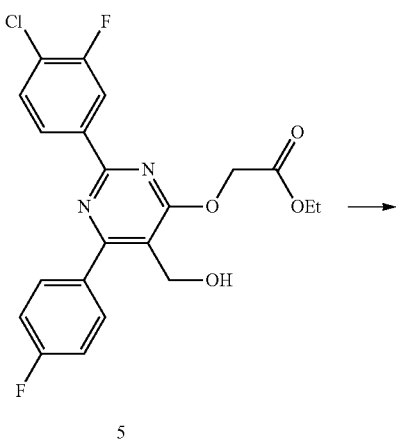

5

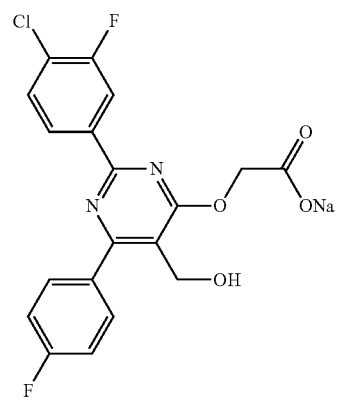

6

A mixture of Compound 1 (1.00 g, 4.16 mmol), phosphoryl chloride (5.25 g, 56.3 mmol), and DMF (640 μL, 8.32 μmol) was refluxed for 39 hours. After cooling, the volatiles were removed under reduced pressure. The residue was dissolved in toluene, concentrated under reduced pressure, then re-dissolved in toluene, treated with activated charcoal, and filtered through Celite® pad. The filtrate was concentrated under reduced pressure. The residue was purified by silica gel column chromatography (hexane→hexane:ethyl acetate=49:1) to give Compound 2 (284 mg, 22%) as a solid.

$^1$H NMR (500 MHz, DMSO-d6): 7.86 (1H, dd, J=7.9, 8.3 Hz), 8.06 (1H, dd, J=1.9, 8.3 Hz), 8.18 (1H, dd, J=1.9, 10.4 Hz), 10.2 (1H, s).

Compound 3 was prepared by reacting and treating in the same manner as in Example 186 using Compound 2.

Compound 3: MS: 373/375 [M+H]$^+$, APCI.

Compound 4 was prepared by reacting and treating in the same manner as in Example 186 using Compound 3.

Compound 4: $^1$H NMR (500 MHz, DMSO-d6): 1.22 (3H, t, J=7.1 Hz), 4.21 (2H, q, J=7.1 Hz), 5.25 (2H, s), 7.41 (2H, dd, J=8.8, 8.8 Hz), 7.82-7.86 (3H, m), 8.24-8.29 (2H, m), 10.11 (1H, s).

To a solution of Compound 4 (52 mg, 120 μmol) in THF (2 mL) and EtOH (1 mL) was added sodium borohydride (4.6 mg, 120 μmol) at room temperature. The mixture was stirred for 1 day. The mixture was diluted with water, and extracted with ethyl acetate. The organic layer was washed with brine, dried over anhydrous magnesium sulfate, and concentrated under reduced pressure. The residue was purified by silica gel column chromatography (hexane→hexane:ethyl acetate=7:3) to give Compound 5 (38 mg, 73%) as a solid.

MS: 435/437 [M+H]$^+$, APCI.

Compound 6 was prepared by reacting and treating in the same manner as in Example 186 using Compound 5.

Compound 6: MS: 405/407 [M-Na]−, ESI.

Example 204

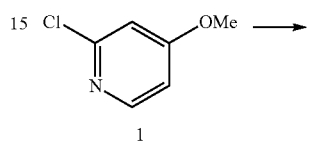

1

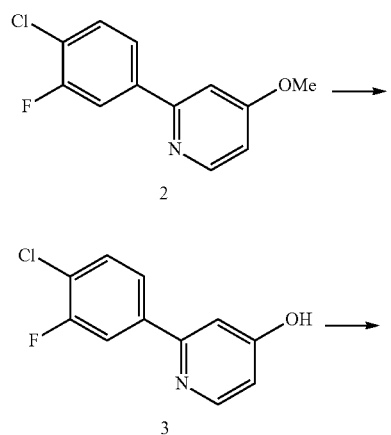

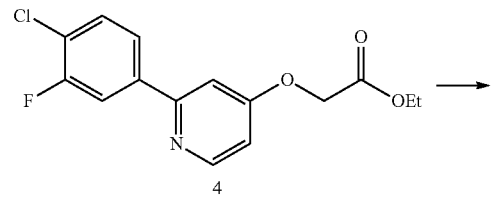

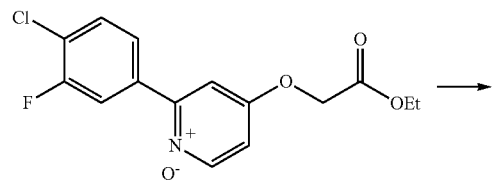

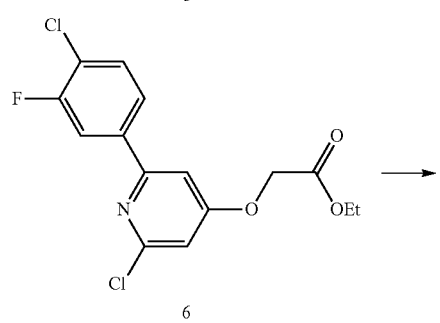

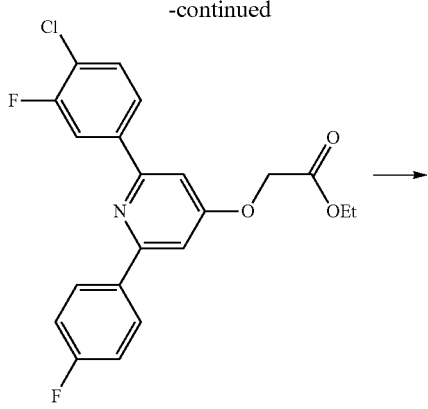

7

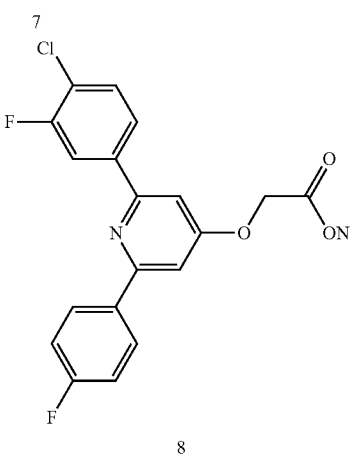

8

Compound 2 was prepared by reacting and treating in the same manner as in Example 186 using Compound 1.

Compound 2: MS: 238/240 [M+H]+, APCI.

A mixture of Compound 2 (1.0 g, 4.2 mmol) and pyridine hydrochloride (2.43 g, 21 mmol) was stirred at 200° C. for 10 minutes. After cooling, the reaction mixture was diluted with ethyl acetate and washed with water, dried over anhydrous magnesium sulfate, and concentrated under reduced pressure. The residue was triturated with diisopropyl ether to give Compound 3 (815 mg, 87%) as a solid.

Compound 3: MS: 222/224 [M−H]−, ESI.

To a solution of Compound 3 (815 mg, 3.7 mmol) in DMF (10.0 mL) was added sodium hydride (60%, 951 mg, 23.8 mol) at 0° C. and the mixture was stirred at 0° C. for 30 minutes. Then ethyl bromoacetate (450 μL, 4.1 μmol) was added thereto at 0° C. and the mixture was stirred at room temperature overnight. The reaction mixture was quenched with ice-water and extracted with diethyl ether. The organic layer was washed with water, dried over anhydrous magnesium sulfate, and concentrated under reduced pressure. The residue was purified by silica gel column chromatography (hexane:ethyl acetate=19:1→3:1) to give Compound 4 (820 mg, 72%) as a solid.

Compound 4: MS: 310/312 [M+H]+, APCI.

To a solution of Compound 4 (2.12 g, 3.7 mmol) in dichloromethane (30.0 mL) was added m-chloro perbenzoic acid (65%, 2.73 g, 10.3 mmol) at 0° C. and the mixture was stirred at room temperature for 6 hours, then stirred at 50° C. for 2 hours. After cooling, the reaction mixture was diluted with ethyl acetate and washed with saturated aqueous sodium bicarbonate, dried over anhydrous magnesium sulfate, and concentrated under reduced pressure. The residue was purified by silica gel column chromatography (chloroform→chloroform:methanol=19:1) to give Compound 5 (1.66 g, 74%) as a solid.

MS: 326/328 [M+H]+, APCI.

To a solution of Compound 5 (1.65 g, 5.1 mmol) in triethylamine (847 μL, 6.1 mmol) was added phosphoryl chloride (0.93 g, 6.1 mmol) at 0° C. and the mixture was stirred at room temperature for 2 hours. The reaction mixture was quenched with saturated aqueous sodium bicarbonate and extracted with ethyl acetate. The organic layer was washed with water, dried over anhydrous magnesium sulfate, and concentrated under reduced pressure. The residue was purified by silica gel column chromatography (hexane→hexane:ethyl acetate=50:50) to give Compound 6 (509 mg, 29%) as a solid.

MS: 344/346 [M+H]+, APCI.

Compound 7 was prepared by reacting and treating in the same manner as in Example 186 using Compound 6.

Compound 7: MS: 404/406 [M+H]+, APCI.

Compound 8 was prepared by reacting and treating in the same manner as in Example 186 using Compound 7.

Compound 8: MS: 374/376 [M−Na]−, ESI.

Example 205

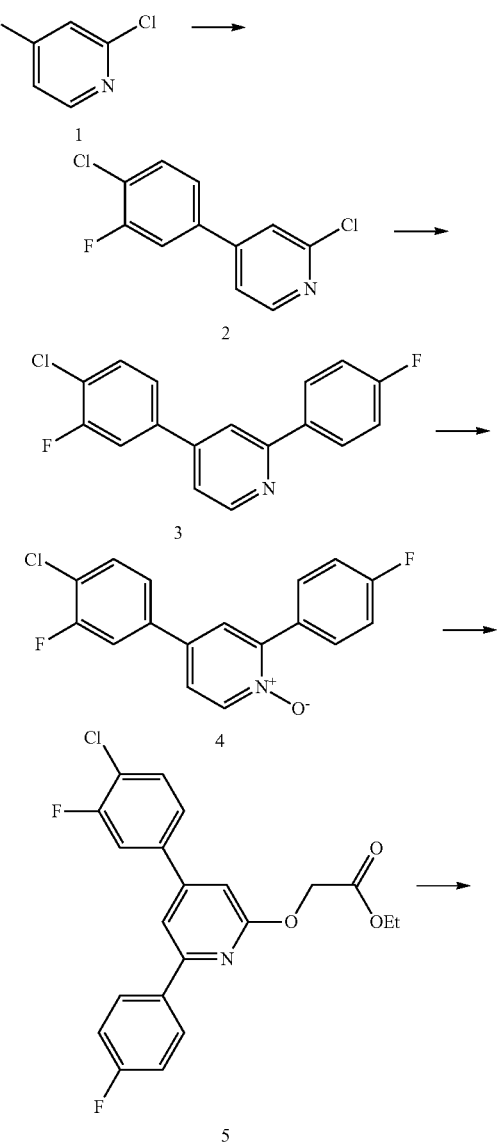

-continued

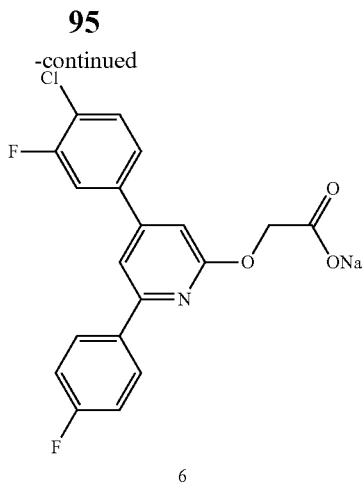
6

Compound 2 was prepared by reacting and treating in the same manner as in Example 186 using Compound 1.

Compound 2: MS: 242/244 [M+H]+, APCI.

Compound 3 was prepared by reacting and treating in the same manner as in Example 186 using Compound 2.

Compound 3: MS: 302/304 [M+H]+, APCI.

Compound 4 was prepared by reacting and treating in the same manner as in Example 204 using Compound 3.

Compound 4: MS: 318/320 [M+H]+, APCI.

To a solution of Compound 4 (200 mg, 629 μmmol) and p-toluene sulfonylchloride (156 mg, 818 μmol) in ethyl glycolate (1.5 mL) was added dropwise triethylamine (175 μL, 1.26 mmol) at 0° C. and the mixture was stirred at room temperature for 18 hours. The reaction mixture was diluted with ethyl acetate and washed with water, dried over anhydrous magnesium sulfate, and concentrated under reduced pressure. The residue was purified by silica gel column chromatography (hexane→hexane:ethyl acetate=80:20) to give Compound 5 (109 mg, 43%) as a solid.

MS: 404/406 [M+H]+, APCI.

Compound 6 was prepared by reacting and treating in the same manner as in Example 186 using Compound 5.

Compound 6: MS: 374/376 [M-Na]−, ESI.

Example 206

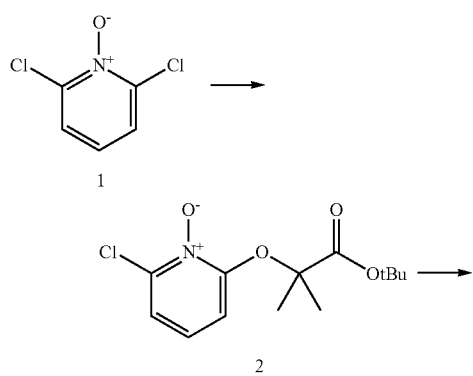

-continued

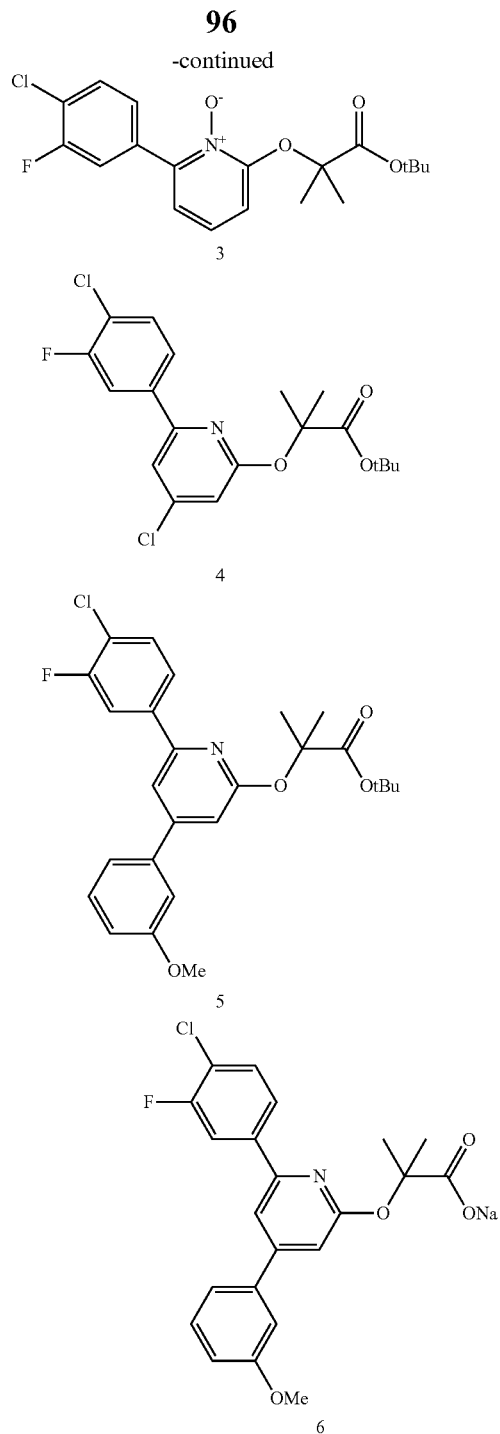

Compound 2 was prepared by reacting and treating in the same manner as in Example 186 using Compound 1.
Compound 2: MS: 288/290 [M+H]+, APCI.

Compound 3 was prepared by reacting and treating in the same manner as in Example 186 using Compound 2.
Compound 3: MS: 382/384 [M+H]+, APCI.

To a solution of Compound 3 (106 mg, 0.28 mmol) in dichloromethane (1 mL) was added triphosgene (55 mg, 0.19 mmol) at −10° C. and the mixture was stirred at the same temperature for 15 minutes. Triethylamine (77 μL, 0.55 mmol) was slowly introduced and the mixture was stirred at −10 to −5° C. for 30 minutes. Water was added to the mixture, which was neutralized with 2 M aqueous sodium hydroxide followed by extraction with chloroform. The organic layer was washed with brine, dried over anhydrous sodium sulfate, and concentrated under reduced pressure. The residue was purified by silica gel column chromatography (hexane→hexane:ethyl acetate=9:1) to give Compound 4 (64 mg, 57%) as a solid.

MS: 400/402 [M+14]+, APCI.

Compound 5 was prepared by reacting and treating in the same manner as in Example 186 using Compound 4.

Compound 5: MS: 472/474 [M+H]+, APCI.

A solution of Compound 5 (163 mg, 0.61 mmol) in trifluoroacetic acid (5 mL) was stirred at 40° C. for 2 hours. Then the mixture was concentrated under reduced pressure. The obtained free acid (121 mg, 0.29 mmol) was treated in the same manner as in Example 206 to give Compound 6 (96 mg, 36% from Compound 5) as a solid.

MS: 414/416 [M-Na]−, ESI.

Example 207

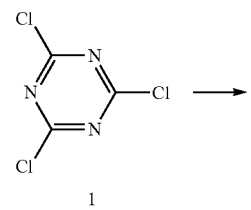
1

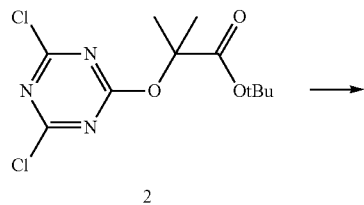
2

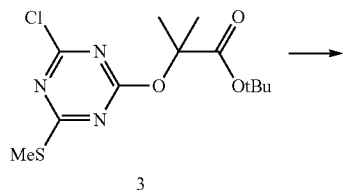
3

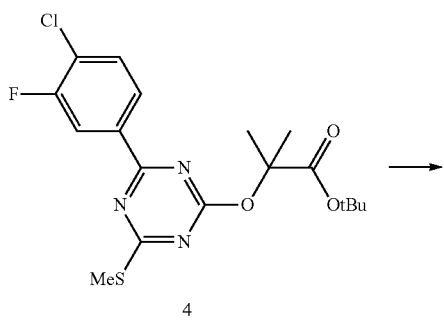
4

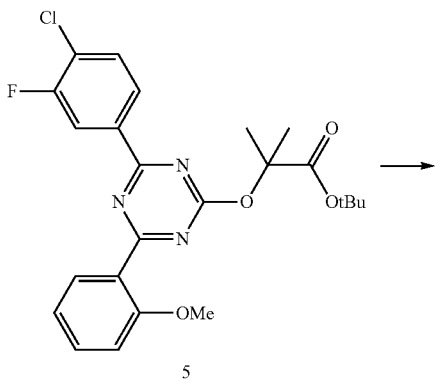
5

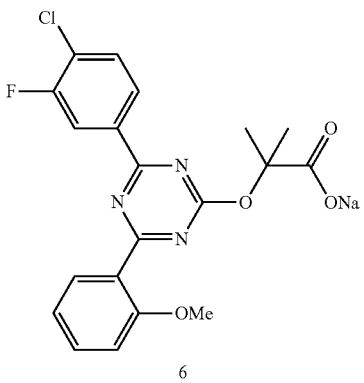
6

Compound 2 was prepared by reacting and treating in the same manner as in Example 186 using Compound 1.

Compound 2: $^1$H NMR (400 MHz, CDCl$_3$): δ 1.44 (9H, s), 1.72 (6H, s).

A solution of Compound 2 (154 mg, 0.50 mmol), sodium thiomethoxide (38.5 mg, 0.55 mmol) and H$_2$O (9 μL, 0.5 mmol) in ethyl acetate (1 mL) was stirred at room temperature for 4.5 hours. The reaction mixture was filtered and concentrated under reduced pressure. The residue was purified by silica gel column chromatography (hexane→hexane:ethyl acetate=19:1) to give Compound 3 (65.8 mg, 41%) as a solid.

Compound 3: MS: 320/322 [M+H]+, APCI.

Compound 4 was prepared by reacting and treating in the same manner as in Example 186 using Compound 3.

Compound 4: MS: 414/416 [M+H]+, APCI.

A mixture of Compound 4 (38.8 mg, 94 μmol), 2-methoxyphenylboronic acid (16 mg, 103 μmol), dichlorobis(triphenylphosphine)palladium (9.8 mg, 14 μmol), copper(I) thiophene-2-carboxylate (54 mg, 282 μmol) and THF (1 mL) was stirred at 50° C. for 2.5 hours under argon atmosphere. After cooling, the reaction mixture was diluted with ethyl acetate, filtered through Celite® pad, and concentrated under reduced pressure. The residue was purified by silica gel column chromatography (hexane→hexane:ethyl acetate=9:1) to give Compound 5 (31 mg, 70%) as a solid.

MS: 474/476 [M+H]+, APCI.

Compound 6 was prepared by reacting and treating in the same manner as in Example 206 using Compound 5.

Compound 6: MS: 416/418 [M-Na]−, ESI.

Example 208

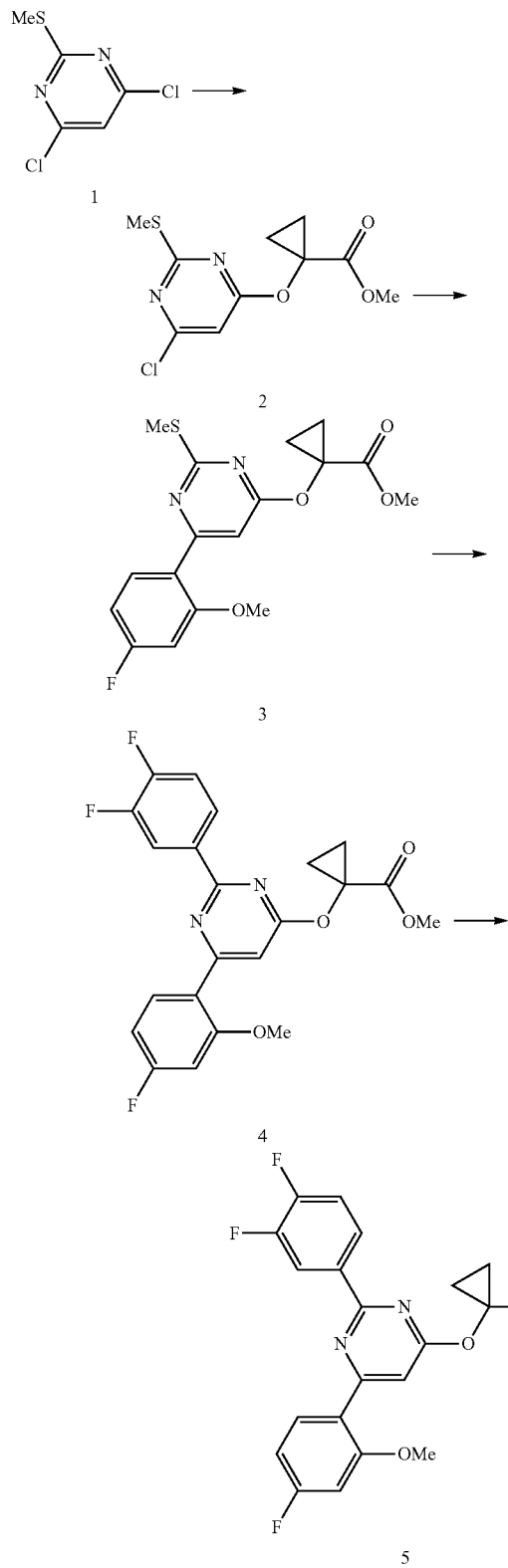

To a solution of Compound 1 (5.00 g, 25.6 mmol) and methyl 1-hydroxy-1-cyclopropane carboxylate (3.97 g, 30.8 mmol) in THF (100 mL) was added sodium hydride (60%, 1.23 g, 30.8 mol) at −78° C. and the mixture was stirred at room temperature for 3 hours. The reaction mixture was quenched with 1 M aqueous citric acid and extracted with ethyl acetate. The organic layer was washed with water and brine, dried over anhydrous sodium sulfate, and concentrated under reduced pressure. The residue was purified by silica gel column chromatography (hexane:ethyl acetate=15:1) to give Compound 2 (6.91 g, 98%) as a solid.

MS: 275/277 [M+H]$^+$, APCI.

Compound 3 was prepared by reacting and treating in the same manner as in Example 186 using Compound 2.

Compound 3: MS: 365 [M+H]$^+$, APCI.

A mixture of Compound 3 (150 mg, 412 μmol), 3,4-difluorophenylboronic acid (195 mg, 1.23 mmol), tetrakis(triphenylphosphine)palladium(0) (48 mg, 41 μmol), copper(I) thiophene-2-carboxylate (238 mg, 1.23 mmol) and THF (5 mL) was refluxed for 1.5 hours under argon atmosphere. After cooling, the reaction mixture was diluted with saturated aqueous ammonium hydroxide, extracted with ethyl acetate. The organic layer was washed with water and brine, dried over sodium sulfate, and concentrated under reduced pressure. The residue was purified by silica gel column chromatography (hexane:ethyl acetate=10:1) to give Compound 4 (167 mg, 94%) as a powder.

Compound 4: MS: 431 [M+H]$^+$, APCI.

Compound 5 was prepared by reacting and treating in the same manner as in Example 186 using Compound 4.

Compound 5: MS: 415 [M-Na]−, ESI.

Example 209

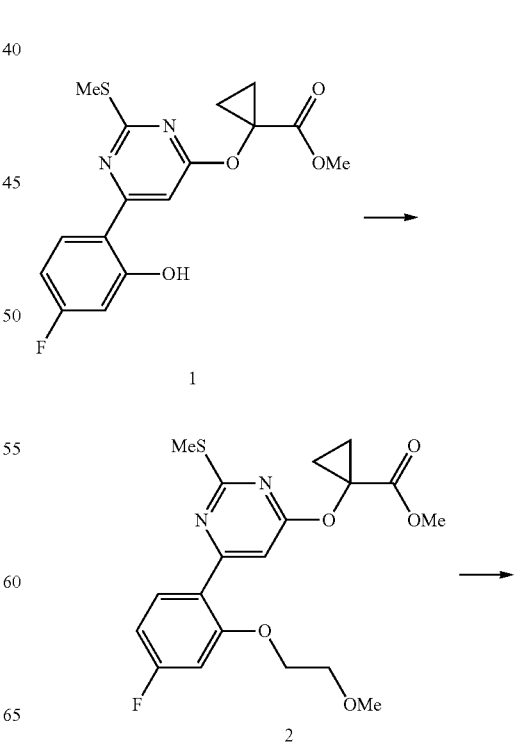

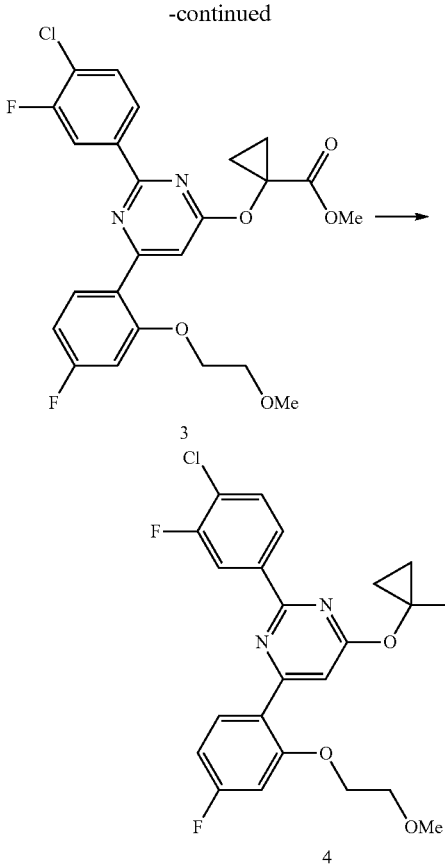

Compound 2 was prepared by reacting and treating in the same manner as in Example 200 using Compound 1.
Compound 2: MS: 409 [M+H]$^+$, APCI.
Compound 3 was prepared by reacting and treating in the same manner as in Example 207 using Compound 2.
Compound 3: MS: 491/493 [M+H]$^+$, APCI.
Compound 4 was prepared by reacting and treating in the same manner as in Example 186 using Compound 3.
Compound 4: MS: 475/477 [M-Na]−, ESI.
Corresponding starting compounds were treated in the similar manner to any of the above Examples to give the following compounds.

| Example | R | MS (APCI) |
|---|---|---|
| 210 | phenyl | 387/389 [M + H]+ |
| 211 | 4-methoxyphenyl | 417/419 [M + H]+ |
| 212 | 2-fluorophenyl | 405/407 [M + H]+ |
| 213 | 2-methoxyphenyl | 417/419 [M + H]+ |
| 214 | 3-methoxyphenyl | 417/419 [M + H]+ |
| 215 | 4-ethoxyphenyl | 431/433 [M + H]+ |
| 216 | 4-methoxymethylphenyl | 431/433 [M + H]+ |
| 217 | 2-methylthiophenyl | 433/435 [M + H]+ |
| 218 | 3-methylthiophenyl | 433/435 [M + H]+ |
| 219 | 2-trifluoromethyl | 455/457 [M + H]+ |
| 220 | 3-trifluoromethyl | 455/457 [M + H]+ |
| 221 | 2-ethoxyphenyl | 431/433 [M + H]+ |
| 222 | (5-methyl-2-ethoxypyridinyl) | 432/434 [M + H]+ |
| 223 | (4-methyl-1-n-propylpyrazolyl) | 419/421 [M + H]+ |
| 224 | (5-methyl-2-chlorothienyl) | 427/429 [M + H]+ |
| 225 | (4-methyl-2,5-dimethoxyphenyl) | 447/449 [M + H]+ |
| 226 | (4-methyl-5-fluoro-2-methoxyphenyl) | 435/437 [M + H]+ |
| 227 | (3-methyl-2-ethoxypyridinyl) | 432/434 [M + H]+ |
| 228 | (3-methyl-2,6-dimethoxypyridinyl) | 448/450 [M + H]+ |
| 229 | (4-methyl-1-isobutylpyrazolyl) | 433/435 [M + H]+ |
| 230 | (4-methyl-1-(3-methylbutyl)pyrazolyl) | 447/449 [M + H]+ |
| 231 | (3-methyl-2-fluoro-6-methoxyphenyl) | 435/437 [M + H]+ |

| | | |
|---|---|---|
| 232 |  | 435/437 [M + H]+ |
| 233 |  | 435/437 [M + H]+ |
| 234 |  | 418/420 [M + H]+ |
| 235 |  | 412/414 [M + H]+ |
| 236 |  | 412/414 [M + H]+ |
| 237 |  | 435/437 [M + H]+ |
| 238 |  | 431/433 [M + H]+ |
| 239 | | 429/431 [M + H]+ |
| 240 | | 429/431 [M + H]+ |
| 241 | | 435/437 [M + H]+ |
| 242 | | 435/437 [M + H]+ |
| Example | R | MS (APCl) |
|---|---|---|
| 243 | | 386/388 [M + H]+ |
| 244 | | 404/406 [M + H]+ |
| 245 | | 417/419 [M + H]+ |
| Example | R | MS (APCl) |
|---|---|---|
| 246 | | 403/405 [M + H]+ |
| 247 | | 415/417 [M + H]+ |
| 248 | | 433/435 [M + H]+ |
| 249 | | 428/430 [M + H]+ |

-continued
| Example | R | MS (APCI) |
|---|---|---|
| 250 | 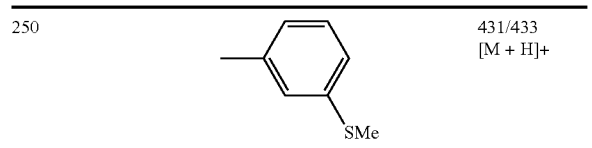 | 431/433 [M + H]+ |
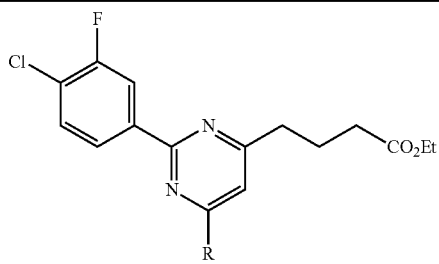
| Example | R | MS (APCI) |
|---|---|---|
| 251 | 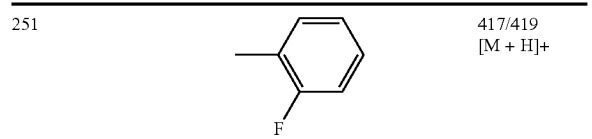 | 417/419 [M + H]+ |
| 252 | 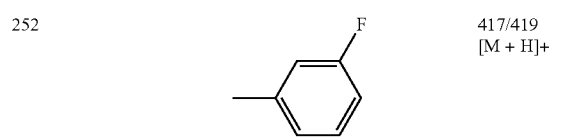 | 417/419 [M + H]+ |
| 253 | 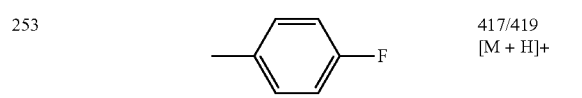 | 417/419 [M + H]+ |
| 254 | 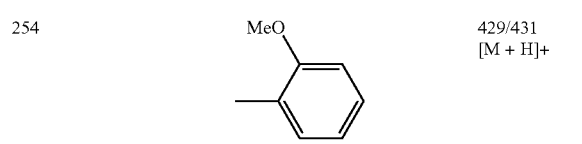 | 429/431 [M + H]+ |
| 255 | 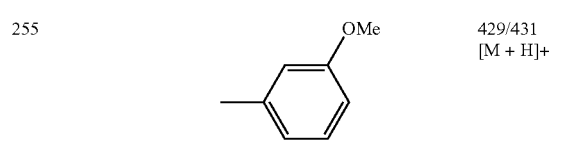 | 429/431 [M + H]+ |
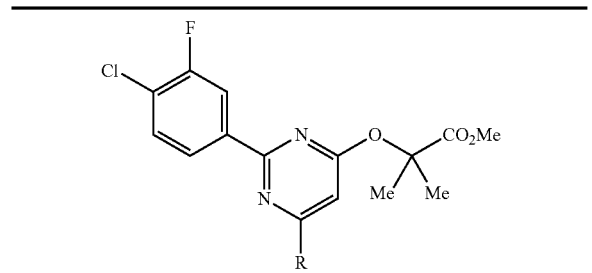
| Example | R | MS (APCI) |
|---|---|---|
| 256 | 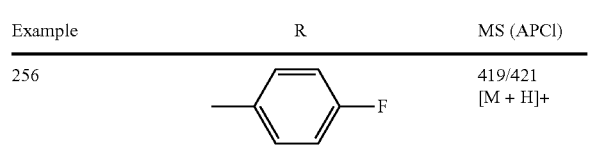 | 419/421 [M + H]+ |
| 257 | 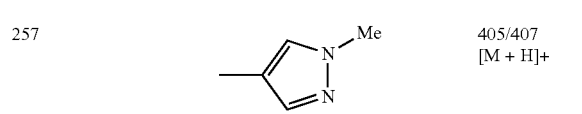 | 405/407 [M + H]+ |
-continued
| | | |
|---|---|---|
| 258 | 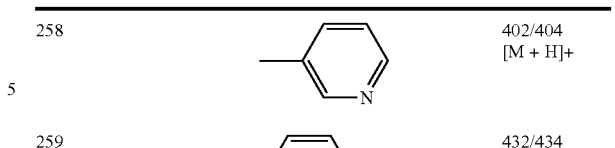 | 402/404 [M + H]+ |
| 259 | 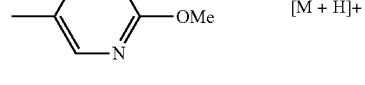 | 432/434 [M + H]+ |
| 260 | 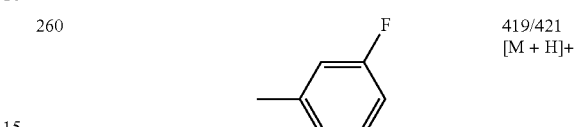 | 419/421 [M + H]+ |
| 261 | 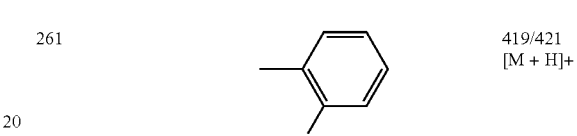 | 419/421 [M + H]+ |
| 262 | 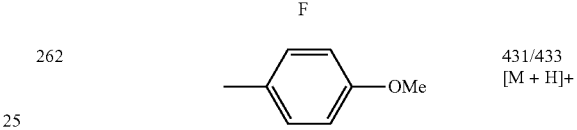 | 431/433 [M + H]+ |
| 263 | 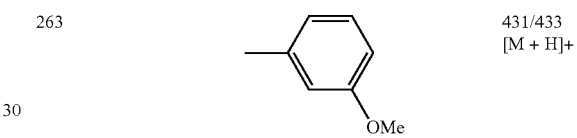 | 431/433 [M + H]+ |
| 264 | 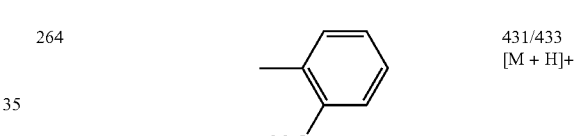 | 431/433 [M + H]+ |
| 265 | 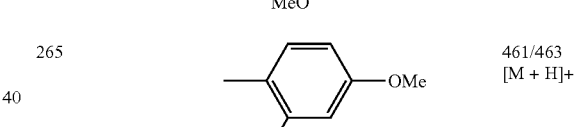 | 461/463 [M + H]+ |
| 266 | 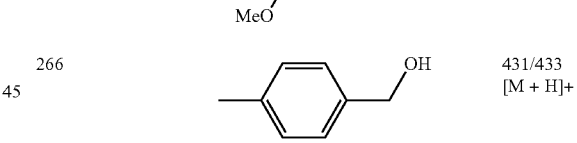 | 431/433 [M + H]+ |
| 267 | 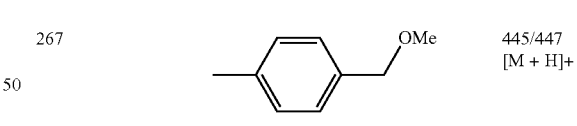 | 445/447 [M + H]+ |
| 268 | 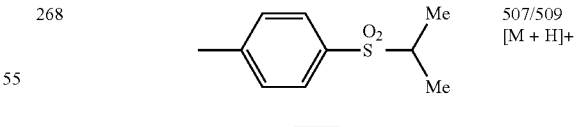 | 507/509 [M + H]+ |
| 269 | 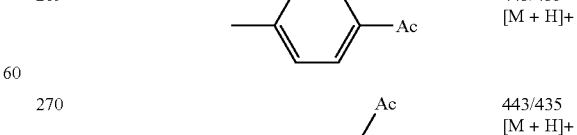 | 443/435 [M + H]+ |
| 270 | 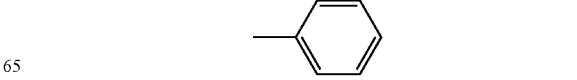 | 443/435 [M + H]+ |

107
-continued
| | | |
|---|---|---|
| 271 | 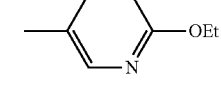 | 443/435 [M + H]+ |
| 272 | 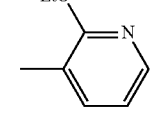 | 446/448 [M + H]+ |
| 273 | 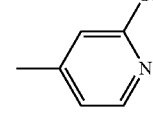 | 446/448 [M + H]+ |
| 274 | 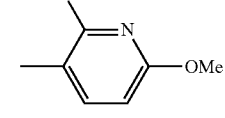 | 432/434 [M + H]+ |
| 275 | 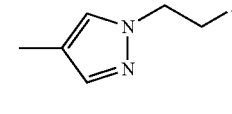 | 462/464 [M + H]+ |
| 276 | 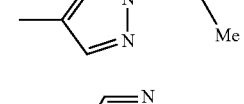 | 433/435 [M + H]+ |
| 277 | 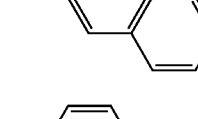 | 447/449 [M + H]+ |
| 278 | 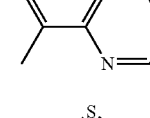 | 452/454 [M + H]+ |
| 279 | 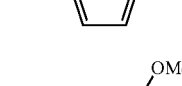 | 452/454 [M + H]+ |
| 280 | 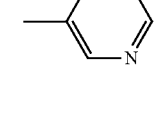 | 449/451 [M + H]+ |
| 281 | 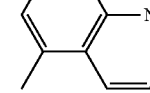 | 432/434 [M + H]+ |
| 282 | 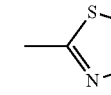 | 452/454 [M + H]+ |
108
-continued
| | | |
|---|---|---|
| 283 | 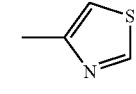 | 408/410 [M + H]+ |
| 284 | 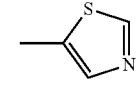 | 408/410 [M + H]+ |
| 285 | 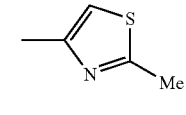 | 408/410 [M + H]+ |
| 286 | 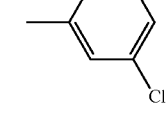 | 422/424 [M + H]+ |
| 287 | 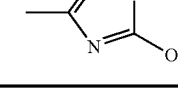 | 436/438 [M + H]+ |
| 288 | 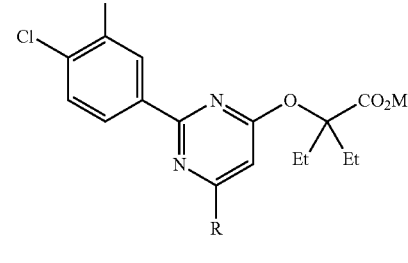 | 438/440 [M + H]+ |
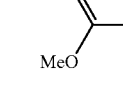
| Example | R | MS (APCl) |
|---|---|---|
| 289 | 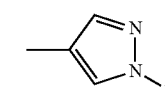 | 459/461 [M + H]+ |
| 290 | 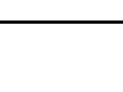 | 430/432 [M + H]+ |
| 291 | | 433/435 [M + H]+ |

-continued
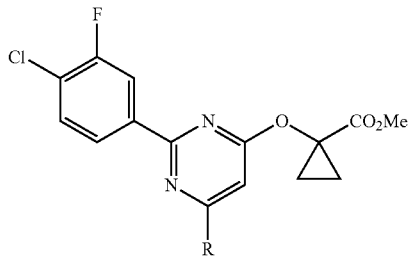
| Example | R | MS (APCl) |
|---|---|---|
| 292 |  | 417/419 [M + H]+ |
| 293 | 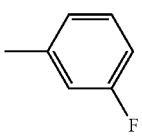 | 417/419 [M + H]+ |
| 294 |  | 417/419 [M + H]+ |
| 295 | 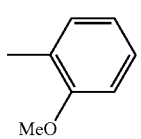 | 429/431 [M + H]+ |
| 296 | 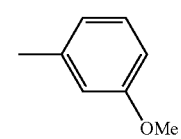 | 429/431 [M + H]+ |
| 297 | 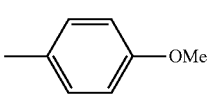 | 429/431 [M + H]+ |
| 298 | 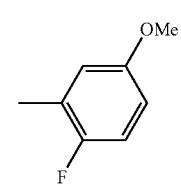 | 447/449 [M + H]+ |
| 299 | 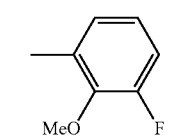 | 447/449 [M + H]+ |
| 300 | 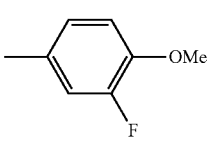 | 447/449 [M + H]+ |
-continued
| | | |
|---|---|---|
| 301 |  | 447/449 [M + H]+ |
| 302 | 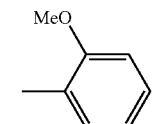 | 447/449 [M + H]+ |
| 303 | 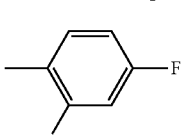 | 447/449 [M + H]+ |
| 304 | 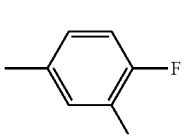 | 447/449 [M + H]+ |
| 305 | 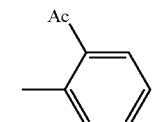 | 459/461 [M + H]+ |
| 306 | 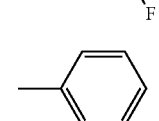 | 441/443 [M + H]+ |
| 307 | 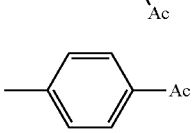 | 441/443 [M + H]+ |
| 308 | 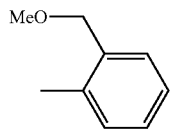 | 443/445 [M + H]+ |
| 309 | 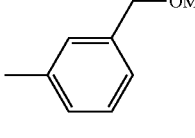 | 443/445 [M + H]+ |
| 310 | 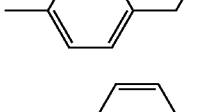 | 443/445 [M + H]+ |
| 311 | 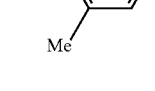 | 413/415 [M + H]+ |

111
-continued
112
-continued
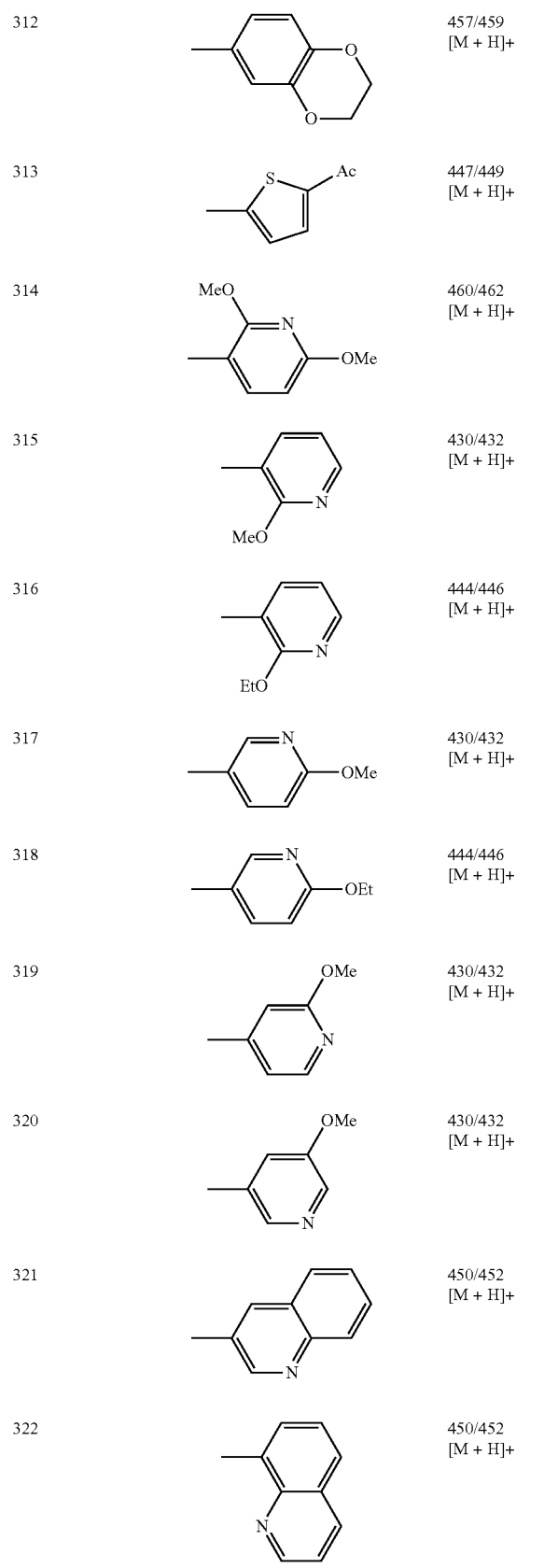
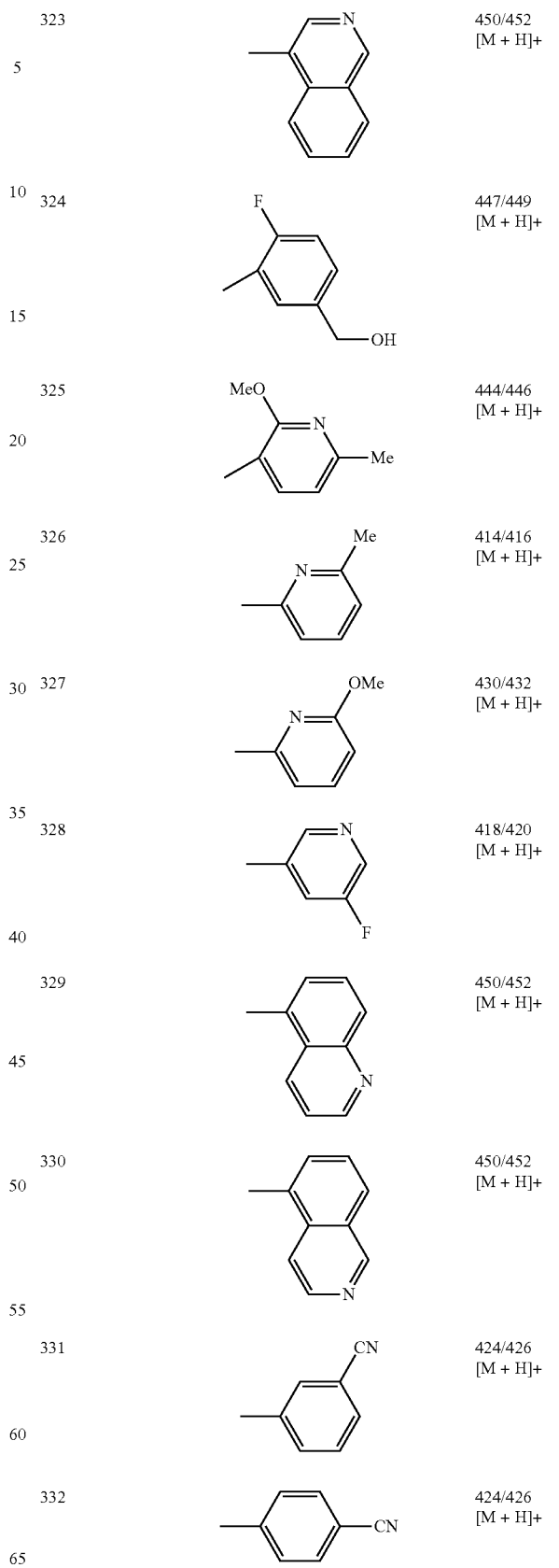
| # | MS | # | MS |
|---|---|---|---|
| 312 | 457/459 [M + H]+ | 323 | 450/452 [M + H]+ |
| 313 | 447/449 [M + H]+ | 324 | 447/449 [M + H]+ |
| 314 | 460/462 [M + H]+ | 325 | 444/446 [M + H]+ |
| 315 | 430/432 [M + H]+ | 326 | 414/416 [M + H]+ |
| 316 | 444/446 [M + H]+ | 327 | 430/432 [M + H]+ |
| 317 | 430/432 [M + H]+ | 328 | 418/420 [M + H]+ |
| 318 | 444/446 [M + H]+ | 329 | 450/452 [M + H]+ |
| 319 | 430/432 [M + H]+ | 330 | 450/452 [M + H]+ |
| 320 | 430/432 [M + H]+ | 331 | 424/426 [M + H]+ |
| 321 | 450/452 [M + H]+ | 332 | 424/426 [M + H]+ |
| 322 | 450/452 [M + H]+ | | |

| | | | | | | |
|---|---|---|---|---|---|---|
| 333 | 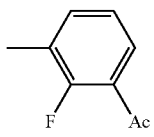 | 459/461 [M + H]+ | | 346 | 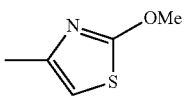 | 420/422 [M + H]+ |
| 334 | 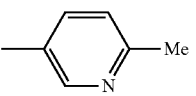 | 414/416 [M + H]+ | | 347 | 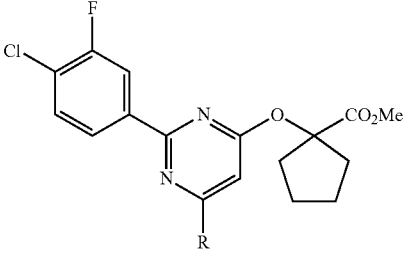 | 434/436 [M + H]+ |
| 335 | 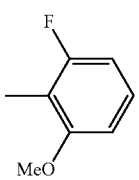 | 447/449 [M + H]+ | | 348 | 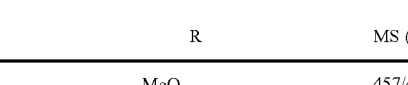 | 436/438 [M + H]+ |
| 336 | 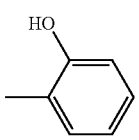 | 415/417 [M + H]+ | | | | |
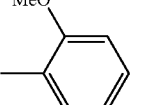
| Example | R | MS (APCl) |
|---|---|---|
| 349 | 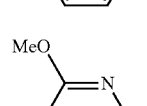 | 457/459 [M + H]+ |
| 337 | 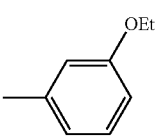 | 443/445 [M + H]+ | | | | |
| 338 | 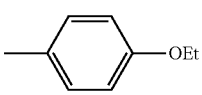 | 443/445 [M + H]+ | | 350 | 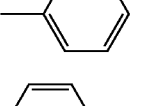 | 458/460 [M + H]+ |
| 339 | 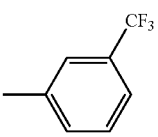 | 467/469 [M + H]+ | | 351 | 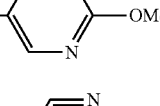 | 458/460 [M + H]+ |
| 340 | 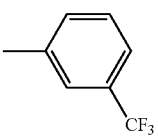 | 467/469 [M + H]+ | | 352 | 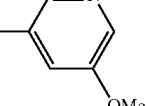 | 458/460 [M + H]+ |
| 341 | 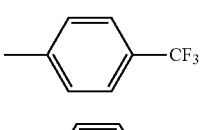 | 467/469 [M + H]+ | | | | |
| 342 | 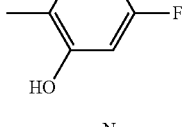 | 433/435 [M + H]+ | | 353 | 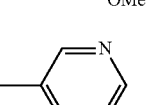 | 446/448 [M + H]+ |
| 343 | 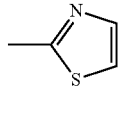 | 406/408 [M + H]+ | | | | |
| 344 | 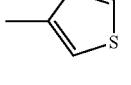 | 406/408 [M + H]+ | | 354 | 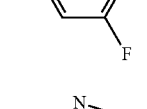 | 434/436 [M + H]+ |
| 345 | 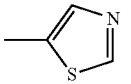 | 406/408 [M + H]+ | | 355 | 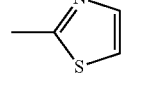 | 434/436 [M + H]+ |

-continued
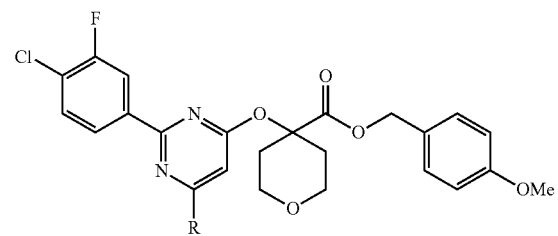
| Example | R | MS (APCl) |
|---|---|---|
| 356 | 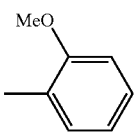 | 579/581 [M + H]+ |
| 357 |  | 597/599 [M + H]+ |
| 358 | 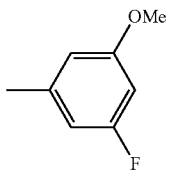 | 597/599 [M + H]+ |
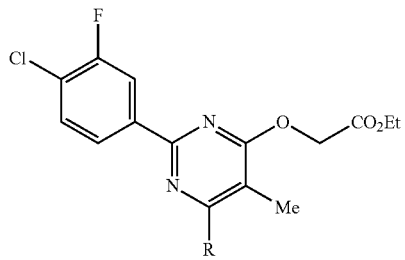
| Example | R | MS (APCl) |
|---|---|---|
| 359 | 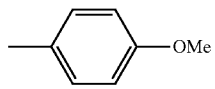 | 431/433 [M + H]+ |
| 360 | 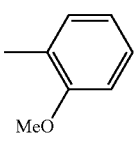 | 431/433 [M + H]+ |
| 361 | 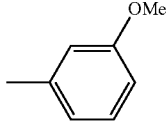 | 431/433 [M + H]+ |
| 362 | 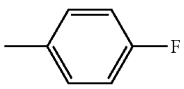 | 419/421 [M + H]+ |
-continued
| | | |
|---|---|---|
| 363 |  | 419/421 [M + H]+ |
| 364 | 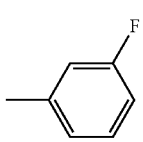 | 419/421 [M + H]+ |
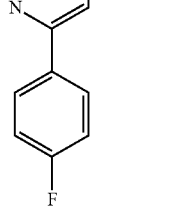
| Example | R | MS (APCl) |
|---|---|---|
| 365 | 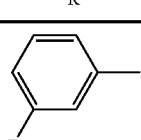 | 371 [M + H]+ |
| 366 | 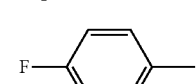 | 371 [M + H]+ |
| 367 | 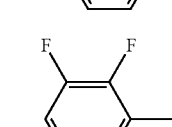 | 389 [M + H]+ |
| 368 | 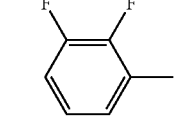 | 389 [M + H]+ |
| 369 | 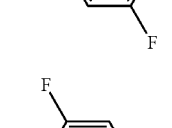 | 389 [M + H]+ |
| 370 | 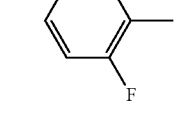 | 383 [M + H]+ |
| 371 | 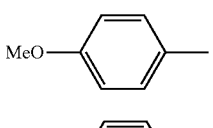 | 396 [M + H]+ |
| 372 | 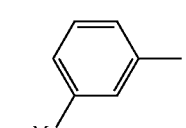 | 367 [M + H]+ |

| | | |
|---|---|---|
| 373 | 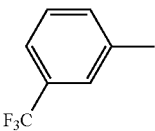 | 421 [M + H]+ |
| 374 | 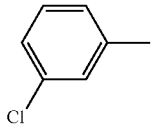 | 387/389 [M + H]+ |
| 375 | 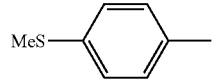 | 399 [M + H]+ |
| 376 | 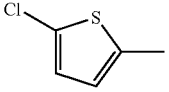 | 393/395 [M + H]+ |
| 377 | 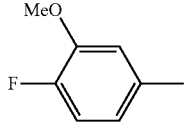 | 401 [M + H]+ |
| 378 | 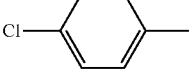 | 387/389 [M + H]+ |
| 379 | 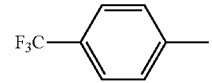 | 421 [M + H]+ |
| 380 | 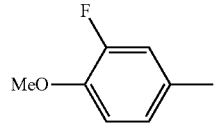 | 401 [M + H]+ |
| 381 | 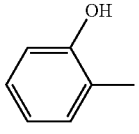 | 369 [M + H]+ |
| 382 | 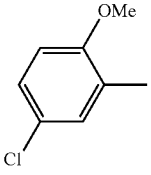 | 417/419 [M + H]+ |
| 383 | 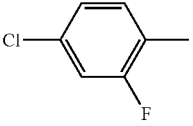 | 405/407 [M + H]+ |
| 384 | 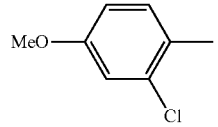 | 417/419 [M + H]+ |
| 385 | 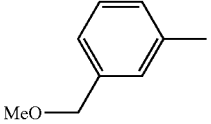 | 397 [M + H]+ |
| 386 | 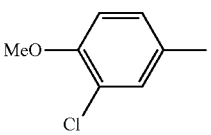 | 417/419 [M + H]+ |
| 387 | 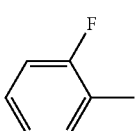 | 401 [M + H]+ |
| 388 | 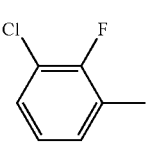 | 405/407 [M + H]+ |
| 389 | 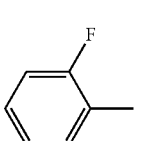 | 405/407 [M + H]+ |
| 390 | 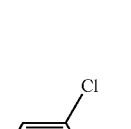 | 417/419 [M + H]+ |
| 391 | 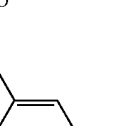 | 405/407 [M + H]+ |
| 392 | 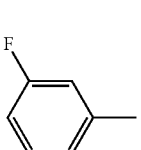 | 401 [M + H]+ |

-continued
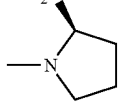
| Example | R | MS (APCl) |
|---|---|---|
| 393 | 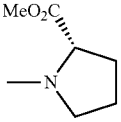 | 430/432 [M + H]+ |
| 394 | 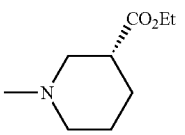 | 430/432 [M + H]+ |
| 395 | 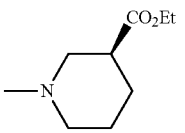 | 458/460 [M + H]+ |
| 396 | 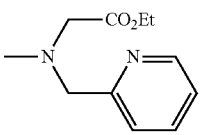 | 458/460 [M + H]+ |
| 397 | 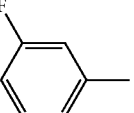 | 495/497 [M + H]+ |
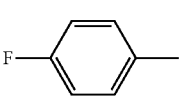
| Example | R | MS (APCl) |
|---|---|---|
| 398 | 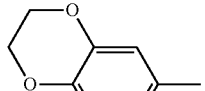 | 413 [M + H]+ |
| 399 | 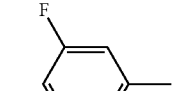 | 413 [M + H]+ |
-continued
| | | |
|---|---|---|
| 400 | 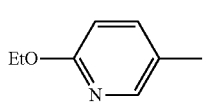 | 453 [M + H]+ |
| 401 | 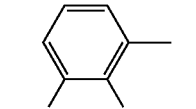 | 431 [M + H]+ |
| 402 | 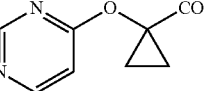 | 440 [M + H]+ |
| 403 | 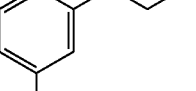 | 431 [M + H]+ |
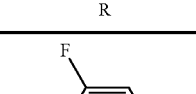
| Example | R | MS (APCl) |
|---|---|---|
| 404 | (2,3-difluorophenyl) | 475 [M + H]+ |
| 405 | (3,5-difluorophenyl) | 475 [M + H]+ |
(structure with CO2Et)
| Example | R | MS (APCl) |
|---|---|---|
| 406 | MeO-phenyl | 417/419 [M + H]+ |

| | | |
|---|---|---|
| 407 | MeO—(2-methoxy-5-methylpyridine) | 418/420 [M + H]+ |
| 408 | (toluene) | 387/389 [M + H]+ |
Example 409
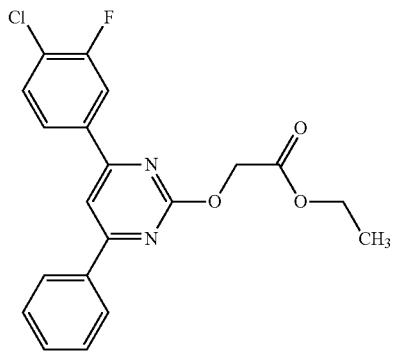 [SMILES: CCOC(=O)COc1nc(-c2ccccc2)cc(-c2ccc(Cl)c(F)c2)n1]
MS: 387/389 [M+H]+ (APCI).
Example 410
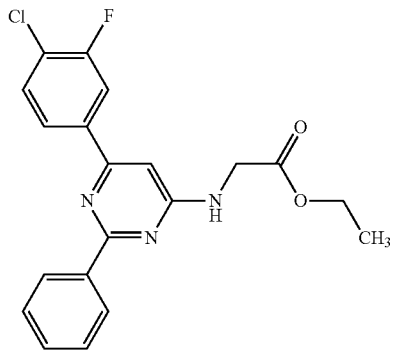 [SMILES: CCOC(=O)CNc1cc(-c2ccc(Cl)c(F)c2)nc(-c2ccccc2)n1]
MS: 386/388 [M+H]+ (APCI).
Example 411
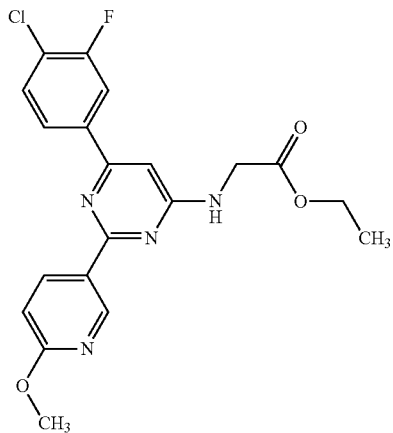 [SMILES: CCOC(=O)CNc1cc(-c2ccc(Cl)c(F)c2)nc(-c2ccc(OC)nc2)n1]
MS: 417/419 [M+H]+ (APCI).
Example 412
Cl, F, phenyl-pyrimidine-NH-CH2-CO2Et structure
MS: 386/388 [M+H]+ (APCI).
R-pyridine-O-CH2-CO2Et with 3-fluoro-4-chlorophenyl structure
| Example | R | MS (APCI) |
|---|---|---|
| 413 | 3-fluorophenyl | 404/406 [M + H]+ |
| 414 | 2-fluorophenyl | 404/406 [M + H]+ |
| 415 | 4-methoxyphenyl | 416/418 [M + H]+ |
| 416 | 3-methoxyphenyl | 416/418 [M + H]+ |
| 417 | 2-methoxyphenyl | 416/418 [M + H]+ |

123
-continued

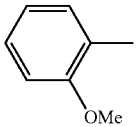

| Example | R | MS (APCl) |
|---|---|---|
| 418 | 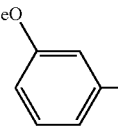 | 416/418 [M + H]+ |
| 419 | 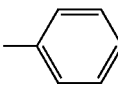 | 416/418 [M + H]+ |
| 420 | 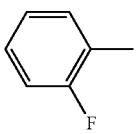 | 416/418 [M + H]+ |
| 421 | 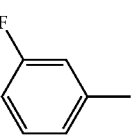 | 404/406 [M + H]+ |
| 422 | 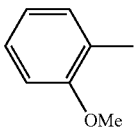 | 404/406 [M + H]+ |

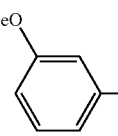

| Example | R | MS (APCl) |
|---|---|---|
| 423 | 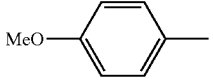 | 416/418 [M + H]+ |
| 424 | 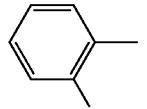 | 416/418 [M + H]+ |

124
-continued

| | | |
|---|---|---|
| 425 | 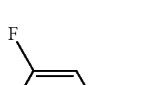 | 416/418 [M + H]+ |
| 426 | 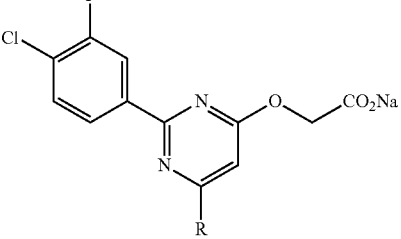 | 404/406 [M + H]+ |
| 427 | 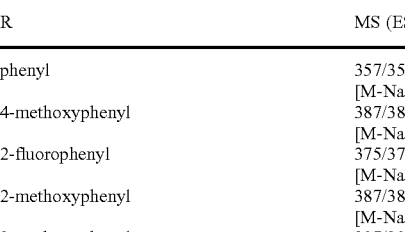 | 404/406 [M + H]+ |

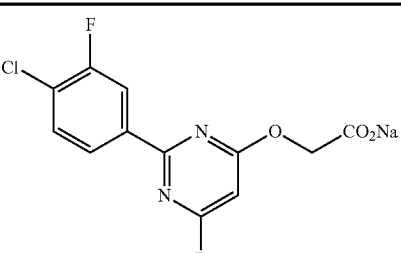

| Example | R | MS (ESI) |
|---|---|---|
| 428 | phenyl | 357/359 [M-Na]- |
| 429 | 4-methoxyphenyl | 387/389 [M-Na]- |
| 430 | 2-fluorophenyl | 375/377 [M-Na]- |
| 431 | 2-methoxyphenyl | 387/389 [M-Na]- |
| 432 | 3-methoxyphenyl | 387/389 [M-Na]- |
| 433 | 4-ethoxyphenyl | 401/403 [M-Na]- |
| 434 | 4-methoxymethylphenyl | 401/403 [M-Na]- |
| 435 | 2-methylthiophenyl | 403/405 [M-Na]- |
| 436 | 3-methylthiophenyl | 403/405 [M-Na]- |
| 437 | 2-trifluoromethylphenyl | 425/427 [M-Na]- |
| 438 | 3-trifluoromethylphenyl | 425/427 [M-Na]- |
| 439 | 2-ethoxyphenyl | 401/403 [M-Na]- |

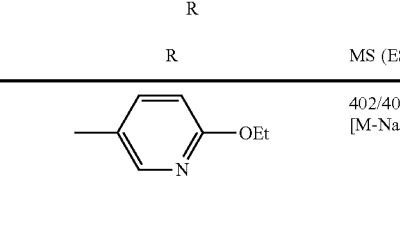

| Example | R | MS (ESI) |
|---|---|---|
| 440 | 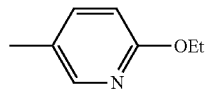 | 402/404 [M-Na]- |

125
-continued
| | | |
|---|---|---|
| 441 | 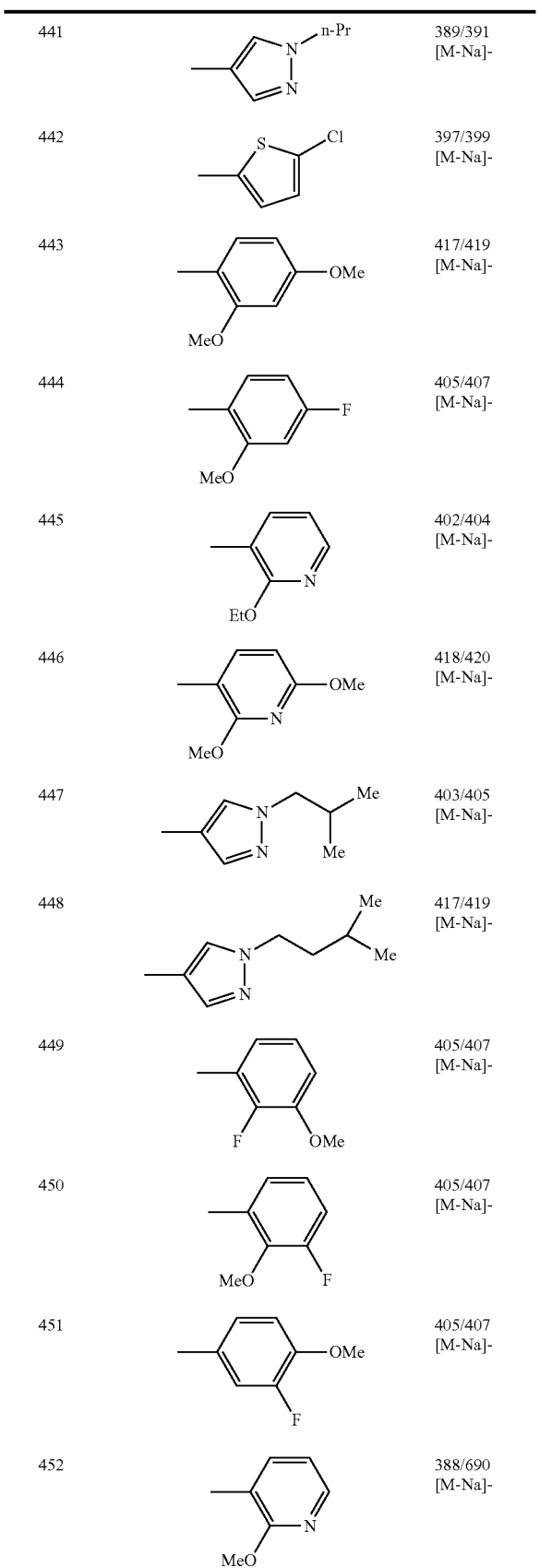 | 389/391 [M-Na]- |
| 442 | | 397/399 [M-Na]- |
| 443 | | 417/419 [M-Na]- |
| 444 | | 405/407 [M-Na]- |
| 445 | | 402/404 [M-Na]- |
| 446 | | 418/420 [M-Na]- |
| 447 | | 403/405 [M-Na]- |
| 448 | | 417/419 [M-Na]- |
| 449 | | 405/407 [M-Na]- |
| 450 | | 405/407 [M-Na]- |
| 451 | | 405/407 [M-Na]- |
| 452 | | 388/690 [M-Na]- |
126
-continued
| | | |
|---|---|---|
| 453 | 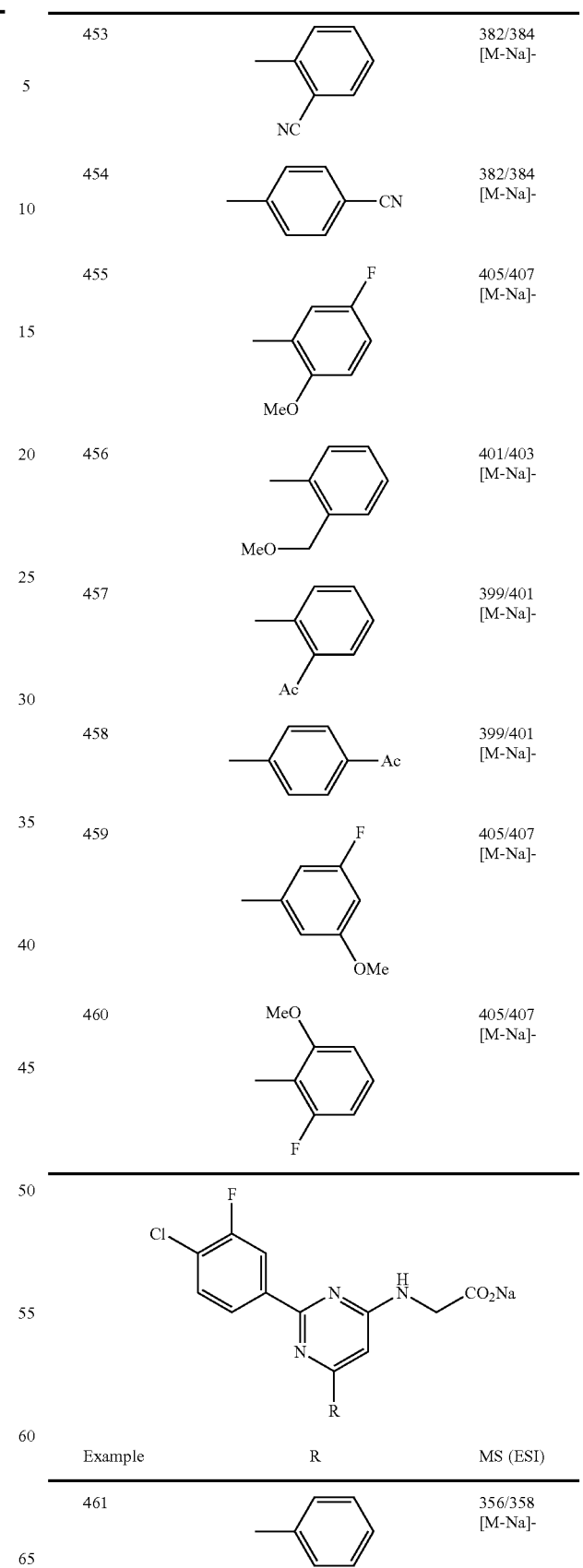 | 382/384 [M-Na]- |
| 454 | | 382/384 [M-Na]- |
| 455 | | 405/407 [M-Na]- |
| 456 | | 401/403 [M-Na]- |
| 457 | | 399/401 [M-Na]- |
| 458 | | 399/401 [M-Na]- |
| 459 | | 405/407 [M-Na]- |
| 460 | | 405/407 [M-Na]- |
| Example | R | MS (ESI) |
|---|---|---|
| 461 | | 356/358 [M-Na]- |

127

-continued

| | | |
|---|---|---|
| 462 | 4-F-C6H4- | 374/376 [M-Na]- |
| 463 | 5-Me-2-OMe-pyridin-yl | 387/389 [M-Na]- |

[Structure: 2-(4-chloro-3-fluorophenyl)-6-R-pyrimidin-4-yl propanoate sodium salt]

| Example | R | MS (ESI) |
|---|---|---|
| 464 | 3-F-C6H4- | 373/375 [M-Na]- |
| 465 | 2-OMe-C6H4- | 385/387 [M-Na]- |
| 466 | 3-F-5-OMe-C6H3- | 403/405 [M-Na]- |
| 467 | 3-NMe2-C6H4- | 398/400 [M-Na]- |
| 468 | 3-SMe-C6H4- | 401/403 [M-Na]- |

128

-continued

[Structure: 2-(4-chloro-3-fluorophenyl)-6-R-pyrimidin-4-yl butanoate sodium salt]

| Example | R | MS (ESI) |
|---|---|---|
| 469 | 3-F-2-Me-C6H3- (2-F, methyl) | 387/389 [M-Na]- |
| 470 | 3-F-C6H4- | 387/389 [M-Na]- |
| 471 | 4-F-C6H4- | 387/389 [M-Na]- |
| 472 | 2-OMe-C6H4- | 399/401 [M-Na]- |
| 473 | 3-OMe-C6H4- | 399/401 [M-Na]- |

[Structure: 2-(4-chloro-3-fluorophenyl)-6-R-pyrimidin-4-yloxy-2-methylpropanoate sodium salt]

| Example | R | MS (ESI) |
|---|---|---|
| 474 | 4-F-C6H4- | 403/405 [M-Na]- |
| 475 | 1-Me-pyrazol-4-yl | 389/391 [M-Na]- |
| 476 | pyridin-3-yl | 386/388 [M-Na]- |

| # | Structure | Mass |
|---|---|---|
| 477 | 5-methyl-2-methoxypyridine | 416/418 [M-Na]- |
| 478 | 3-fluorophenyl (methyl) | 403/405 [M-Na]- |
| 479 | 2-fluorophenyl (methyl) | 403/405 [M-Na]- |
| 480 | 4-methoxyphenyl (methyl) | 415/417 [M-Na]- |
| 481 | 3-methoxyphenyl (methyl) | 415/417 [M-Na]- |
| 482 | 2-methoxyphenyl (methyl) | 415/417 [M-Na]- |
| 483 | 2,4-dimethoxyphenyl (methyl) | 445/447 [M-Na]- |
| 484 | 4-(hydroxymethyl)phenyl (methyl) | 415/417 [M-Na]- |
| 485 | 4-(methoxymethyl)phenyl (methyl) | 429/431 [M-Na]- |
| 486 | 4-(isopropylsulfonyl)phenyl (methyl) | 491/493 [M-Na]- |
| 487 | 4-acetylphenyl (methyl) | 427/429 [M-Na]- |
| 488 | 3-acetylphenyl (methyl) | 427/429 [M-Na]- |
| 489 | 2-acetylphenyl (methyl) | 427/429 [M-Na]- |
| 490 | 5-methyl-2-ethoxypyridine | 430/432 [M-Na]- |
| 491 | 3-methyl-2-ethoxypyridine | 430/432 [M-Na]- |
| 492 | 4-methyl-2-methoxypyridine | 416/418 [M-Na]- |
| 493 | 3-methyl-2,6-dimethoxypyridine | 446/448 [M-Na]- |
| 494 | 4-methyl-1-propylpyrazole | 417/419 [M-Na]- |
| 495 | 4-methyl-1-isobutylpyrazole | 431/433 [M-Na]- |
| 496 | 3-methylquinoline | 436/438 [M-Na]- |
| 497 | 8-methylquinoline | 436/438 [M-Na]- |
| 498 | 5-methyl-2-acetylthiophene | 433/435 [M-Na]- |
| 499 | 5-methyl-3-methoxypyridine | 416/418 [M-Na]- |
| 500 | 5-methylquinoline | 436/438 [M-Na]- |
| 501 | 2-methylthiazole | 392/394 [M-Na]- |
| 502 | 4-methylthiazole | 392/394 [M-Na]- |

-continued

| | | |
|---|---|---|
| 503 | 5-methyl-thiadiazole | 392/394 [M-Na]- |
| 504 | 4-methyl-2-Me-thiazole | 406/408 [M-Na]- |
| 505 | 5-methyl-2-Cl-pyridine | 420/422 [M-Na]- |
| 506 | 4-methyl-2-OMe-thiazole | 422/424 [M-Na]- |

Structure: 2-(4-chloro-3-fluorophenyl)-6-R-pyrimidin-4-yl O-C(Et)(Et)-CO2Na

| Example | R | MS (ESI) |
|---|---|---|
| 507 | 2-MeO-phenyl | 443/445 [M-Na]- |
| 508 | pyridin-3-yl | 414/416 [M-Na]- |
| 509 | 1-Me-pyrazol-4-yl | 417/419 [M-Na]- |

Structure: 2-(4-chloro-3-fluorophenyl)-6-R-pyrimidin-4-yl O-cyclopropyl-CO2Na

| Example | R | MS (ESI) |
|---|---|---|
| 510 | 2-F-phenyl | 401/403 [M-Na]- |

-continued

| Example | R | MS (ESI) |
|---|---|---|
| 511 | 3-F-phenyl | 401/403 [M-Na]- |
| 512 | 4-F-phenyl | 401/403 [M-Na]- |
| 513 | 2-MeO-phenyl | 413/415 [M-Na]- |
| 514 | 3-MeO-phenyl | 413/415 [M-Na]- |
| 515 | 4-MeO-phenyl | 413/415 [M-Na]- |
| 516 | 4-F-3-MeO-phenyl | 431/433 [M-Na]- |
| 517 | 2-MeO-3-F-phenyl | 431/433 [M-Na]- |
| 518 | 4-MeO-3-F-phenyl | 431/433 [M-Na]- |
| 519 | 3-F-5-MeO-phenyl | 431/433 [M-Na]- |
| 520 | 2-MeO-4-F-phenyl | 431/433 [M-Na]- |
| 521 | 4-F-2-MeO-phenyl | 431/433 [M-Na]- |

-continued
| | | |
|---|---|---|
| 522 | 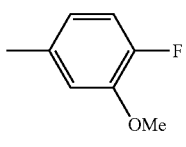 | 431/433 [M-Na]- |
| 523 | 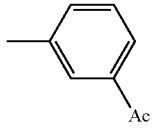 | 425/427 [M-Na]- |
| 524 | 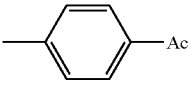 | 425/427 [M-Na]- |
| 525 | 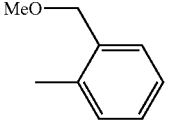 | 427/429 [M-Na]- |
| 526 | 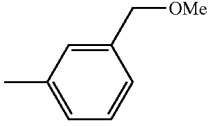 | 427/429 [M-Na]- |
| 527 | 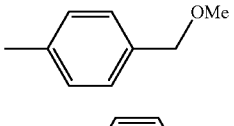 | 427/429 [M-Na]- |
| 528 | 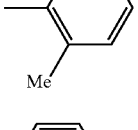 | 397/399 [M-Na]- |
| 529 | 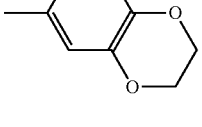 | 441/443 [M-Na]- |
| 530 | 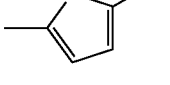 | 431/433 [M-Na]- |
| 531 | 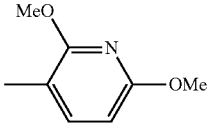 | 444/446 [M-Na]- |
| 532 | 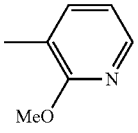 | 414/416 [M-Na]- |
| 533 | 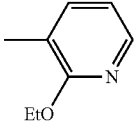 | 428/430 [M-Na]- |
-continued
| | | |
|---|---|---|
| 534 | 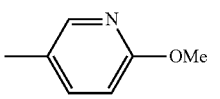 | 414/416 [M-Na]- |
| 535 | 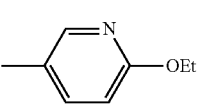 | 428/430 [M-Na]- |
| 536 | 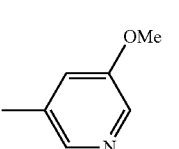 | 414/416 [M-Na]- |
| 537 | 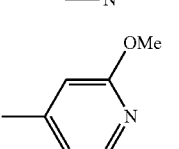 | 414/416 [M-Na]- |
| 538 | 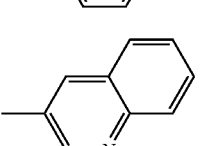 | 434/436 [M-Na]- |
| 539 | 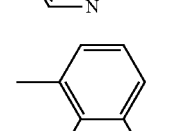 | 434/436 [M-Na]- |
| 540 | 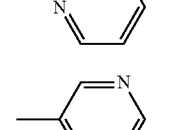 | 434/436 [M-Na]- |
| 541 | 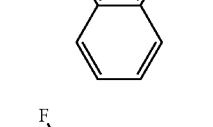 | 431/433 [M-Na]- |
| 542 | 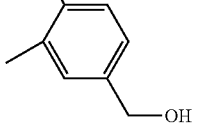 | 428/430 [M-Na]- |
| 543 | 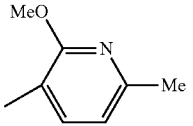 | 398/400 [M-Na]- |
| 544 | 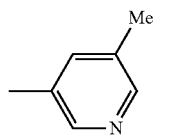 | 414/416 [M-Na]- |

| Example | R | MS (ESI) |
|---|---|---|
| 545 | 3-fluoro-5-methylpyridine | 402/404 [M-Na]- |
| 546 | 4-methylquinoline | 434/436 [M-Na]- |
| 547 | 5-methylisoquinoline | 434/436 [M-Na]- |
| 548 | 3-methylbenzonitrile | 408/410 [M-Na]- |
| 549 | 4-methylbenzonitrile | 408/410 [M-Na]- |
| 550 | 2,5-dimethylpyridine | 398/400 [M-Na]- |
| 551 | 3-fluoro-2-methyl-6-methoxybenzene | 431/433 [M-Na]- |
| 552 | 2-methylphenol | 399//401 [M-Na]- |
| 553 | 3-ethoxytoluene | 427/429 [M-Na]- |
| 554 | 4-ethoxytoluene | 427/429 [M-Na]- |
| 555 | 3-(trifluoromethyl)toluene | 451/453 [M-Na]- |

| Example | R | MS (ESI) |
|---|---|---|
| 556 | 3-(trifluoromethyl)toluene | 451/453 [M-Na]- |
| 557 | 4-(trifluoromethyl)toluene | 451/453 [M-Na]- |
| 558 | 5-fluoro-2-methylphenol | 417/419 [M-Na]- |
| 559 | 2-methylthiazole | 390/392 [M-Na]- |
| 560 | 4-methylthiazole | 390/392 [M-Na]- |
| 561 | 5-methylthiazole | 390/392 [M-Na]- |
| 562 | 2,4-dimethylthiazole | 404/406 [M-Na]- |
| 563 | 3-chloro-5-methylpyridine | 418/420 [M-Na]- |
| 564 | 2-methoxy-4-methylthiazole | 420/422 [M-Na]- |

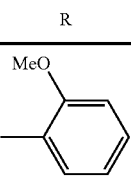

| Example | R | MS (ESI) |
|---|---|---|
| 565 | 2-methoxytoluene | 441/443 [M-Na]- |
| 566 | 2-methoxy-3-methylpyridine | 442/444 [M-Na]- |

-continued
| | | |
|---|---|---|
| 567 | 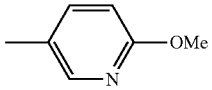 | 442/444 [M-Na]- |
| 568 | 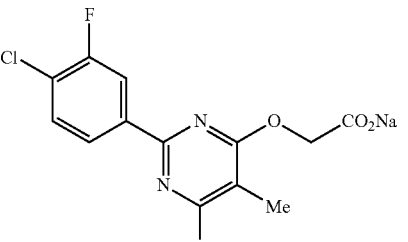 | 442/444 [M-Na]- |
| 569 | 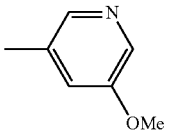 | 430/432 [M-Na]- |
| 570 | 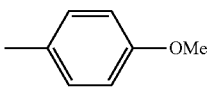 | 418/420 [M-Na]- |
| 571 | 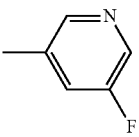 | 418/420 [M-Na]- |
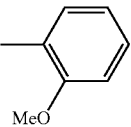
| Example | R | MS (ESI) |
|---|---|---|
| 572 | 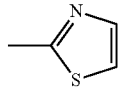 | 475/477 [M-Na]- |
| 573 | 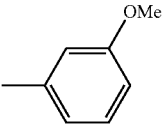 | 475/477 [M-Na]- |
-continued
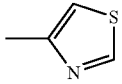
| Example | R | MS (ESI) |
|---|---|---|
| 574 | 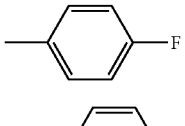 | 401/403 [M-Na]- |
| 575 | 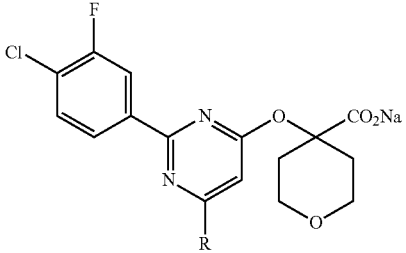 | 401/403 [M-Na]- |
| 576 | 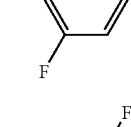 | 401/403 [M-Na]- |
| 577 | 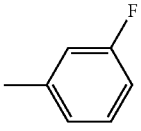 | 389/391 [M-Na]- |
| 578 | 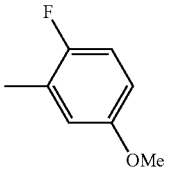 | 389/391 [M-Na]- |
| 579 | 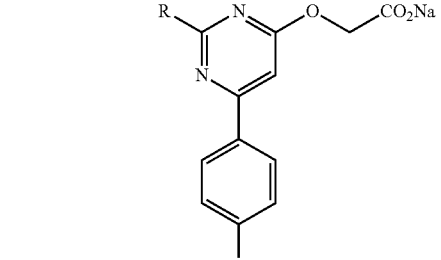 | 389/391 [M-Na]- |
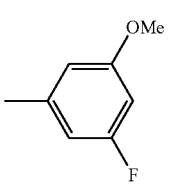
| Example | R | MS (ESI) |
|---|---|---|
| 580 | 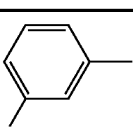 | 341 [M-Na]- |
| 581 | 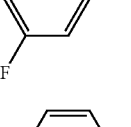 | 341 [M-Na]- |

| | 139 -continued | | | 140 -continued | |
|---|---|---|---|---|---|
| 582 | 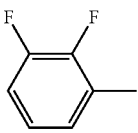 2,3-difluoro-phenyl | 359 [M-Na]- | 595 | 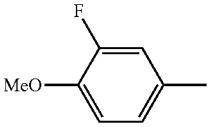 3-fluoro-4-methoxy-phenyl | 371 [M-Na]- |
| 583 | 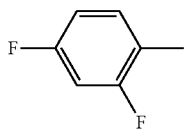 2,5-difluoro-phenyl | 359 [M-Na]- | 596 | 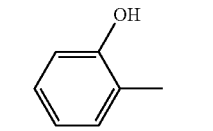 2-hydroxy-phenyl | 339 [M-Na]- |
| 584 | 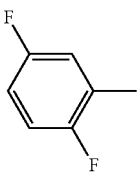 2,4-difluoro-phenyl | 359 [M-Na]- | 597 | 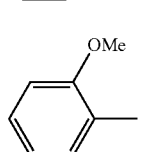 | 387/389 [M-Na]- |
| 585 | 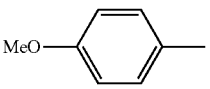 4-methoxy-phenyl | 353 [M-Na]- | | | |
| 586 | 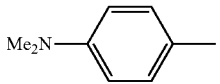 4-dimethylamino-phenyl | 366 [M-Na]- | 598 | 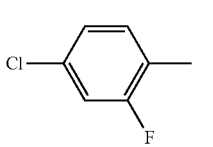 | 375/377 [M-Na]- |
| 587 | 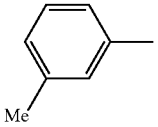 3-methyl-phenyl | 337 [M-Na]- | 599 | 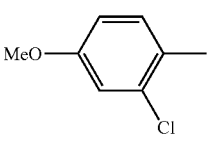 | 387/389 [M-Na]- |
| 588 | 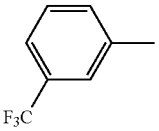 3-trifluoromethyl-phenyl | 391 [M-Na]- | 600 | 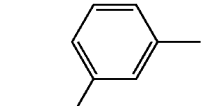 | 367 [M-Na]- |
| 589 | 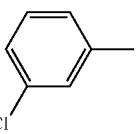 3-chloro-phenyl | 357/359 | 601 | 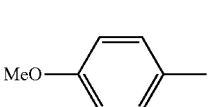 | 387/389 [M-Na]- |
| 590 | 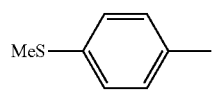 4-methylthio-phenyl | 369 [M-Na]- | 602 | 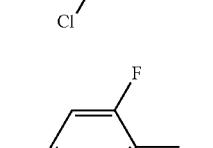 | 371 [M-Na]- |
| 591 | 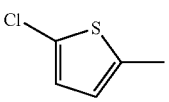 5-chloro-thienyl | 363/365 [M-Na]- | | | |
| 592 | 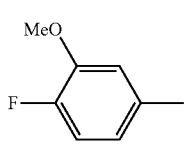 | 371 [M-Na]- | 603 | 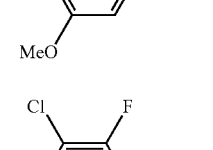 | 375/377 [M-Na]- |
| 593 | 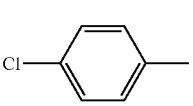 4-chloro-phenyl | 357/359 [M-Na]- | 604 | 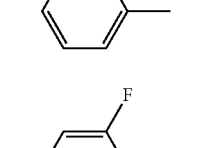 | 375/377 [M-Na]- |
| 594 | 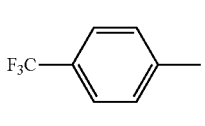 4-trifluoromethyl-phenyl | 391 [M-Na]- | | | |

-continued
| | | |
|---|---|---|
| 605 | 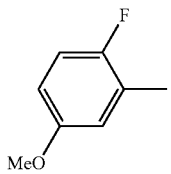 (F, MeO substituted phenyl) | 387/389 [M-Na]- |
| 606 | 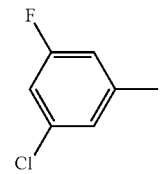 (F, Cl substituted phenyl) | 375/377 [M-Na]- |
| 607 | 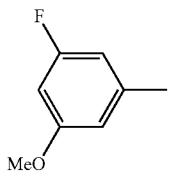 (F, MeO substituted phenyl) | 371 [M-Na]- |
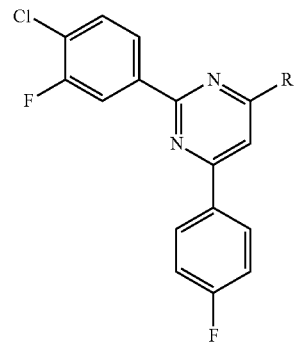
| Example | R | MS (ESI) |
|---|---|---|
| 608 | 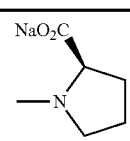 | 414/416 [M-Na]- |
| 609 | 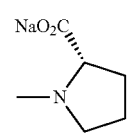 | 414/416 [M-Na]- |
| 610 | 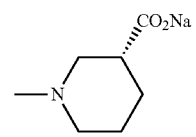 | 428/430 [M-Na]- |
| 611 | 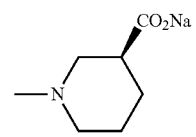 | 428/430 [M-Na]- |
| 612 | 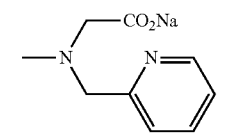 | 465/467 [M-Na]- |
-continued
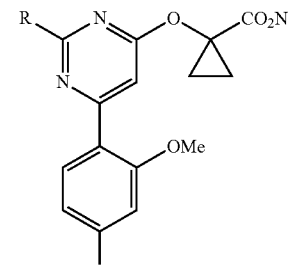
| Example | R | MS (ESI) |
|---|---|---|
| 613 | 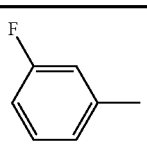 | 397 [M-Na]- |
| 614 | 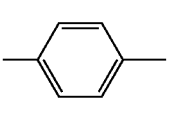 | 397 [M-Na]- |
| 615 | 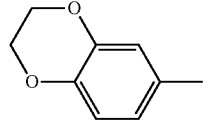 | 437 [M-Na]- |
| 616 | 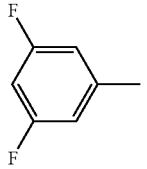 | 415 [M-Na]- |
| 617 | 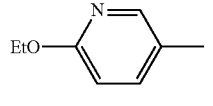 | 424 [M-Na]- |
| 618 | 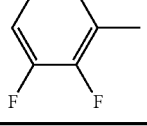 | 415 [M-Na]- |
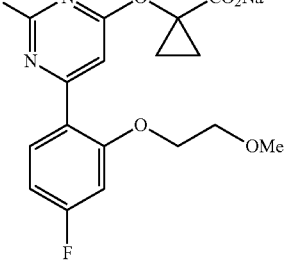
| Example | R | MS (ESI) |
|---|---|---|
| 619 | 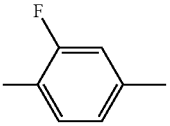 | 459 [M-Na]- |

-continued
| | | |
|---|---|---|
| 620 | 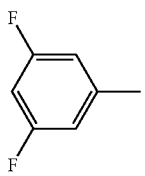 | 459 [M-Na]- |
| | 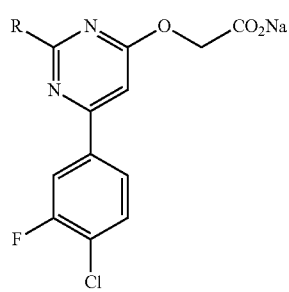 | |
| Example | R | MS (ESI) |
|---|---|---|
| 621 | 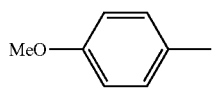 | 387/389 [M-Na]- |
| 622 | 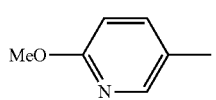 | 388/390 [M-Na]- |
| 623 | 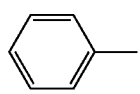 | 357/359 [M-Na]- |
Example 624
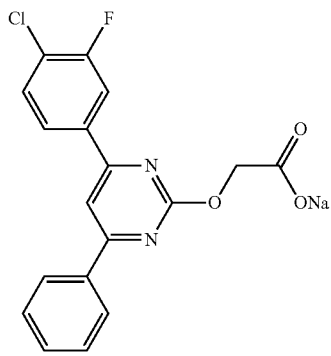
MS: 357/359[M-Na]− (ESI).
Example 625
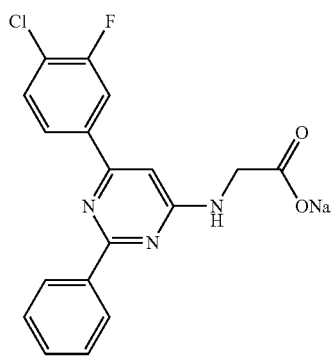
MS: 356/358[M-Na]− (ESI).
Example 626
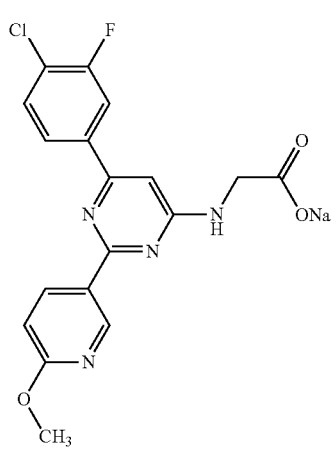
MS: 387/389[M-Na]− (ESI).
Example 627
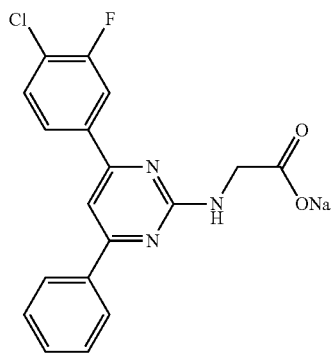
MS: 356/358[M-Na]− (ESI).

| Example | R | MS (ESI) |
|---|---|---|
| 628 | 3-fluorophenyl | 374/376 [M-Na]- |
| 629 | 2-fluorophenyl | 374/376 [M-Na]- |
| 630 | 4-methoxyphenyl | 386/388 [M-Na]- |
| 631 | 3-methoxyphenyl | 386/388 [M-Na]- |
| 632 | 2-methoxyphenyl | 386/388 [M-Na]- |

| Example | R | MS (ESI) |
|---|---|---|
| 633 | 2-methoxyphenyl | 386/388 [M-Na]- |
| 634 | 3-methoxyphenyl | 386/388 [M-Na]- |
| 635 | 4-methoxyphenyl | 386/388 [M-Na]- |
| 636 | 2-fluorophenyl | 374/376 [M-Na]- |
| 637 | 3-fluorophenyl | 374/376 [M-Na]- |

| Example | R | MS (ESI) |
|---|---|---|
| 638 | 2-methoxyphenyl | 386/388 [M-Na]- |
| 639 | 3-methoxyphenyl | 386/388 [M-Na]- |
| 640 | 4-methoxyphenyl | 386/388 [M-Na]- |
| 641 | 2-fluorophenyl | 374/376 [M-Na]- |
| 642 | 3-fluorophenyl | 374/376 [M-Na]- |

Example 643

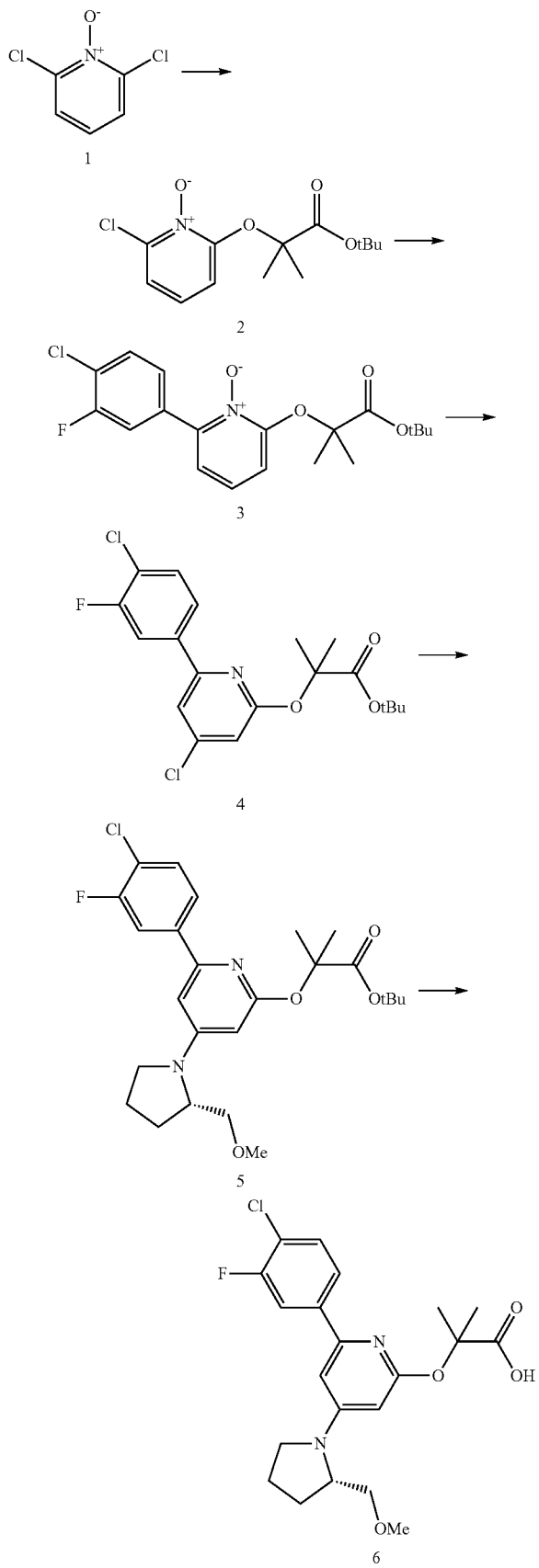 [SMILES: [O-][n+]1c(Cl)cccc1Cl ; CC(C)(C)OC(=O)C(C)(C)Oc1cccc(Cl)[n+]1[O-] ; CC(C)(C)OC(=O)C(C)(C)Oc1cccc(-c2ccc(Cl)c(F)c2)[n+]1[O-] ; CC(C)(C)OC(=O)C(C)(C)Oc1cc(Cl)cc(-c2ccc(Cl)c(F)c2)n1 ; COC[C@@H]1CCCN1c1cc(OC(C)(C)C(=O)OC(C)(C)C)nc(-c2ccc(Cl)c(F)c2)c1 ; COC[C@@H]1CCCN1c1cc(OC(C)(C)C(=O)O)nc(-c2ccc(Cl)c(F)c2)c1]

To a solution of tert-butyl 2-hydroxyisobutyrate (6.41 g, 40 mmol) in tetrahydrofuran (50 mL) was added sodium hydride (60%, 1.60 g, 40 mmol) at −10° C. and the mixture was stirred for 30 minutes. 2,6-Dichloropyridine N-oxide was added thereto, and the mixture was stirred at the same temperature for 30 minutes followed by at room temperature for 5 hours. The mixture was cooled to 0° C. and 10% aqueous citric acid was added thereto until the mixture became neutral. After the addition of ethyl acetate, the insoluble material was filtered off through Celite® pad. The filtrate was dried over anhydrous sodium sulfate, and concentrated under reduced pressure. The residue was purified by silica gel column chromatography (hexane:ethyl acetate=1:1→ethyl acetate) to give Compound 2 (3.69 g, 64%) as a oil.

MS: 288/290 [M+H]+, APCI.

A suspension of Compound 2 (1.849 g, 6.43 mmol), 4-chloro-3-fluorophenylboronic acid 1.681 g, 9.64 mmol), dichlorobis(triphenylphosphine)palladium (450 mg, 641 µmol) and 2 M aqueous sodium carbonate (6.45 mL, 12.9 mmol) in 1,2-dimethoxyethane (35 mL) was refluxed for 7 hours under argon atmosphere. After cooling, ethyl acetate and water were added thereto, and the mixture was filtered through Celite® pad. The two layers were separated and the organic layer was washed with water and brine, dried over anhydrous sodium sulfate, and concentrated under reduced pressure. The residue was purified by silica gel column chromatography (hexane:ethyl acetate=9:1→1:1) to give Compound 3 (2.086 g, 85%) as a solid.

MS: 382/384 [M+H]+, APCI.

To a solution of Compound 3 (106 mg, 0.28 mmol) in dichloromethane (1 mL) was added triphosgene (55 mg, 0.19 mmol) at −10° C. and the mixture was stirred at the same temperature for 15 minutes. Triethylamine (77 µL, 0.55 mmol) was slowly introduced and the mixture was stirred at −10 to −5° C. for 30 minutes. Water was added thereto, which was neutralized with 2 M aqueous sodium hydroxide followed by extraction with chloroform. The organic layer was washed with brine, dried over anhydrous sodium sulfate, and concentrated under reduced pressure. The residue was purified by silica gel column chromatography (hexane→hexane: ethyl acetate=9:1) to give Compound 4 (64 mg, 57%) as a solid.

MS: 400/402 [M+H]+, APCI.

A mixture of Compound 4 (57.8 mg, 161 µmol) and (S)-2-(methoxymethyl)pyrrolidine (371 mg, 3.22 mmol) was refluxed for 8 hours. After cooling, the mixture was diluted with ethyl acetate, washed with 1 M aqueous citric acid, and filtered through Chem Elute® (Varian Inc.), and the filtrate was concentrated under reduced pressure. The residue was purified by silica gel column chromatography (hexane→hexane:ethyl acetate=17:3) to give Compound 5 (49.6 mg, 64%) as a viscous oil.

MS: 479/481 [M+H]+, APCI.

A mixture of Compound 5 (58.3 mg, 122 µmol) and trifluoroacetic acid (1 mL) was stirred at room temperature overnight. The volatile was removed under reduced pressure. The residue was diluted with ethyl acetate, washed with water and brine, dried over anhydrous sodium sulfate, concentrated under reduced pressure. The residue was crystallized from acetone-water to give Compound 6 (37.3 mg, 72%) as powders.

MS: 421/423 [M−H]−, APCI.

Example 644

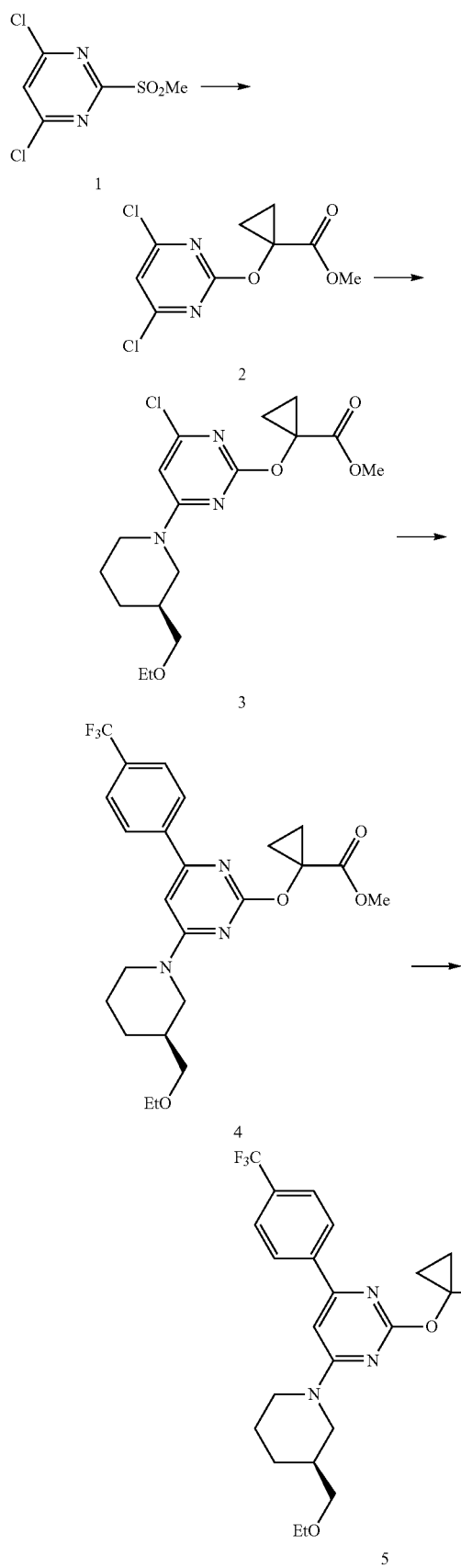

To a solution of Compound 1 (2.00 g, 8.81 mmol) and methyl 1-hydroxy-1-cyclopropane carboxylate (1.36 g, 10.6 mmol) in THF (40 mL) was added sodium hydride (60%, 423 mg, 10.6 mmol) at −78° C. and the mixture was stirred at room temperature for 1.5 hours. The reaction mixture was quenched with 1 M aqueous citric acid and extracted with ethyl acetate. The organic layer was washed with water and brine, dried over anhydrous sodium sulfate, and concentrated under reduced pressure. The residue was purified by silica gel column chromatography (hexane→hexane:ethyl acetate=4:1) to give Compound 2 (1.95 g, 84%) as a solid.

MS: 263/265 [M+H]$^+$, APCI.

To a suspension of Compound 2 (200 mg, 760 μmol) and (S)-3-(ethoxymethyl)piperidine hydrochloride (143 mg, 798 μmol) in THF (7.60 mL) was added triethylamine (265 μl, 1.90 mmol) at 0° C. and the mixture was stirred at room temperature overnight. The reaction mixture was poured into water and extracted with ethyl acetate. The organic layer was concentrated under reduced pressure. The residue was purified by silica gel column chromatography (hexane:ethyl acetate=9:1→7:3) to give Compound 3 (270 mg, 97%) as a viscous oil.

MS: 370/372 [M+H]$^+$, APCI.

A suspension of Compound 3 (88.0 mg, 238 μmol), 4-(trifluoromethyl)phenylboronic acid (69.1 mg, 357 μmol), dichlorobis(triphenylphosphine)palladium (17.0 mg, 23.8 μmol) and 2 M aqueous sodium carbonate (357 μL, 714 μmol) in 1,2-dimethoxyethane (2.38 mL) was refluxed for 2 hours under argon atmosphere. Additional 4-(trifluoromethyl)phenylboronic acid (138 mg, 714 μmol), dichlorobis(triphenylphosphine)palladium (17.0 mg, 23.8 μmol) and 2 M aqueous sodium carbonate (535 μL, 1.07 mmol) were added and the mixture was refluxed for 2 hours under argon atmosphere. Additional 4-(trifluoromethyl)phenylboronic acid (138 mg, 714 μmol) and dichlorobis(triphenylphosphine)palladium (17.0 mg, 23.8 μmol) were added and the mixture was refluxed for 14 hours under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane→hexane:ethyl acetate=4:1) to give Compound 4 (106 mg, 93%) as a viscous oil.

MS: 480 [M+H]$^+$, APCI.

Compound 5 was prepared by reacting and treating in the same manner as in Example 1 using Compound 4.

Compound 5: MS: 464 [M-Na]−, ESI.

Example 645

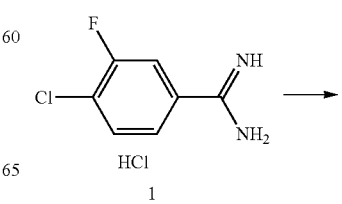

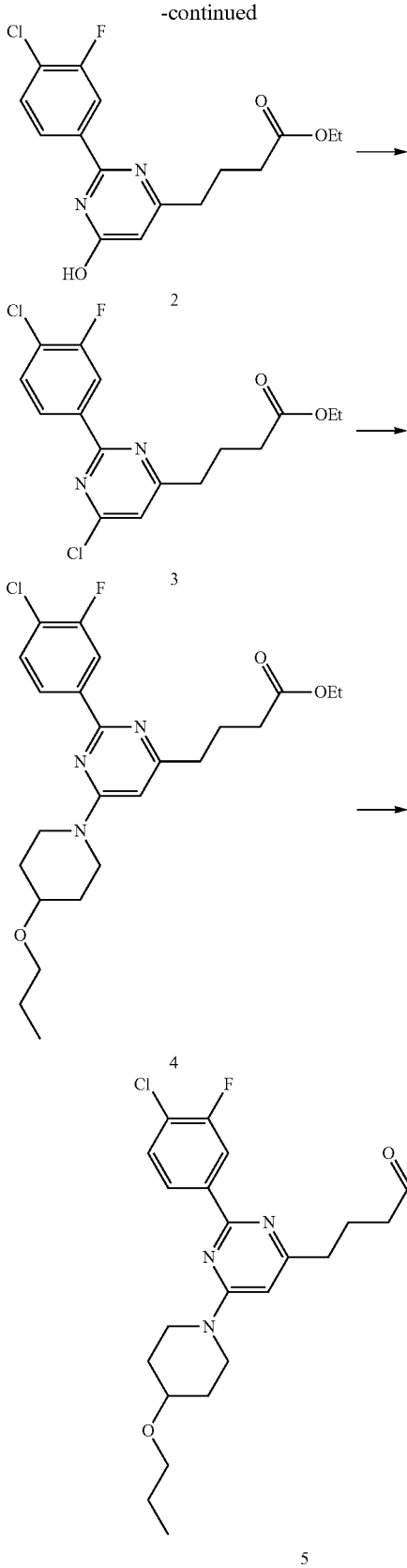

3-oxopimelate (1.31 g, 5.74 mmol) were added thereto at 0° C., and the mixture was refluxed for 10 hours. Additional diethyl 3-oxopimelate (661 mg, 2.87 mmol) was added and the mixture was refluxed for 15 hours. Additional diethyl 3-oxopimelate (661 mg, 2.87 mmol) was added and the mixture was refluxed for 24 hours. After cooling, the precipitate was collected by filtration and rinsed with water to give Compound 2 (665 mg, 41%) as powders.

MS: 339/341 [M+H]$^+$, APCI.

A mixture of Compound 2 (768 mg, 2.36 mmol) and phosphoryl chloride (7.68 mL) was refluxed for 15 minutes. After cooling, the reaction mixture was concentrated under reduced pressure. The residue was dissolved in chloroform, filtered through a silica gel pad, and concentrated under reduced pressure to give Compound 3 (770 mg, 91%) as a viscous oil.

MS: 357/359 [M+H]$^+$, APCI.

To a solution of Compound 3 (62.1 mg, 174 µmol) in THF (867 µL) were added 4-propoxypiperidine hydrochloride (625 mg, 348 µmol) and triethylamine (96.9 µl, 695 µmol), and the mixture was stirred at room temperature overnight. The reaction mixture was poured into water and extracted with ethyl acetate. The organic layer was concentrated under reduced pressure. The residue was purified by silica gel column chromatography (hexane→hexane:ethyl acetate=17:3) to give Compound 4 (76.9 mg, 95%) as a viscous oil.

MS: 464/466 [M+H]$^+$, APCI.

Compound 5 was prepared by reacting and treating in the same manner as in Example 1 using Compound 4.

Compound 5: MS: 434/436 [M-Na]–, ESI.

Example 646

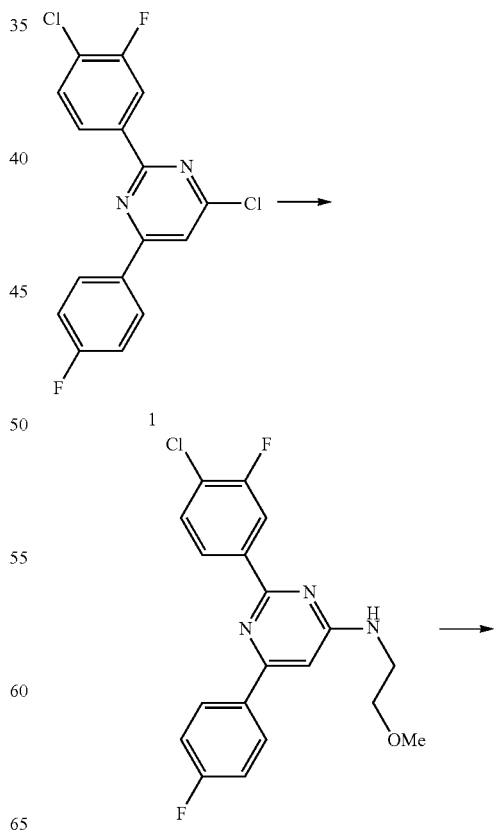

A solution of sodium ethoxide was prepared by dissolving sodium hydride (60%, 191 mg, 4.78 mmol) in absolute EtOH (9.57 mL). Compound 1 (1.00 g, 4.78 mmol) and diethyl

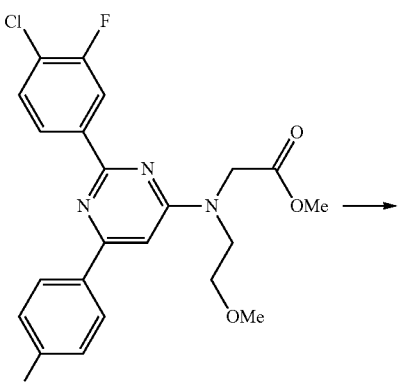

3

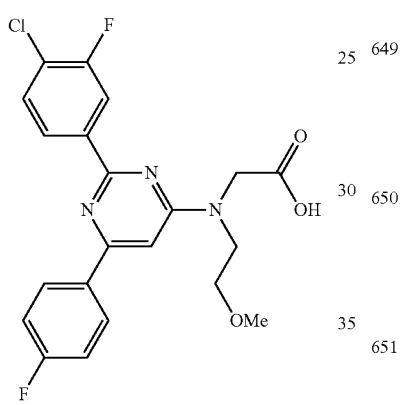

4

Compound 2 was prepared by reacting and treating in the same manner as in Example 190 using Compound 1.

Compound 2: MS: 376/378 [M+H]⁺, APCI.

To a solution of Compound 2 (70 mg, 0.186 mmol) in DMF (2 mL) was added sodium hydride (60%, 9.3 mg, 0.233 mmol) at room temperature and the mixture was stirred for 30 minutes. Methyl bromoacetate (19.4 μL, 0.205 mmol) was added thereto and the mixture was stirred at room temperature for 3 hours. The reaction mixture was quenched with water, and extracted with ethyl acetate and chloroform. The organic layer was dried over anhydrous magnesium sulfate and concentrated under reduced pressure. The residue was purified by silica gel column chromatography (hexane:ethyl acetate=9:1→3:1) to give Compound 3 (50.2 mg, 63%) as a solid.

MS: 448/450 [M+H]⁺, APCI.

Compound 4 was prepared by reacting and treating in the same manner as in Example 186 using Compound 3.

Compound 4: MS: 432/434 [M−H]−, ESI.

Corresponding starting compounds were treated in the similar manner to any of the above Examples to give the following compounds.

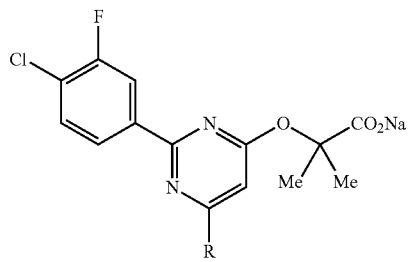

| Example | R | MS (ESI) |
|---|---|---|
| 647 | 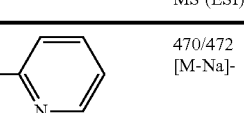 | 470/472 [M-Na]- |
| 648 | 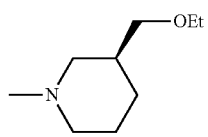 | 450/452 [M-Na]- |
| 649 | 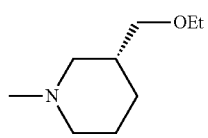 | 450/452 [M-Na]- |
| 650 | 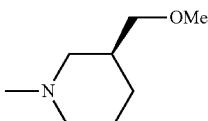 | 436/438 [M-Na]- |
| 651 | 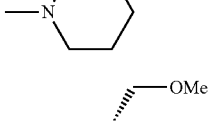 | 436/438 [M-Na]- |
| 652 | 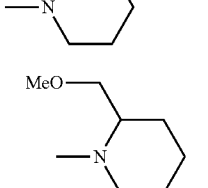 | 436/438 [M-Na]- |
| 653 | 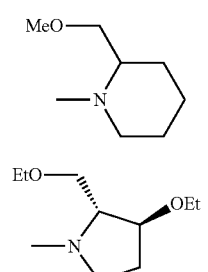 | 480/482 [M-Na]- |
| 654 | 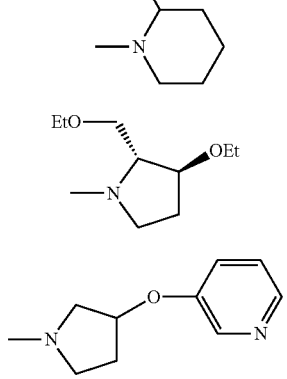 | 471/473 [M-Na]- |
| 655 | 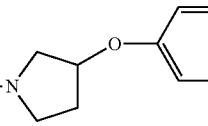 | 436/438 [M-Na]- |
| 656 |  | 436/438 [M-Na]- |

| | | 155 -continued | | |
|---|---|---|---|---|
| 657 | 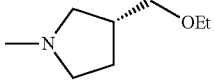 | | | 436/438 [M-Na]- |
| 658 | 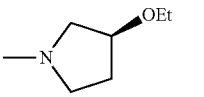 | | | 422/424 [M-Na]- |
| 659 | 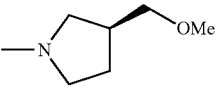 | | | 422/424 [M-Na]- |
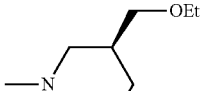
| Example | R | M | MS (ESI) |
|---|---|---|---|
| 660 |  | H | 466/468 [M-H]- |
| 661 |  | Na | 470/472 [M-Na]- |
| 662 | 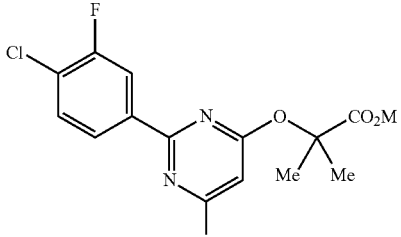 | Na | 480/482 [M-Na]- |
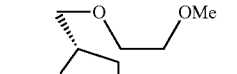
| Example | R | MS (ESI) |
|---|---|---|
| 663 | 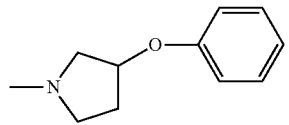 | 468/470 [M-Na]- |
| 664 |  | 469/471 [M-Na]- |
| | | 156 -continued | |
|---|---|---|---|
| 665 | 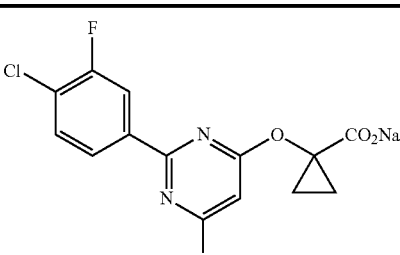 | | 420/422 [M-Na]- |
| 666 | 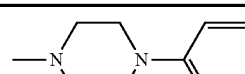 | | 448/450 [M-Na]- |
| 667 | 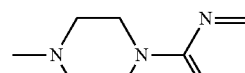 | | 448/450 [M-Na]- |
| 668 | | | 434/436 [M-Na]- |
| 669 | | | 434/436 [M-Na]- |
| 670 | | | 478/780 [M-Na]- |
| 671 | | | 468/470 [M-Na]- |
| 672 | | | 469/471 [M-Na]- |
| 673 | | | 434/436 [M-Na]- |
| 674 | | | 434/436 [M-Na]- |
| 675 | | | 434/436 [M-Na]- |
| 676 | | | 420/422 [M-Na]- |
| 677 | | | 420/422 [M-Na]- |

157
-continued
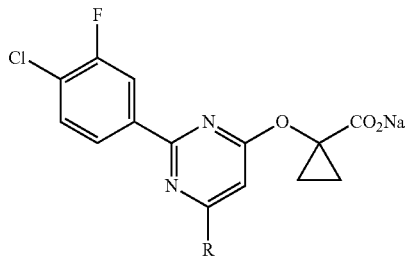
| Example | R | MS (ESI) |
|---|---|---|
| 678 | 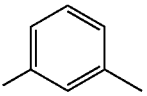 | 478/480 [M-Na]- |
| 679 |  | 434/436 [M-Na]- |
| 680 | 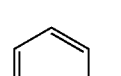 | 462/464 [M-Na]- |
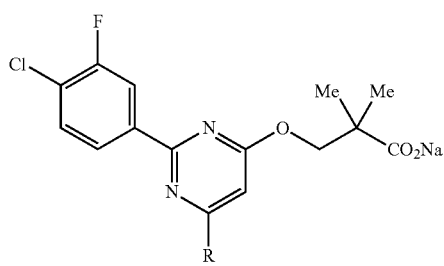
| Example | R | MS (ESI) |
|---|---|---|
| 681 | 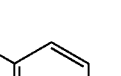 | 436/438 [M-Na]- |
| 682 | 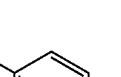 | 450/452 [M-Na]- |
| 683 | | 450/452 [M-Na]- |
158
Example 684
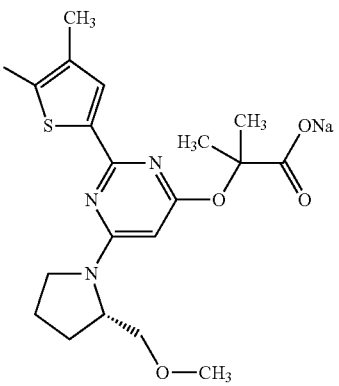
MS: 424/426[M-Na]− (ESI).
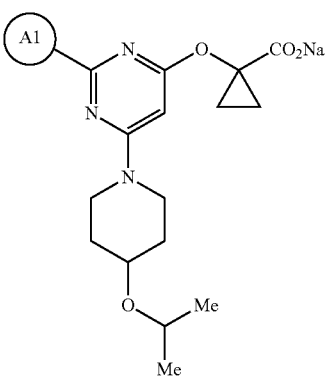
| Example | Ring A1 | MS (ESI) |
|---|---|---|
| 685 | 3-CF3-phenyl | 464 [M-Na]- |
| 686 | 4-CF3-phenyl | 464 [M-Na]- |
| 687 | 3-Cl-phenyl | 430/432 [M-Na]- |
| 688 | 4-Cl-phenyl | 430/432 [M-Na]- |
| 689 | 3-Cl-4-F-phenyl | 448/450 [M-Na]- |

159
-continued

| | | |
|---|---|---|
| 690 | Cl, F, Me-phenyl | 448/450 [M-Na]- |
| 691 | 2,3-dichloro-5-methylthiophene | 470/472 [M-Na]- |

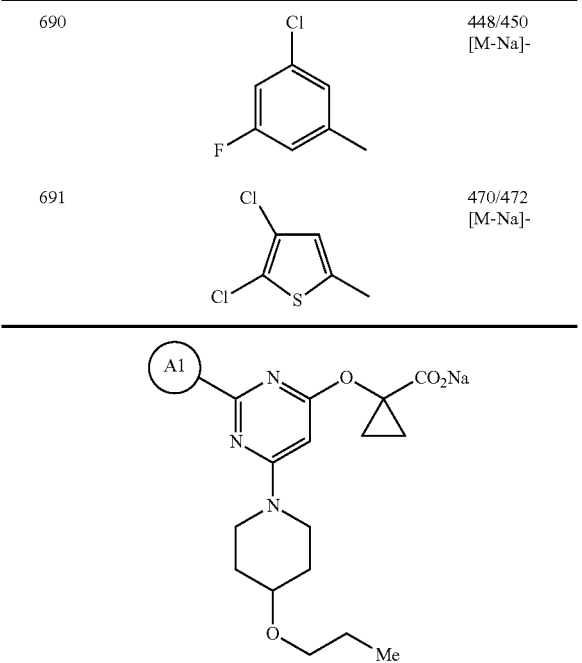

| Example | Ring A1 | MS (ESI) |
|---|---|---|
| 692 | 3-CF₃-phenyl | 464 [M-Na]- |
| 693 | 4-CF₃-phenyl | 464 [M-Na]- |
| 694 | 3-Cl-phenyl | 430/432 [M-Na]- |
| 695 | 4-Cl-phenyl | 430/432 [M-Na]- |
| 696 | 4-F-3-Cl-phenyl | 448/450 [M-Na]- |
| 697 | 3-Cl-5-F-phenyl | 448/450 [M-Na]- |

160
-continued

| | | |
|---|---|---|
| 698 | 2,3-dichloro-5-methylthiophene | 470/472 [M-Na]- |

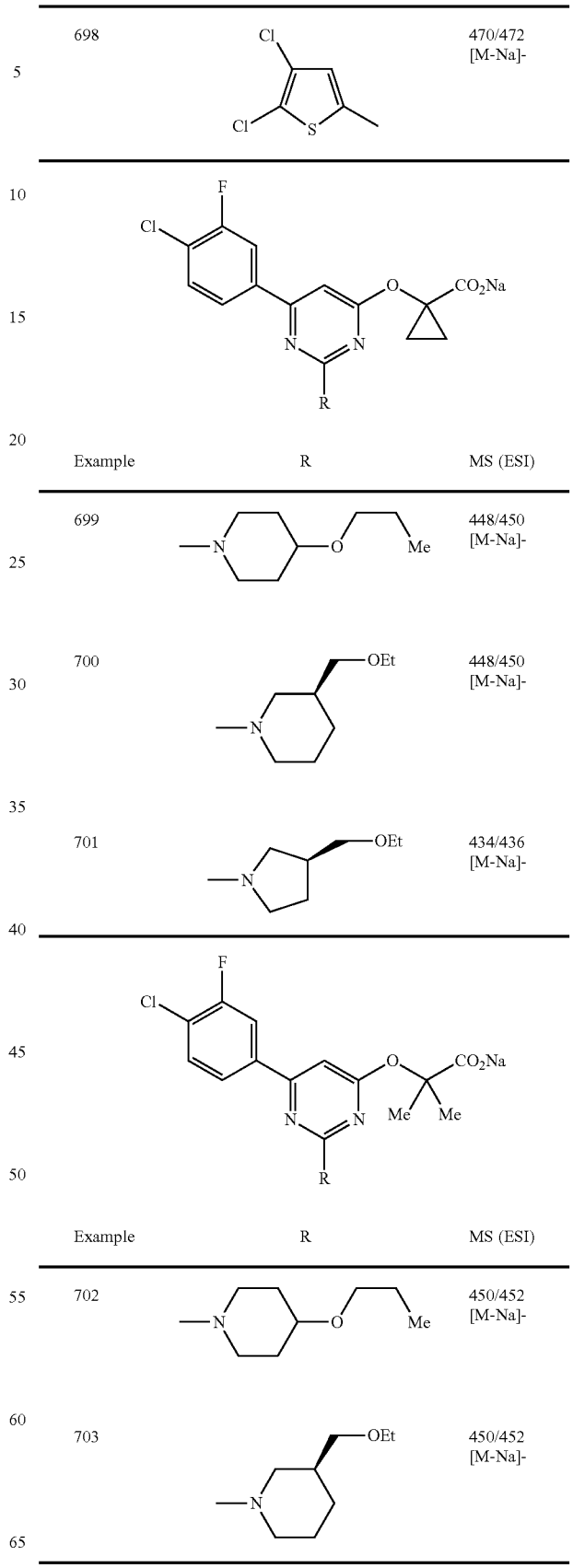

| Example | R | MS (ESI) |
|---|---|---|
| 699 | 1-methyl-4-(2-propoxy)piperidine | 448/450 [M-Na]- |
| 700 | 1-methyl-3-(ethoxymethyl)piperidine | 448/450 [M-Na]- |
| 701 | 1-methyl-3-(ethoxymethyl)pyrrolidine | 434/436 [M-Na]- |

| Example | R | MS (ESI) |
|---|---|---|
| 702 | 1-methyl-4-(2-propoxy)piperidine | 450/452 [M-Na]- |
| 703 | 1-methyl-3-(ethoxymethyl)piperidine | 450/452 [M-Na]- |

Example 704
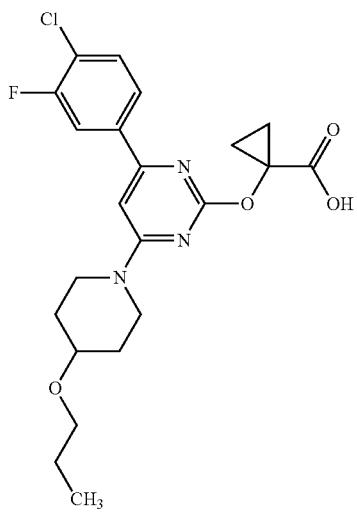 [SMILES: CCCOC1CCN(c2cc(-c3ccc(Cl)c(F)c3)nc(OC3(C(=O)O)CC3)n2)CC1]
MS: 448/450[M−H]− (ESI).
Example 705
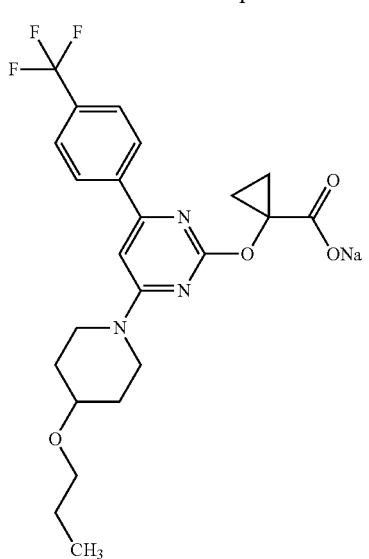
MS: 464[M-Na]− (ESI).
Example 706
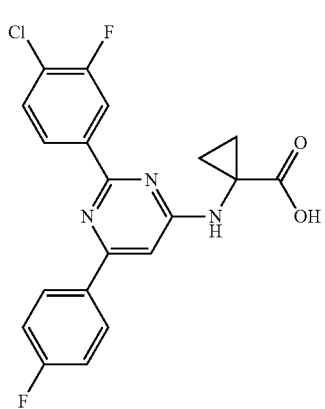 [SMILES: O=C(O)C1(Nc2cc(-c3ccc(F)cc3)nc(-c3ccc(Cl)c(F)c3)n2)CC1]
MS: 400/402[M-Na]− (ESI).
Example 707
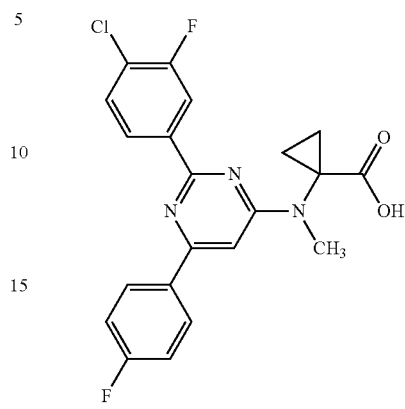
MS: 414/416 [M-Na]− (ESI).
Example 708
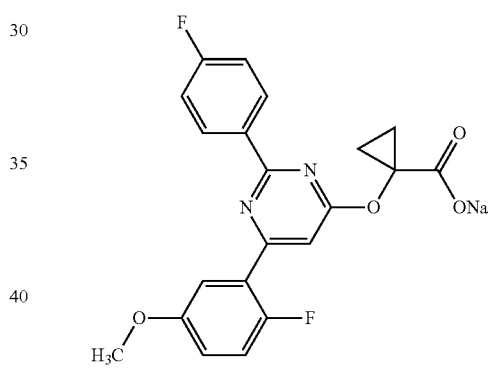
MS: 397[M-Na]− (ESI).
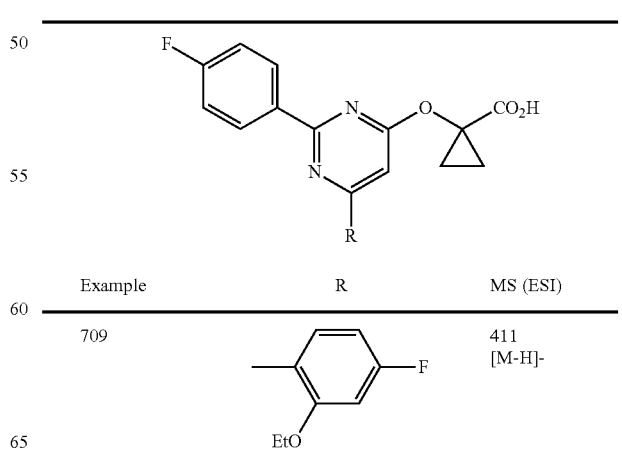
| Example | R | MS (ESI) |
|---|---|---|
| 709 | (4-fluoro-2-methyl-6-ethoxyphenyl) | 411 [M-H]- |

-continued
| Example | | MS (ESI) |
|---|---|---|
| 710 | (4-fluoro-2-methylphenoxy isopropyl group) | 425 [M-H]- |
| Example | R | MS (ESI) |
|---|---|---|
| 711 | 5-chloro-2-methylthiophene | 415/417 [M-Na]- |
| 712 | 2,3-dichloro-5-methylthiophene | 449/451 [M-Na]- |
| 713 | 5-chloro-3-methyl-2-methylthiophene | 429/431 [M-Na]- |
| Example | R | MS (ESI) |
|---|---|---|
| 714 | 4-fluorophenyl | 441 [M-H]- |
| 715 | 4-chlorophenyl | 457/459 [M-H]- |
Example 716
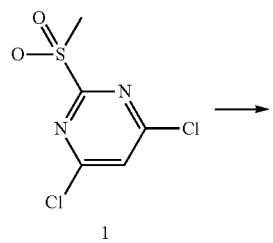
1
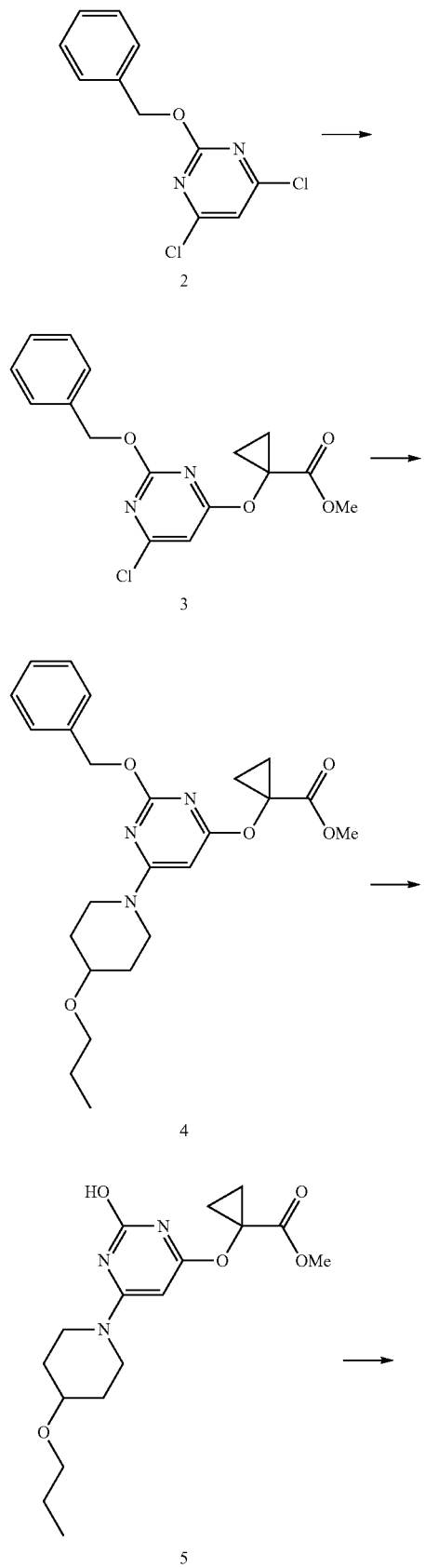

-continued

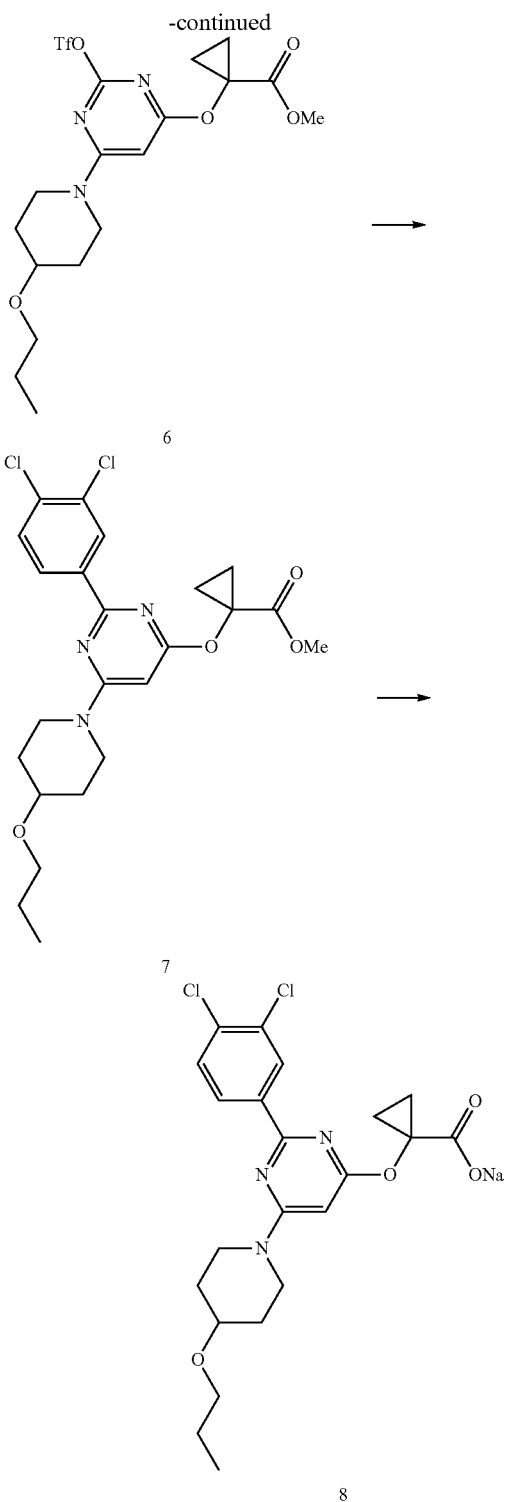

To a solution of Compound 1 (6.00 g, 26.4 mmol) and benzyl alcohol (2.87 mL, 27.7 mmol) in THF (120 mL) was added sodium hydride (60%, 1.16 g, 29.1 mmol) at −78° C. The mixture was warmed to room temperature, and was stirred at the same temperature for 4 hours. Water and ethyl acetate were added thereto. The two layers were separated, and the organic layer was washed with water and brine, dried over anhydrous sodium sulfate, filtered, and concentrated under reduced pressure. The residue was purified by silica gel column chromatography (hexane→ethyl acetate) to give Compound 2 (3.47 g, 51%) as a viscous oil.

MS: 255/257 [M+H]$^+$, APCI.

To a solution of Compound 2 (3.26 g, 12.8 mmol) and methyl 1-hydroxy-1-cyclopropane carboxylate (1.81 g, 14.1 mmol) was added sodium hydride (60%, 562 mg, 14.1 mmol) at −78° C. The mixture was warmed to room temperature, and was stirred at the same temperature for 2 hours. Water and ethyl acetate were added thereto. The two layers were separated, and the organic layer was washed with water and brine, dried over anhydrous sodium sulfate, filtered, and concentrated under reduced pressure. The residue was purified by silica gel column chromatography (hexane:ethyl acetate=19:1→83:17) to give Compound 3 (3.85 g, 90%) as an oil.

MS: 335/337 [M+H]$^+$, APCI.

A mixture of Compound 3 (1.50 g, 4.48 mmol), 4-propoxypiperidine hydrochloride (1.21 g, 6.72 mmol), and triethylamine (1.87 mL, 13.4 mmol) in THF (22.4 mL) was stirred at room temperature for 2 days. Then, 4-propoxypiperidine hydrochloride (0.16 g, 0.89 mmol) was added thereto, and the mixture was stirred at 50° C. overnight. Water and ethyl acetate were added thereto. The two layers were separated, and the aqueous layer was extracted with ethyl acetate. The combined organic layer was dried over anhydrous sodium sulfate, filtered, and concentrated under reduced pressure. The residue was purified by silica gel column chromatography (hexane:ethyl acetate=19:1→3:1) to give Compound 4 (1.77 g, 89%) as an oil.

MS: 442 [M+H]$^+$, APCI.

A suspension of Compound 4 (1.75 g, 3.96 mmol) and palladium on carbon (5%, 700 mg) in methanol (35 mL) was stirred at room temperature under hydrogen atmosphere. After 3 hours, the insoluble was filtered off, and the filtrate was concentrated under reduced pressure to give Compound 5 (1.36 g, 98%) as a foam.

MS: 352 [M+H]$^+$, APCI.

To a solution of Compound 5 (1.10 g, 3.14 mmol) in THF (22 mL) were added sodium tert-butoxide (604 mg, 6.29 mmol) and N-phenyl-bis(trifluoromethanesulfonimide) (2.25 g, 6.29 mmol) at 0° C., and the mixture was stirred at room temperature overnight. The mixture was cooled back to 0° C., and sodium tert-butoxide (604 mg, 6.29 mmol) and N-phenyl-bis(trifluoromethanesulfonimide) (2.25 g, 6.29 mmol) were added thereto. The mixture was stirred at room temperature for 4 hours. Then, the mixture was cooled back to 0° C., and sodium tert-butoxide (604 mg, 6.29 mmol) and N-phenyl-bis(trifluoromethanesulfonimide) (2.25 g, 6.29 mmol) were added thereto. The mixture was stirred at room temperature overnight. Water was added thereto, and the mixture was extracted with ethyl acetate. The organic layer was dried over anhydrous sodium sulfate, filtered, and concentrated under reduced pressure. The residue was purified by silica gel column chromatography (hexane→hexane:ethyl acetate=4:1) to give Compound 6 (1.00 g, 66%) as an oil.

MS: 484 [M+H]$^+$, APCI.

A suspension of Compound 6 (90 mg, 186 μmol), 3,4-dichlorophenylboronic acid (107 mg, 559 μmol), tetrakis(triphenylphosphine)palladium (44 mg, 37 μmol) and 2 M aqueous sodium carbonate (280 μL, 560 μmol) in 1,2-dimethoxyethane (1.86 mL) was refluxed overnight under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane:ethyl acetate=9:1→7:3) to give Compound 7 (76 mg, 85%) as a viscous oil.

MS: 480/482 [M+H]$^+$, APCI.

Compound 8 was prepared by reacting and treating in the same manner as in Example 1 using Compound 7.

Compound 8: MS: 464/466 [M-Na]−, ESI.

Example 717

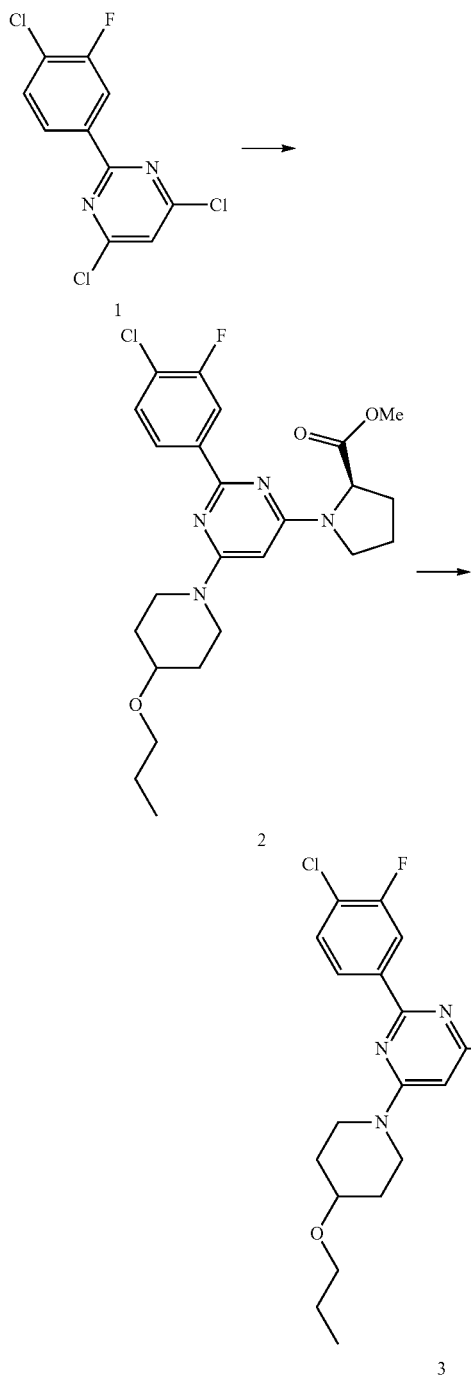

A mixture of Compound 1 (80 mg, 288 μmol), D-proline methyl ester hydrochloride (53 mg, 317 μmol), and triethylamine (100 μL, 721 μmol) in 1-methyl-2-pyrrolidinone (2.88 mL) was stirred at room temperature overnight. The mixture was diluted with ethyl acetate, and washed with water. The organic layer was dried over anhydrous sodium sulfate, filtered, and concentrated under reduced pressure. The residue was combined with 4-propoxypiperidine hydrochloride (156 mg, 867 μmol), sodium methanesulfinate (30 mg, 289 μmol), N,N-diisopropylethylamine (151 μL, 867 μmol), and 1-methyl-2-pyrrolidinone (2.1 mL), and the mixture was stirred at room temperature overnight, followed by at 50° C. for 3 hours. 4-Propoxypiperidine hydrochloride (156 mg, 867 μmol) and N,N-diisopropylethylamine (151 μL, 867 μmol) were added thereto. The mixture was stirred at 50° C. overnight, diluted with water, and extracted with ethyl acetate. The organic layer was dried over anhydrous sodium sulfate, filtered, and concentrated under reduced pressure. The residue was purified by silica gel column chromatography (hexane→hexane:ethyl acetate=22:3) to give Compound 2 (104 mg, 76%) as an oil.

MS: 477/479 [M+H]+, APCI.

Compound 3 was prepared by reacting and treating in the same manner as in Example 1 using Compound 2.

Compound 3: MS: 461/463 [M-Na]−, ESI.

Example 718

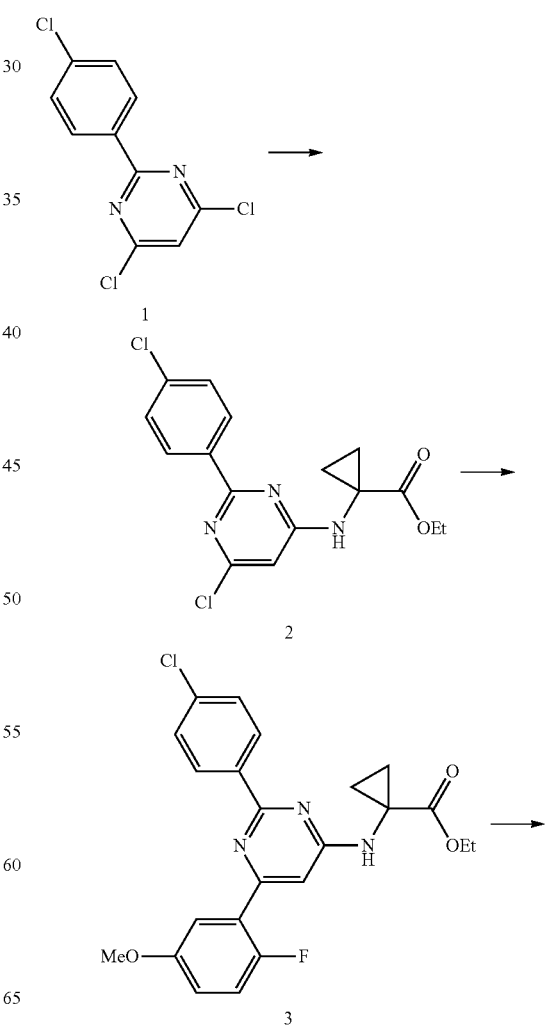

-continued

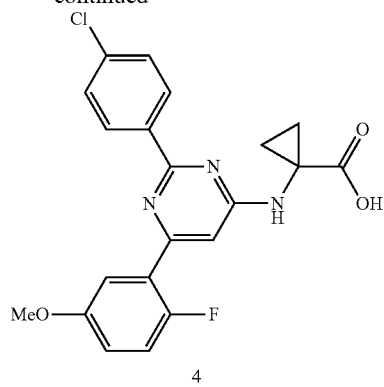

4

A mixture of Compound 1 (2.00 g, 7.71 mmol), ethyl 1-amino-1-cyclopropane carboxylate hydrochloride (1.53 g, 9.25 mmol), and triethylamine (2.69 mL, 19.3 mmol) in 1-methyl-2-pyrrolidinone (38.5 mL) was stirred at 50° C. overnight. The mixture was diluted with ethyl acetate, and washed with water. The organic layer was dried over anhydrous sodium sulfate, filtered, and concentrated under reduced pressure. The residue was purified by silica gel column chromatography (hexane:ethyl acetate=19:1→3:1) to give Compound 2 (2.01 g, 74%) as a solid.

MS: 352/354 [M+H]+, APCI.

A suspension of Compound 2 (100 mg, 284 mmol), 2-fluoro-5-methoxyphenylboronic acid 74 mg, 435 μmol), dichlorobis(triphenylphosphine)palladium (20 mg, 28 μmol) and 2 M aqueous sodium carbonate (426 μL, 852 μmol) in 1,2-dimethoxyethane (2.0 mL) was refluxed overnight under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane:ethyl acetate=19:1→3:1) to give Compound 3 (106 mg, 84%) as powders.

MS: 442/444 [M+H]+, APCI.

Compound 4 was prepared by reacting and treating in the same manner as in Example 1 using Compound 3.

Compound 4: MS: 412/414 [M−H]−, ESI.

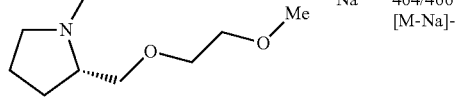

| Example | R | R' | MS (ESI) |
|---|---|---|---|
| 719 | | Na | 464/466 [M-Na]- |
| 720 | | H | 448/450 [M-H]- |
| 721 | | H | 448/450 [M-H]- |
| 722 | | Na | 460/462 [M-Na]- |
| 723 | | Na | 448/450 [M-Na]- |
| 724 | | Na | 448/450 [M-Na]- |
| 725 | | Na | 448/450 [M-Na]- |
| 726 | | Na | 462/464 [M-Na]- |
| 727 | | Na | 462/464 [M-Na]- |

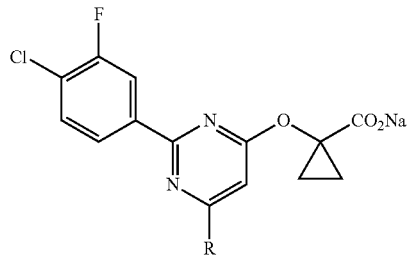

| Example | R | MS (ESI) |
|---|---|---|
| 728 | | 458/460 [M-Na]- |
| 729 | | 462/464 [M-Na]- |
| 730 | | 420/422 [M-Na]- |

-continued
| | | | |
|---|---|---|---|
| 731 | 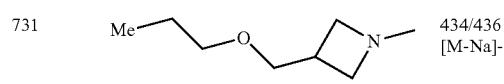 | 434/436 [M-Na]- | |
| 732 | 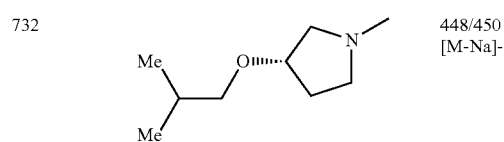 | 448/450 [M-Na]- | |
| 733 | 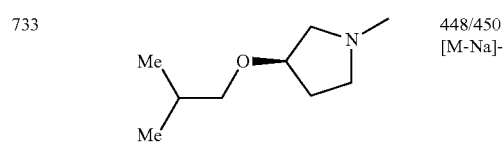 | 448/450 [M-Na]- | |
| 734 | 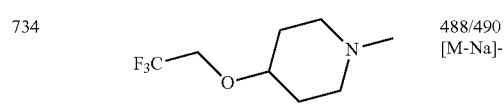 | 488/490 [M-Na]- | |
| 735 | 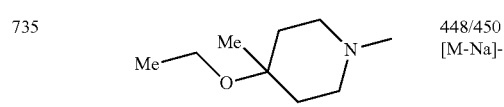 | 448/450 [M-Na]- | |
| 736 | 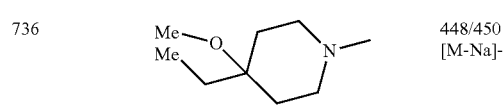 | 448/450 [M-Na]- | |
| 737 | 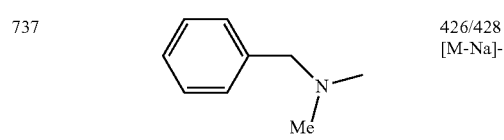 | 426/428 [M-Na]- | |
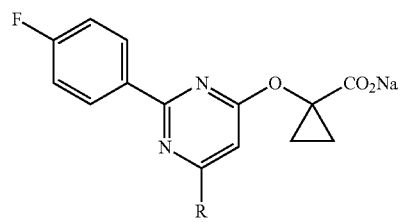
| Example | R | MS (ESI) |
|---|---|---|
| 738 | 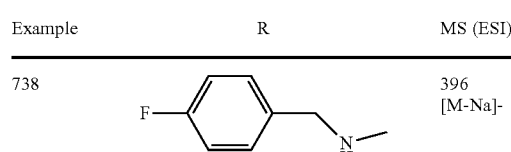 | 396 [M-Na]- |
| 739 | 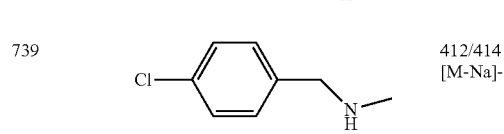 | 412/414 [M-Na]- |
| 740 | 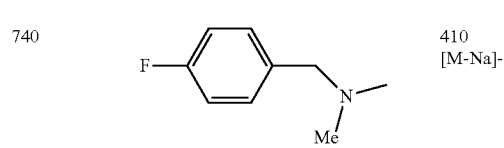 | 410 [M-Na]- |
-continued
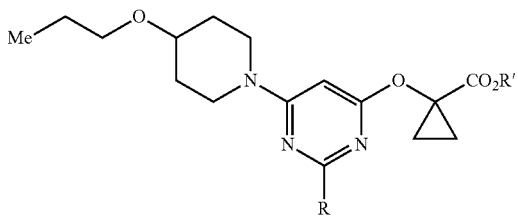
| Example | R | R' | MS (ESI) |
|---|---|---|---|
| 741 | 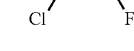 | H | 448/450 [M-H]- |
| 742 | 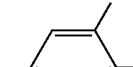 | Na | 448/450 [M-Na]- |
| 743 | 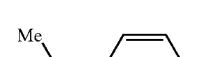 | Na | 438 [M-Na]- |
| 744 | 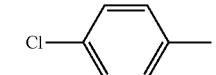 | Na | 448/450 [M-Na]- |
| 745 | 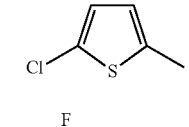 | Na | 436/438 [M-Na]- |
| 746 | 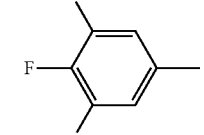 | Na | 450 [M-Na]- |
| 747 | 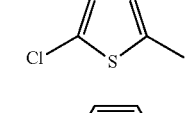 | Na | 450/452 [M-Na]- |
| 748 | 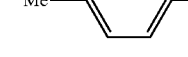 | Na | 410 [M-Na]- |
| 749 | 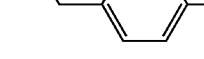 | Na | 424 [M-Na]- |
| 750 | 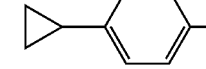 | Na | 436 [M-Na]- |

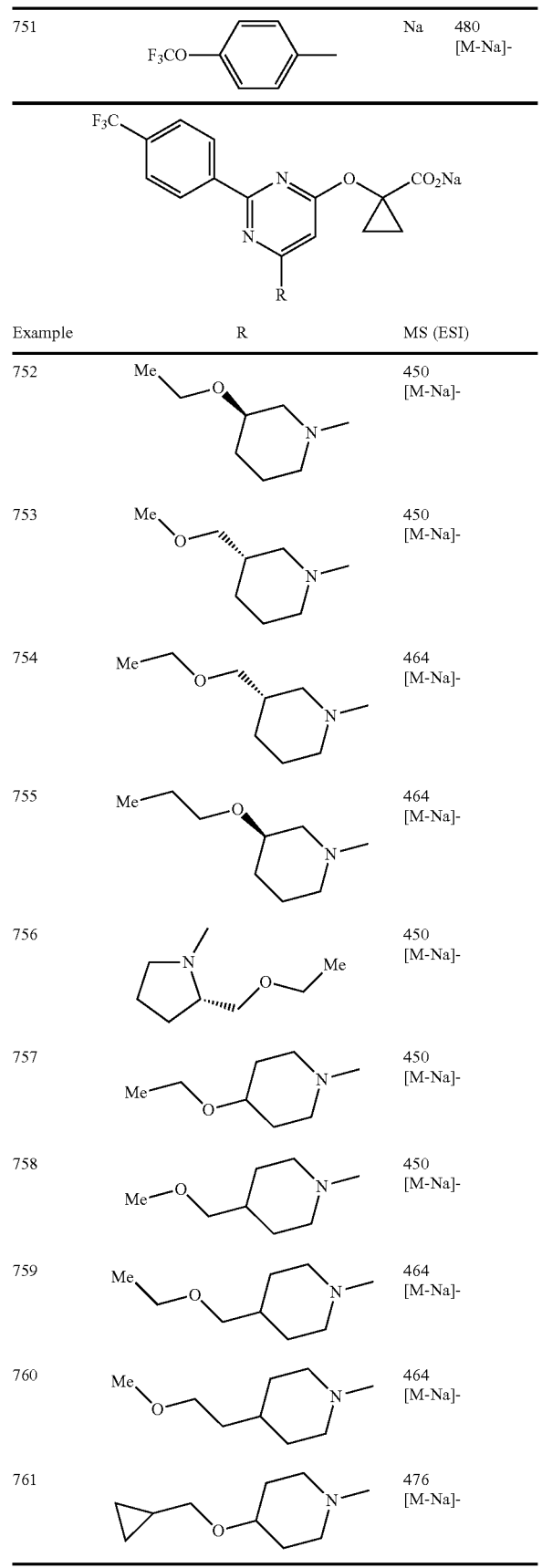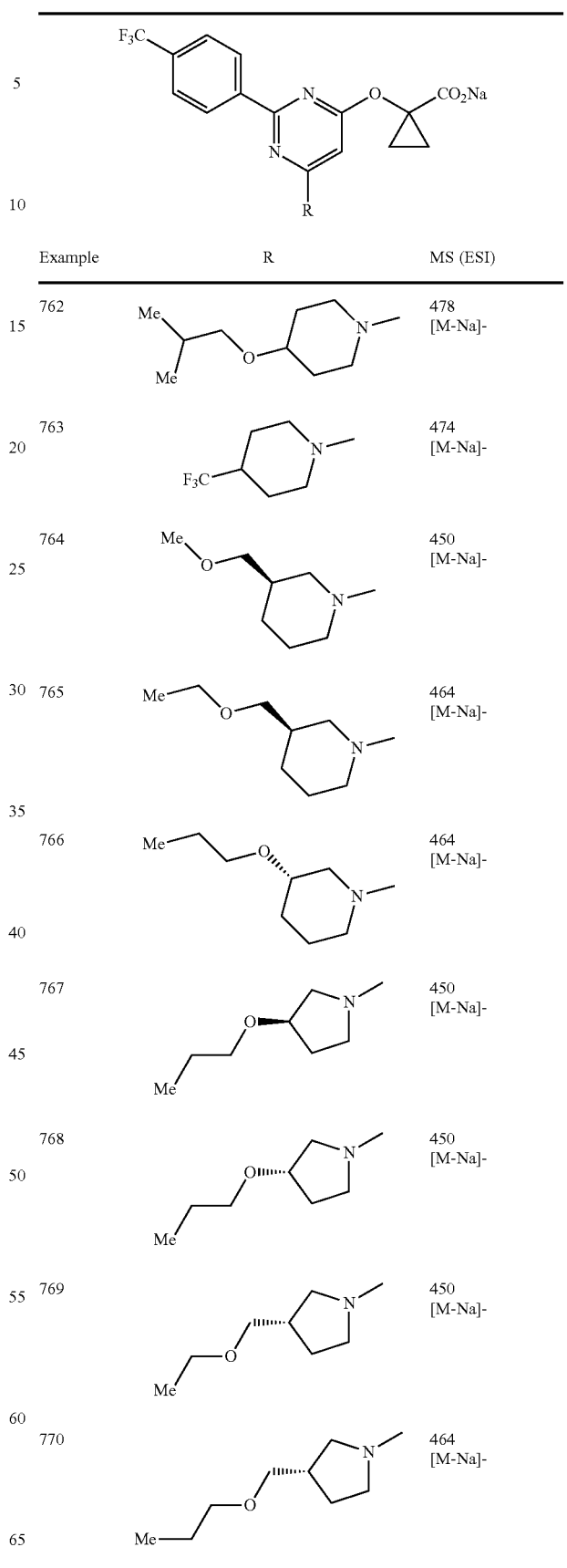

-continued
| Example | R | MS (ESI) |
|---|---|---|
| 771 | 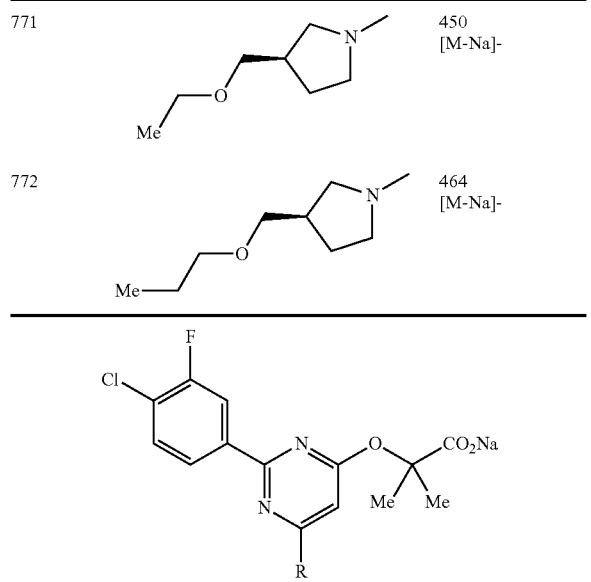 | 450 [M-Na]- |
| 772 | | 464 [M-Na]- |
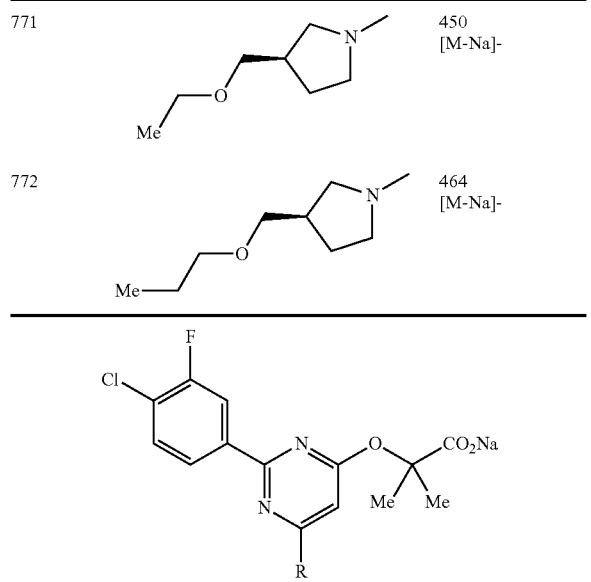
| Example | R | MS (ESI) |
|---|---|---|
| 773 | | 450/452 [M-Na]- |
| 774 | | 450/452 [M-Na]- |
| 775 | | 464/466 [M-Na]- |
| 776 | | 464/466 [M-Na]- |
| 777 | | 466/468 [M-Na]- |
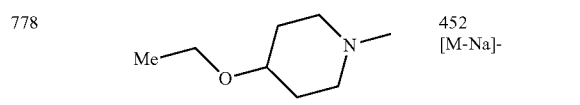
| Example | R | MS (ESI) |
|---|---|---|
| 778 | | 452 [M-Na]- |
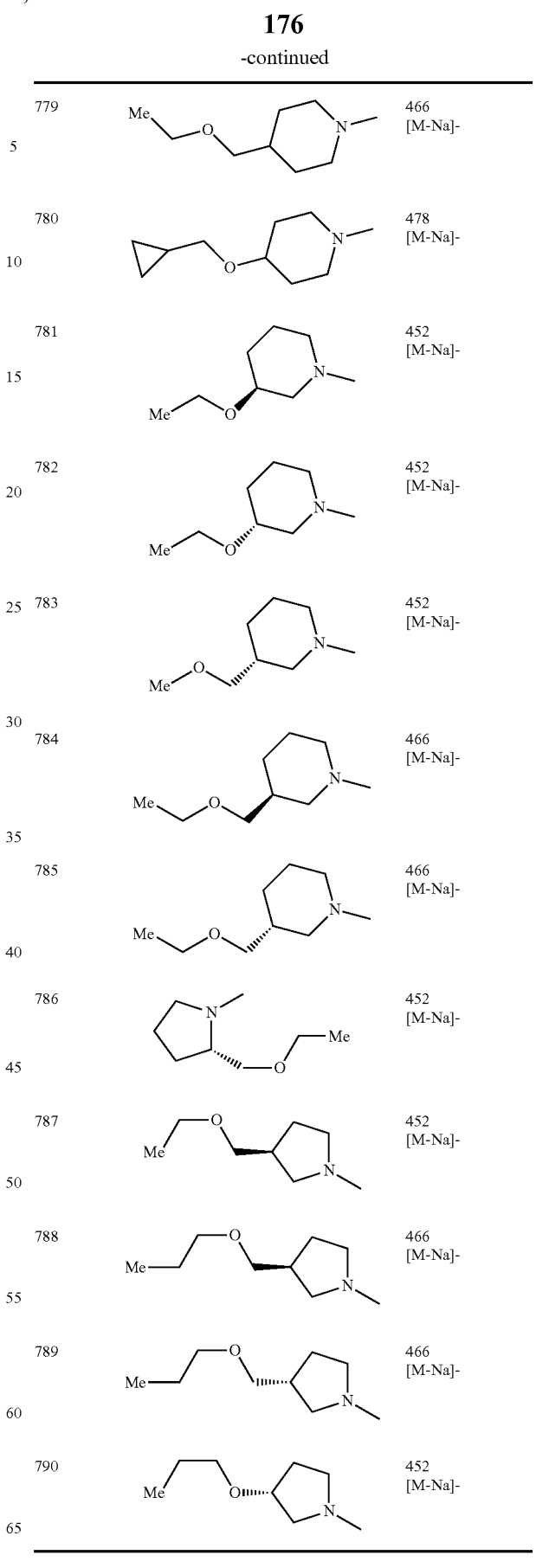
-continued
| Example | R | MS (ESI) |
|---|---|---|
| 779 | | 466 [M-Na]- |
| 780 | | 478 [M-Na]- |
| 781 | | 452 [M-Na]- |
| 782 | | 452 [M-Na]- |
| 783 | | 452 [M-Na]- |
| 784 | | 466 [M-Na]- |
| 785 | | 466 [M-Na]- |
| 786 | | 452 [M-Na]- |
| 787 | | 452 [M-Na]- |
| 788 | | 466 [M-Na]- |
| 789 | | 466 [M-Na]- |
| 790 | | 452 [M-Na]- |

177
-continued

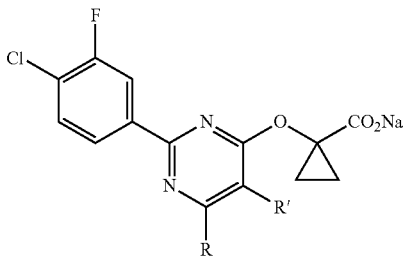

| Example | R | R' | MS (ESI) |
|---|---|---|---|
| 791 | Me~O~(N-Me piperidin-4-yl) | F | 466/468 [M-Na]- |
| 792 | Me2CH-O-(N-Me piperidin-4-yl) | F | 466/468 [M-Na]- |
| 793 | Me~O~(N-Me piperidin-4-yl) | Me | 462/464 [M-Na]- |
| 794 | Me2CH-O-(N-Me piperidin-4-yl) | Me | 462/464 [M-Na]- |
| 795 | Me~O~(N-Me piperidin-4-yl) | OMe | 478/480 [M-Na]- |
| 796 | Me2CH-O-(N-Me piperidin-4-yl) | OMe | 478/480 [M-Na]- |

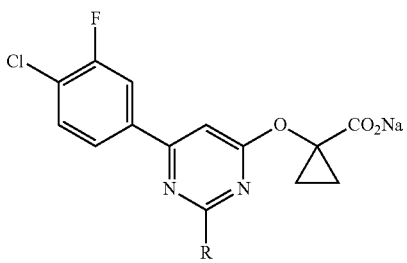

| Example | R | MS (ESI) |
|---|---|---|
| 797 | iBu-O-(N-Me piperidin-4-yl) | 462/464 [M-Na]- |
| 798 | Me(CH2)3-O-(N-Me piperidin-4-yl) | 462/464 [M-Na]- |
| 799 | Me-O-(CH2)3-(N-Me piperidin-4-yl) | 462/464 [M-Na]- |

178
-continued

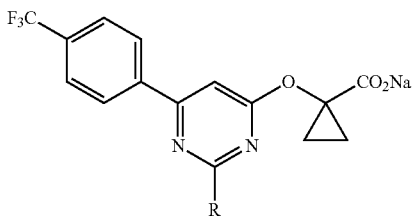

| Example | R | MS (ESI) |
|---|---|---|
| 800 | Me~(CH2)2~O~(N-Me piperidin-4-yl) | 464 [M-Na]- |
| 801 | Me~(CH2)2~O~(3S-N-Me piperidin-3-yl) | 464 [M-Na]- |
| 802 | MeO-CH2-(N-Me piperidin-3-yl) | 450 [M-Na]- |
| 803 | Me-CH2-O-CH2-(N-Me piperidin-3-yl) | 464 [M-Na]- |
| 804 | Me(CH2)2-O-CH2-(N-Me pyrrolidin-3-yl) | 464 [M-Na]- |
| 805 | Me(CH2)2-O-CH2-(N-Me pyrrolidin-3-yl) | 464 [M-Na]- |
| 806 | Me(CH2)3-O-(N-Me piperidin-4-yl) | 478 [M-Na]- |
| 807 | Me2CH-O-(N-Me piperidin-4-yl) | 464 [M-Na]- |
| 808 | Me-CH2-O-CH2-(N-Me piperidin-4-yl) | 464 [M-Na]- |
| 809 | Me-O-(CH2)2-(N-Me piperidin-4-yl) | 464 [M-Na]- |
| 810 | Me-O-(CH2)3-(N-Me piperidin-4-yl) | 478 [M-Na]- |

| | | -continued |
|---|---|---|
| 811 | 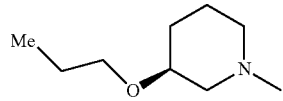 | 464 [M-Na]- |
| 812 | 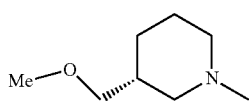 | 450 [M-Na]- |
| 813 | 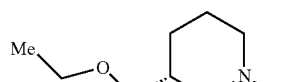 | 464 [M-Na]- |
Example 814
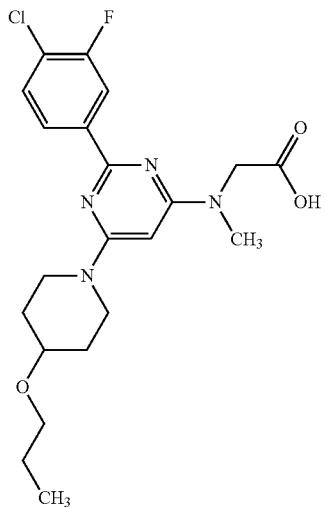 [SMILES: CCCOC1CCN(c2cc(N(C)CC(=O)O)nc(-c3ccc(Cl)c(F)c3)n2)CC1]
MS 435/437[M-Na]– (ESI).
Example 815
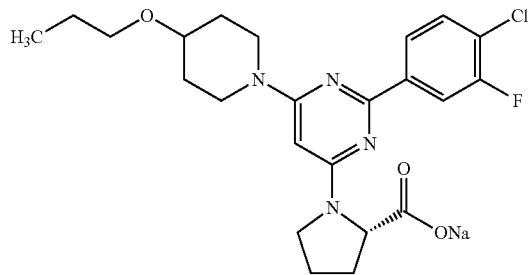
MS: 461/463[M-Na]– (ESI).
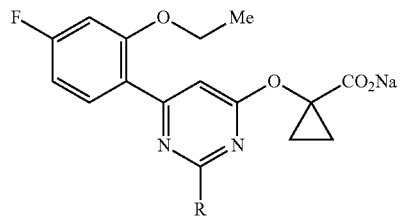
| Example | R | MS (ESI) |
|---|---|---|
| 816 | 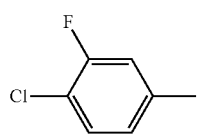 | 445/447 [M-Na]- |
| 817 | 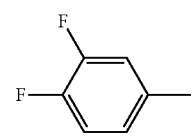 | 429 [M-Na]- |
| 818 | 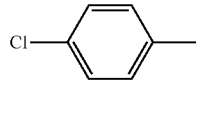 | 472/429 [M-Na]- |
| 819 | 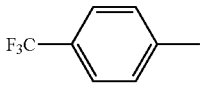 | 461 [M-Na]- |
| 820 | 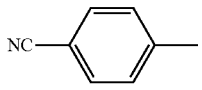 | 418 [M-Na]- |
| 821 | 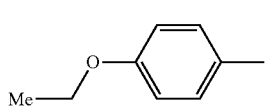 | 437 [M-Na]- |
| 822 | 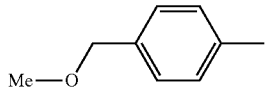 | 437 [M-Na]- |
| 823 | 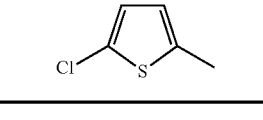 | 433/435 [M-Na]- |

Example 824
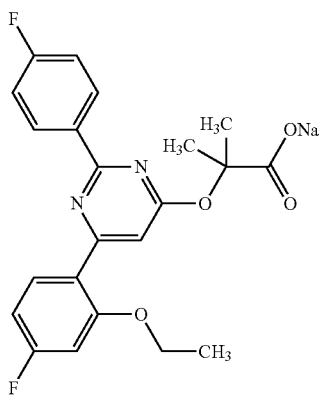
MS: 413[M-Na]– (ESI).
| Example | R | MS (ESI) |
|---|---|---|
| 825 | 4-F-C6H4 | 429 [M-Na]- |
| 826 | 3,4-diF-C6H3 | 447 [M-Na]- |
| Example | R | R' | MS (ESI) |
|---|---|---|---|
| 827 | 4-F-C6H4 | Na | 417 [M-Na]- |
| 828 | 4-MeO-C6H4 | Na | 429 [M-Na]- |
| 829 | 4-(MeOCH2)-C6H4 | Na | 443 [M-Na]- |
| 830 | 2-MeO-5-methylpyridin-? | Na | 430 [M-Na]- |
| 831 | 5-F-2-OMe-4-methylphenyl | Na | 447 [M-Na]- |
| 832 | 4-F-2-methyl-... OMe | Na | 447 [M-Na]- |
| 833 | 2-EtO-5-methylpyridin-? | H | 444 [M-H]- |
| 834 | 2-EtO-3-methylpyridin-? | H | 444 [M-H]- |
| Example | R | R' | MS (ESI) |
|---|---|---|---|
| 835 | 5-F-2-methylphenyl (Me) | H | 381 [M-H]- |
| 836 | 3-Cl-... F | H | 401/403 [M-H]- |
| 837 | 2-Cl-... F | H | 401/403 [M-H]- |
| 838 | 4-CF3-C6H4 | H | 417 [M-H]- |
| 839 | 4-cyclopropylpyridin-? | H | 389 [M-H]- |

-continued
| | | | |
|---|---|---|---|
| 840 | 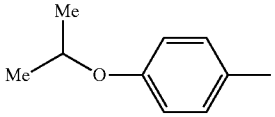 | H | 407 [M-H]- |
| 841 | 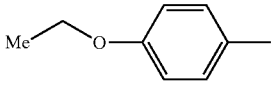 | H | 393 [M-H]- |
| 842 | 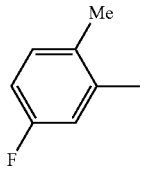 | H | 381 [M-H]- |
| 843 | 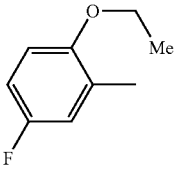 | Na | 411 [M-Na]- |
| 844 | 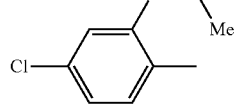 | Na | 427/429 [M-Na]- |
| 845 | 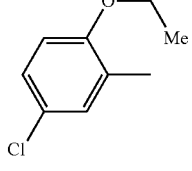 | Na | 427/429 [M-Na]- |
| 846 | 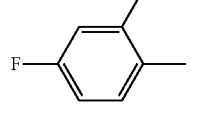 | H | 411 [M-H]- |
| 847 | 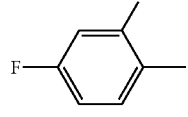 | H | 392 [M-H]- |
| 848 | 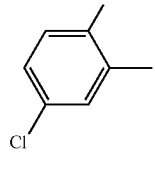 | H | 397/399 [M-Na]- |
| 849 | 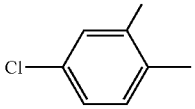 | H | 397/399 [M-Na]- |
-continued
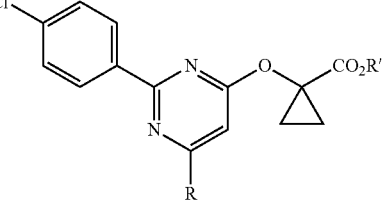
| Example | R | R' | MS (ESI) |
|---|---|---|---|
| 850 | 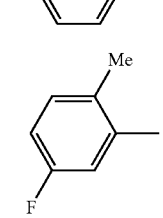 | Na | 427/429 [M-H]- |
| 851 | 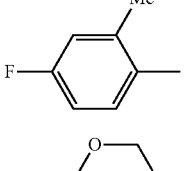 | Na | 397/399 [M-Na]- |
| 852 | 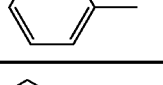 | Na | 397/399 [M-Na]- |
| 853 | 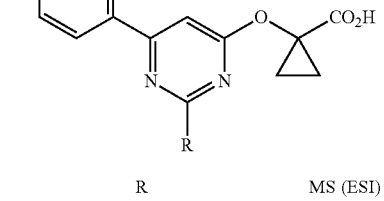 | H | 410/412 [M-Na]- |
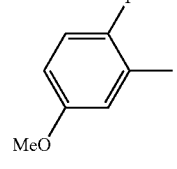
| Example | R | MS (ESI) |
|---|---|---|
| 854 | 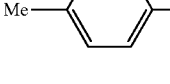 | 397 [M-H]- |
| 855 | 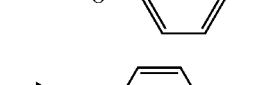 | 363 [M-H]- |
| 856 | 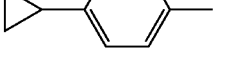 | 393 [M-H]- |
| 857 |  | 389 [M-H]- |

Example 858
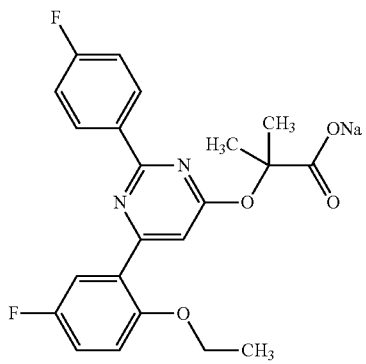
MS: 413[M-Na]– (ESI).
Example 859
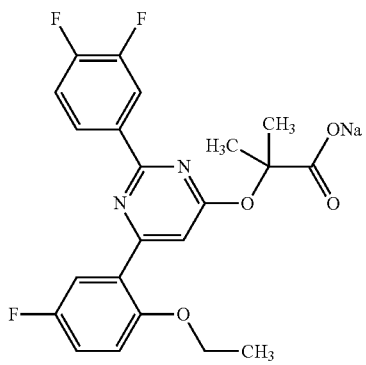
MS: 431[M-Na]– (ESI).
Example 860
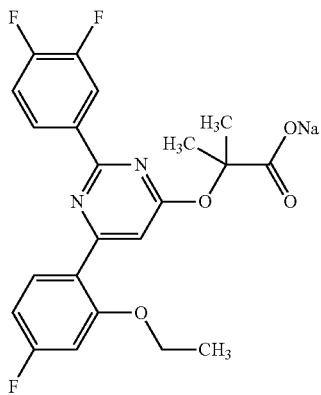
MS: 431[M-Na]– (ESI).
Example 861
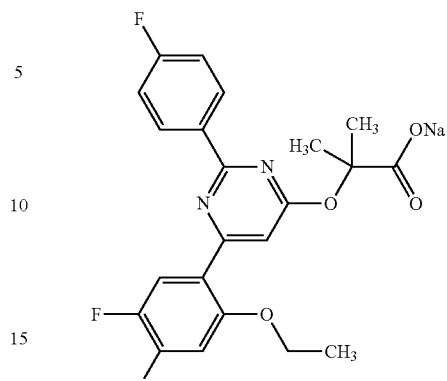
MS: 431[M-Na]– (ESI).
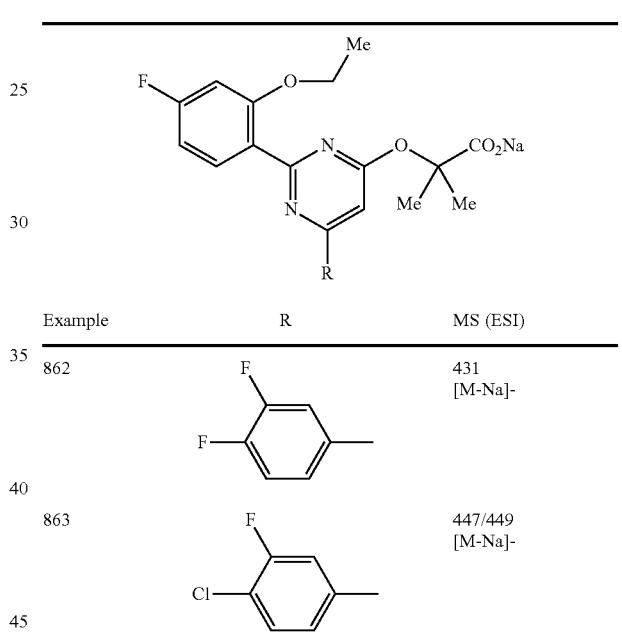
| Example | R | MS (ESI) |
|---|---|---|
| 862 | ![2,3-difluorophenyl] | 431 [M-Na]- |
| 863 | ![3-fluoro-4-chlorophenyl] | 447/449 [M-Na]- |
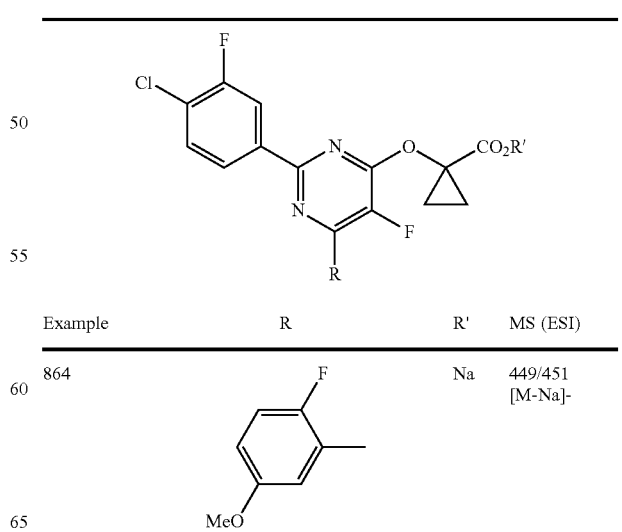
| Example | R | R' | MS (ESI) |
|---|---|---|---|
| 864 | ![4-fluoro-3-methoxyphenyl with MeO] | Na | 449/451 [M-Na]- |

-continued
| Ex. | R | | MS (ESI) |
|---|---|---|---|
| 865 | 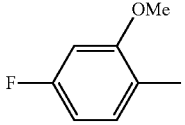 | Na | 449/451 [M-Na]- |
| 866 | 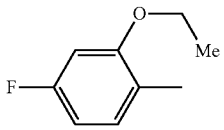 | Na | 463/465 [M-Na]- |
| 867 | 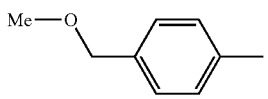 | H | 445/447 [M-H]- |
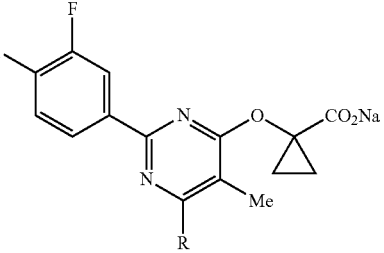
| Example | R | MS (ESI) |
|---|---|---|
| 868 | 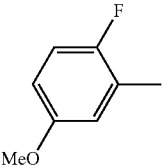 | 445/447 [M-Na]- |
| 869 | 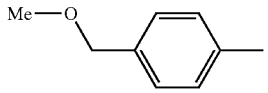 | 441/443 [M-Na]- |
| 870 | 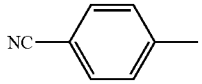 | 422/424 [M-Na]- |
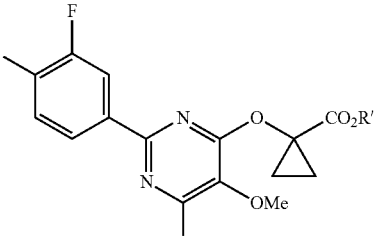
| Example | R | R' | MS (ESI) |
|---|---|---|---|
| 871 |  | Na | 457/459 [M-Na]- |
| 872 | 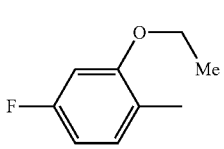 | Na | 475/477 [M-Na]- |
-continued
| Ex. | R | | MS (ESI) |
|---|---|---|---|
| 873 | 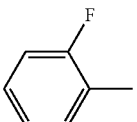 | Na | 461/463 [M-Na]- |
| 874 | 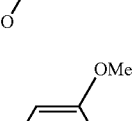 | H | 461/463 [M-H]- |
| Example | R | MS (ESI) |
|---|---|---|
| 875 | 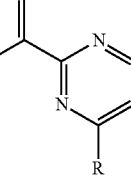 | 416 [M-H]- |
| 876 |  | 388 [M-H]- |
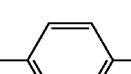
| Example | R | MS (ESI) |
|---|---|---|
| 877 | 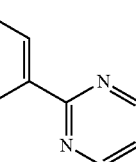 | 412/414 [M-H]- |
| 878 | 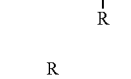 | 412/414 [M-H]- |
| 879 | 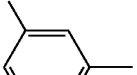 | 396/398 [M-H]- |

Example 880

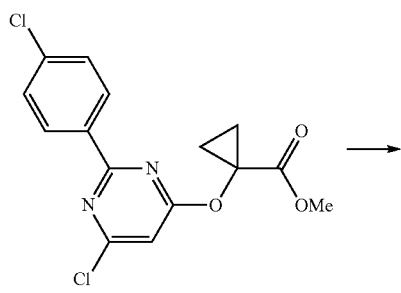

1

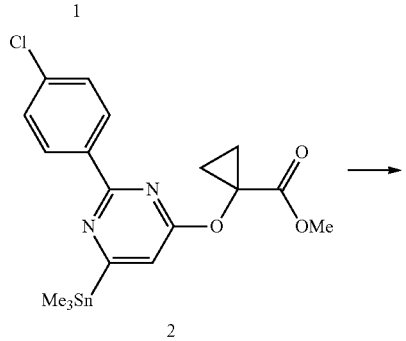

2

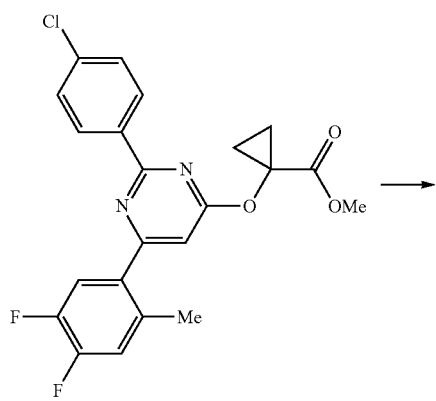

3

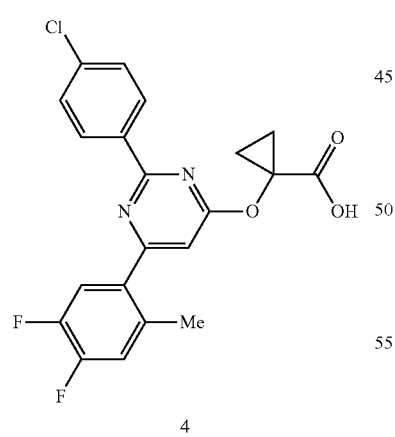

4

A suspension of Compound 1 (3.00 g, 8.85 mmol), hexamethylditin (3.67 mL, 17.7 mmol), and tetrakis(triphenylphosphine)palladium (358 mg, 310 μmol) in 1,4-dioxane (53.1 mL) was refluxed for 1.5 hours under argon atmosphere. After cooling to room temperature, the volatile was removed under reduced pressure, and the residue was purified by alumina gel column chromatography (hexane:ethyl acetate=97:3) to give Compound 2 (2.55 g, 62%) as a solid.

MS: 465/467/469 [M+H]$^+$, APCI.

A suspension of Compound 2 (100 mg, 214 μmol), 2-bromo-4,5-difluorotoluene (53.1 mg, 257 μmol), and dichlorobis(triphenylphosphine)palladium (15.0 mg, 21.4 μmol) in toluene (4.28 mL) was refluxed for 20 hours under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane:ethyl acetate=19:1) to give Compound 3 (55.3 mg, 60%) as a solid.

MS: 431/433 [M+H]$^+$, APCI.

Compound 4 was prepared by reacting and treating in the same manner as in example 186 using Compound 3.

Compound 4: MS: 415/417 [M−H]−, ESI.

Example 881

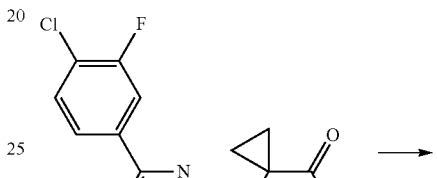

1

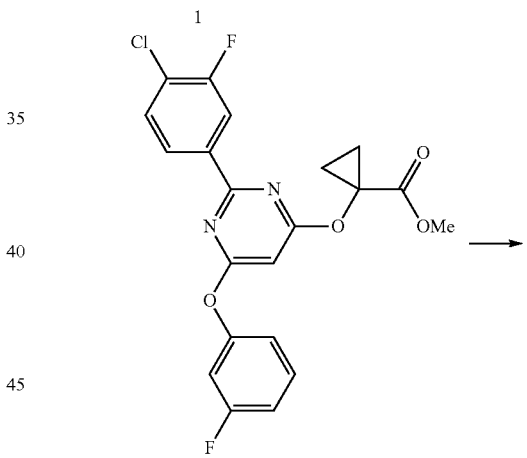

2

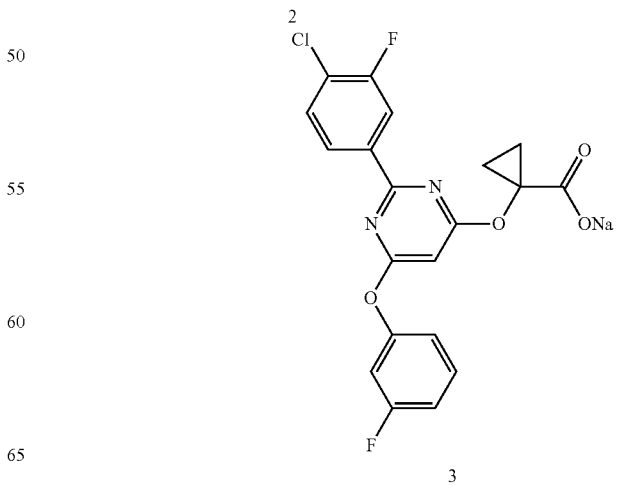

3

A suspension of Compound 1 (50.0 mg, 140 μmol), 3-fluorophenol (24.3 mg, 210 μmol), and potassium carbonate (57.7 mg, 420 μmol) in DMSO (1.40 mL) was stirred at room temperature overnight. The reaction mixture was quenched with saturated aqueous ammonium hydroxide and extracted with ethyl acetate. The organic layer was washed with water, filtered through Chem Elut® (Varian Inc.), and concentrated under reduced pressure. The residue was purified by silica gel column chromatography (hexane→hexane:ethyl acetate=15:1) to give Compound 2 (56.8 mg, 94%) as a solid.

MS: 433/435 [M+H]$^+$, APCI.

Compound 3 was prepared by reacting and treating in the same manner as in Example 1 using Compound 2.

Compound 3: MS: 417/419 [M-Na]-, ESI.

Example 882

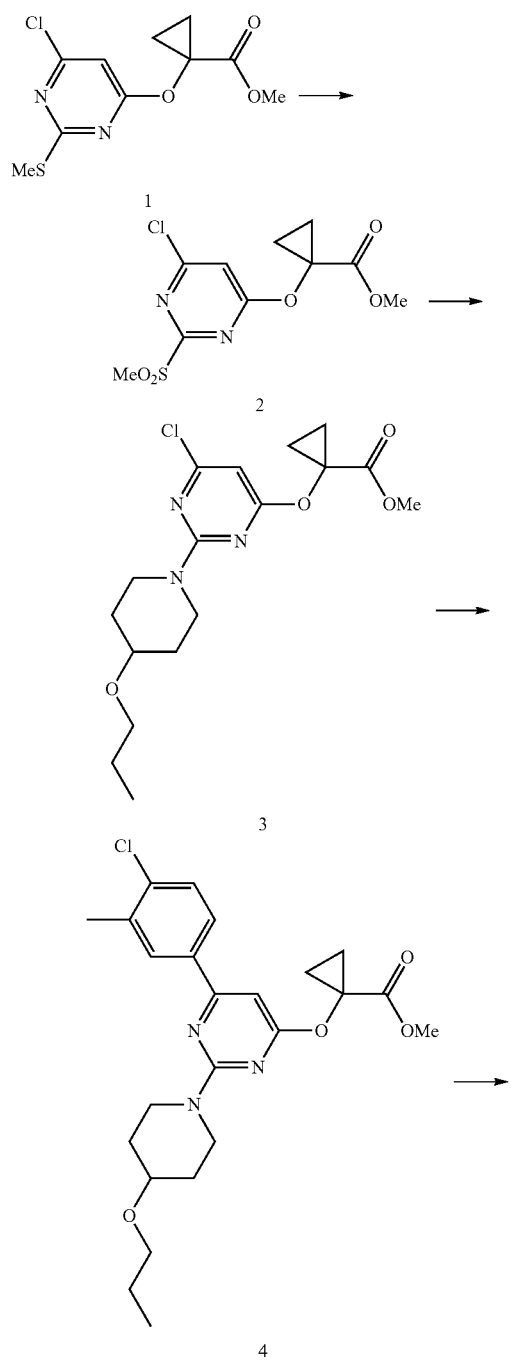

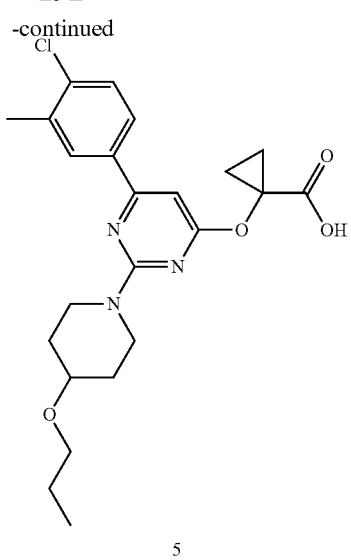

To a solution of Compound 1 (10.0 g, 36.4 mmol) in chloroform (182 mL) was added 3-chloroperoxybenzoic acid (18.4 g, 80.1 mmol) at 0° C. and the mixture was stirred at the same temperature for 1.5 hours, then stirred at room temperature for 2 hours. Additional 3-chloroperoxybenzoic acid (2.51 g, 10.9 mmol) was added at 0° C. and the mixture was stirred at room temperature overnight. Saturated aqueous sodium sulfite and saturated aqueous sodium bicarbonate were added thereto and the mixture was extracted with chloroform. The organic layer was washed with saturated aqueous sodium bicarbonate and brine, dried over anhydrous sodium sulfate, and concentrated under reduced pressure. The residue was triturated with diisopropyl ether to give Compound 2 (11.0 g, 98%) as powders.

MS: 307/309 [M+H]$^+$, APCI.

To a suspension of Compound 2 (1.10 g, 3.26 mmol) and 4-propoxypiperidine hydrochloride (644 mg, 3.59 mmol) in THF (16.3 mL) was added N,N-diisopropylethylamine (1.42 ml, 8.15 mmol) at 0° C. and the mixture was stirred at room temperature overnight. The reaction mixture was poured into water and extracted with ethyl acetate. The organic layer was filtered through Chem Elute® (Varian Inc.), and concentrated under reduced pressure. The residue was purified by silica gel column chromatography (hexane:ethyl acetate=4:1→1:1) to give Compound 3 (537 mg, 45%) as a solid.

MS: 370/372 [M+H]$^+$, APCI.

A suspension of Compound 3 (80.0 mg, 216 μmol), 4-chloro-3-methylphenylboronic acid 47.9 mg, 281 μmol), dichlorobis(triphenylphosphine)palladium (15.5 mg, 21.6 μmol) and 2 M aqueous sodium carbonate (216 μL, 433 μmol) in 1,2-dimethoxyethane (2.16 mL) was refluxed overnight under argon atmosphere. After cooling, the reaction mixture was diluted with ethyl acetate, filtered through Chem Elut® (Varian Inc.) and Bond Elut® (Varian Inc.), and concentrated under reduced pressure. The residue was purified by silica gel column chromatography (hexane→hexane:ethyl acetate=17:3) to give Compound 4 (103 mg, quant.) as a viscous oil.

MS: 460/462 [M+H]$^+$, APCI.

Compound 5 was prepared by reacting and treating in the same manner as in Example 1 using Compound 4.

Compound 5: MS: 444/446 [M-H]-, ESI.

Example 883

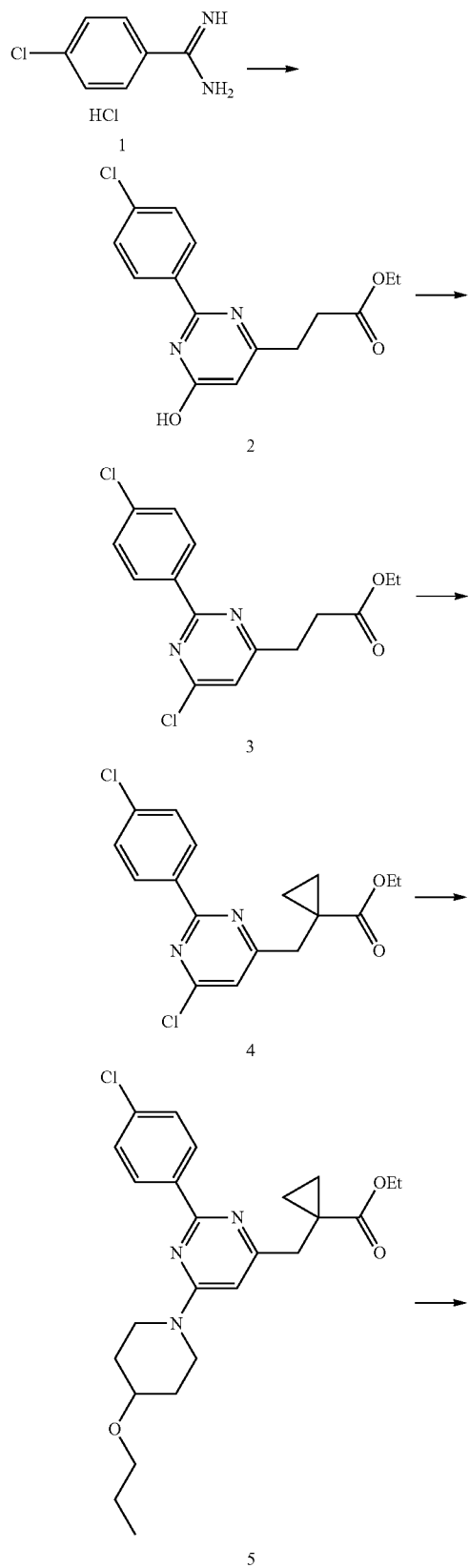

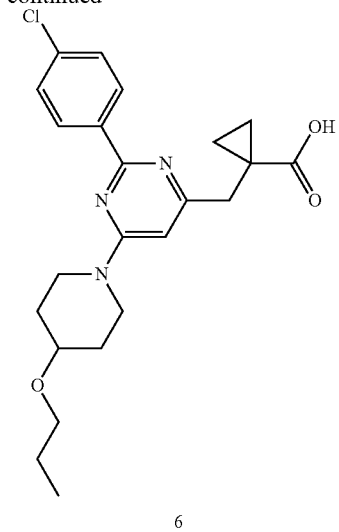

A solution of sodium ethoxide was prepared by dissolving sodium hydride (60%, 345 mg, 8.84 mmol) in absolute EtOH (15.0 mL). Compound 1 (1.50 g, 7.78 mmol) and 3-oxohexanedioic acid diethyl ether (2.04 g, 9.42 mmol) were added thereto at 0° C., and the mixture was refluxed for 12 hours. After cooling, the reaction mixture was concentrated under reduced pressure. The residue was dissolved in water and acidified with 2 M hydrochloric acid. The precipitate was collected by filtration to give Compound 2 (1.80 g, 75%) as a solid.

MS: 307/309 [M+H]+, APCI.

A mixture of Compound 2 (1.00 g, 3.26 mmol) and phosphoryl chloride (9.12 mL) was refluxed for 1 hour. After cooling, the reaction mixture was concentrated under reduced pressure. The residue was poured into water and extracted with ethyl acetate. The organic layer was concentrated under reduced pressure. The residue was purified by silica gel column chromatography (hexane→hexane:ethyl acetate=17:3) to give Compound 3 (660 mg, 62%) as a solid.

MS: 325/327 [M+H]+, APCI.

To a solution of Compound 3 (472 mg, 1.45 mmol) in THF (9.40 mL) were added sodium hexamethyldisilylamide (3.38 ml, 3.48 mmol) at −78° C., and the mixture was stirred at −78° C. for 30 minutes. To the reaction mixture was added ethylene dibromide (379 μl, 4.35 mmol) at −78° C., and the mixture was stirred at −78° C. for 3 hours. The reaction mixture was poured into water and extracted with ethyl acetate. The organic layer was concentrated under reduced pressure. The residue was purified by silica gel column chromatography (hexane→hexane:ethyl acetate=17:3) to give a crude product of Compound 4 (180 mg).

To the solution of the crude product of Compound 4 (90.0 mg) in 1-methyl-2-pyrrolidone (1.80 mL) were added 4-propoxypiperidine hydrochloride (92.1 mg, 512 μmol) and N,N-diisopropylethylamine (179 μl, 1.03 mmol), and the mixture was stirred at 50° C. overnight. The reaction mixture was poured into water and extracted with ethyl acetate. The organic layer was concentrated under reduced pressure. The residue was purified by silica gel column chromatography (hexane→hexane:ethyl acetate=17:3) to give Compound 5 (39.3 mg, 12% from Compound 3) as a solid.

MS: 458/460 [M+H]+, APCI.

Compound 6 was prepared by reacting and treating in the same manner as in Example 1 using Compound 5.

Compound 6: MS: 431/433 [M−H]−, ESI.

Example 884a

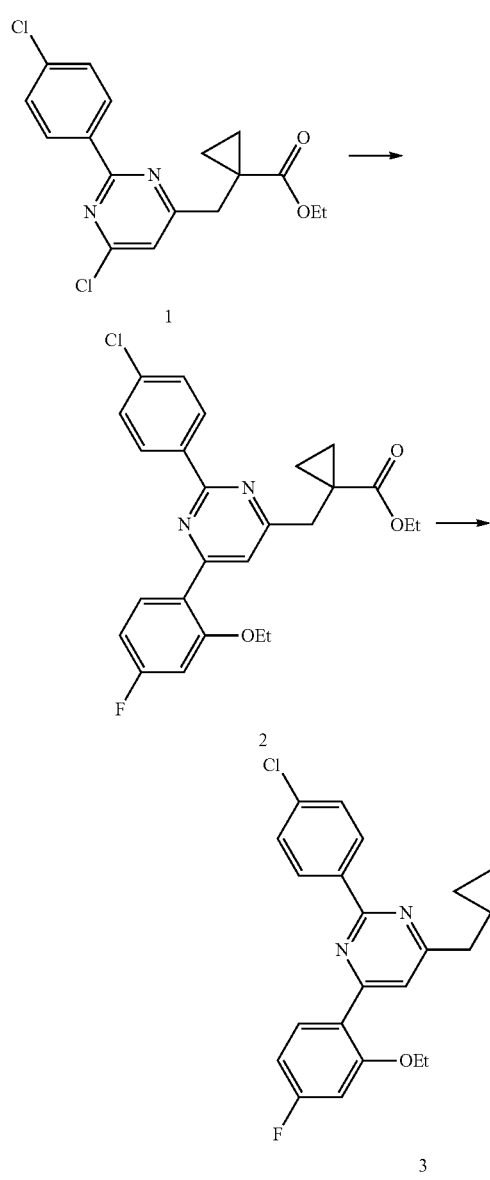

Compound 2 was prepared by reacting and treating in the same manner as in Example 186 using Compound 1.
Compound 2: MS: 455/457 [M+H]+, APCI.
Compound 3 was prepared by reacting and treating in the same manner as in Example 186 using Compound 2.
MS: 425/427 [M−Na]−, ESI.

Example 884b

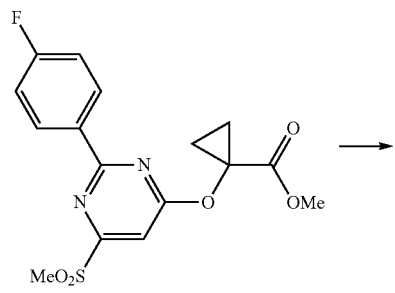

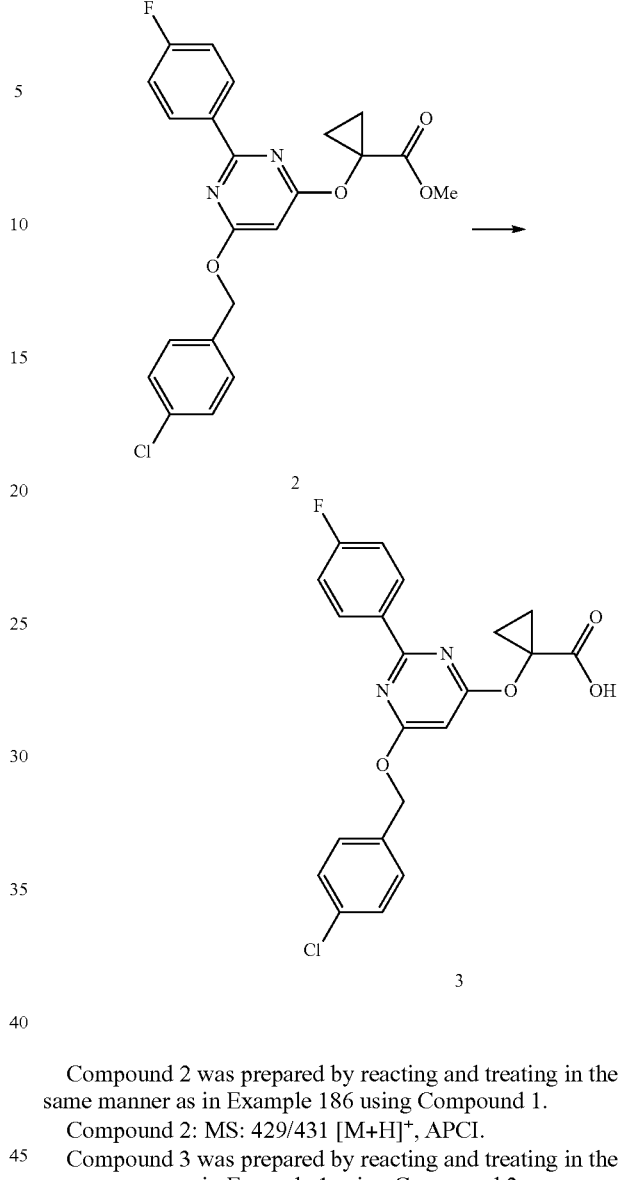

Compound 2 was prepared by reacting and treating in the same manner as in Example 186 using Compound 1.
Compound 2: MS: 429/431 [M+H]+, APCI.
Compound 3 was prepared by reacting and treating in the same manner as in Example 1 using Compound 2.
Compound 3: MS: 413/415 [M−H]−, ESI.

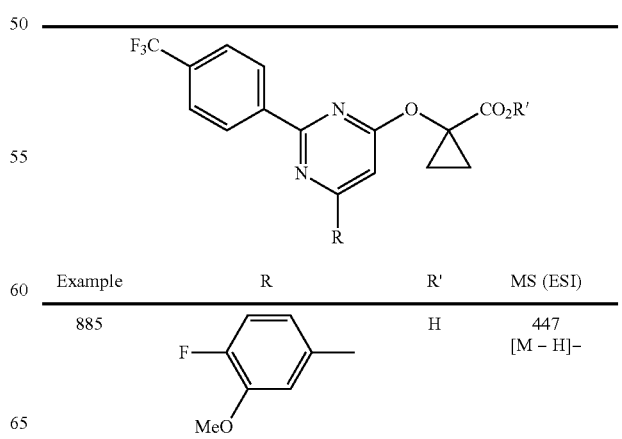

| Example | R | R' | MS (ESI) |
|---|---|---|---|
| 885 | 3-F, 4-MeO phenyl | H | 447 [M − H]− |

| | | | |
|---|---|---|---|
| 886 | 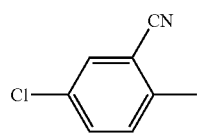 | Na | 424 [M – Na]– |
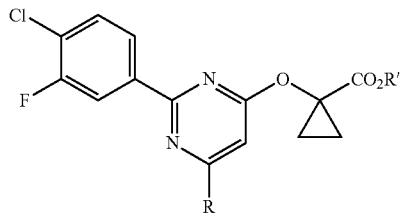
| Example | R | R' | MS (ESI) |
|---|---|---|---|
| 887 | 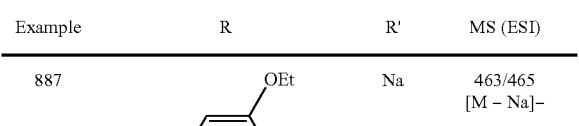 | Na | 463/465 [M – Na]– |
| 888 | 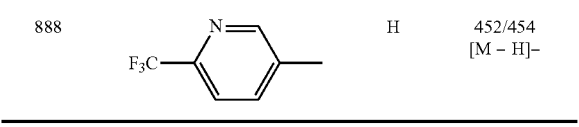 | H | 452/454 [M – H]– |
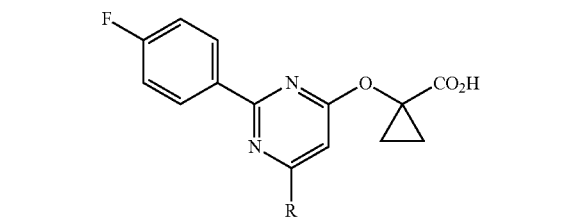
| Example | R | | MS (ESI) |
|---|---|---|---|
| 889 | 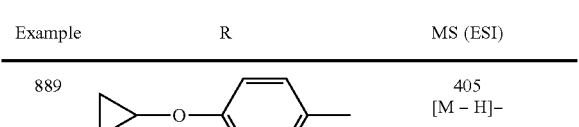 | | 405 [M – H]– |
| 890 | 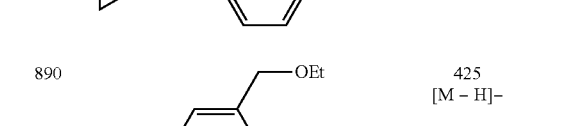 | | 425 [M – H]– |
| 891 | 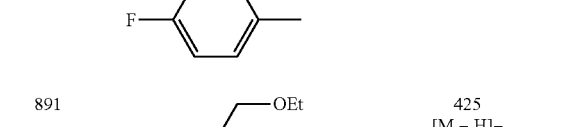 | | 425 [M – H]– |
| 892 | 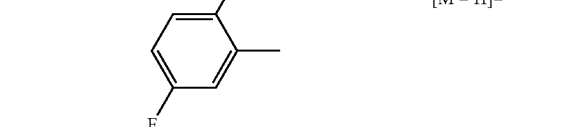 | | 395 [M – H]– |
| | | |
|---|---|---|
| 893 | 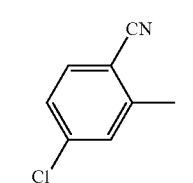 | 408/410 [M – H]– |
| 894 | 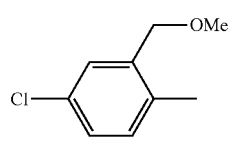 | 408/410 [M – H]– |
| 895 | 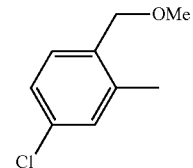 | 427/429 [M – H]– |
| 896 | 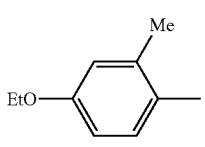 | 427/429 [M – H]– |
| 897 | 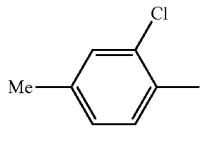 | 407 [M – H]– |
| 898 | 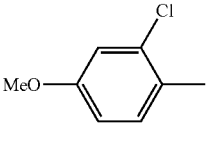 | 397/399 [M – H]– |
| 899 | 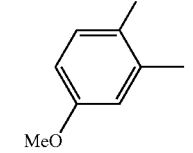 | 413/415 [M – H]– |
| 900 | 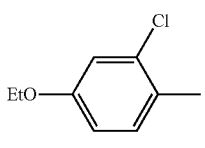 | 413/415 [M – H]– |
| 901 | 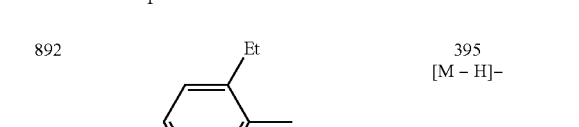 | 427/429 [M – H]– |
| 902 |  | 421 [M – H]– |

| Example | R (structure) | MS (ESI) |
|---|---|---|
| 903 | 2-methyl-5-(trifluoromethyl)benzyl with OMe (F₃C-phenyl-CH₂-OMe, Me) | 461 [M – H]– |
| 904 | 2-methyl-4-(trifluoromethyl)benzyl with OMe | 461 [M – H]– |
| 905 | 2-methyl-3-methyl-5-(trifluoromethyl)phenyl (F₃C, Me, Me) | 431 [M – H]– |
| 906 | 2,3-dimethyl-5-(trifluoromethyl)phenyl | 431 [M – H]– |
| 907 | 4-fluoro-2-(trifluoromethyl)-methylphenyl (CF₃, F, Me) | 435 [M – H]– |
| 908 | 2-(trifluoromethyl)-4-fluoro-6-methylphenyl | 435 [M – H]– |
| 909 | 2,3-difluoro-6-methylphenyl (F, Me, F) | 399 [M – H]– |
| 910 | 4,5-difluoro-2-methylphenyl (Me, F, F) | 399 [M – H]– |
| 911 | 6-ethoxy-2-methyl-3-methylpyridinyl (EtO-pyridine-Me, Me) | 408 [M – H]– |
| 912 | 2-(trifluoromethyl)-3-methylpyridinyl (CF₃, Me) | 418 [M – H]– |
| 913 | 5-chloro-2-methyl-3-methylthiophene (Me, Cl, S, Me) | 403/405 [M – H]– |
| 914 | 2,5-dichloro-3-methylthiophene (Cl, S, Cl, Me) | 423/425 [M – H]– |
| 915 | 2-cyclopropyl-4-methyl-5-methylthiazole | 410 [M – H]– |

<br/>

Structure: 2-(4-chlorophenyl)-6-R-pyrimidin-4-yl-oxy-cyclopropane-carboxylate CO₂R'

| Example | R | R' | MS (ESI) |
|---|---|---|---|
| 916 | 5-fluoro-2-methylbenzyl with OEt | H | 441/443 [M – H]– |
| 917 | 4-fluoro-2-methylbenzyl with OEt | H | 441/443 [M – H]– |
| 918 | 5-chloro-2-methyl-3-cyanophenyl (CN, Cl, Me) | H | 424/426 [M – H]– |
| 919 | 4-chloro-2-methyl-cyanophenyl (CN, Me, Cl) | H | 424/426 [M – H]– |
| 920 | 4-fluoro-2-methylbenzyl with OMe | H | 427/429 [M – H]– |

| | 201 -continued | | |
|---|---|---|---|
| 921 | 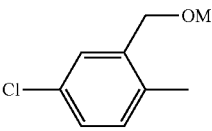 | H | 443/445 [M − H]− |
| 922 | 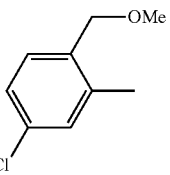 | H | 443/445 [M − H]− |
| 923 | 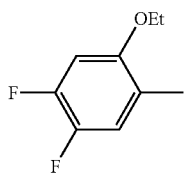 | Na | 445/447 [M − Na]− |
| 924 | 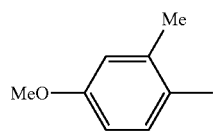 | H | 409/411 [M − H]− |
| 925 | 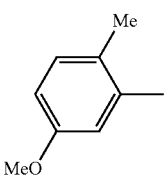 | H | 409/411 [M − H]− |
| 926 | 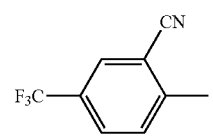 | Na | 458/460 [M − Na]− |
| 927 | 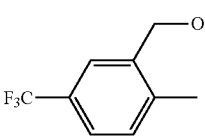 | H | 477/479 [M − H]− |
| 928 | 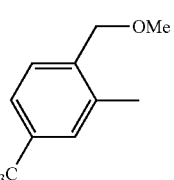 | H | 477/479 [M − H]− |
| 929 | 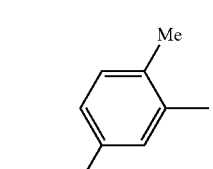 | H | 437/439 [M − H]− |
| 930 | 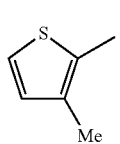 | H | 385/387 [M − H]− |
| | 202 -continued | | |
|---|---|---|---|
| 931 | 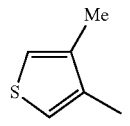 | H | 385/387 [M − H]− |
| 932 | 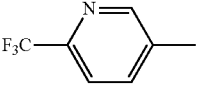 | H | 434/436 [M − H]− |
| 933 | 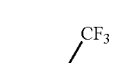 | H | 434/436 [M − H]− |
| 934 | 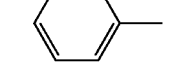 | Na | 413/415 [M − Na]− |
| 935 | 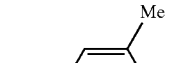 | Na | 424/426 [M − Na]− |
| 936 | 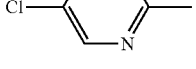 | H | 424/426 [M − H]− |
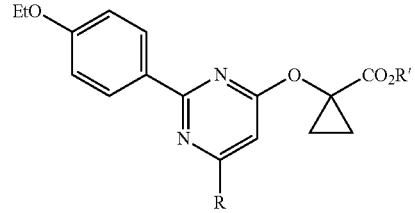
| Example | R | R' | MS (ESI) |
|---|---|---|---|
| 937 | 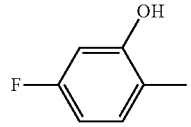 | Na | 409 [M − Na]− |
| 938 | 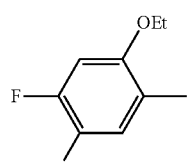 | Na | 455 [M − Na]− |
| 939 |  | Na | 453/455 [M − Na]− |
| 940 | 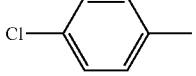 | H | 444 [M − H]− |

203
-continued

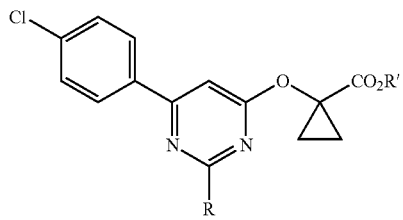

| Example | R | R' | MS (ESI) |
|---|---|---|---|
| 941 | 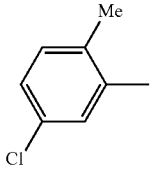 (F, OMe, Me on benzene) | H | 413/415 [M − H]− |
| 942 | 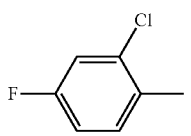 (F, OEt on benzene) | H | 427/429 [M − H]− |
| 943 | 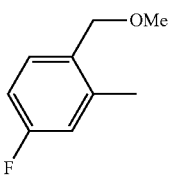 (Me, Me, F on benzene) | H | 397/399 [M − H]− |
| 944 | 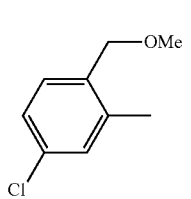 (Me, F on benzene) | H | 397/399 [M − H]− |
| 945 | 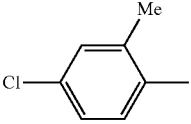 (F₃C-pyridine-Me) | H | 434/436 [M − H]− |
| 946 | 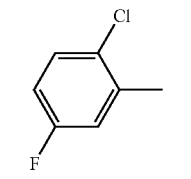 (CN, Cl, Me benzene) | H | 424/426 [M − H]− |

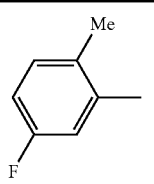

| Example | R | R' | MS (ESI) |
|---|---|---|---|
| 947 | 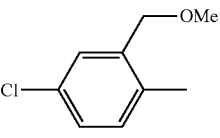 (Me, F benzene) | H | 381 [M − H]− |

204
-continued

| 948 | 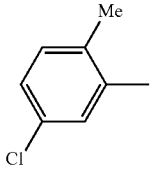 (Me, Me, Cl benzene) | H | 397/399 [M − H]− |
|---|---|---|---|
| 949 | 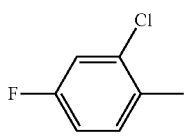 (Cl, F, Me benzene) | H | 401/403 [M − H]− |
| 950 | 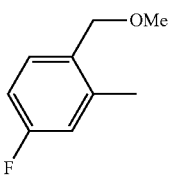 (OMe-CH₂, F, Me benzene) | H | 411 [M − H]− |
| 951 | 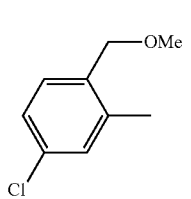 (OMe-CH₂, Cl benzene) | H | 427/429 [M − H]− |
| 952 | 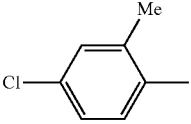 (Me, Me, Cl benzene) | H | 397 [M − H]− |
| 953 | 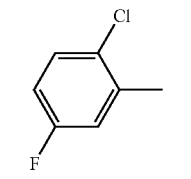 (Cl, F benzene) | H | 401/403 [M − H]− |
| 954 | 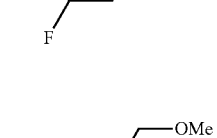 (OMe-CH₂, F benzene) | H | 411 [M − H]− |
| 955 | 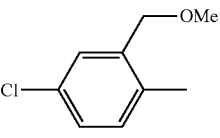 (OMe-CH₂, Cl, Me benzene) | H | 427/429 [M − H]− |

205
-continued
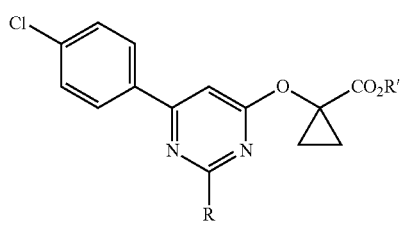
| Example | R | R' | MS (ESI) |
|---|---|---|---|
| 956 | 4-F, 2-Me-benzyl-OMe | H | 427/429 [M − H]− |
| 957 | 4-Cl, 2-Me-benzyl-OMe | H | 443/445 [M − H]− |
| 958 | 5-F, 2-Me-benzyl-OMe | H | 427/429 [M − H]− |
| 959 | 5-Cl, 2-Me-benzyl-OMe | H | 443/445 [M − H]− |
| 960 | 4-Cl, 2-Me-benzonitrile (CN) | H | 424/426 [M − H]− |
206
Example 961
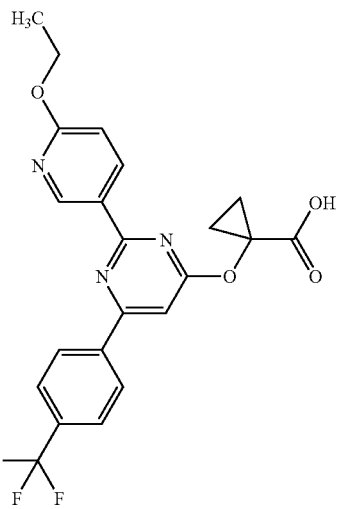
MS: 444[M−H]− (ESI).
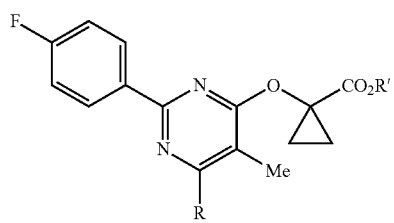
| Example | R | R' | MS (ESI) |
|---|---|---|---|
| 962 | 4-Cl-phenyl | H | 397/399 [M − H]− |
| 963 | 4-F-phenyl | H | 381 [M − H]− |
| 964 | 4-Me-phenyl | H | 377 [M − H]− |
| 965 | 4-EtO-phenyl | H | 407 [M − H]− |
| 966 | 4-(MeOCH2)-phenyl | H | 407 [M − H]− |
| 967 | 4-(cyclopropyloxy)-phenyl | Na | 419 [M − Na]− |

207 -continued

| Example | R (aryl) | R' | MS (ESI) |
|---|---|---|---|
| 968 | 3,5-dimethylphenyl (Me, Me) | H | 377 [M − H]− |
| 969 | 3-fluoro-4-methylphenyl (F) | H | 381 [M − H]− |
| 970 | 3-chloro-4-methylphenyl (Cl) | H | 397/399 [M − H]− |
| 971 | 3-ethoxy-4-methylphenyl (EtO) | H | 407 [M − H]− |
| 972 | 2-ethoxy-4-fluoro-methylphenyl (OEt, F) | H | 425 [M − H]− |
| 973 | 4-fluoro-2-methylphenyl (Me, F) | H | 395 [M − H]− |
| 974 | 2-ethoxy-4-fluorophenyl (OEt, F) | Na | 425 [M − Na]− |
| 975 | 4-chloro-2-methoxyphenyl (OMe, Cl) | Na | 427/429 [M − Na]− |
| 976 | 5-chloro-2-methoxyphenyl (OMe, Cl) | Na | 427/429 [M − Na]− |

208 -continued

Structure: 2-(4-fluorophenyl)-5-methyl-6-R-pyrimidin-4-yl)oxy-1-cyclopropanecarboxylic acid sodium salt.

| Example | R | MS (ESI) |
|---|---|---|
| 977 | 2-ethoxy-5-methyl-fluorophenyl (EtO, F) | 425 [M − Na]− |
| 978 | 3-ethoxy-5-fluorophenyl (EtO, F) | 425 [M − Na]− |
| 979 | 3-ethoxy-4-fluorophenyl (EtO, F) | 425 [M − Na]− |
| 980 | 4-chloro-3-methoxyphenyl (MeO, Cl) | 427/429 [M − Na]− |
| 981 | 2-fluoro-4-ethoxyphenyl (F, EtO) | 425 [M − Na]− |
| 982 | 2-chloro-4-methoxyphenyl (Cl, MeO) | 427/429 [M − Na]− |
| 983 | 3-chloro-4-methoxyphenyl (Cl, MeO) | 427/429 [M − Na]− |
| 984 | 2,3-difluorophenyl (F, F) | 399 [M − Na]− |
| 985 | 2,4-difluorophenyl (F, F) | 399 [M − Na]− |

| Example | R (aryl) | | MS (ESI) |
|---|---|---|---|
| 986 | 3,4-difluorophenyl | | 399 [M − Na]− |
| 987 | 3,5-difluorophenyl | | 399 [M − Na]− |
| 988 | 3,4,5-trifluorophenyl | | 417 [M − Na]− |

Structure: 2-(4-fluorophenyl)-5-methyl-6-R-pyrimidin-4-yl 1-(CO₂R')cyclopropane

| Example | R | R' | MS (ESI) |
|---|---|---|---|
| 989 | 2-chloro-4-fluoro-6-methylphenyl | Na | 415/417 [M − Na]− |
| 990 | 2-chloro-3-fluoro-6-methylphenyl | Na | 415/417 [M − Na]− |
| 991 | 2-chloro-4-fluorophenyl (methyl) | Na | 415/417 [M − Na]− |
| 992 | 4-cyano-2-chlorophenyl | H | 422/424 [M − H]− |
| 993 | 2-chloro-5-methyl-phenyl (MeO) | Na | 427/429 [M − Na]− |
| 994 | 3-chloro-5-methyl (MeO) | H | 427/429 [M − H]− |
| 995 | 4-fluoro-2,6-dimethylphenyl | Na | 395 [M − Na]− |
| 996 | 4-fluoro-2-methoxy-5-methylphenyl | Na | 411 [M − Na]− |
| 997 | 3-fluoro-5-methoxy-methylphenyl | Na | 411 [M − Na]− |
| 998 | 4-fluoro-3-methoxy-methylphenyl | Na | 411 [M − Na]− |
| 999 | 4-fluoro-3-methyl (Me) | Na | 395 [M − Na]− |
| 1000 | 3,5-dimethyl-fluorophenyl | Na | 395 [M − Na]− |
| 1001 | 4-fluoro-3-methylphenyl (Me) | Na | 395 [M − Na]− |
| 1002 | 2-fluoro-4-methylphenyl (Me) | Na | 395 [M − Na]− |
| 1003 | 3-fluoro-4-methoxyphenyl | Na | 411 [M − Na]− |

211
-continued
| | | | |
|---|---|---|---|
| 1004 | 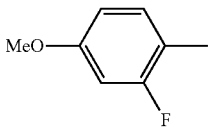 | Na | 411 [M − Na]− |
| 1005 | 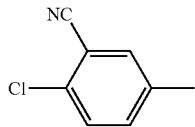 | Na | 422/424 [M − Na]− |
| 1006 | 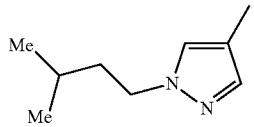 | Na | 423 [M − Na]− |
| 1007 | 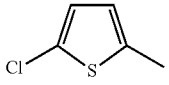 | Na | 403/405 [M − Na]− |
| 1008 | 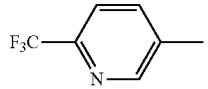 | Na | 432 [M − Na]− |
| 1009 | 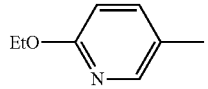 | Na | 408 [M − Na]− |
| 1010 | 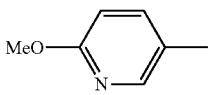 | Na | 394 [M − Na]− |
| 1011 | 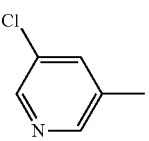 | Na | 398/400 [M − Na]− |
| 1012 | 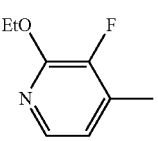 | H | 426 [M − H]− |
| 1013 | 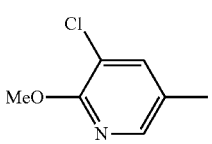 | H | 428/430 [M − H]− |
| 1014 | 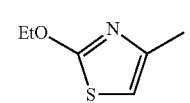 | Na | 414 [M − Na]− |
212
-continued
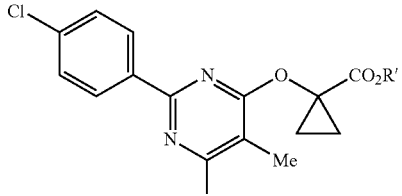
| Example | R | R' | MS (ESI) |
|---|---|---|---|
| 1015 |  | H | 397/399 [M − H]− |
| 1016 | 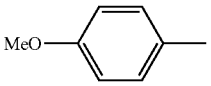 | H | 409 [M − H]− |
| 1017 | 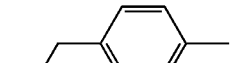 | H | 423/425 [M − H]− |
| 1018 |  | H | 397/399 [M − H]− |
| 1019 | 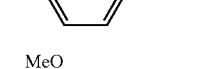 | H | 409/411 [M − H]− |
| 1020 |  | H | 423/425 [M − H]− |
| 1021 | 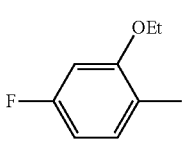 | H | 441/443 [M − H]− |
| 1022 | 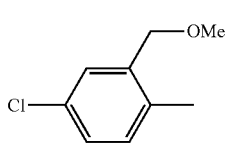 | H | 457/459 [M − H]− |
| 1023 | 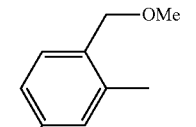 | H | 457/459 [M − H]− |
| 1024 | 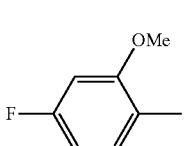 | Na | 427/429 [M − Na]− |

-continued
| | | | |
|---|---|---|---|
| 1025 | 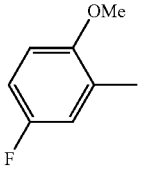 | Na | 427/429 [M − Na]− |
| 1026 | 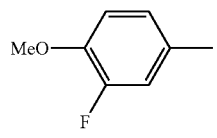 | Na | 427/429 [M − Na]− |
| 1027 | 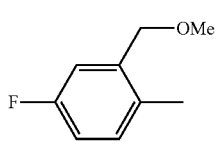 | Na | 441/443 [M − Na]− |
| 1028 | 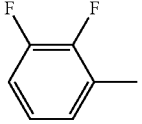 | Na | 415/417 [M − Na]− |
| 1029 | 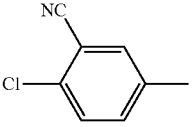 | Na | 438/440 [M − Na]− |
| 1030 | 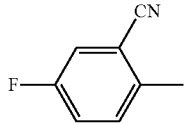 | Na | 422/424 [M − Na]− |
| 1031 | 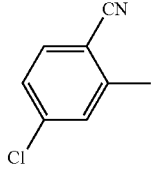 | Na | 438/440 [M − Na]− |
| 1032 | 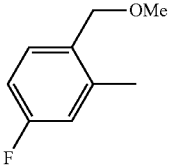 | Na | 441/443 [M − Na]− |
| 1033 | 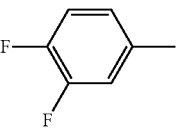 | Na | 415/417 [M − Na]− |
Example 1034
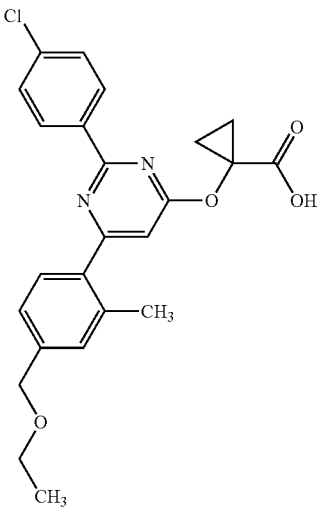 [SMILES: CCOCc1ccc(-c2cc(OC3(C(=O)O)CC3)nc(-c3ccc(Cl)cc3)n2)c(C)c1]
MS 437/439[M−H]− (ESI).
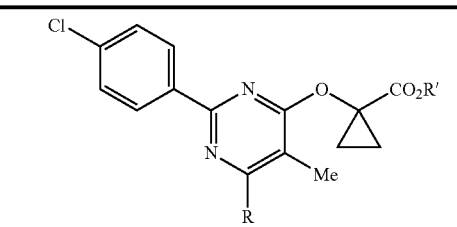
| Example | R | R' | MS (ESI) |
|---|---|---|---|
| 1035 | 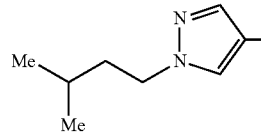 | Na | 437/441 [M − Na]− |
| 1036 | 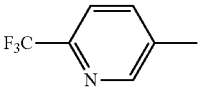 | Na | 448/450 [M − Na]− |
| 1037 | 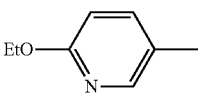 | Na | 424/426 [M − Na]− |
| 1038 | 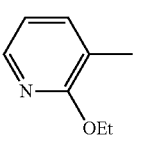 | Na | 424/426 [M − Na]− |
| 1039 | 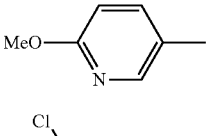 | Na | 410/412 [M − Na]− |
| 1040 | 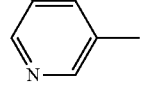 | Na | 414/416 [M − Na]− |

-continued

| Example | Structure | R | MS (ESI) |
|---|---|---|---|
| 1041 | 3-EtO, 4-F, 5-methyl pyridine | H | 442/444 [M − H]− |
| 1042 | 3-Cl, 2-MeO, 5-methyl pyridine | H | 444/446 [M − H]− |
| 1043 | 4-methyl, 2-EtO thiazole | Na | 430/432 [M − Na]− |
| 1044 | 5-Cl, 2-methyl thiophene | Na | 419/421 [M − Na]− |

Structure: 4-(4-fluorophenyl)-pyrimidin-2-yloxy-cyclopropane-CO2Na with R substituent

| Example | R | MS (ESI) |
|---|---|---|
| 1045 | 4-cyclopropylphenyl | 389 [M − Na]− |
| 1046 | 5-Cl, 2-methylphenyl (Me) | 397/399 [M − Na]− |
| 1047 | 2-OEt, 5-F phenyl | 411 [M − Na]− |
| 1048 | 5-Cl, 2-methyl, OMe-benzyl | 427/429 [M − Na]− |
| 1049 | 4-CF3 phenyl | 417 [M − Na]− |
| 1050 | 4-Cl, 2-methylphenyl (Me) | 397/399 [M − H]− |

-continued

Structure: 4-(4-chlorophenyl)-pyrimidin-2-yloxy-cyclopropane-CO2Na with R substituent

| Example | R | MS (ESI) |
|---|---|---|
| 1051 | 4-chlorophenyl | 399/401 [M − Na]− |
| 1052 | 2-methyl, 5-F phenyl (Me) | 397/399 [M − Na]− |
| 1053 | 5-Cl, 2-methyl, OMe-benzyl | 443/445 [M − Na]− |
| 1054 | 2-methyl, 4-F phenyl (Me) | 397/399 [M − H]− |
| 1055 | 2-OEt, 5-F phenyl | 427/429 [M − Na]− |

Example 1056

Structure: 2-(3,4-difluorophenyl)-4-(4,5-difluoro-2-ethoxyphenyl)-pyrimidin-6-yloxy-2-methylpropanoic acid sodium salt MS: 449 [M−Na]− (ESI).

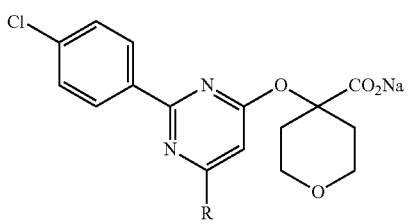

| Example | R | MS (ESI) |
|---|---|---|
| 1057 | 4-cyclopropylphenyl | 449/451 [M − Na]− |
| 1058 | 4-chlorophenyl | 443/445 [M − Na]− |
| 1059 | 3-chlorophenyl | 443/445 [M − Na]− |
| 1060 | 4-chloro-2-methylphenyl | 457/459 [M − Na]− |
| 1061 | 4-chloro-2-ethoxyphenyl | 487/489 [M − Na]− |
| 1062 | 4-ethoxyphenyl | 453/455 [M − Na]− |
| 1063 | 5-chloro-2-thienyl | 449/451 [M − Na]− |
| 1064 | 4-trifluoromethylphenyl | 477/479 [M − Na]− |
| 1065 | 4-chloro-2-methylphenyl | 457/459 [M − Na]− |

-continued

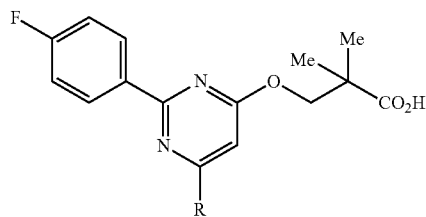

| Example | R | MS (ESI) |
|---|---|---|
| 1066 | 4-fluorophenyl | 383 [M − H]− |
| 1067 | 4-(methoxymethyl)phenyl | 409 [M − H]− |
| 1068 | 5-fluoro-2-methoxyphenyl | 413 [M − H]− |
| 1069 | 2-fluoro-5-methoxyphenyl | 413 [M − H]− |

| Example | R | MS (ESI) |
|---|---|---|
| 1070 | 4-fluorophenyl | 381 [M − Na]− |
| 1071 | 4-ethoxyphenyl | 407 [M − Na]− |
| 1072 | 4-chloro-2-methoxyphenyl | 427/429 [M − Na]− |
| 1073 | 4-fluoro-2-ethoxyphenyl | 425 [M − Na]− |

219
-continued
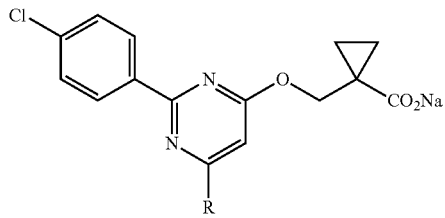
| Example | R | MS (ESI) |
|---|---|---|
| 1074 |  (MeO-benzyl) | 423/425 [M − Na]− |
| 1075 | (5-F, 2-Me, OMe-benzyl) | 441/443 [M − Na]− |
| 1076 | (EtO-pyridyl-Me) | 424/426 [M − Na]− |
| Example | R | R' | R'' | MS (ESI) |
|---|---|---|---|---|
| 1077 | (3-F, 5-MeO-phenyl) | H | F | 396 [M − H]− |
| 1078 | (5-F, 2-Me, 2-OEt-phenyl) | H | Cl | 426/428 [M − H]− |
| 1079 | (MeO-benzyl) | Me | Cl | 422/424 [M − H]− |
220
Example 1080
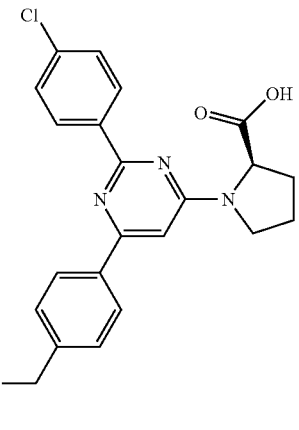
MS: 422/424[M−H]− (ESI).
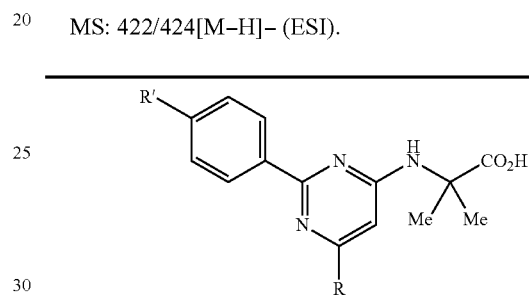
| Example | R | R' | MS (ESI) |
|---|---|---|---|
| 1081 | (MeO-benzyl) | F | 394 [M − H]− |
| 1082 | (5-F, 2-Me, 2-OEt-phenyl) | F | 412 [M − H]− |
| 1083 | (NC-phenyl-Me) | Cl | 393/395 [M + H]+ |
Example 1084
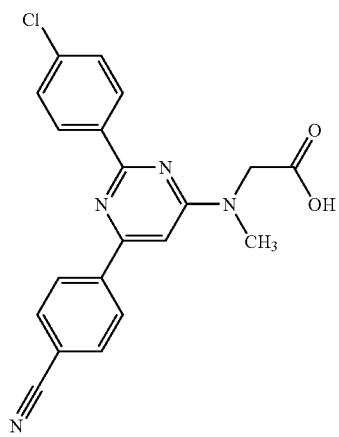 [SMILES: CN(CC(=O)O)c1cc(-c2ccc(C#N)cc2)nc(-c2ccc(Cl)cc2)n1]
MS: 377/379[M−H]− (ESI).

| Example | R | MS (ESI) |
|---|---|---|
| 1085 | 4-(F₃C)-C₆H₄- | 432/434 [M – H]– |
| 1086 | 4-(cyclopropyl)-C₆H₄- | 404/406 [M – H]– |
Example 1087
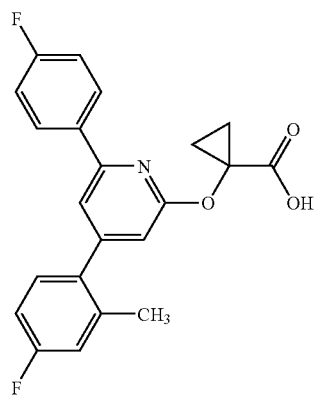 [SMILES: Cc1cc(F)ccc1-c1cc(OC2(C(=O)O)CC2)nc(-c2ccc(F)cc2)c1]
MS: 380[M–H]– (ESI).
| Example | R | R' | MS (ESI) |
|---|---|---|---|
| 1088 | 5-Cl-2-Me-C₆H₃- | Na | 414/416 [M – Na]– |
| 1089 | 5-Cl-2-OEt-C₆H₃- | H | 444/446 [M – H]– |
| 1090 | 5-Cl-2-(CH₂OMe)-C₆H₃- | H | 444/446 [M – H]– |
| 1091 | 4-Cl-2,3-diMe-C₆H₂- | Na | 414/416 [M – Na]– |
| 1092 | 4-F₃C-2,3-diMe-C₆H₂- | H | 448/450 [M – H]– |
| 1093 | 4-F₃C-2,3-diMe-C₆H₂- | Na | 448/450 [M – Na]– |
| 1094 | 4-F₃CO-2,3-diMe-C₆H₂- | Na | 464/466 [M – Na]– |
| Example | R | R' | MS (ESI) |
|---|---|---|---|
| 1095 | 7-F-2-Me-1,2,3,4-tetrahydroisoquinolin-yl | Na | 438/440 [M – Na]– |
| 1096 | 6-F-2-Me-1,2,3,4-tetrahydroisoquinolin-yl | Na | 438/440 [M – Na]– |
| 1097 | 3-Cl-6-Me-5,6,7,8-tetrahydro-1,6-naphthyridin-yl | H | 455/457 [M – H]– |

223
-continued
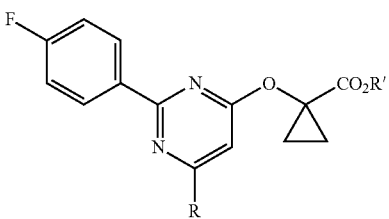
| Example | R | R' | MS (ESI) |
|---|---|---|---|
| 1098 | 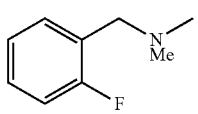 | Na | 410 [M − Na]− |
| 1099 | 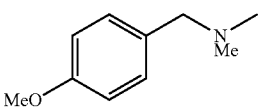 | H | 410 [M − H]− |
| 1100 | 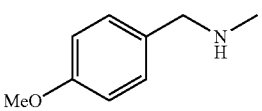 | H | 422 [M − H]− |
| 1101 | 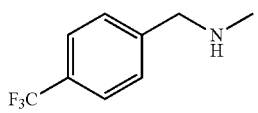 | H | 408 [M − H]− |
| 1102 | 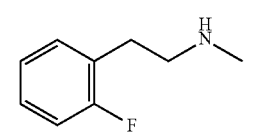 | H | 446 [M − H]− |
| 1103 | 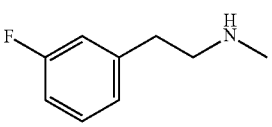 | Na | 410 [M − Na]− |
| 1104 | 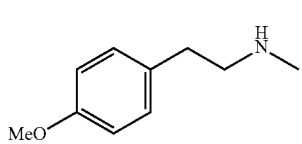 | Na | 410 [M − Na]− |
| 1105 | 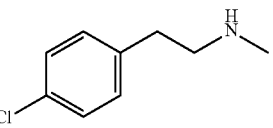 | Na | 422 [M − Na]− |
| 1106 | 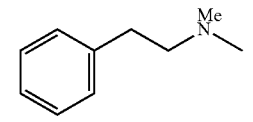 | Na | 426/428 [M − Na]− |
| 1107 | | Na | 406 [M − Na]− |
224
-continued
| | R | R' | MS (ESI) |
|---|---|---|---|
| 1108 | 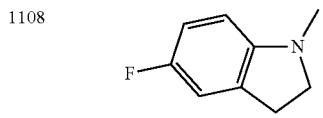 | Na | 408 [M − Na]− |
| 1109 | 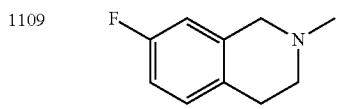 | Na | 422 [M − Na]− |
| 1110 | 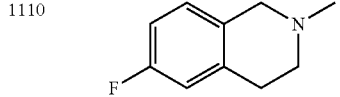 | Na | 422 [M − Na]− |
| 1111 | 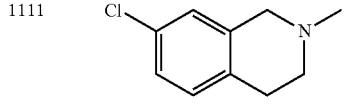 | Na | 438/440 [M − Na]− |
| 1112 | 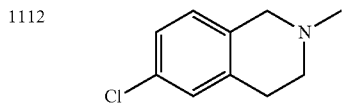 | H | 438/440 [M − H]− |
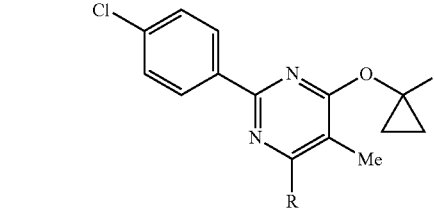
| Example | R | R' | MS (ESI) |
|---|---|---|---|
| 1113 | 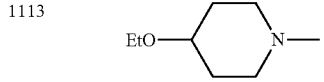 | H | 430/432 [M − H]− |
| 1114 | 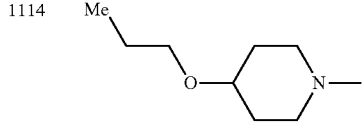 | H | 444/446 [M − H]− |
| 1115 | 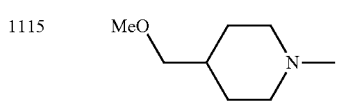 | H | 430/432 [M − H]− |
| 1116 | 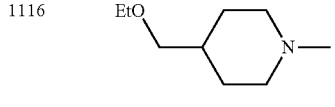 | H | 444/446 [M − H]− |
| 1117 | 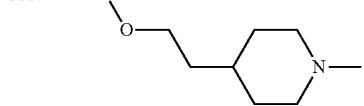 | H | 444/446 [M − H]− |
| 1118 | 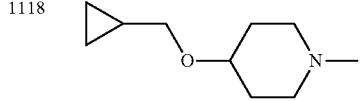 | H | 456/458 [M − H]− |

225
-continued
| | | | | |
|---|---|---|---|---|
| 1119 | Me 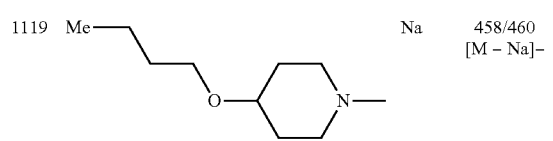 | | Na | 458/460 [M − Na]− |
| 1120 | MeO 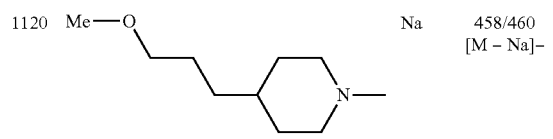 | | Na | 458/460 [M − Na]− |
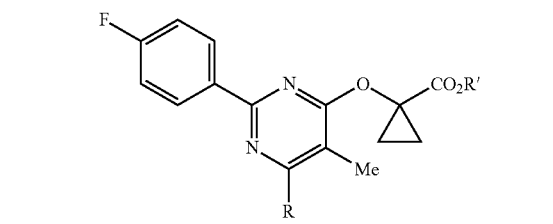
| Example | R | R' | MS (ESI) |
|---|---|---|---|
| 1121 | Me 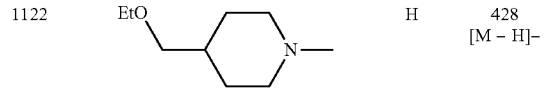 | H | 428 [M − H]− |
| 1122 | EtO 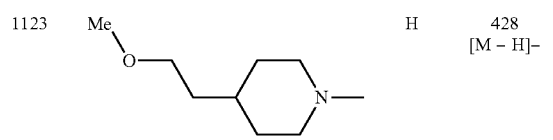 | H | 428 [M − H]− |
| 1123 | Me 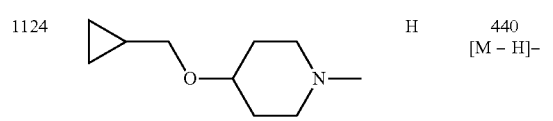 | H | 428 [M − H]− |
| 1124 | 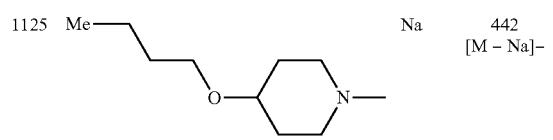 | H | 440 [M − H]− |
| 1125 | Me 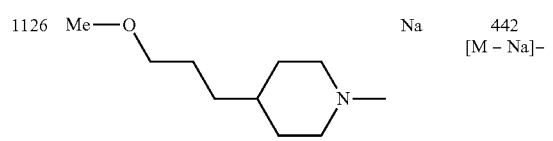 | Na | 442 [M − Na]− |
| 1126 | MeO 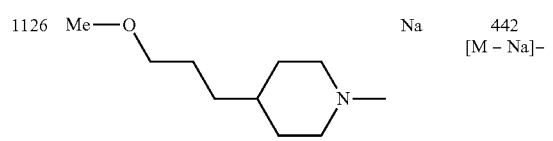 | Na | 442 [M − Na]− |
226
-continued
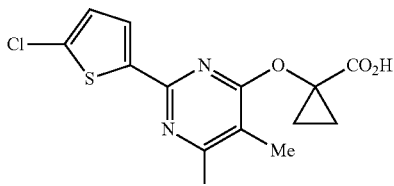
| Example | R | MS (ESI) |
|---|---|---|
| 1127 | EtO  | 436/438 [M − H]− |
| 1128 | MeO 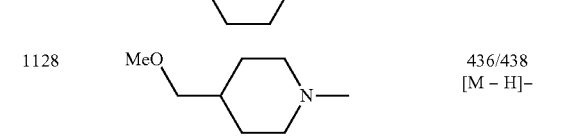 | 436/438 [M − H]− |
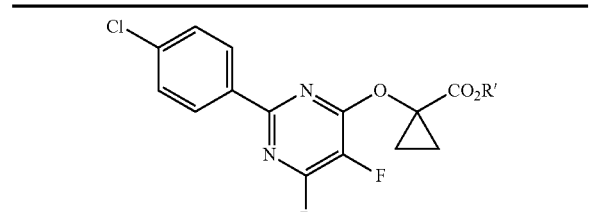
| Example | R | R' | MS (ESI) |
|---|---|---|---|
| 1129 | Me 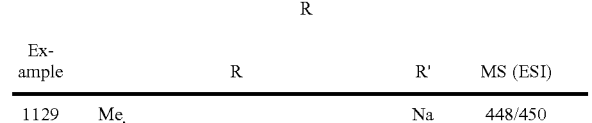 | Na | 448/450 [M − Na]− |
| 1130 | Me-Me 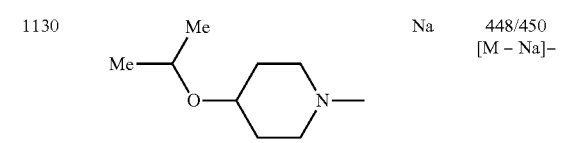 | Na | 448/450 [M − Na]− |
| 1131 | EtO 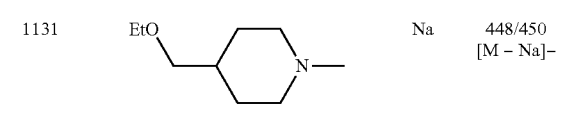 | Na | 448/450 [M − Na]− |
| 1132 | MeO 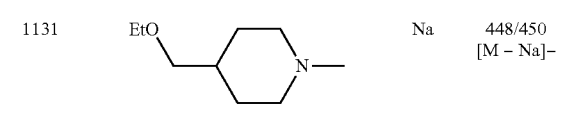 | Na | 448/450 [M − Na]− |
| 1133 | Me 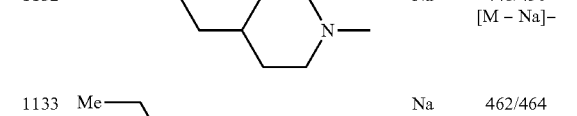 | Na | 462/464 [M − Na]− |
| 1134 | Me-O 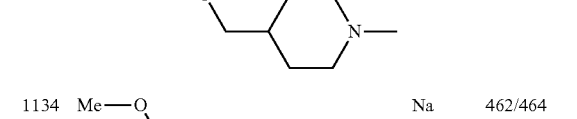 | Na | 462/464 [M − Na]− |
| 1135 | 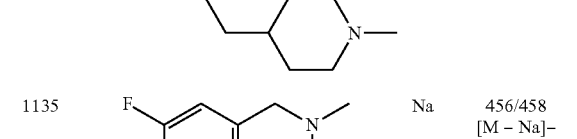 | Na | 456/458 [M − Na]− |

227
-continued
| 1136 | 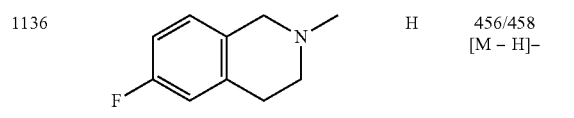 | H | 456/458 [M − H]− |
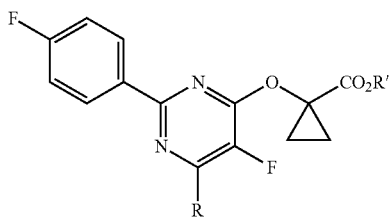
| Example | R | R' | MS (ESI) |
|---|---|---|---|
| 1137 | 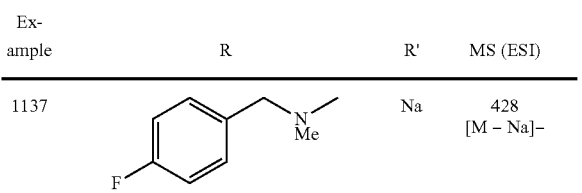 | Na | 428 [M − Na]− |
| 1138 | 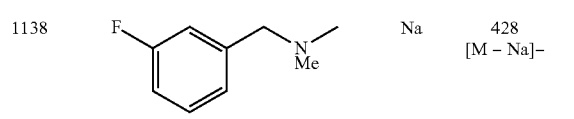 | Na | 428 [M − Na]− |
| 1139 | 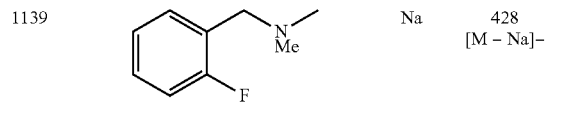 | Na | 428 [M − Na]− |
| 1140 | 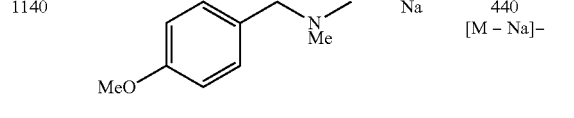 | Na | 440 [M − Na]− |
| 1141 | 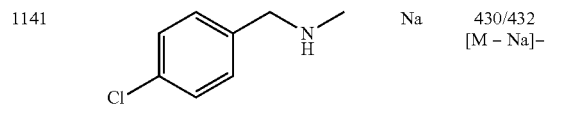 | Na | 430/432 [M − Na]− |
| 1142 | 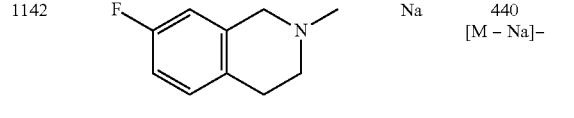 | Na | 440 [M − Na]− |
| 1143 | 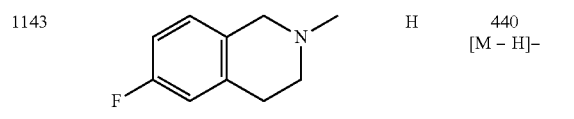 | H | 440 [M − H]− |
| 1144 | 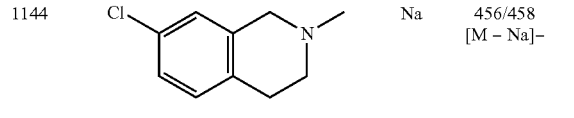 | Na | 456/458 [M − Na]− |
| 1145 | 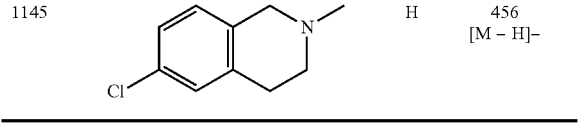 | H | 456 [M − H]− |
228
-continued
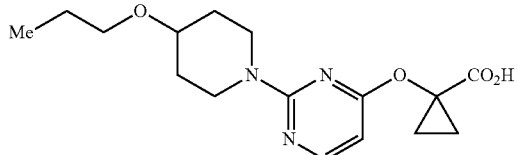
| Example | R | MS (ESI) |
|---|---|---|
| 1146 | 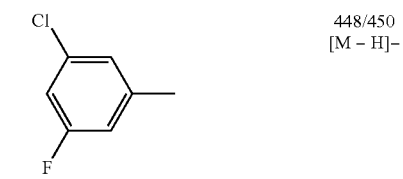 | 448/450 [M − H]− |
| 1147 | 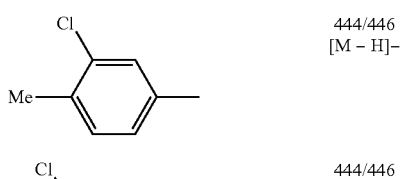 | 448/450 [M − H]− |
| 1148 | 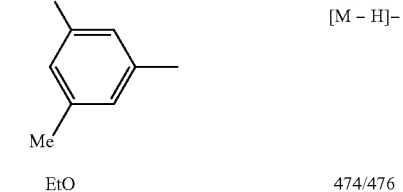 | 444/446 [M − H]− |
| 1149 | 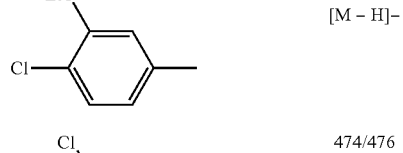 | 444/446 [M − H]− |
| 1150 | 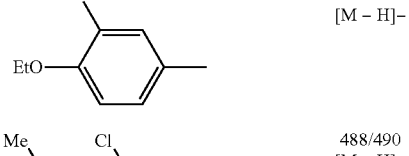 | 474/476 [M − H]− |
| 1151 | 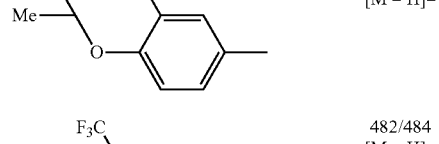 | 474/476 [M − H]− |
| 1152 | 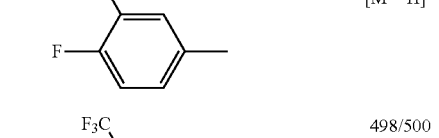 | 488/490 [M − H]− |
| 1153 | 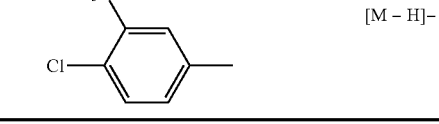 | 482/484 [M − H]− |
| 1154 | | 498/500 [M − H]− |

229
-continued
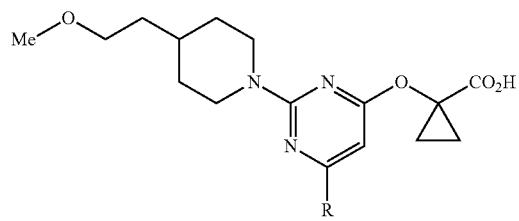
| Example | R | MS (ESI) |
|---|---|---|
| 1155 | 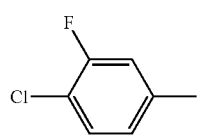 | 448/450 [M − H]− |
| 1156 | 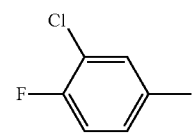 | 448/450 [M − H]− |
| 1157 | 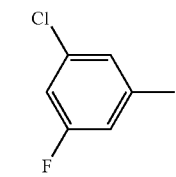 | 448/450 [M − H]− |
| 1158 | 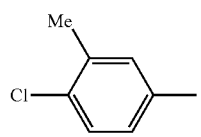 | 444/446 [M − H]− |
| 1159 | 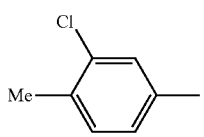 | 444/446 [M − H]− |
| 1160 | 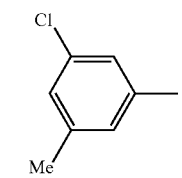 | 444/446 [M − H]− |
| 1161 | 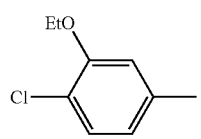 | 474/476 [M − H]− |
| 1162 | 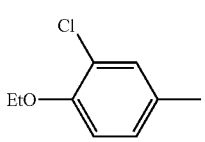 | 474/476 [M − H]− |
230
-continued
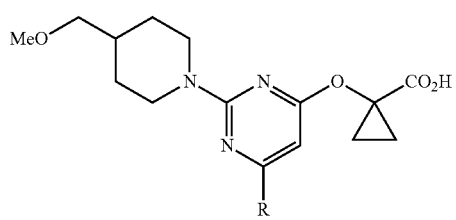
| Example | R | MS (ESI) |
|---|---|---|
| 1163 | 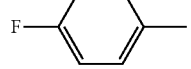 | 434/436 [M − H]− |
| 1164 | 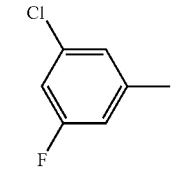 | 434/436 [M − H]− |
| 1165 | 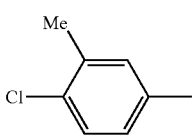 | 430/432 [M − H]− |
| 1166 | 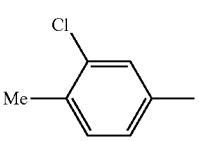 | 430/432 [M − H]− |
| 1167 | 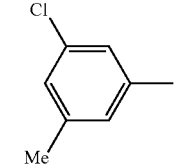 | 430/432 [M − H]− |
| 1168 | 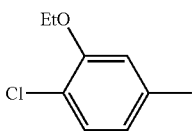 | 460/462 [M − H]− |
| 1169 | 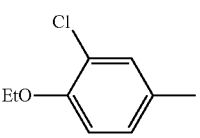 | 460/462 [M − H]− |

| | 231 -continued | | | | 232 -continued | |
|---|---|---|---|---|---|---|

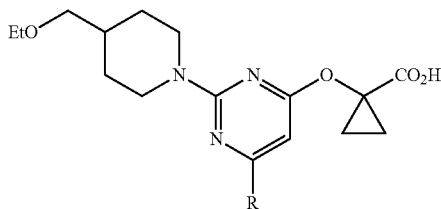

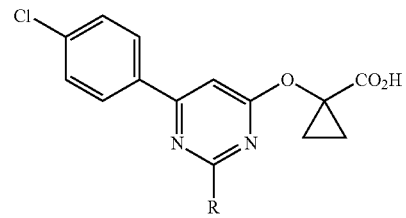

| Example | R | MS (ESI) | | Example | R | MS (ESI) |
|---|---|---|---|---|---|---|
| 1170 | F, Cl-phenyl | 448/450 [M − H]− | | 1178 | MeO-ethyl-piperidine-N-Me | 430 [M − H]− |
| 1171 | Cl, F-phenyl | 448/450 [M − H]− | | 1179 | cyclopropylmethoxy-piperidine-N-Me | 442/444 [M − H]− |
| 1172 | Cl, F-phenyl | 448/450 [M − H]− | | 1180 | Me-ethoxy-piperidine-N-Me | 430/432 [M − H]− |
| 1173 | Me, Cl-phenyl | 444/446 [M − H]− | | 1181 | EtO-methyl-piperidine-N-Me | 430/432 [M − H]− |
| 1174 | Cl, Me-phenyl | 444/446 [M − H]− | | 1182 | isobutoxy-piperidine-N-Me | 444/446 [M − H]− |
| 1175 | Cl, Me-phenyl | 444/446 [M − H]− | | 1183 | Me-ethoxy-piperidine-N-Me (S) | 430/432 [M − H]− |
| | | | | 1184 | Me-ethoxy-piperidine-N-Me (R) | 430/432 [M − H]− |
| 1176 | EtO, Cl-phenyl | 474/476 [M − H]− | | 1185 | 4-F-benzyl-NH-Me | 412/414 [M − H]− |
| | | | | 1186 | 3-F-benzyl-NH-Me | 412/414 [M − H]− |
| | | | | 1187 | 4-MeO-benzyl-NH-Me | 424/426 [M − H]− |
| 1177 | Cl, EtO-phenyl | 474/476 [M − H]− | | 1188 | 4-F-benzyl-N(Me)Me | 426/428 [M − H]− |

| Example | R | R' | MS (ESI) |
|---|---|---|---|
| 1189 | 3-F-C6H4-CH2-N(Me)- | | 426/428 [M − H]− |
| 1190 | 4-MeO-C6H4-CH2-N(Me)- | | 438/440 [M − H]− |
| 1191 | 7-F-2-Me-tetrahydroisoquinolin-2-yl | | 438/440 [M − H]− |
| 1192 | 6-F-2-Me-tetrahydroisoquinolin-2-yl | | 438/440 [M − H]− |

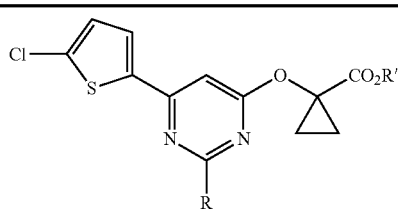

| Example | R | R' | MS (ESI) |
|---|---|---|---|
| 1193 | 1-Me-4-EtO-piperidin-1-yl | Na | 422/424 [M − Na]− |
| 1194 | 1-Me-4-(MeCH2CH2O)-piperidin-1-yl | Na | 436/438 [M − Na]− |
| 1195 | 1-Me-4-(MeCH2CH2CH2O)-piperidin-1-yl | Na | 450/452 [M − Na]− |
| 1196 | 1-Me-4-(MeOCH2)-piperidin-1-yl | Na | 422/424 [M − Na]− |
| 1197 | 1-Me-4-(EtOCH2)-piperidin-1-yl | Na | 436/438 [M − Na]− |
| 1198 | 1-Me-4-(MeOCH2CH2)-piperidin-1-yl | Na | 436/438 [M − Na]− |
| 1199 | 1-Me-4-(MeOCH2CH2CH2)-piperidin-1-yl | Na | 450/452 [M − Na]− |
| 1200 | 1-Me-4-(Me2CHCH2O)-piperidin-1-yl | Na | 450/452 [M − Na]− |

| Example | R | R' | MS (ESI) |
|---|---|---|---|
| 1201 | 1-Me-4-(cyclopropyl-CH2-O)-piperidin-1-yl | Na | 448/450 [M − Na]− |
| 1202 | 7-F-2-Me-tetrahydroisoquinolin-2-yl | Na | 444/446 [M − Na]− |
| 1203 | 6-F-2-Me-tetrahydroisoquinolin-2-yl | H | 444/446 [M − H]− |
| 1204 | 6-Cl-2-Me-tetrahydroisoquinolin-2-yl | H | 460/462 [M − H]− |
| 1205 | 3-Cl-6-Me-5,6,7,8-tetrahydro-1,6-naphthyridin-6-yl | H | 461/463 [M − H]− |

| Example | R | R' | MS (ESI) |
|---|---|---|---|
| 1206 | 1-Me-4-EtO-piperidin-1-yl | H | 436/438 [M − H]− |
| 1207 | 1-Me-4-(MeOCH2)-piperidin-1-yl | H | 436/438 [M − H]− |
| 1208 | 1-Me-4-(MeOCH2CH2)-piperidin-1-yl | H | 450/452 [M − H]− |
| 1209 | 1-Me-4-(cyclopropyl-CH2-O)-piperidin-1-yl | H | 462/464 [M − H]− |
| 1210 | 1-Me-4-(MeCH2CH2O)-piperidin-1-yl | H | 450/452 [M − H]− |
| 1211 | 1-Me-4-(EtOCH2)-piperidin-1-yl | H | 450/452 [M − H]− |

-continued

| | | | | |
|---|---|---|---|---|
| 1212 | Me-CH(Me)-CH2-O-[4-(N-Me)piperidine] | H | 464/466 [M − H]− | |
| 1213 | Me-CH2-CH2-O-[(3S)-(N-Me)piperidine] | H | 450/452 [M − H]− | |
| 1214 | Me-CH2-CH2-CH2-O-[4-(N-Me)piperidine] | Na | 464/466 [M − Na]− | |
| 1215 | MeO-CH2-CH2-CH2-[4-(N-Me)piperidine] | Na | 464/466 [M − Na]− | |

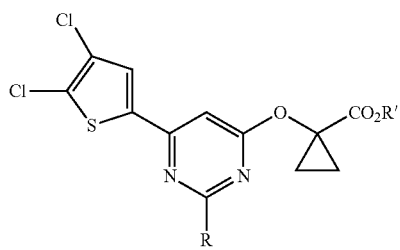

| Example | R | R' | MS (ESI) |
|---|---|---|---|
| 1216 | EtO-[4-(N-Me)piperidine] | H | 456/458 [M − H]− |
| 1217 | MeO-CH2-[4-(N-Me)piperidine] | H | 456/458 [M − H]− |
| 1218 | MeO-CH2-CH2-[4-(N-Me)piperidine] | H | 470/472 [M − H]− |
| 1219 | cyclopropyl-CH2-O-[4-(N-Me)piperidine] | H | 482/484 [M − H]− |
| 1220 | Me-CH2-CH2-O-[4-(N-Me)piperidine] | H | 470/472 [M − H]− |
| 1221 | EtO-CH2-[4-(N-Me)piperidine] | H | 470/472 [M − H]− |
| 1222 | Me-CH(Me)-CH2-O-[4-(N-Me)piperidine] | H | 484/486 [M − H]− |

-continued

| | | | |
|---|---|---|---|
| 1223 | Me-CH2-CH2-O-[(3S)-(N-Me)piperidine] | H | 470/472 [M − H]− |
| 1224 | Me-CH2-CH2-CH2-O-[4-(N-Me)piperidine] | Na | 484/486 [M − Na]− |
| 1225 | MeO-CH2-CH2-CH2-[4-(N-Me)piperidine] | Na | 484/486 [M − Na]− |
| 1226 | (3S)-MeO-(N-Me)piperidine | Na | 442/444 [M − Na]− |
| 1227 | (3S)-EtO-(N-Me)piperidine | Na | 456/458 [M − Na]− |

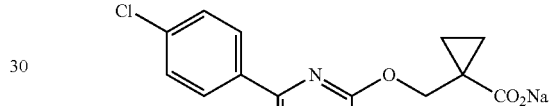

| Example | R | MS (ESI) |
|---|---|---|
| 1228 | (3S)-EtO-(N-Me)piperidine | 430/432 [M − Na]− |
| 1229 | (3R)-EtO-(N-Me)piperidine | 430/432 [M − Na]− |

[Structure: 4-chlorophenyl-pyrimidine with NH-cyclopropyl-CO2H and R substituent]

| Example | R | MS (ESI) |
|---|---|---|
| 1230 | 4-Me-(N-Me)piperidine | 385/387 [M − H]− |

| Example | | MS (ESI) |
|---|---|---|
| 1231 | 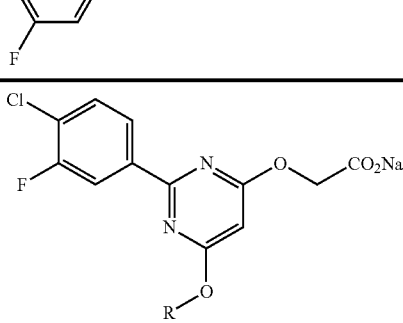 | 481/483 [M − H]− |
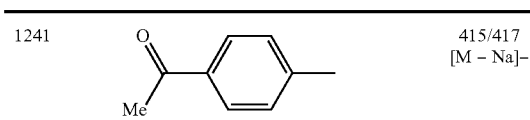
| Example | R | MS (ESI) |
|---|---|---|
| 1232 |  | 373/375 [M − Na]− |
| 1233 | | 391/393 [M − Na]− |
| 1234 | | 391/393 [M − Na]− |
| 1235 | | 391/393 [M − Na]− |
| 1236 | | 409/411 [M − Na]− |
| 1237 | | 421/423 [M − Na]− |
| 1238 | | 409/411 [M − Na]− |
| 1239 | | 417/419 [M − Na]− |
| 1240 | | 398/400 [M − Na]− |
| 1241 | 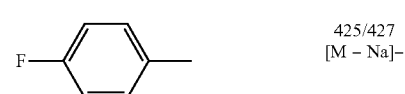 | 415/417 [M − Na]− |
| 1242 | | 407/409 [M − Na]− |
| 1243 | 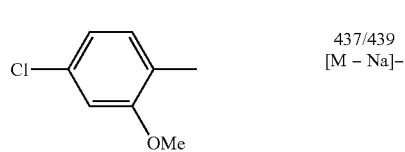 | 409/411 [M − Na]− |
| 1244 | | 425/427 [M − Na]− |
| 1245 | 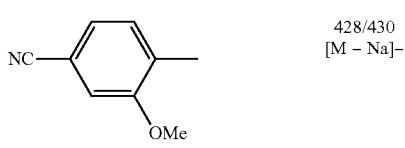 | 437/439 [M − Na]− |
| 1246 | | 428/430 [M − Na]− |
| 1247 | 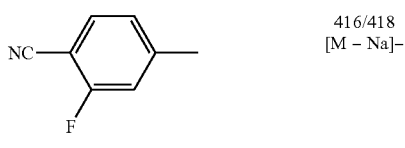 | 416/418 [M − Na]− |
| 1248 | | 445/447 [M − Na]− |
| 1249 | 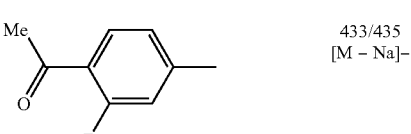 | 433/435 [M − Na]− |
| 1250 | 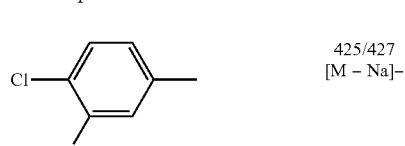 | 425/427 [M − Na]− |
| 1251 | 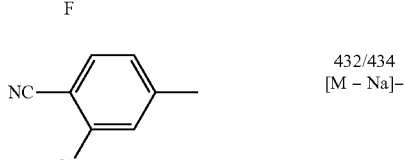 | 432/434 [M − Na]− |

239
-continued
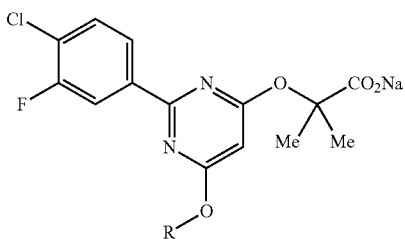
| Example | R | MS (ESI) |
|---|---|---|
| 1252 | 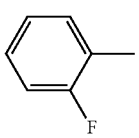 | 419/421 [M − Na]− |
| 1253 | 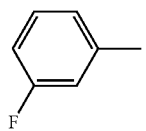 | 419/421 [M − Na]− |
| 1254 | 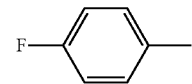 | 419/421 [M − Na]− |
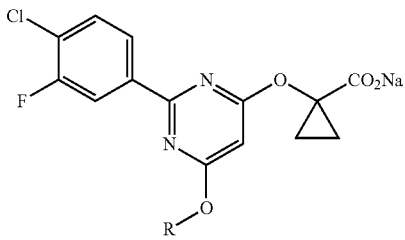
| Example | R | MS (ESI) |
|---|---|---|
| 1255 | 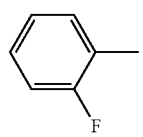 | 417/419 [M − Na]− |
| 1256 | 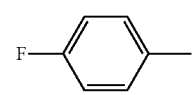 | 417/419 [M − Na]− |
240
-continued
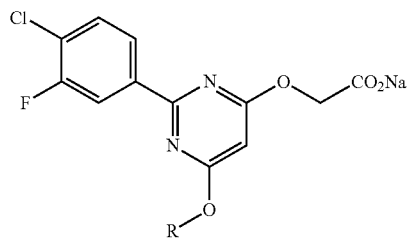
| Example | R | MS (ESI) |
|---|---|---|
| 1257 | 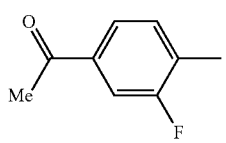 | 433/435 [M − Na]− |
| 1258 | 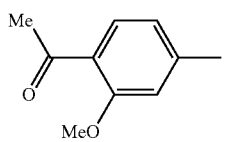 | 445/447 [M − Na]− |
| 1259 | 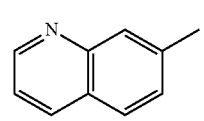 | 424/426 [M − Na]− |
| 1260 | 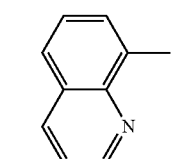 | 424/426 [M − Na]− |
| 1261 | 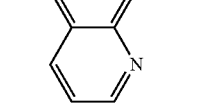 | 449/451 [M − Na]− |
| 1262 | 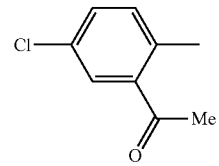 | 433/435 [M − Na]− |
| 1263 | 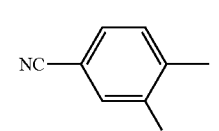 | 433/435 [M − Na]− |

-continued
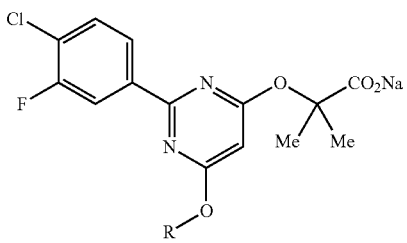
| Example | R | MS (ESI) |
|---|---|---|
| 1264 | 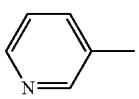 | 402/404 [M − Na]− |
| 1265 | 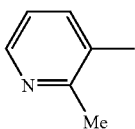 | 416/418 [M − Na]− |
| 1266 | 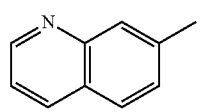 | 452/454 [M − Na]− |
| 1267 | 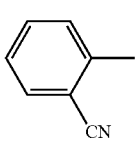 | 426/428 [M − Na]− |
| 1268 | 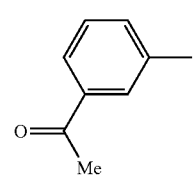 | 443/445 [M − Na]− |
| 1269 | 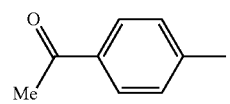 | 443/445 [M − Na]− |
| 1270 | 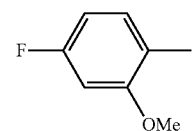 | 449/451 [M − Na]− |
| 1271 | 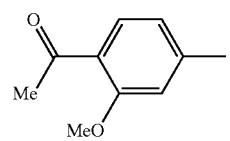 | 473/475 [M − Na]− |
| 1272 | 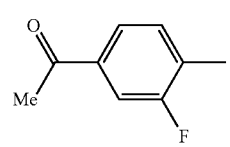 | 461/463 [M − Na]− |
-continued
| | | |
|---|---|---|
| 1273 | 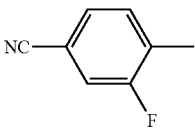 | 444/446 [M − Na]− |
| 1274 | 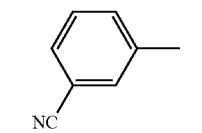 | 426/428 [M − Na]− |
| 1275 | 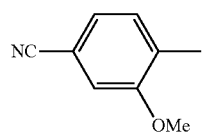 | 456/458 [M − Na]− |
| 1276 | 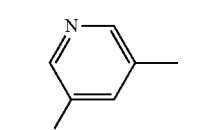 | 436/438 [M − Na]− |
| 1277 | 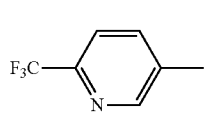 | 470/472 [M − Na]− |
| 1278 | 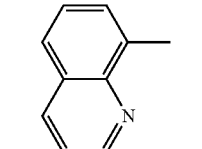 | 452/454 [M − Na]− |
| 1279 | 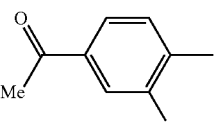 | 473/475 [M − Na]− |
Example 1280
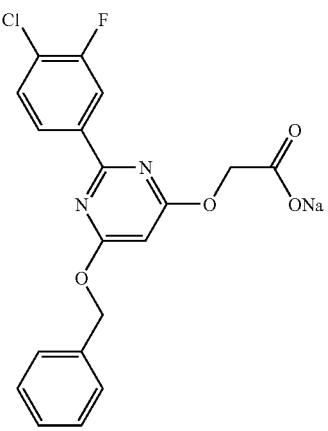
MS: 387/389[M-Na]− (ESI).

| Example | R | R' | MS (ESI) |
|---------|---|----|----------|
| 1281 | 4-F-benzyl | Cl | 413/415[M − H]− |
| 1282 | 3-F-benzyl | Cl | 413/415[M − H]− |
| 1283 | 3-Cl-benzyl | F | 413/415[M − H]− |

| Example | R | R' | MS (ESI) |
|---------|---|----|----------|
| 1284 | 4-F-benzyl | H | 413/415[M − H]− |
| 1285 | 3-F-benzyl | H | 413/415[M − H]− |
| 1286 | 3,4-diF-benzyl | H | 431/433[M − H]− |
| 1287 | 3,5-diF-benzyl | H | 431/433[M − H]− |
| 1288 | 4-F-3-MeO-benzyl | H | 443/445[M − H]− |
| 1289 | 3-MeO-benzyl | Na | 425/427[M − Na]− |

| Example | R | MS (ESI) |
|---------|---|----------|
| 1290 | 3-F-phenylpropyl | 411[M − Na]− |
| 1291 | 3-MeO-phenylpropyl | 423[M − Na]− |

| Example | R | MS (ESI) |
|---------|---|----------|
| 1292 | 4-F-benzyl | 419/421[M − H]− |
| 1293 | 3-F-benzyl | 419/421[M − H]− |
| 1294 | 2,4-diF-benzyl | 437/439[M − H]− |

-continued

| | | |
|---|---|---|
| 1295 | [2,5-difluoro-ethylphenyl] | 437/439[M – H]– |
| 1296 | [3,4-difluoro-ethylphenyl] | 437/439[M – H]– |
| 1297 | [3,5-difluoro-ethylphenyl] | 437/439[M – H]– |
| 1298 | [3-ethyl-5-methoxyphenyl] | 431/433[M – H]– |

Example 1299

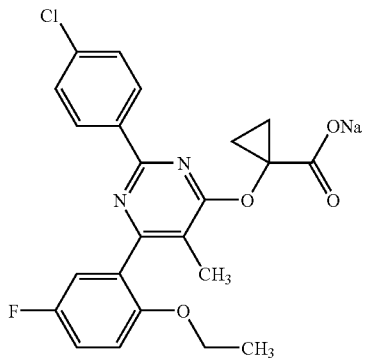

MS: 441/443[M-Na]– (ESI).

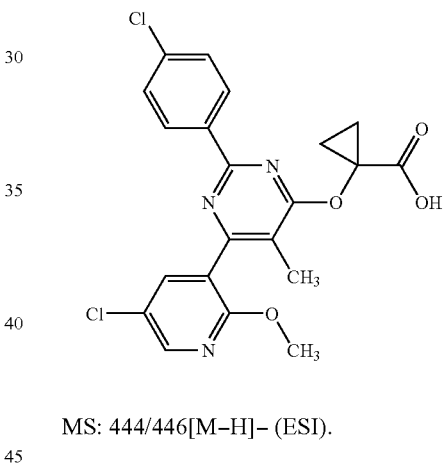

| Example | R | MS (ESI) |
|---|---|---|
| 1300 | [5-cyclopropyl-2-methylphenyl-CH2-OMe] | 449/451[M – H]– |

-continued

[structure: 2-(4-chlorophenyl)-pyrimidine with O-cyclopropyl-CO2H and R substituent]

| Example | R | MS (ESI) |
|---|---|---|
| 1301 | [3-methyl-4-(CF3)pyridin-yl] | 434/436[M – H]– |

Example 1302

[structure with 5-chloro-2-methoxypyridin-3-yl and CH3]

MS: 444/446[M–H]– (ESI).

[structure: 2-(4-chlorophenyl)-pyrimidine with O-cyclopropyl-CO2H and R substituent]

| Example | R | MS (ESI) |
|---|---|---|
| 1303 | [5-chloro-3-methyl-2-ethoxypyridin-yl] | 444/446[M – H]– |

247
-continued
| | | |
|---|---|---|
| 1304 | 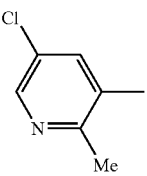 | 414/416[M − H]− |
| 1305 | 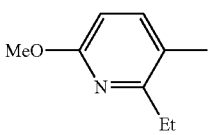 | 424/426[M − H]− |
| 1306 | 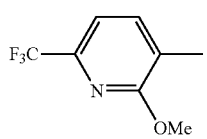 | 464/466[M − H]− |
| 1307 | 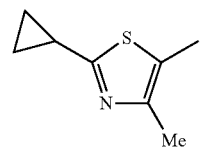 | 426/428[M − H]− |
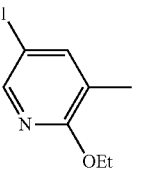
| Example | R | MS (ESI) |
|---|---|---|
| 1308 | 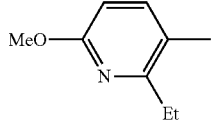 | 421[M − H]− |
| 1309 | 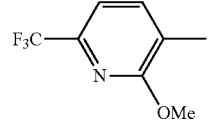 | 433[M − H]− |
| 1310 | 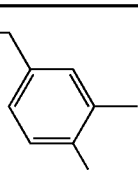 | 403/405[M − H]− |
| 1311 | 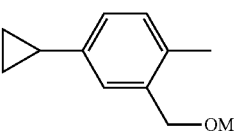 | 398/400[M − H]− |
248
-continued
| | | |
|---|---|---|
| 1312 | 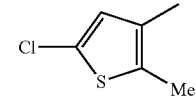 | 428/430[M − H]− |
| 1313 | 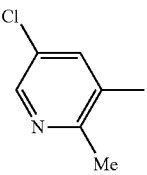 | 408[M − H]− |
| 1314 | 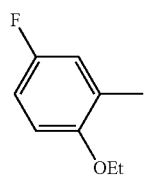 | 448[M − H]− |
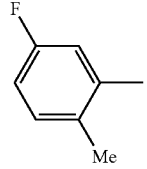
| Example | R | MS (ESI) |
|---|---|---|
| 1315 | 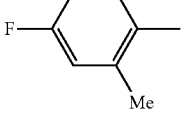 | 433/435[M − H]− |
| 1316 | 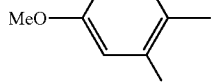 | 403/405[M − H]− |
| 1317 | 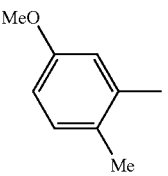 | 403/405[M − H]− |
| 1318 | MeO-aryl-Me,Me | 415/417[M − H]− |
| 1319 | MeO-aryl-Me,Me | 415/417[M − H]− |

| Example | R | MS (ESI) |
|---|---|---|
| 1320 | 5-fluoro-2-methylbenzyl methyl ether | 433/435[M − H]− |
| 1321 | 4-fluoro-2-methylbenzyl methyl ether | 433/435[M − H]− |
| 1322 | 5-chloro-2-methylbenzyl methyl ether | 499/451[M − H]− |
| 1323 | 4-chloro-2-methylbenzyl methyl ether | 499/451[M − H]− |

Scaffold: 2-(5-chlorothien-2-yl)-5-methyl-6-R-pyrimidin-4-yloxy-cyclopropanecarboxylic acid

| Example | R | MS (ESI) |
|---|---|---|
| 1324 | 1-methyl-4-(propoxy)piperidine | 450/452[M − H]− |
| 1325 | 1-methyl-4-(ethoxymethyl)piperidine | 450/452[M − H]− |
| 1326 | 1-methyl-4-(2-methoxyethyl)piperidine | 450/452[M − H]− |

Scaffold: 2-(5-chlorothien-2-yl)-5-fluoro-6-R-pyrimidin-4-yloxy-cyclopropanecarboxylic acid

| Example | R | MS (ESI) |
|---|---|---|
| 1327 | 1-methyl-4-ethoxypiperidine | 440/442[M − H]− |
| 1328 | 1-methyl-4-(methoxymethyl)piperidine | 440/442[M − H]− |
| 1329 | 1-methyl-4-(propoxy)piperidine | 454/456[M − H]− |
| 1330 | 1-methyl-4-(ethoxymethyl)piperidine | 454/456[M − H]− |
| 1331 | 1-methyl-4-(2-methoxyethyl)piperidine | 454/456[M − H]− |

Scaffold: 2-(4,5-dichlorothien-2-yl)-5-fluoro-6-R-pyrimidin-4-yloxy-cyclopropanecarboxylic acid

| Example | R | MS (ESI) |
|---|---|---|
| 1332 | 1-methyl-4-ethoxypiperidine | 474/476[M − H]− |
| 1333 | 1-methyl-4-(methoxymethyl)piperidine | 474/476[M − H]− |
| 1334 | 1-methyl-4-(propoxy)piperidine | 488/490[M − H]− |
| 1335 | 1-methyl-4-(ethoxymethyl)piperidine | 488/490[M − H]− |
| 1336 | 1-methyl-4-(2-methoxyethyl)piperidine | 488/490[M − H]− |

Corresponding starting compounds are treated in the similar manner to any of the above Examples to give the following intermediates.

| Reference example | Structure | MS (APCI) |
|---|---|---|
| 1 | 2-(4-chloro-3-fluorophenyl)-6-chloropyrimidin-4-yl O-CH₂C(O)OCH₂CH₃ | 345/347 [M + H]⁺ |
| 2 | 2-(4-chloro-3-fluorophenyl)-6-chloropyrimidin-4-yl O-cyclopropyl-C(O)OCH₃ | 357/359 [M + H]⁺ |
| 3 | 2-(4-chloro-3-fluorophenyl)-6-chloropyrimidin-4-yl O-C(Et)(Et)C(O)OCH₃ | 387/389 [M + H]⁺ |
| 4 | 2-(4-chloro-3-fluorophenyl)-6-chloropyrimidin-4-yl O-cyclopentyl-C(O)OCH₃ | 385/387 [M + H]⁺ |
| 5 | 2-(4-chloro-3-fluorophenyl)-6-chloropyrimidin-4-yl O-(tetrahydropyran-4-yl)-C(O)O-CH₂-(4-methoxyphenyl) | 507/509 [M + H]⁺ |

| | | |
|---|---|---|
| 6 | 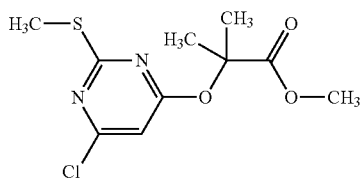 | 277/279 [M + H]+ |
| 7 | 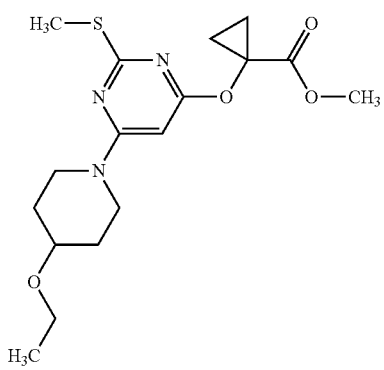 [SMILES: CCOC1CCN(c2cc(OC3(C(=O)OC)CC3)nc(SC)n2)CC1] | 368 [M + H]+ |
| 8 | 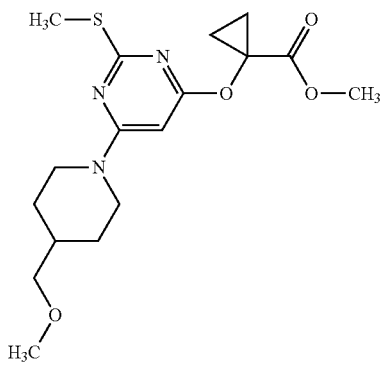 [SMILES: COCC1CCN(c2cc(OC3(C(=O)OC)CC3)nc(SC)n2)CC1] | 368 [M + H]+ |
| 9 | 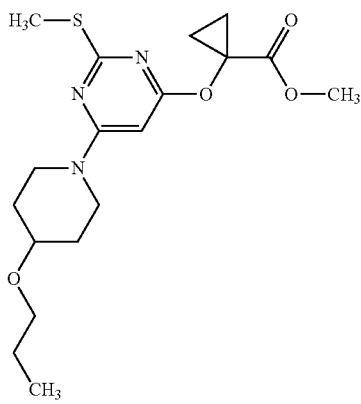 [SMILES: CCCOC1CCN(c2cc(OC3(C(=O)OC)CC3)nc(SC)n2)CC1] | 382 [M + H]+ |

-continued
| | | |
|---|---|---|
| 10 | 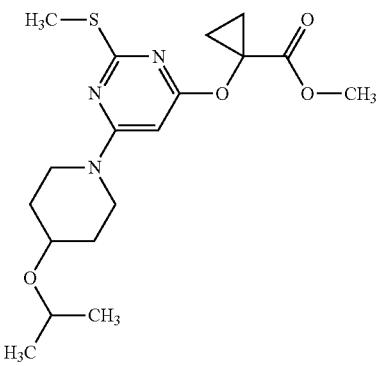 [SMILES: COC(=O)C1(Oc2cc(N3CCC(OC(C)C)CC3)nc(SC)n2)CC1] | 382 [M + H]+ |
| 11 | 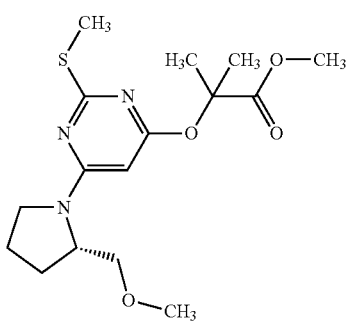 [SMILES: COC[C@@H]1CCCN1c1cc(OC(C)(C)C(=O)OC)nc(SC)n1] | 356 [M + H]+ |
| 12 | 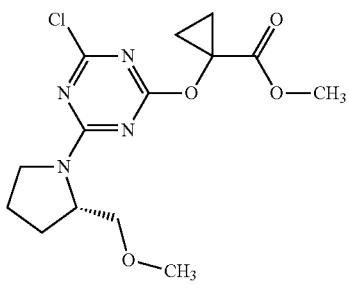 [SMILES: COC[C@@H]1CCCN1c1nc(Cl)nc(OC2(C(=O)OC)CC2)n1] | 343/345 [M + H]+ |
| 13 | 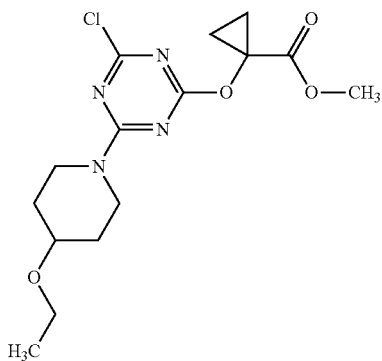 [SMILES: CCOC1CCN(c2nc(Cl)nc(OC3(C(=O)OC)CC3)n2)CC1] | 357/359 [M + H]+ |

| | | |
|---|---|---|
| 14 | 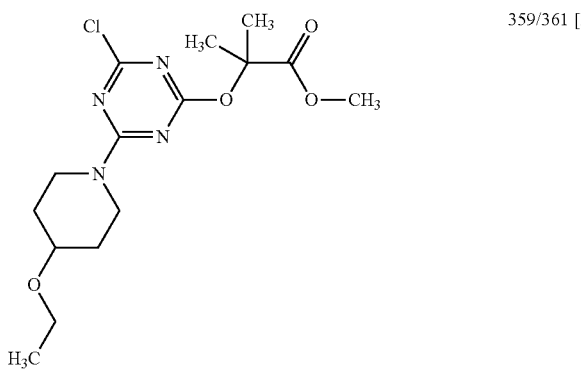 | 359/361 [M + H]⁺ |
| 15 | 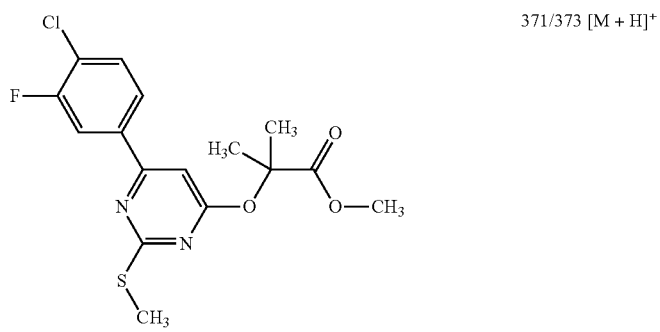 | 371/373 [M + H]⁺ |
| 16 | 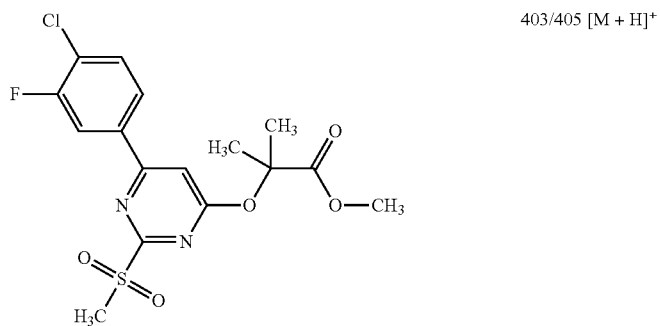 | 403/405 [M + H]⁺ |
| 17 | 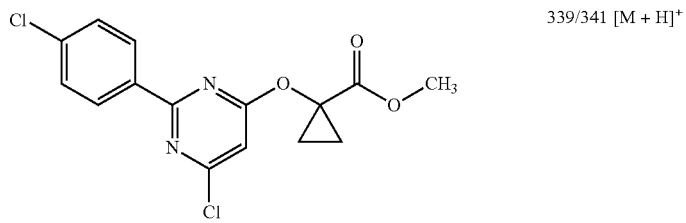 | 339/341 [M + H]⁺ |
| 18 | 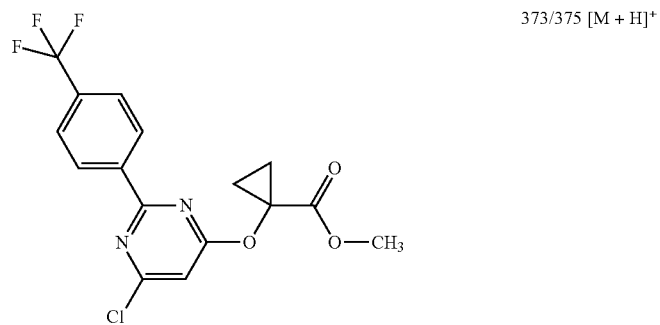 | 373/375 [M + H]⁺ |

-continued
| | | |
|---|---|---|
| 19 | 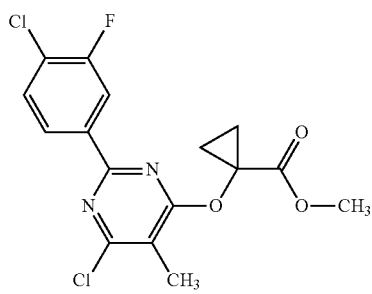 [SMILES: COC(=O)C1(Oc2nc(-c3ccc(Cl)c(F)c3)nc(Cl)c2C)CC1] | 371/373 [M + H]+ |
| 20 | 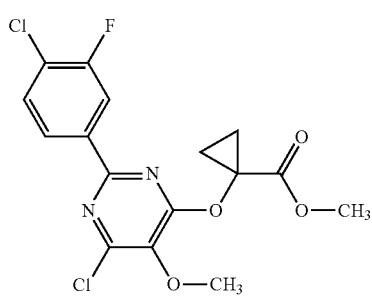 [SMILES: COC(=O)C1(Oc2nc(-c3ccc(Cl)c(F)c3)nc(Cl)c2OC)CC1] | 387/389 [M + H]+ |
| 21 | 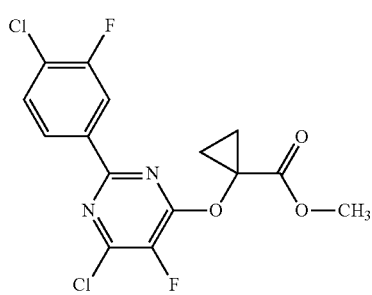 [SMILES: COC(=O)C1(Oc2nc(-c3ccc(Cl)c(F)c3)nc(Cl)c2F)CC1] | 375/377 [M + H]+ |
| 22 | 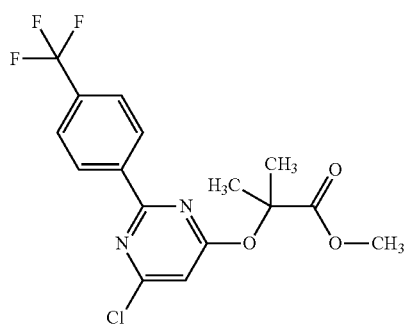 [SMILES: COC(=O)C(C)(C)Oc1cc(Cl)nc(-c2ccc(C(F)(F)F)cc2)n1] | 375/377 [M + H]+ |
| 23 | 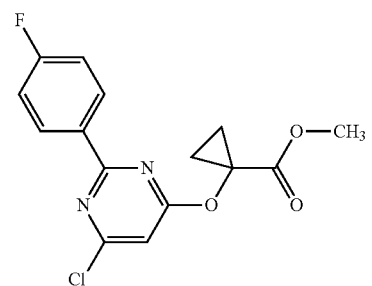 [SMILES: COC(=O)C1(Oc2cc(Cl)nc(-c3ccc(F)cc3)n2)CC1] | 323/325 [M + H]+ |

-continued
| | | |
|---|---|---|
| 24 | 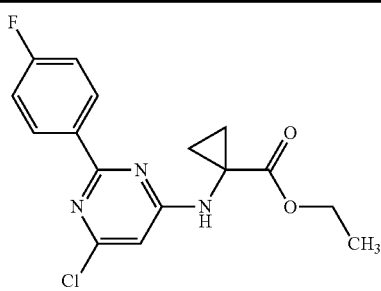 | 336/338 [M + H]+ |
| 25 | 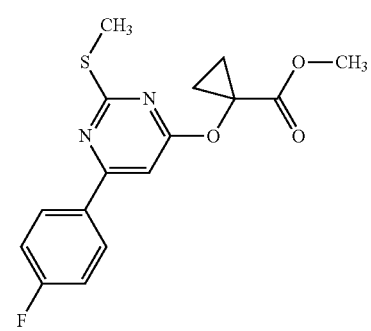 [SMILES: COC(=O)C1(Oc2cc(-c3ccc(F)cc3)nc(SC)n2)CC1] | 335 [M + H]+ |
| 26 | 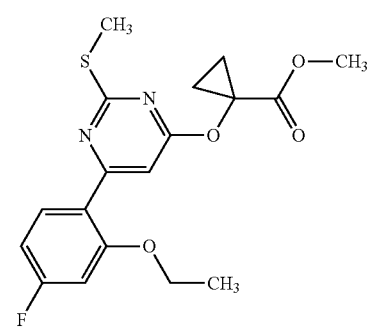 [SMILES: CCOc1cc(F)ccc1-c1cc(OC2(C(=O)OC)CC2)nc(SC)n1] | 379 [M + H]+ |
| 27 | 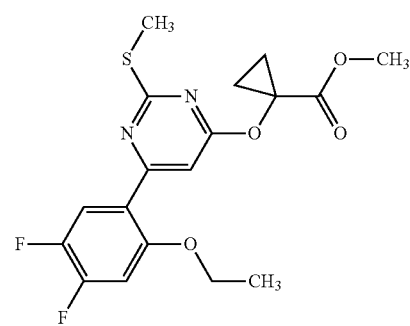 [SMILES: CCOc1cc(F)c(F)cc1-c1cc(OC2(C(=O)OC)CC2)nc(SC)n1] | 397 [M + H]+ |
| 28 | 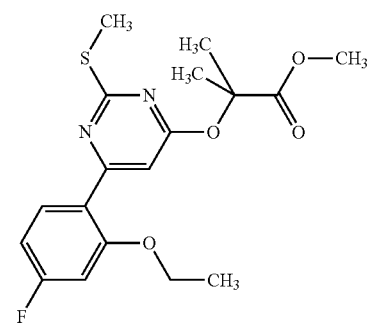 [SMILES: CCOc1cc(F)ccc1-c1cc(OC(C)(C)C(=O)OC)nc(SC)n1] | 381 [M + H]+ |

| | | |
|---|---|---|
| 29 | 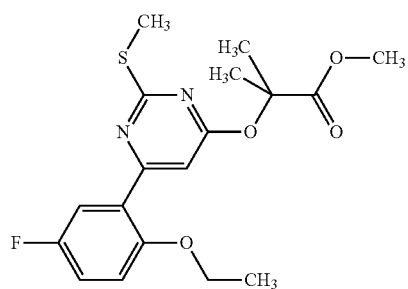 [SMILES: CCOc1ccc(F)cc1-c1cc(OC(C)(C)C(=O)OC)nc(SC)n1] | 381 [M + H]+ |
| 30 | 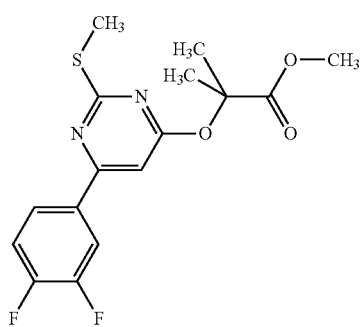 [SMILES: COC(=O)C(C)(C)Oc1cc(-c2ccc(F)c(F)c2)nc(SC)n1] | 355 [M + H]+ |
| 31 | 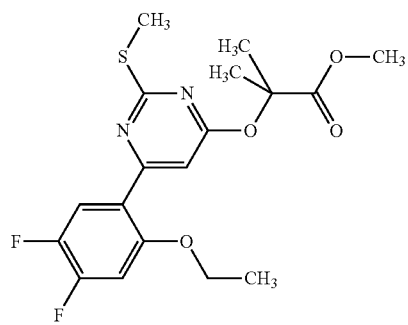 [SMILES: CCOc1cc(F)c(F)cc1-c1cc(OC(C)(C)C(=O)OC)nc(SC)n1] | 399 [M + H]+ |
| 32 | 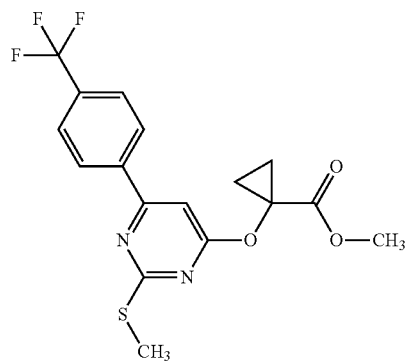 | 385 [M + H]+ |

-continued
| | | |
|---|---|---|
| 33 | 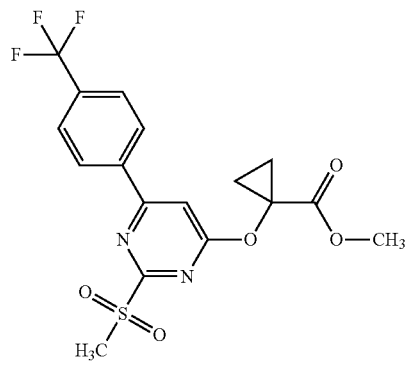 [SMILES: COC(=O)C1(Oc2cc(-c3ccc(C(F)(F)F)cc3)nc(S(C)(=O)=O)n2)CC1] | 417 [M + H]+ |
| 34 | 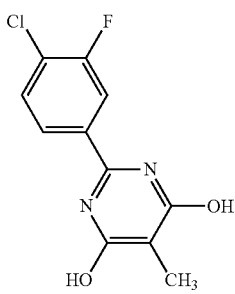 [SMILES: Cc1c(O)nc(-c2ccc(Cl)c(F)c2)nc1O] | 255/257 [M + H]+ |
| 35 | 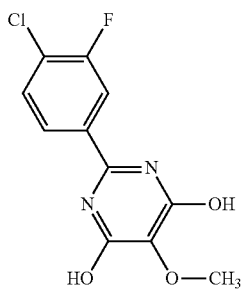 [SMILES: COc1c(O)nc(-c2ccc(Cl)c(F)c2)nc1O] | 271/273 [M + H]+ |
| 36 | 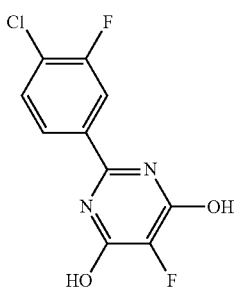 [SMILES: Oc1nc(-c2ccc(Cl)c(F)c2)nc(O)c1F] | 259/261 [M + H]+ |
| 37 | 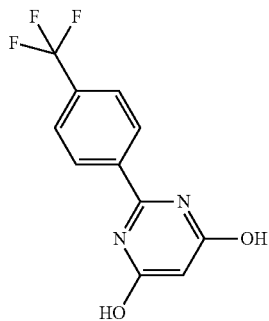 [SMILES: Oc1cc(O)nc(-c2ccc(C(F)(F)F)cc2)n1] | 257 [M + H]+ |

-continued
| | | |
|---|---|---|
| 38 | 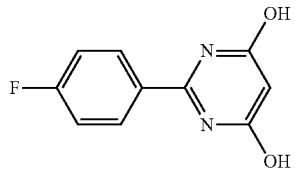 | 207 [M + H]⁺ |
| 39 | 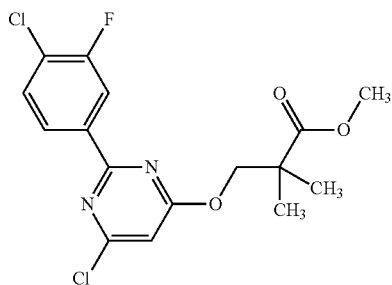 [SMILES: COC(=O)C(C)(C)COc1cc(Cl)nc(-c2ccc(Cl)c(F)c2)n1] | 373/375 [M + H]⁺ |
| 40 | 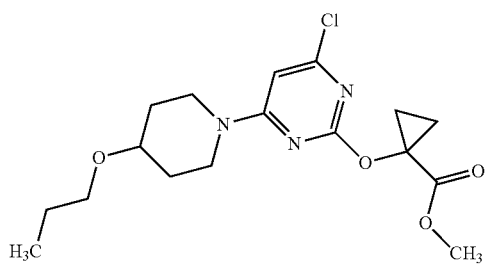 [SMILES: CCCOC1CCN(c2cc(Cl)nc(OC3(C(=O)OC)CC3)n2)CC1] | 370/372 [M + H]⁺ |
| 41 | 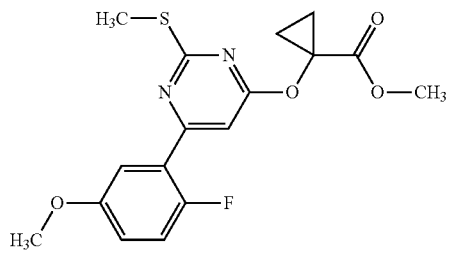 | 365 [M + H]⁺ |
| 42 | 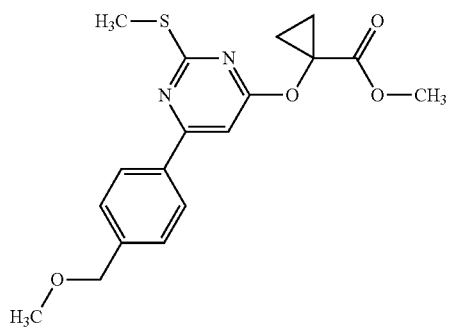 | 361 [M + H]⁺ |

| | | |
|---|---|---|
| 43 | 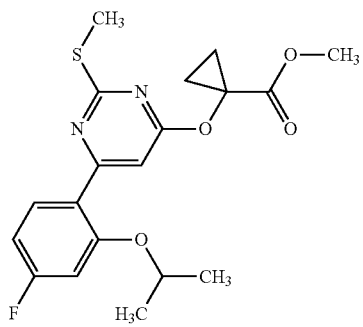 [SMILES: COC(=O)C1(Oc2cc(-c3ccc(F)cc3OC(C)C)nc(SC)n2)CC1] | 393 [M + H]+ |
| 44 | 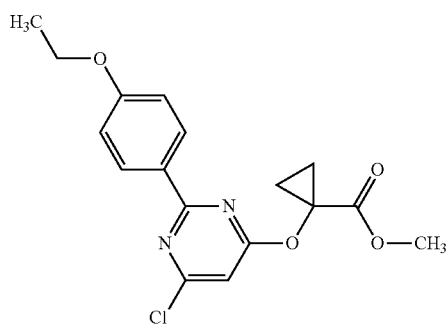 [SMILES: CCOc1ccc(-c2nc(Cl)cc(OC3(C(=O)OC)CC3)n2)cc1] | 349/351 [M + H]+ |
| 45 | 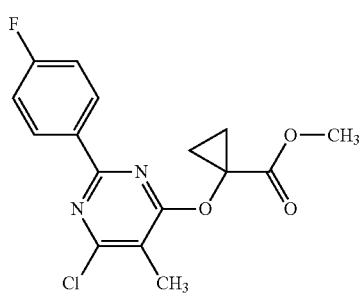 [SMILES: COC(=O)C1(Oc2nc(-c3ccc(F)cc3)nc(Cl)c2C)CC1] | 337 [M + H]+ |
| 46 | 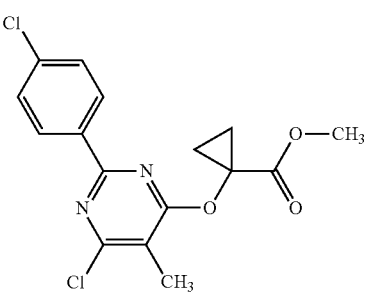 [SMILES: COC(=O)C1(Oc2nc(-c3ccc(Cl)cc3)nc(Cl)c2C)CC1] | 353/355 [M + H]+ |
| 47 | 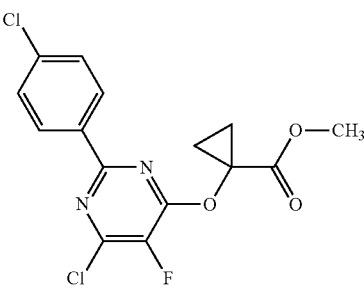 [SMILES: COC(=O)C1(Oc2nc(-c3ccc(Cl)cc3)nc(Cl)c2F)CC1] | 357/359 [M + H]+ |

-continued
| | | |
|---|---|---|
| 48 | 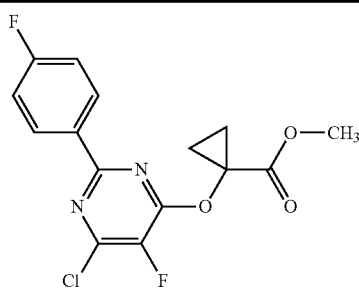 | 341/343 [M + H]+ |
| 49 | 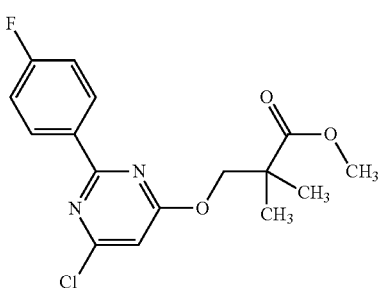 [SMILES: COC(=O)C(C)(C)COc1cc(Cl)nc(-c2ccc(F)cc2)n1] | 339/341 [M + H]+ |
| 50 | 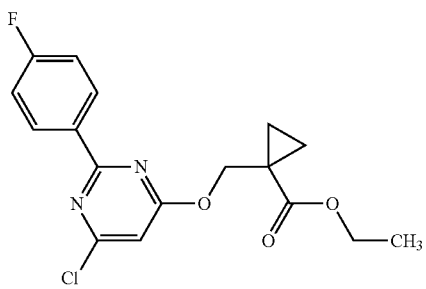 [SMILES: CCOC(=O)C1(COc2cc(Cl)nc(-c3ccc(F)cc3)n2)CC1] | 351/353 [M + H]+ |
| 51 | 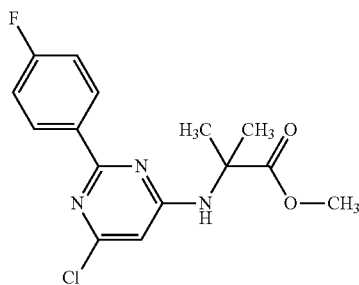 [SMILES: COC(=O)C(C)(C)Nc1cc(Cl)nc(-c2ccc(F)cc2)n1] | 324/326 [M + H]+ |
| 52 | 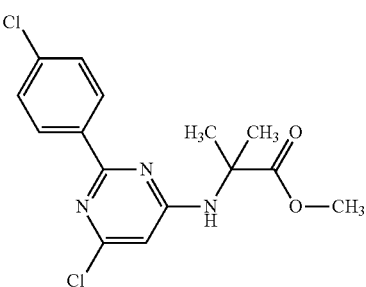 [SMILES: COC(=O)C(C)(C)Nc1cc(Cl)nc(-c2ccc(Cl)cc2)n1] | 340/342 [M + H]+ |

-continued
| | | |
|---|---|---|
| 53 | 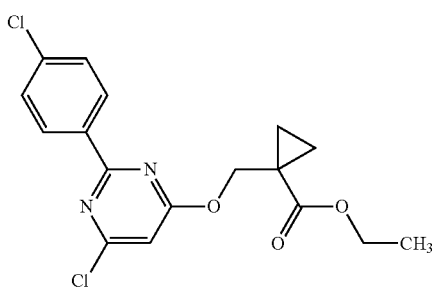 [SMILES: CCOC(=O)C1(COc2cc(Cl)nc(-c3ccc(Cl)cc3)n2)CC1] | 367/369 [M + H]+ |
| 54 | 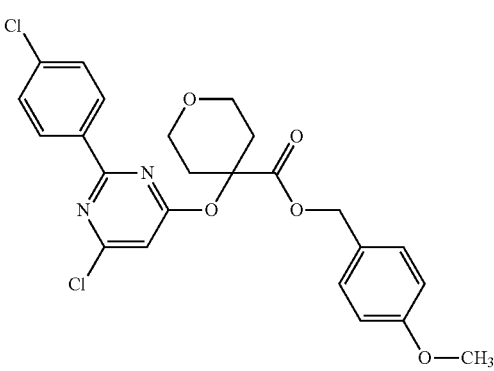 [SMILES: COc1ccc(COC(=O)C2(Oc3cc(Cl)nc(-c4ccc(Cl)cc4)n3)CCOCC2)cc1] | 489/491 [M + H]+ |
| 55 | 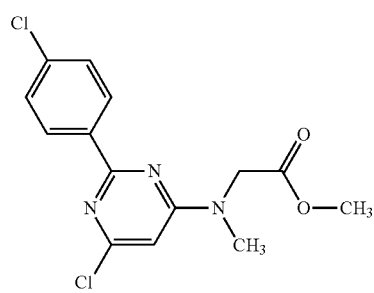 [SMILES: COC(=O)CN(C)c1cc(Cl)nc(-c2ccc(Cl)cc2)n1] | 326/328 [M + H]+ |
| 56 | 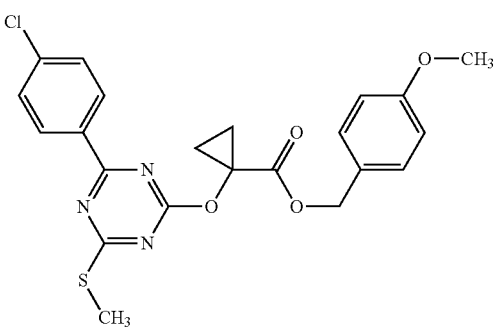 [SMILES: COc1ccc(COC(=O)C2(Oc3nc(SC)nc(-c4ccc(Cl)cc4)n3)CC2)cc1] | 458/460 [M + H]+ |
| 57 | 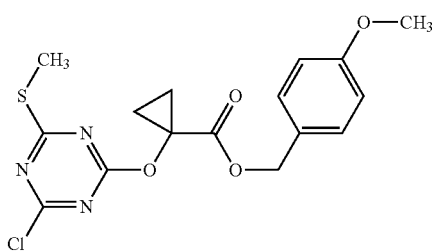 [SMILES: COc1ccc(COC(=O)C2(Oc3nc(Cl)nc(SC)n3)CC2)cc1] | 382/384 [M + H]+ |

-continued
| | | |
|---|---|---|
| 58 | 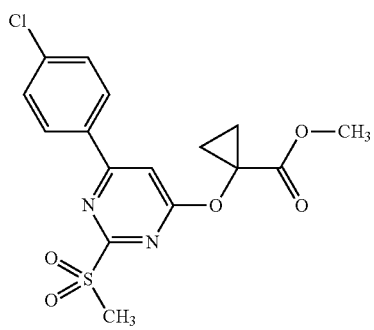 [SMILES: COC(=O)C1(Oc2cc(-c3ccc(Cl)cc3)nc(S(C)(=O)=O)n2)CC1] | 383/385 [M + H]+ |
| 59 | 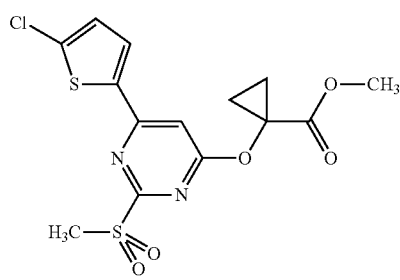 [SMILES: COC(=O)C1(Oc2cc(-c3ccc(Cl)s3)nc(S(C)(=O)=O)n2)CC1] | 389/391 [M + H]+ |
| 60 | 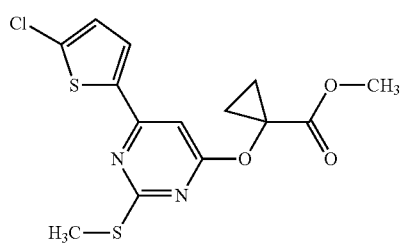 [SMILES: COC(=O)C1(Oc2cc(-c3ccc(Cl)s3)nc(SC)n2)CC1] | 357/359 [M + H]+ |
| 61 | 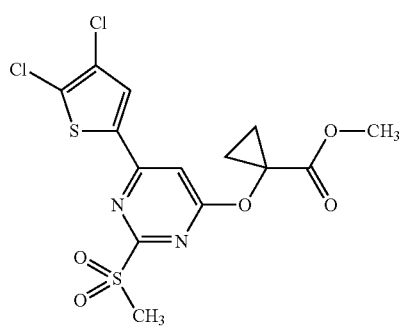 [SMILES: COC(=O)C1(Oc2cc(-c3cc(Cl)c(Cl)s3)nc(S(C)(=O)=O)n2)CC1] | 423/425 [M + H]+ |
| 62 | 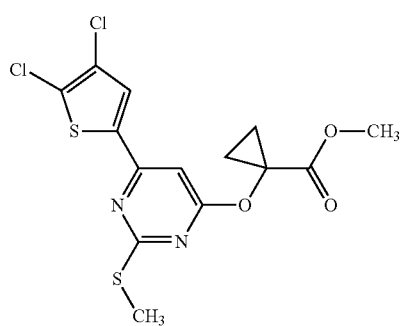 [SMILES: COC(=O)C1(Oc2cc(-c3cc(Cl)c(Cl)s3)nc(SC)n2)CC1] | 391/393 [M + H]+ |

-continued
| | | |
|---|---|---|
| 63 | 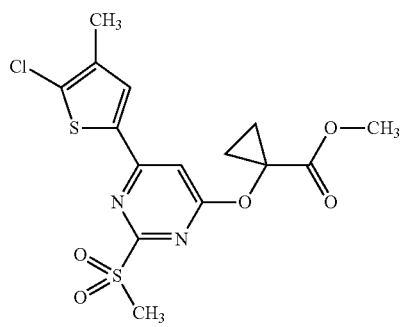 | 403/405 [M + H]+ |
| 64 | 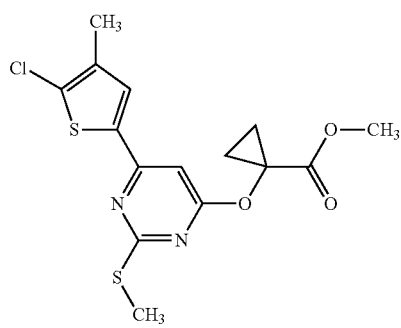 [SMILES: COC(=O)C1(Oc2cc(-c3cc(C)c(Cl)s3)nc(SC)n2)CC1] | 371/373 [M + H]+ |
| 65 | 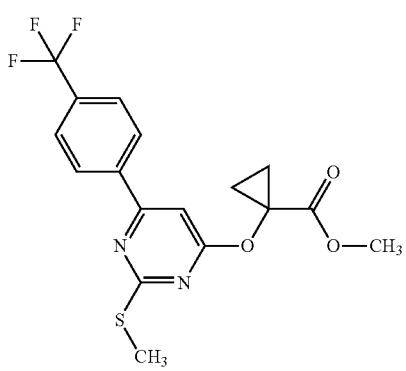 [SMILES: COC(=O)C1(Oc2cc(-c3ccc(C(F)(F)F)cc3)nc(SC)n2)CC1] | 385 [M + H]+ |
| 66 | 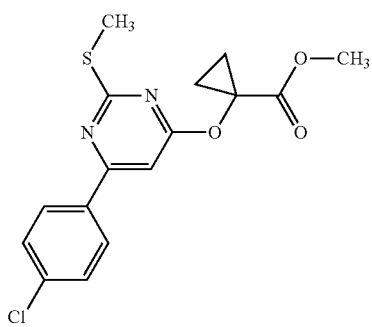 [SMILES: COC(=O)C1(Oc2cc(-c3ccc(Cl)cc3)nc(SC)n2)CC1] | 351/353 [M + H]+ |
| 67 | 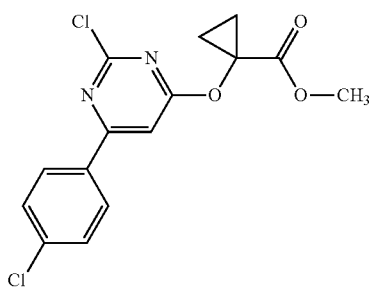 [SMILES: COC(=O)C1(Oc2cc(-c3ccc(Cl)cc3)nc(Cl)n2)CC1] | 339/341 [M + H]+ |

-continued
| 68 | 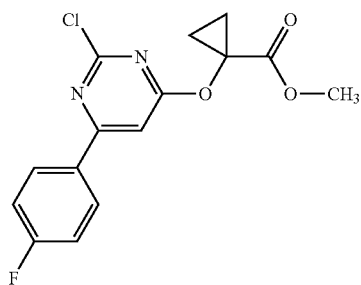 [SMILES: COC(=O)C1(Oc2cc(-c3ccc(F)cc3)nc(Cl)n2)CC1] | 323/325 [M + H]+ |
| 69 | 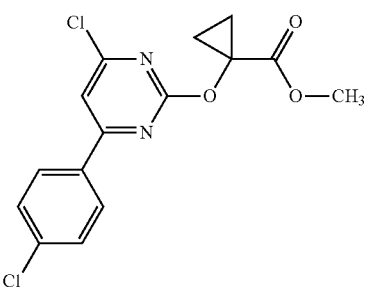 [SMILES: COC(=O)C1(Oc2nc(Cl)cc(-c3ccc(Cl)cc3)n2)CC1] | 339/341 [M + H]+ |
| 70 | 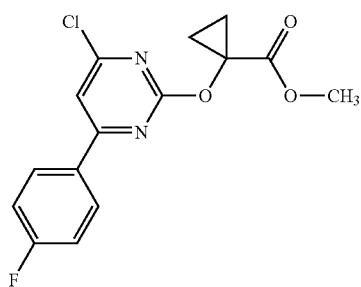 [SMILES: COC(=O)C1(Oc2nc(Cl)cc(-c3ccc(F)cc3)n2)CC1] | 323/325 [M + H]+ |
| 71 | 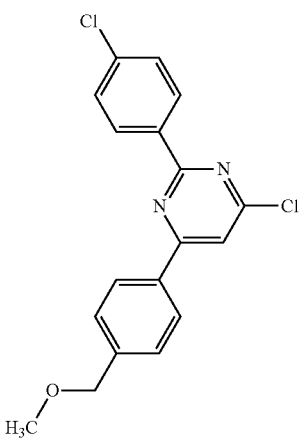 [SMILES: COCc1ccc(-c2cc(Cl)nc(-c3ccc(Cl)cc3)n2)cc1] | 345/347 [M + H]+ |
| 72 | 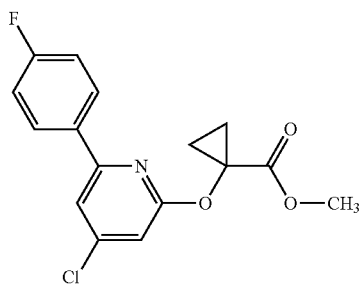 [SMILES: COC(=O)C1(Oc2cc(Cl)cc(-c3ccc(F)cc3)n2)CC1] | 322/324 [M + H]+ |

-continued
| | | |
|---|---|---|
| 73 | 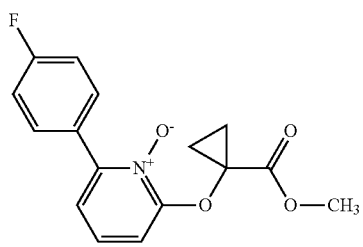 [SMILES: COC(=O)C1(Oc2cccc(-c3ccc(F)cc3)[n+]2[O-])CC1] | 304 [M + H]+ |
| 74 | 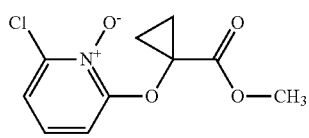 [SMILES: COC(=O)C1(Oc2cccc(Cl)[n+]2[O-])CC1] | 244/246 [M + H]+ |
| 75 | 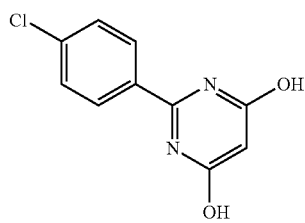 [SMILES: Oc1cc(O)nc(-c2ccc(Cl)cc2)n1] | 223/225 [M + H]+ |
| 76 | 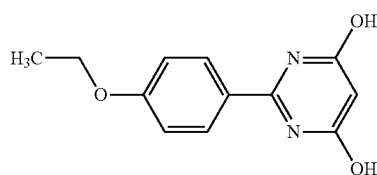 [SMILES: CCOc1ccc(-c2nc(O)cc(O)n2)cc1] | 233 [M + H]+ |
| 77 | 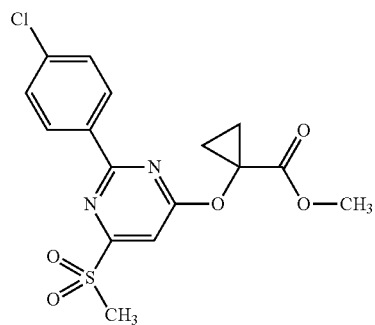 [SMILES: COC(=O)C1(Oc2cc(S(C)(=O)=O)nc(-c3ccc(Cl)cc3)n2)CC1] | 383/385 [M + H]+ |
| 78 | 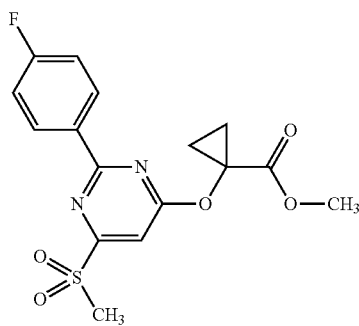 [SMILES: COC(=O)C1(Oc2cc(S(C)(=O)=O)nc(-c3ccc(F)cc3)n2)CC1] | 367 [M + H]+ |

-continued
| | | |
|---|---|---|
| 79 | 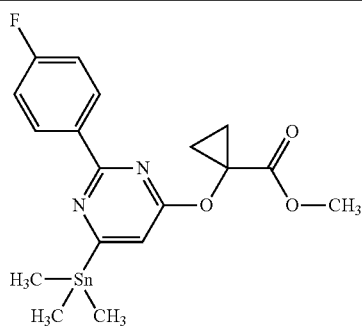 | 449/451/453 [M + H]+ |
| 80 | 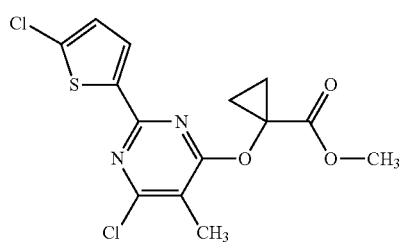 [SMILES: COC(=O)C1(Oc2nc(-c3ccc(Cl)s3)nc(Cl)c2C)CC1] | 359/361 [M + H]+ |
| 81 | 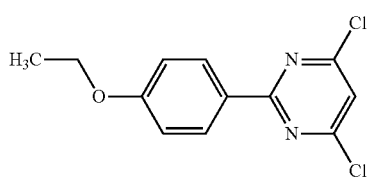 [SMILES: CCOc1ccc(-c2nc(Cl)cc(Cl)n2)cc1] | 269/271 [M + H]+ |
| 82 | 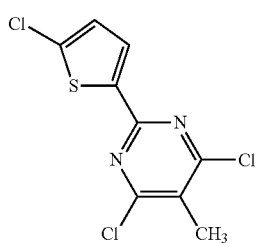 | 279/281 [M + H]+ |
| 83 | 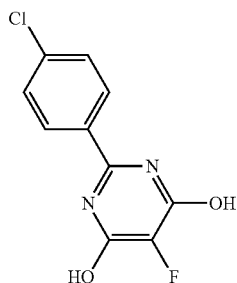 [SMILES: Oc1nc(-c2ccc(Cl)cc2)nc(O)c1F] | 241/243 [M + H]+ |
| 84 | 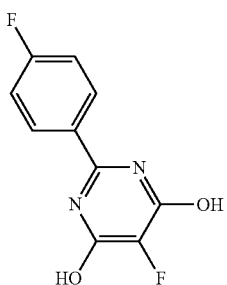 [SMILES: Oc1nc(-c2ccc(F)cc2)nc(O)c1F] | 223 [M − H]− |

-continued
| | | |
|---|---|---|
| 85 | 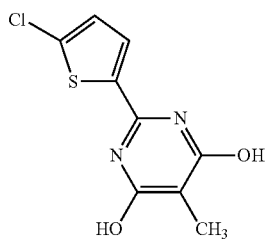 | 243/245 [M + H]+ |
| 86 | 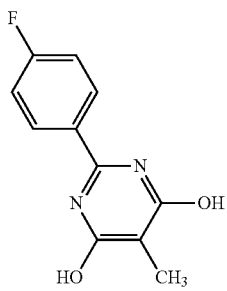 [SMILES: Cc1c(O)nc(-c2ccc(F)cc2)nc1O] | 221 [M + H]+ |
| 87 | 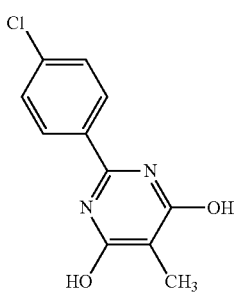 [SMILES: Cc1c(O)nc(-c2ccc(Cl)cc2)nc1O] | 237/239 [M + H]+ |
| 88 | 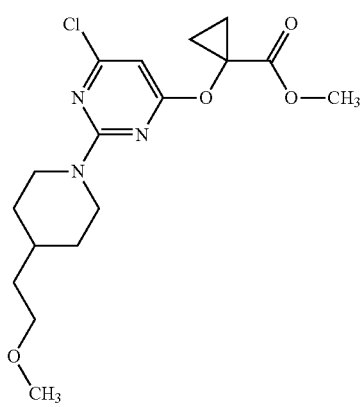 [SMILES: COCCC1CCN(c2nc(Cl)cc(OC3(C(=O)OC)CC3)n2)CC1] | 370/372 [M + H]+ |
| 89 | 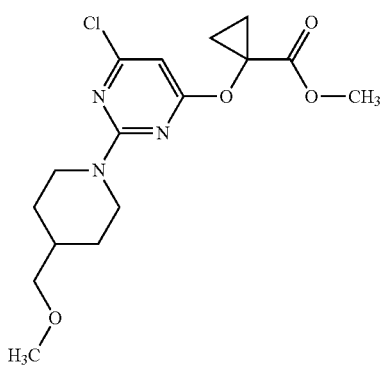 [SMILES: COCC1CCN(c2nc(Cl)cc(OC3(C(=O)OC)CC3)n2)CC1] | 356/358 [M + H]+ |

| | | |
|---|---|---|
| 90 | 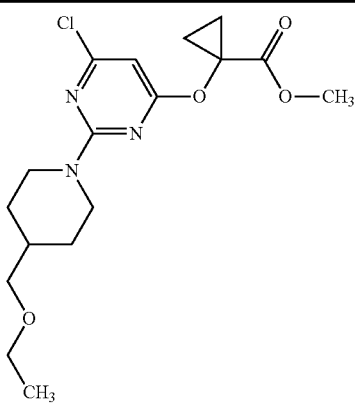 | 370/372 [M + H]+ |
| 91 | 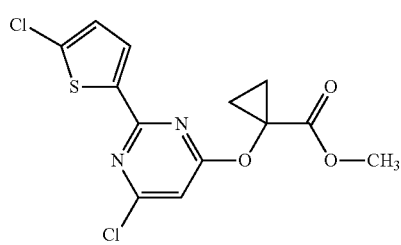 [SMILES: COC(=O)C1(Oc2cc(Cl)nc(-c3ccc(Cl)s3)n2)CC1] | 345/347 [M + H]+ |
| 92 | 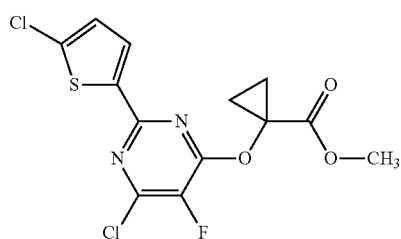 [SMILES: COC(=O)C1(Oc2nc(-c3ccc(Cl)s3)nc(Cl)c2F)CC1] | 363/365 [M + H]+ |
| 93 | 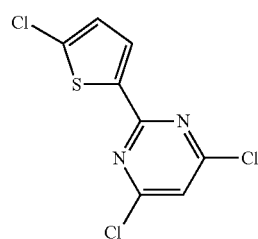 [SMILES: Clc1cc(Cl)nc(-c2ccc(Cl)s2)n1] | 265/267 [M + H]+ |
| 94 | 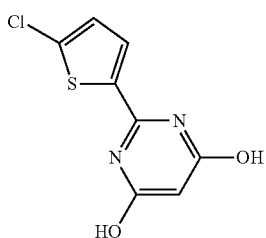 [SMILES: Oc1cc(O)nc(-c2ccc(Cl)s2)n1] | 229/231 [M + H]+ |
| 95 | 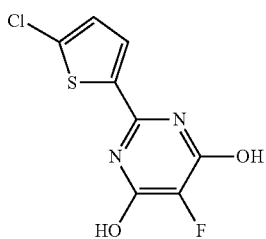 [SMILES: Oc1nc(-c2ccc(Cl)s2)nc(O)c1F] | 247/249 [M + H]+ |

| | | |
|---|---|---|
| 96 | 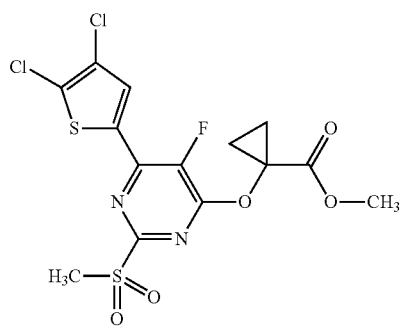 [SMILES: COC(=O)C1(Oc2nc(S(C)(=O)=O)nc(-c3cc(Cl)c(Cl)s3)c2F)CC1] | 441/443 [M + H]⁺ |
| 97 | 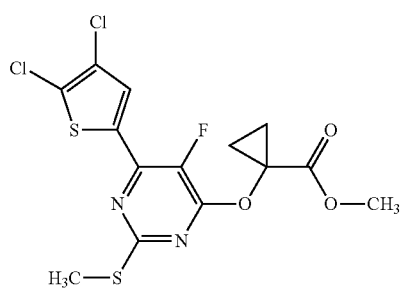 [SMILES: COC(=O)C1(Oc2nc(SC)nc(-c3cc(Cl)c(Cl)s3)c2F)CC1] | 409/411 [M + H]⁺ |
| 98 | 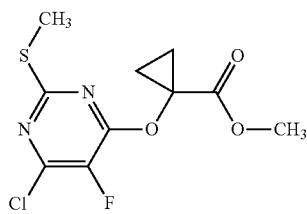 [SMILES: COC(=O)C1(Oc2nc(SC)nc(Cl)c2F)CC1] | 293/295 [M + H]⁺ |
| Reference example | Structure | |
|---|---|---|
| 99 | 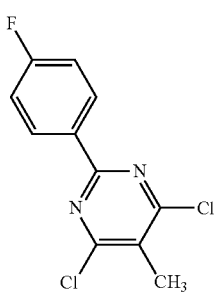 [SMILES: Cc1c(Cl)nc(-c2ccc(F)cc2)nc1Cl] | ¹H NMR (500 MHz, DMSO-d₆): δ 2.45 (3H, s), 7.36-7.41 (2H, m), 8.30-8.35 (2H, m) |
| 100 | 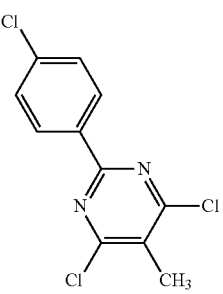 [SMILES: Cc1c(Cl)nc(-c2ccc(Cl)cc2)nc1Cl] | ¹H NMR (500 MHz, DMSO-d₆): δ 2.45 (3H, s), 7.61-7.64 (2H, m), 8.26-8.29 (2H, m) |

| | | |
|---|---|---|
| 101 | 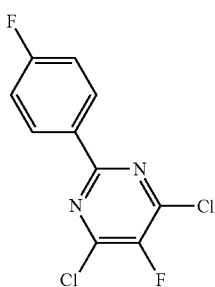 [SMILES: Fc1ccc(-c2nc(Cl)c(F)c(Cl)n2)cc1] | ¹H NMR (500 MHz, DMSO-d₆): δ 7.37-7.42 (2H, m), 8.29-8.33 (2H, m) |
| 102 | 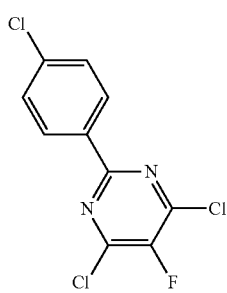 [SMILES: Fc1c(Cl)nc(-c2ccc(Cl)cc2)nc1Cl] | ¹H NMR (500 MHz, DMSO-d₆): δ 7.63-7.65 (2H, m), 8.24-8.27 (2H, m) |
| 103 | 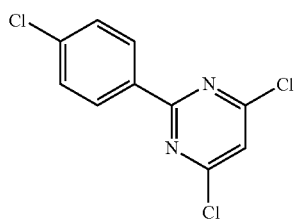 [SMILES: Clc1ccc(-c2nc(Cl)cc(Cl)n2)cc1] | ¹H NMR (400 MHz, CDCl₃): δ 7.29 (1H, s), 7.46 (2H, d, J = 8.8 Hz), 8.38 (2H, d, J = 8.8 Hz) |
| 104 | 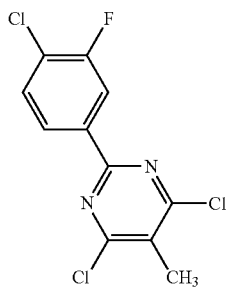 [SMILES: Cc1c(Cl)nc(-c2ccc(Cl)c(F)c2)nc1Cl] | ¹H NMR (500 MHz, DMSO-d₆): δ 2.46 (3H, s), 7.80 (1H, t, J = 8.2 Hz), 8.09-8.16 (2H, m) |
| 105 | 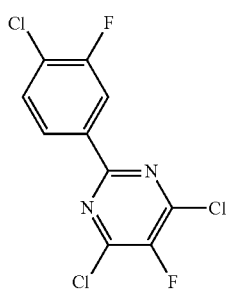 [SMILES: Fc1cc(-c2nc(Cl)c(F)c(Cl)n2)ccc1Cl] | ¹H NMR (400 MHz, DMSO-d₆): δ 7.81 (1H, dd, J = 7.3, 8.2 Hz), 8.08-8.15 (2H, m) |

| | | |
|---|---|---|
| 106 | 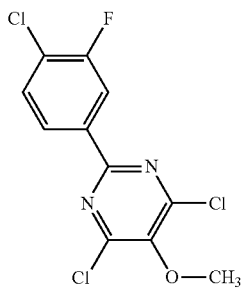 [SMILES: COc1c(Cl)nc(-c2ccc(Cl)c(F)c2)nc1Cl] | $^1$H NMR (400 MHz, DMSO-d$_6$): δ 3.97 (3H, s), 7.79 (1H, dd, J = 7.6, 8.2 Hz), 8.07-8.12 (2H, m) |
| 107 | 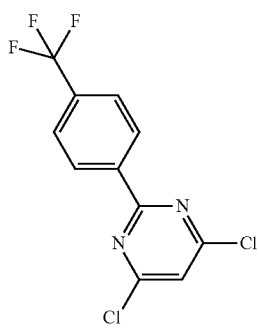 [SMILES: FC(F)(F)c1ccc(-c2nc(Cl)cc(Cl)n2)cc1] | $^1$H NMR (400 MHz, CDCl$_3$): δ 7.35 (1H, s), 7.75 (2H, d, J = 8.5 Hz), 8.57 (2H, d, J = 8.2 Hz) |
| 108 | 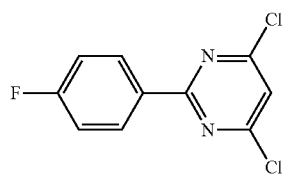 | $^1$H NMR (400 MHz, CDCl$_3$): δ 7.13-7.20 (1H, m), 7.27 (1H, s), 8.43-8.50 (2H, m) |
| 109 | 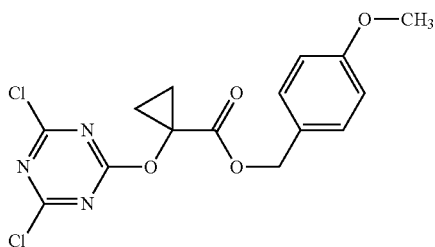 [SMILES: COc1ccc(COC(=O)C2(Oc3nc(Cl)nc(Cl)n3)CC2)cc1] | $^1$H NMR (400 MHz, CDCl3): δ 1.40 (2H, dd, J = 6.0, 8.8 Hz), 1.71 (2H, dd, J = 6.0, 8.8 Hz), 3.81 (3H, s), 5.12 (2H, s), 6.84-6.88 (2H, m), 7.16-7.20 (2H, m) |
| 110 | 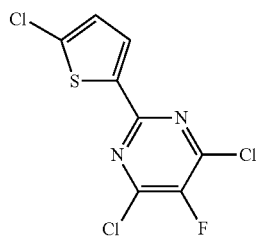 [SMILES: Fc1c(Cl)nc(-c2ccc(Cl)s2)nc1Cl] | $^1$H NMR (400 MHz, CDCl3): δ 6.96 (1H, d, J = 3.9 Hz), 7.76 (1H, d, J = 4.5 Hz) |

Experimental Example 1

Methods for Testing Compounds on Human BKαβ1 Channels Expressed Cho Cells

Cell Culture:

CHO cells expressing human BKαβ1 were cultured in T75 or 6 well cell culture cluster. Medium: DMEM/F12+10% FBS+0.5 mg/mL G418/genetecin+0.1 mg/mL Hygromycin. Split cells every 3-4 days at 80-90% confluence. Use cells for experiments 60-72 hrs after re-passage and at ~90% confluence.

Cell Preparation:

Trypsin solution (0.05% Trypsin+0.1% EDTA), Ca$^{2+}$ free PBS and culture medium were warmed to 37° C. Inspect the T75 flask for cell confluence. Remove culture medium and add warm Ca$^{2+}$ free PBS to wash cells. Remove Ca$^{2+}$ free PBS and add warm Trypsin solution. Put the T75 flask back to 37° C. incubator for about 4.5 minutes. Stop Trypsin activity by adding culture medium. Spin the cells down. Suspend cells in 120-160 μL external solution for BK current recording and use the cells as soon as possible.

Electrophysiology:

PatchXpress Sealchip 16 electrodes (AVIVA Biosciences) and PatchXpress 7000A (Axon Instruments, Inc) were used for BK current recording. Flat bottom 1.5 mL glass vial (HiPep Laboratories) were used for containing external solutions (±compounds). The holes in the sealchip (equivalent to patch electrode) had resistance about 1.5 MΩ. Cell membrane capacitance was compensated and access resistance was also compensated by 40%. Voltage-clamp protocol: Holding voltage=0 mV. Record BK current during 200-ms steps between +80 to +120 mV in 10 mV increments and 2 sec inter-pulse interval. On-line digital leak subtraction was performed by a P/−4 procedure. After whole-cell configuration was established, 2 minute was used to optimize access resistance. Then the chamber was washed with control bath solution for 1 minute to remove excessive cells. Control bath solution was added with robotic pipette and control BK current was recorded after 1 minute equilibrium time. For each drug concentration, 45 μL drug solution was added three times with "suction before adding" mode which left old solution. For each drug addition, 1 minute equilibrium time was given. BK current was measured at each drug concentrations (usually within 3.5 minutes after first drug addition). Calculate % change of BK current at the voltage step when the control BK current first exceeding 200 pA. If the control BK current was less than 200 pA at 120 mV, the cell was not used. % changes were calculated as $100*(I_d-I_c)/I_c$, where $I_d$ was the current amplitude in the presence of drug and $I_c$ was the control current amplitude.

Calculation of $EC_{100}$:

$EC_{100}$ was defined as the drug concentration causing 100% increase of BK current calculated by the method described above. $EC_{100}$ was determined by the data points just below and above 100%. % Increase of BK current was plotted against log [drug concentration]. A straight line connected two data points flanking 100%. From this straight line, the concentration corresponding to 100% increase of BK current was determined as $EC_{100}$.

Solutions for Manual Patch-Clamp and PatchXpress:

Compounds were dissolved in DMSO to make 10 mM stock solutions. Subsequent dilutions were made with external solution. The testing drug concentrations were 0.1, 0.3, 1, 3 and 10 μM depending on the potency of compounds. The highest DMSO concentration was 0.1%. External solution (in mM): 140 NaCl, 4 KCl, 1 $MgCl_2$, 2 $CaCl_2$, 10 Glucose, 10 HEPES; pH=7.4 with NaOH. Internal solution (in mM): 140 KCl, 5 EGTA, 1 $MgCl_2$, 5 MgATP, 0.2 $CaCl_2$, 5 HEPES; pH=7.2 with KOH.

A result of the selected compounds of the present invention is shown in the following Table 1.

TABLE 1

| Example | $EC_{100}$ (μM) |
|---|---|
| 5 | 0.78 |
| 6 | 1.61 |
| 12 | 1.39 |
| 16 | 1.91 |
| 17 | 2.47 |
| 31 | 0.14 |
| 33 | 1.75 |
| 36 | 0.59 |
| 37 | 0.69 |
| 39 | 0.25 |
| 47 | 0.33 |
| 50 | 1.05 |
| 51 | 1.09 |
| 54 | 1.31 |
| 59 | 0.51 |
| 62 | 1.5 |
| 63 | 1.28 |

TABLE 1-continued

| Example | $EC_{100}$ (μM) |
|---|---|
| 65 | 1.43 |
| 67 | 1.92 |
| 69 | 2.56 |
| 76 | 2.96 |
| 78 | 1.41 |
| 88 | 1.38 |
| 199 | 1.14 |
| 206 | 0.68 |
| 207 | 1.91 |
| 208 | 0.38 |
| 209 | 0.27 |
| 474 | 0.36 |
| 485 | 1.83 |
| 497 | 0.31 |
| 506 | 1.38 |
| 512 | 0.14 |
| 518 | 0.1 |
| 519 | 0.12 |
| 520 | 0.32 |
| 522 | 0.39 |
| 526 | 0.36 |
| 527 | 0.37 |
| 529 | 0.12 |
| 533 | 0.5 |
| 534 | 0.36 |
| 548 | 0.29 |
| 549 | 0.33 |
| 552 | 0.2 |
| 553 | 0.1 |
| 555 | 0.3 |
| 556 | 0.03 |
| 558 | 0.04 |
| 559 | 0.36 |
| 563 | 0.01 |
| 565 | 0.28 |
| 566 | 0.56 |
| 570 | 2.15 |
| 572 | 1.07 |
| 573 | 0.05 |
| 612 | 0.41 |
| 613 | 0.12 |
| 619 | 0.49 |
| 646 | 1.23 |
| 664 | 1.29 |
| 706 | 0.16 |
| 709 | 0.12 |
| 710 | 0.14 |
| 888 | 0.48 |
| 889 | 0.04 |
| 892 | 0.55 |
| 895 | 0.53 |
| 897 | 0.62 |
| 900 | 0.36 |
| 905 | 0.14 |
| 906 | 0.15 |
| 918 | 0.2 |
| 921 | 0.1 |
| 922 | 0.11 |
| 928 | 0.13 |
| 935 | 0.41 |
| 957 | 0.38 |
| 965 | 0.38 |
| 967 | 0.32 |
| 977 | 0.13 |
| 978 | 0.12 |
| 982 | 0.1 |
| 993 | 0.13 |
| 996 | 0.58 |
| 999 | 0.14 |
| 1000 | 0.14 |
| 1007 | 0.1 |
| 1015 | 0.34 |
| 1016 | 0.5 |
| 1021 | 0.31 |
| 1023 | 0.92 |
| 1034 | 0.17 |
| 1047 | 0.19 |

TABLE 1-continued

| Example | EC$_{100}$ (μM) |
|---|---|
| 1050 | 0.22 |
| 1052 | 0.38 |
| 1055 | 0.13 |
| 1068 | 0.46 |
| 1073 | 0.36 |
| 1087 | 0.36 |
| 1088 | 0.14 |
| 1091 | 0.03 |
| 1092 | 0.02 |
| 1093 | 0.04 |
| 1094 | 0.03 |
| 1095 | 0.3 |
| 1096 | 0.11 |
| 1098 | 0.11 |
| 1100 | 0.38 |
| 1108 | 0.36 |
| 1109 | 0.07 |
| 1110 | 0.3 |
| 1111 | 0.12 |
| 1114 | 0.41 |
| 1115 | 1.74 |
| 1116 | 1.31 |
| 1118 | 0.42 |
| 1119 | 0.73 |
| 1122 | 0.9 |
| 1123 | 0.95 |
| 1125 | 0.5 |
| 1126 | 0.77 |
| 1129 | 0.61 |
| 1131 | 0.23 |
| 1132 | 0.41 |
| 1133 | 1.29 |
| 1148 | 0.13 |
| 1153 | 0.34 |
| 1182 | 1.03 |
| 1191 | 0.02 |
| 1192 | 0.04 |
| 1194 | 0.91 |
| 1197 | 0.15 |
| 1202 | 0.2 |
| 1203 | 0.01 |
| 1208 | 0.96 |
| 1215 | 0.39 |
| 1216 | 0.54 |
| 1217 | 0.19 |
| 1218 | 0.15 |
| 1227 | 0.37 |
| 1281 | 0.12 |
| 1286 | 1.2 |
| 1290 | 0.26 |

Experimental Example 2

Inhibitory Effect on the Rhythmic Bladder Contractions in Anesthetized Rats

Female Sprague-Dawley rats (9 to 12 weeks old weighing between 200 to 300 g) were anethethized with urethane (subcutaneously administered with a dose of 1.2 g/kg). Both ureters were cannulated to excrete urine. A cannula was inserted into the bladder via the urethra and secured with a ligature around the urethral opening and connected to a three-way stopcock. The ends were connected to a pressure transducer for measurement of bladder pressure and to a infusion pump for intravesical infusion of saline. A cannula was inserted in the femoral vein for intravenous (i.v.) drug administration. Following a over 20 minute post-surgical stabilization period and emptying of urine in the bladder, saline was infused into the bladder (50 μl/min) to evoke the micturition reflex. After the rhythmic bladder contractions had occurred, the saline infusion rate into the bladder was changed to 5 μl/min in order to maintain these contractions. Compounds were administered after stable rhythmic bladder contraction was obtained over 15 minutes. All compounds were dissolved in saline containing 10% dimethyl acetamide for intravenous administration (1 ml/kg). When iberiotoxin, a large conductance calcium-activated K channel blocker (0.15 mg/kg, i.v.) was administered for comparison purposes, it was administered 5 minutes before drug administration.

The frequencies (contractions per minute) of rhythmic bladder contractions were calculated for 10 minutes before and after drug administration. The efficacy of compounds expressed as percent of inhibition in frequency, which calculated from the following formula:

(1−frequency after dosing/frequency before dosing)× 100(%)

As a result, compounds of the present invention decreased the frequency of bladder rhythmic contraction without changing the amplitude of contraction. A compound of example 5 shows 78% inhibition (10 mg/kg) in the model. A percent of inhibition in frequency of the selected compounds of the present invention at 10 mg/kg is shown in the following Table 2.

TABLE 2

| Example | |
|---|---|
| 12 | A |
| 22 | A |
| 31 | B |
| 52 | A |
| 59 | B |
| 497 | B |
| 527 | A |
| 534 | B |
| 565 | B |
| 567 | B |
| 612 | A |
| 619 | B |
| 693 | A |
| 977 | B |
| 1091 | B |
| 1110 | B |
| 1227 | B |

A: inhibition(%) > 50,
B: 50 > inhibition(%) > 30

Experimental Example 3

Methods for Testing Compounds on Inhibiting COXs

Activities of inhibiting COXs can be investigated by the manner described in Proc. Natl. Acad. Sci. USA 96, 7563, 1996.

As a result, compounds of the present invention are less or no potent COXs inhibitors. A result of COXs inhibition of the selected compounds (Example Nos. 1, 3, 12, 188, 474, 497, 507, 513, 527, 533, 562, and 638) are: ratWB Cox-1 IC50>30 μM and ratWB IC50>30 μM.

INDUSTRIAL APPLICABILITY

The compound of formula (A) or a pharmaceutically acceptable salt thereof which is an active ingredient of the present invention has an excellent large conductance calcium-activated K channel opening activity and hyperpolarizes a membrane electric potential of cells, so that it is useful for a prophylactic, relief and/or treatment agent of, for example, hypertension, irritable bowel syndrome, chronic heart failure, angina, cardiac infarction, cerebral infarction, subarachnoid hemorrhage, cerebral vasospasm, cerebral hypoxia, peripheral blood vessel disorder, anxiety, erectile dysfunction, urolithiasis and pain accompanied thereby, pollakiuria, urinary incontinence, nocturnal enuresis, asthma, chronic obstructive pulmonary disease (COPD), cough accompanied by asthma or COPD, intracerebral hemorrhage, traumatic encephalopathy, interstitial cystitis, prostatitis, pain accompanied by prostatitis, overactive bladder and the like.

Also, the compound of formula (A) or a pharmaceutically acceptable salt thereof has no or a low toxicity, so that it has high safety as a medicine.

The invention claimed is:

1. A compound of formula (A):

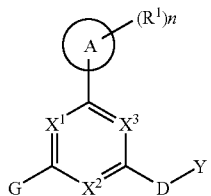

wherein ring A is an aromatic ring or a heteroaromatic ring;

$R^1$ is independently a halogen, cyano, an alkylthio, a cycloalkyl, an alkanoyl, an amino optionally substituted by alkyl(s), an alkylsulfonyl, an alkoxy optionally substituted by one to three substituent(s) independently selected from a halogen, an alkoxy and hydroxy, or an alkyl optionally substituted by one to three substituent(s) independently selected from a halogen, an alkoxy and hydroxy;

n is 0, 1, 2, 3 or 4;

Each of $X^1$, $X^2$ and $X^3$ is independently $CR^2$ or nitrogen, provided that one of $X^1$, $X^2$ and $X^3$ is $CR^2$ and the others are nitrogens;

$R^2$ is independently hydrogen, a halogen, an alkoxy optionally substituted by one to three substituent(s) independently selected from a halogen, an alkoxy and hydroxy, or an alkyl optionally substituted by one or more substituent(s) independently selected from halogen, an alkoxy and hydroxy;

Y is carboxy, tetrazolyl or an alkoxycarbonyl;

D is a group of formula:

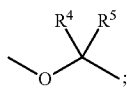

wherein $R^4$ and $R^5$, taken together with the atom(s) to which they are bonded, form a cyclopropane ring optionally substituted by one or more alkyl(s);

G is —$NR^{10}R^{11}$, —$OR^{14}$, a phenyl optionally substituted by one or more $R^{15}$(s) or a group of formula:

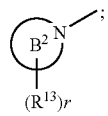

$R^{10}$ is an alkyl substituted by one or more substituent(s) independently selected from an alkoxy, hydroxy, and a group of formula:

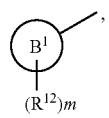

or a cycloalkyl optionally substituted by one or more $R^{12}$(s);

$R^{11}$ is hydrogen, or an alkyl optionally substituted by one to three substituent(s) independently selected from an alkoxy and hydroxy;

$R^{12}$ is independently a halogen, cyano, an alkylthio, a cycloalkyl, an alkanoyl, an amino optionally substituted by alkyl(s), an alkylsulfonyl, an alkoxy optionally substituted by one to three substituent(s) independently selected from a halogen, an alkoxy and hydroxy, or an alkyl optionally substituted by one to three substituent(s) independently selected from a halogen, an alkoxy and hydroxy;

$R^{13}$ is independently hydroxy, an alkoxy optionally substituted by one to three substituent(s) independently selected from a halogen, an alkoxy, a cycloalkyl and hydroxy, an alkylsulfonyl, oxo, a halogen, cyano, an aryl, a heteroary, an aryloxy, a heteroaryloxy, an alkoxycarbnyl or an alkyl optionally substituted by one to three substituent(s) independently selected from a halogen, hydroxy, and an optionally substituted alkoxy;

$R^{14}$ is an alkyl substituted by a group of formula

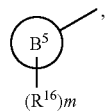

or a group of formula

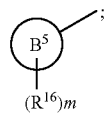

Ring $B^1$ is a carbocyclic ring, a heterocyclic ring, an aromatic ring or a heteroaromatic ring;

Ring $B^2$ is a nitrogen containing heterocyclic ring;

Ring $B^5$ is a carbocyclic ring, a heterocyclic ring, an aromatic ring or a heteroaromatic ring;

$R^{15}$ is independently a halogen, cyano, an alkylthio, a cycloalkyl, a cycloalkyloxy, an alkanoyl, an amino optionally substituted by alkyl(s), an alkylsulfonyl, an alkoxy optionally substituted by one to three substituent(s) independently selected from a halogen, an alkoxy, a cycloalkyl and hydroxy, or an alkyl optionally substituted by one to three substituent(s) independently selected from a halogen, an alkoxy and hydroxy;

$R^{16}$ is independently a halogen, cyano, an alkylthio, a cycloalkyl, an alkanoyl, an amino optionally substituted by alkyl(s), an alkylsulfonyl, an alkoxy optionally substituted by one to three substituent(s) independently selected from a halogen, an alkoxy and hydroxy, or an alkyl optionally substituted by one to three substituent(s) independently selected from a halogen, an alkoxy and hydroxy;

m is 0, 1, 2 or 3; and r is 0, 1, 2 or 3, provided that when G is phenyl optionally substituted by one or more $R^{15}$, Ring A is an aromatic ring;

or a pharmaceutically acceptable salt thereof.

2. The compound according to claim 1 or a pharmaceutically acceptable salt thereof, wherein $R^2$ is hydrogen.

3. The compound according to claim 1 or a pharmaceutically acceptable salt thereof, wherein ring A is benzene.

4. The compound according to claim 1 or a pharmaceutically acceptable salt thereof, wherein $R^1$ is independently a halogen, an alkoxy, or an alkyl optionally substituted by one to three halogen(s).

5. A pharmaceutical composition comprising the compound according to claim 1 or a pharmaceutically acceptable salt thereof as an active ingredient.

6. The compound according to claim 2 or a pharmaceutically acceptable salt thereof, wherein ring A is benzene.

7. The compound according to claim 2 or a pharmaceutically acceptable salt thereof, wherein $R^1$ is independently a halogen, an alkoxy, or an alkyl optionally substituted by one to three halogen(s).

8. The compound according to claim 3 or a pharmaceutically acceptable salt thereof, wherein $R^1$ is independently a halogen, an alkoxy, or an alkyl optionally substituted by one to three halogen(s).

* * * * *